US006647358B2

(12) United States Patent
Grass et al.

(10) Patent No.: US 6,647,358 B2
(45) Date of Patent: *Nov. 11, 2003

(54) PHARMACOKINETIC-BASED DRUG DESIGN TOOL AND METHOD

(75) Inventors: George M. Grass, Tahoe City, CA (US); Glen D. Leesman, Hamilton, MT (US); Daniel A. Norris, San Diego, CA (US); Patrick J. Sinko, Lebanon, NJ (US); John E. Wehrli, Mountain View, CA (US)

(73) Assignee: Lion Bioscience AG, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/320,371

(22) Filed: May 26, 1999

(65) Prior Publication Data

US 2002/0013662 A1 Jan. 31, 2002

Related U.S. Application Data

(60) Provisional application No. 60/100,224, filed on Sep. 14, 1998, provisional application No. 60/109,234, filed on Nov. 18, 1998, provisional application No. 60/100,290, filed on Sep. 14, 1998, and provisional application No. 60/109,232, filed on Nov. 18, 1998.

(51) Int. Cl.[7] .......................... G06N 3/00; G06F 9/455; G06G 7/60
(52) U.S. Cl. .............................. 703/2; 703/11; 702/19
(58) Field of Search ...................... 395/500.02; 709/19; 703/2, 11

(56) References Cited

U.S. PATENT DOCUMENTS

| | | |
|---|---|---|
| 4,335,438 A | 6/1982 | Smolen |
| 4,411,989 A | 10/1983 | Grow |
| 4,775,794 A | 10/1988 | Behmann |
| 4,952,061 A | 8/1990 | Edgar |
| 4,975,581 A | 12/1990 | Robinson et al. |
| 5,331,573 A | 7/1994 | Balaji et al. |
| 5,387,421 A | 2/1995 | Amidon et al. |
| 5,569,452 A | 10/1996 | Amidon et al. |
| 5,579,250 A * | 11/1996 | Balaji et al. .................. 702/19 |
| 5,625,579 A | 4/1997 | Hinsberg, III et al. |
| 5,657,255 A | 8/1997 | Fink et al. |
| 5,680,590 A | 10/1997 | Parti .......................... 195/500 |
| 5,699,268 A | 12/1997 | Schmidt |
| 5,703,792 A | 12/1997 | Chapman |
| 5,705,335 A | 1/1998 | Hendry |
| 5,770,384 A | 6/1998 | Androphy et al. |
| 5,789,160 A | 8/1998 | Eaton et al. |
| 5,807,879 A * | 9/1998 | Rosebrough ................ 514/387 |
| 5,808,918 A | 9/1998 | Fink et al. |
| 5,854,992 A | 12/1998 | Shakhnovich et al. |
| 5,880,972 A | 3/1999 | Horlbeck |
| 5,914,891 A | 6/1999 | McAdams et al. |
| 5,956,501 A | 9/1999 | Brown |
| 5,989,918 A | 11/1999 | Dietz et al. |
| 6,150,416 A | 11/2000 | Kick et al. |

FOREIGN PATENT DOCUMENTS

| | | | |
|---|---|---|---|
| EP | 0 818 744 A2 | 1/1998 | ............ A61K/9/48 |
| EP | 0 918 296 A1 | 5/1999 | ......... G01N/33/487 |
| WO | WO 94/23705 | 10/1994 | ............ A61K/9/48 |
| WO | WO 96/13721 | 5/1996 | ......... G01N/33/487 |
| WO | WO 97/16717 | 5/1997 | .......... G01N/13/00 |
| WO | WO 97/20952 | 6/1997 | ............ C12Q/1/68 |
| WO | WO 97/22000 | 6/1997 | .......... G01N/33/50 |
| WO | WO 97/29091 | 8/1997 | .......... C07D/223/12 |
| WO | WO 97/49987 | 12/1997 | .......... G01N/27/02 |
| WO | WO 98/00231 | 1/1998 | ............ B01J/19/00 |

OTHER PUBLICATIONS

Enslein (A Journal of Molecular and Cellular Toxicology 6(3) 163–169, 1993).*

Database Derwent, Accession, No.: 1995–263280, Carrell et al, 'Biologically active molecule combinatorial library production—by reacting core molecule with tool molecules, especially for preparation of new xanthene derivative serine protease inhibitors', abstract, WO 95/19359 A, Jul. 20, 1995.

Database Dialog, INSPEC Abstract No.: C82024056, Holford, N.H.G. 'DRUGMODEL (pharmacokinetic modelling),' abstract, Proceedings of the fifth annual symposium on computer applications in medicinal care. New York: IEEE, 1981, pp. 603–606.

(List continued on next page.)

*Primary Examiner*—Marjorie Moran
(74) *Attorney, Agent, or Firm*—Arent Fox Kintner Plotkin & Kahn, PLLC

(57) ABSTRACT

The present invention relates to a pharmacokinetic-based design and selection tool (PK tool) and methods for predicting absorption of an administered compound of interest. The methods utilize the tool, and optionally a separately operable component or subsystem thereof. The PK tool includes as computer-readable components: (1) input/output system; (2) physiologic-based simulation model of one or more segments of a mammalian system of interest having one or more physiological barriers to absorption that is based on the selected route of administration; and (3) simulation engine having a differential equation solver. The invention also provides methods for optimizing as well as enabling minimal input requirements a physiologic-based simulation model for predicting in vivo absorption, and optionally one or more additional properties, from either in vitro or in vivo data. The PK tool of the invention may be provided as a computer system, as an article of manufacture in the form of a computer-readable medium, or a computer program product and the like. Subsystems and individual components of the PK tool also can be utilized and adapted in a variety of disparate applications for predicting the fate of an administered compound. The PK tool and methods of the invention can be used to screen and design compound libraries, select and design drugs, as well as predict drug efficacy in mammals from in vitro and/or in vivo data of one or more compounds of interest. The PK tool and methods of the invention also finds use in selecting, designing, and preparing drug compounds, and multi-compound drugs and drug formulations (i.e., drug delivery system) for preparation of medicaments for use in treating mammalian disorders.

382 Claims, 38 Drawing Sheets

OTHER PUBLICATIONS

Holford, N.H.G. 'DRUGMODEL,' Proceedings of the fifth annual symposium on computer applications in medicinal care. New York: IEEE, 1981, pp. 603–606.

Artursson et al., "Caco–2 Monolayers in Experimental and Theoretical Predictions of Drug Transport", *Advanced durg Delivery Reviews* (1996) vol. 22, pp. 67–84.

Audus et al., "The Use of Cultured Epitheelial and Endothelial Cells for Drug Transport and Metabolism Studies", *Pharmaceutical Research* (1990) vol. 7, No. 5, pp. 435–451.

Bailey et al., "The Use of the Intestinal Epithelial Cell Culture Model, Caco–2 in Pharmaceutical Development", *Advanced Drug Delivery Reviews* (1996) vol. 22 pp. 85–103 de Boer et al., "Reconstitution of the Blood–Brain Barrier in Cell Culture for Studies of Drug Transport and Metabolism", *Advanced Drug Deliver Reviews* (1996) vol. 22, pp. 251–264.

Friedberg et al., "Recombinant DNA Technology as an Investigative Tool in Drug Metabolism Research", *Advanced Drug Delivery Reviews* (1996) vol. 22, pp. 187–213.

Grass et al., "Mechanisms of Corneal Drug Penetration III: Modeling of Molecular Transport", *Journal of Pharmaceutical Sciences*, (1988) vol. 77, No. 1, pp. 24–26.

Grass et al., "In Vitro Measurement of Gastrointestinal Tissue Permeability Using a New Diffusion Cell", *Pharmaceutical Research* (1988) vol. 5, No. 6, pp. 372–376.

Hidalgo et al., "Characterization of the Unstirred Water Layer in Caco–2 Cell Monolayers Using a Novel Diffusion Apparatus", *Pharmaceutical Research* (1991) vol. 8, No. 2, pp. 222–227.

Hidalgo et al., "Letter to the Editor: A New Side–by–Side Diffusion Cell for Studying Transport Across Epithelial Cell Monolayers", *In Vivo Cell. Dev. Biol.* (1992) vol. 28A, pp. 578–580.

Hidalgo et al., "Carrier–Mediated Transport and Efflux Mechanisms in Caco–2 Cells", *Advanced Drug Delivery Reviews (1996)* vol. 22, pp. 53–66.

Hu et al., "Membrane Permeability Parameters for Some Amino Acids and β–Lactam Antibiotics: Application of the Boundary Layer Approach", *J. Theor. Biol.* (1988) vol. 131, pp. 107–114.

Jezyk et al., "Permeability Characteristics of Various Intestinal Regions of Rabbit, Dog, and Monkey", *Pharmaceutical Research* (1992) vol. 9, No. 12, pp. 1580–1586.

Kou et al., "Calculation of the Aqueous Diffusion Layer Resistance for Absorption in a Tube: Application to Intestinal Membrane Permeability Determination", *Pharmaceutical Research* (1991) vol. 8, No. 3, pp. 298–305.

Kuhfeld et al., "In Vitro Measurement of Drug Transport Using a New Diffusion Chamber Compatible with Millicell Culture Supports: Performance with Caco–2 Monolayers", *International Journal of Pharmaceutics* (1996) vol. 133, pp. 47–58.

LeCluyse et al., "Strategies for Restoration and Maintenance of Normal Hepatic Structure and Function in Long–Term Cultures of Rat Hepatocytes", *Advanced Drug Delivery Reviews (1996)* vol. 22, pp. 133–186.

Mathias et al., "Respiratory Epithelial Cell Culture Models for Evaluation of Ion and Drug Transport", *Advanced Drug Delivery Reviews* (1996) vol. 22, pp. 215–249.

Maurel, P., "The Use of Adult Human Hepatocytes in Primary Culture and other in Vitro Systems to Investigate Drug Metabolism in Man", *Advanced Drug Delivery Reviews* (1996) vol. 22, pp. 105–132.

Pidgeon et al., "IAM Chromatography: An In Vitro Screen for Predicting Drug Membrance Permeability", *J. Med. Chem.* (1995) vol. 38, pp. 590–594.

Quaroni et al., "Development of Intestinal Cell Culture Models for Drug Transport and Metabolism Studies", *Advanced Drug Delivery Reviews* (1996) vol. 22, pp 3–52.

Rubas et al., "Comparison of the Permeability Characteristics of a Human Colonic Epithelial (Caco–2) Cell Line to Colon of Rabbit, Monkey, and Dog Intestine and Human Drug Absorption", *Pharmaceutical Research* (1993) vol. 10, No. 1, pp. 113–118.

Abstracts from *Pharmaceutical Research* (1992) vol. 9, No. 10—PDD 7046, Lennernas et al., "Solvent Drag and Intestinal Drug Absorption Studied by Human Intestinal Perfusion" and PDD 7048, Karlsson et al., "A New Diffusion Chamber System for the Determination of Drug Permeability Coefficients Across the Human Intestinal Epithelium that are Independent of the Unstirred Water Layer"—p. S–180.

Abstract from *Pharmaceutical Research* (1996) vol. 13, No. 9—PDD 7039, McCarthy et al., "Automated Permeability Analysis of Mixtures Across Caco–2 Cell Monlayers"—p. S–242.

Abstract from *Pharmaceutical Research* (1996) vol. 11, No. 10—APQ 1113, Kuhfeld et al., "An Automated In Vitro Permeability Screen Using Robotics", p. S–39.

Abstract from *Pharmaceutical Research* (1995) vol. 12, No. 9—BIOTEC 2064, Augustijns et al., "Permeability Screen for Synthetic Peptide Combinatorial Libraries Using Caco–2 Cell Monolayers and LC/MS/MS", p. S–94.

Aarons et al., "Computer–assisted Learning Lessons in Drug Disposition and Pharmacokinetics", *Journal of Pharmacological Methods* (1980) vol. 20, pp. 109–123.

Allen, G., "MODFIT: A Pharmacokinetics Computer Program", *Biopharmaceutics & Drug Disposition* (1990) vol. 11, pp. 477–498.

Amidon et al., "Model–Independent Prediction Methods in Pharmacokinetics: Theoretical Considerations", *Mathematical Biosciences* (1975) vol. 25, pp. 259–272.

Amidon et al., "A Theoretical Basis for a Biopharmaceutic Drug Classification: The Correlation of In Vivo Drug Product Dissolution and In Vivo Biavailability", *Pharmaceutical Research* (1995) vol. 12, No. 3, pp. 413–420.

Barbalas et al., "Quantitative Selected Ion Monitoring Processing System: Software and Hardware for the Automated Collection and Analysis of Selected Ion Monitoring Data Acquired for Use in Pharmacokinetic Studies", *Journal of Pharmaceutical Sciences* (1988) vol. 77, No. 8, pp. 679687.

Barvasis et al., "The Pharmacokinetics of Intravenous Anesthetic Drugs Given by Infusion: SPINA*—a Software Program", *European Journal of Anesthesiology* (1989) vol. 6, pp. 435–447.

Beckett et al., "A Model for Steroid Transport Across Biological Membranes", *J. Pharm. Pharmac.*, (1975) vol. 27, pp. 226–234.

Berger et al., "Combining Statistical, Rule–Based, and Physioologic Model–Based Methods to Assist in the Management of Diabetes Mellitus", *Computers and Biomedical Research* (1990) vol. 23, pp. 346–357.

Blakey et al., "Quantitative Structure–Pharmacokinetics Relationships: I. Development of a Whole–Body Physiologically Based Model to Characterize Changes in Pharmcokinetics Across a Homologous Series of Barbiturates in the Rat", *Journal of Pharmacokinetics and Biopharmaceutics*, (1997) vol. 25, No. 3, pp. 377–312.

Bois et al., "Bioequivalence: Performance of Several Measures of Extent of Absorption", *Pharmaceutical Research* (1994) vol. 11, No. 5, pp. 715–722.

Bradshaw, J., "Prediction of Metabolism, Degradation and Toxicity of Xenobiotics", *Pesticide Sci.* (1992) vol. 34, No. 2, p. 185.

Campbell, D.B., "Extrapolation from Animals to Man: The Integration of Pharmacokinetics and Pharmacodynamics" in *Cellular and Molecular Mechanisms of Drugs of Abuse* (1996) Edited by S. F. Ali and Y. Takahashi, pp. 116–135.

Cardot et al., "PKC, A New Pharmacokinetic Software Using SAS", *European Journal of Pharmaceutics and Biopharmaceutics* (1997) vol. 43, pp. 197–199.

Chan et al., "Physiochemical and Drug–delivery Considerations for Oral Drug Bioavailability", *DDT* (1996) vol. 1, No. 11, pp. 461–473.

Chiou, W.L., "Determination of Drug Permeability in a Flat of Distended Stirred Intestine", *International Journal of Clinical Pharmacology and Therapeutics* (1994) vol. 32, No. 9, pp. 474–482.

Combrink et al., "A Comparison of the Standard Approach and the NONMEM Approach in the Estimation of Bioavailability in Man", *J. Pharm Pharmacol.* (1997) vol. 49, pp. 731–733.

Conolly et al., "Biologically Based Pharmacodynamic Models: Tools for Toxicological Research and Risk Assessment", *Ann. Rev. Pharmacol. Toxicol.* (1991) vol. 31, pp. 503–523.

Dijkstra et al., "Simulation of Nutrient Digestion, Absorption and Outflow in the Rumen: Model Description", *American Institute of Nutrition* (1992) pp. 2239–2256.

Dong, M.H., "Microcomputer Programs for Physiologically–based Pharmacokinetic (PB–PK) Modeling", *Computer Methods and Programs in Biomedicine* (1994) vol. 45, pp. 213–221.

Firmer et al., "Simulation of Gastrointestinal Drug Absorption I. Longitudinal Transport in the Small Intestine", *International Journal of Pharmaceutics* (*1988*) vol. 48, pp. 231–246

Franck et al., "KINI: A One Compartment Intravenous Pharmacokinetics Analysis Program", *Computer Methods and Programs in Biomedicine* (1994) vol. 42, pp. 157–165.

Gex–Fabry et al., "Considerations on Data Analysis Using Computer Methods and Currently Available Software for Personal Computers" in *Handbook on Experimental Pharmacology* (1994) vol. 110, pp. 507–527 (Chapter 13).

Grass et al., "A Model to Predict Aqueous Humor and Plasma Pharmacokinetics of Ocularly Applied Drugs", *Investigative Ophthalmology & Visual Science* (1993) vol. 34, No. 7, pp. 2251–2259.

Grass et al., "Evaluation of the Performance of Controlled Release Dosage Forms of Ticlopidine Using In Vitro Intestinal Permeability and Computer Simulations", *Journal of Drug Targeting* (1994) vol. 2, pp. 23–33.

Grass, G.M., "Simulation Models to Predict Oral Drug Absorption from In Vitro Data", *Advanced Drug Delivery Reviews* (1997) vol. 23, pp. 199–219.

Gomeni et al., IGPHARM: Interactive Graphic Package for Pharmacokinetic Analysis, *Computers and Biomedical Research* (1978) vol. 11, pp. 345–361.

Gomeni, R., "Pharm–an Interactive Graphic Program for Individual and Population Pharmacokinetic Parameter Estimation", *Comput. Bio. Med.* (1994) vol. 14, No. 1, pp 25–34.

Hampton et al., "Comparison of MS–DOS and Macintosh Pharmacokinetic Analysis Programs Using a Two–Compartment, Two–Infusion Dosing Scheme", *Clinical Pharmacy* (1991) vol. 10, pp. 206–209.

Hayashi et al., "Pharmacokinetic Analysis of Cimetidine Plasma Concentration Data in Dogs Using a Two Phase Absorption Model", *Pharmaceutical Research* (1994) vol. 11, No. 10, p. S–420.

Hoang, K.T., "Physiologically Based Pharmacokinetic Models: Mathematical Fundamentals and Simulation Implementations", *Toxicology Letters* (1995) vol. 79, pp. 99–106.

Idkaidek et al., "Determination of the Population Pharmacokinetic Parameters of Sustained–Release and Enteric–Coated Oral Formulations, and the Suppository Formulation of Diclofenac Sodium by Simultaneous Data Fitting Using NONMEM", *Biopharmaceutics & Drug Disposition* (1998) vol. 19, pp. 169–174.

Jelliffe, R.W., "The USC*PACK PC Programs for Population Pharmacokinetic Modeling, Modeling of Large Kinetic/Dynamic Systems, and Adaptive Control of Drug Dosage Regimens" *Symposium on Computer Applications in Medical Care: A Conference of the American Medical Informatics Association* (1991) pp. 922–923.

Kalmaz, E.E., "Computer Modeling and Parameter Estimation for Pharmacokinetics and Toxicity Studies", *Journal of American College of Toxicology* (1996) vol. 5, No. 6, p. 607.

Keller et al., "Standardized Structure and Modular Design of a Pharmacokinetic Database", *Computer Methods and Programs in Biomedicine* (1988) vol. 55, pp. 107–115.

Kirkup et al., "A Demonstration of Pharmacokinetics and Physiological Modelling Using a Microcomputer for Data Capture and Analysis", *Computer Applications in the Biosciences* (1986) vol. 2, No. 4, pp. 277–282.

Kwon et al., "Theoretical Considerations on Two Equations for Estimating the Extent of Absorption After Oral Administration of Drugs", *Pharmaceutical Research* (1986) vol. 13, No. 4, pp. 566–569.

Langguth et al., "Variable Gastric Emptying and Discontinuities in Drug Absorption Profiles: Dependence of Rates and Extent of Cimetidine Absorption on Motility Phase and PH", *Biopharmaceutics & Drug Disposition* (1994) vol. 15, pp. 719–746.

Leader et al., "Integrating Pharmacokinetics into Point–of–Care Information Systems", *Clinical Pharmacokinetics* (1996) vol. 31, No. 3, pp. 165–173.

Leahy et al., "Physiologic Based Pharmacokinetic Modelling and QSAR", *Bioactive Compound Design: Possibilities for Industrial Use*, pp. 147–151.

Lincoln et al., "Pharmacokinetic Simulation: A Future Means for Better Control of Cancer Chemotherapy", *Recent Results in Cancer Reseacrh*, pp. 103–107.

Lu et al., "An Interactive Program for Pharmacokinetic Modeling", *Journal of Pharmaceutical Sciences* (1993) vol. 82, No. 5, pp. 537–542.

Luner et al., "Description and Simulation of a Multiple Mixing Tank Model to Predict the Effect of Bile Sequestrants on Bile Salt Excretion", *Journal of Pharmaceutical Sciences* (1993) vol. 82, No. 3, pp. 311–318.

Mazumdar et al., "A Mathematical Study of Simple Exponential Modelling in Biochemical Processes", *Australasian Physical & Engineering Sciences in Medicine* (1991) vol. 14, No. 4, pp. 226–233.

Metzler et al., "Package of Computer Programs for Pharmacokinetic Modeling", *Biometrics, Journal of the Biometric Society* (1974) vol. 30, No. 3, pp. 562–563.

Metzler, C.M. "Commentary to Linear and Nonlinear System Approaches in Pharmacokinetics. How Much Do They Have To Offer? II. The Response Mapping Operator (RMO) Approach", *J. Pharmacokin, Biopharm,* (1988) vol. 16, pp. 543–571.

Murata et al., "Pharmacokinetic Analysis of Single or Multiple–Dose Plasma Drug Concentration Data with a Microcomputer Using Multi–Fraction Absorption Models", *Journal of Pharmaceutical Sciences* (1989) vol. 78, No. 2, pp. 154–159.

Nakai et al., "Evaluation of the Efficiency of Targeting of Antitumor Drugs: Simulation Analysis Based on Pharmacokinetic/Pharmacodynamic Considerations", *J. Drug Targeting* (1996) vol. 8, pp. 448–453.

Nikiforidis et al., "Individualization of Theophylline Infusion Rate on the Basis of a Nonlinear Compartmental Pharmacokinetic Model", *European Journal of Drug Metabolism and Pharmacokinetics* (1997) vol. 22, No. 3, pp. 265–276.

Nogami et al., "Pharmacokinetic Analysis on the Disappearance of Ethoxybenzamide from Plasma. Statistical Treatment of Data of Two Compartmental Model by a Digital Computer", *Chem. Pharm. Bull.* (1969) vol. 17, No. 10, pp. 2097–2104.

Oh et al., "Estimating the Fraction Dose Absorbed from Suspensions of Poorly Soluble Compounds in Humans: A Mathematical Model", *Pharmaceutical Research* (1993) vol. 10, No. 2, pp. 264–270.

Pearce et al., "A Hybrid Computer System for Pharmacokinetic Modeling I. Software Considerations", *Proceedings of the 1981 Summer Computer Simulation Conference* (1981) pp. 117–121.

Pearce et al., "PKDEMO—A Pharmacokinetic Demonstration Simulation Program", *Simulation* (1991) vol. 56, No. 1, pp. 27–30.

Powers et al., "Automated Processing of Data from Pharmacokinetic Investigations", *Computers and Biomedical Research* (1976) vol. 9, pp. 543–548.

Primozic, S., "Pharmacokinetic Modeling and Simulation", *Acta Pharm. Jugosl.* (1990) vol. 40, p. 209.

Ramsay et al., "Pharmacokinetic Simulations Using STELLA: Prediction of In Vivo Performance of Oral Dosage Forms", *Eur. J. Pharm. Biopharm.* (1991) vol. 37, No. 3, pp. 192–197.

Scaf, A.H.J., "Pharmacokinetic Analysis with Rugfit: An Interactive Pharmacokinetic Computer Program", *Biographamaceutics & Drug Disposition (1988)* vol. 9, pp. 415–446.

Seydel et al., "Drug–Membrane Interaction and Accumulation, Conformation Efficacy and Resistance", *Bioactive Compound Design: Possibilities for Industrial Use* pp. 137–146.

Staats et al., "Gastrointestinal Absorption of Xenobiotics in Physiologically Based Pharmacokinetic Models", *Drug Metabolism and Disposition* (1991) vol. 19, No. 1, pp 144–148.

Stigsby et al., "A Computer Model Simulating the Intestinal Absorption of Bile Acids", *Gastroenterology* (1983) pp. 802–807.

Tanswell et al., "TopFit: A PC–Based Pharmacokinetic/Pharmacodynamic Data Analysis Program", *International Journal of Clinical Pharmacology: Therapy and Toxicology* (1993) vol. 31, No. 10, pp. 514–520.

Taylor et al., "The Development og a Nonequilibrium Model for Computer Simulation of Multicomponent Distillation and Absorption Operations", *Distillation and Absorption* (1987) pp. B321–334.

Thomaseth, K., "PANSYM: A Symbolic Equation Generator for Mathematical Modelling, Analysis and control of Metabolic and Pharmacokinetic Systems", *Computer Methods and Programs in Biomedicine* (1994) vol. 42, No. 2, pp. 73–146.

Timcenko et al., "Estimation of Pharmacokinetic Model Parameters", *JAMA Proceedings* (1995) pp. 47–51.

Veng Pedersen, P., "Curve Fitting and Modeling in Pharmacokinetics and Some Practical Experiences with NONLIN and a New Program FUNFIT", *Journal of Pharmacokinetics and Biopharmaceutics* (1977) vol. 5, No. 5, pp. 513–531.

Veng Pedersen et al., "Perspectives in Pharmacokinetics: Linear and Nonlinear System Approaches in Pharmacokinetics: How Much Do They Have to Offer? II. The Response Mapping Operator (RMO) Approach", *Journal of Pharmacokinetics and Biopharmaceutics* (1988) vol. 16, No. 5, pp. 543–571.

Veng Pedersen, P., "Mathematical and Computational Tools of Linear and Non–linear System Analysis in Pharmacokinetics", *Acta Pharm. Jogosl.* (1990) vol. 40, pp. 211–224.

Verotta et al., "Simultaneous Modeling of Pharmacokinetics and Pharmacodynamics: An Improved Algorithm", *Computer Applications in the Biosciences,* (1987) vol. 3, No. 4, pp. 345–349.

Waters et al., "Use of Computerized Data Listings and Activity Profiles of Genetic and Related Effects in the Review of 195 Compounds", *Mutation Research* (1988) vol. 205 pp. 295–312.

Yang et al., "Pharmacokinetics", *Introduction to Biochemical Toxicology*, Edited by E. Hodgson and P.E. Levi, Appleton & Lange, Norwalk, CT, pp. 49–73.

Yu et al., "DeMons—A New Deconvolution Method for Estimating Drug Absorbed at Different Time Intervals and/or Drug Disposition Model Parameters Using a Montonic Cubic Spline", *Biopharmaceutics & Drug Disposition* (1997) vol. 18, No. 6, pp. 475–487.

Zhang et al., "A Computer Model for Oral Transmucosal (OT) Bioavailability Prediction", *Pharmaceutical Research* (1997) vol. 14, No. 10, p. SA–662.

Zhou et al., "Methodology for Using Oral Does Pharmacokinetic Data to Select Drugs for Prolonged Release Formulations and Validation of the Method Using Simulated Data", *Biopharmaceutics & Drug Disposition* (1995) vol. 16, pp. 319–331.

Abstracts from *Pharmaceutical Research* (1995) vol. 12, No. 9, p. S–367—PPDM 8162, Yu et al., "Saturable Small Intestinal Drug Absorption in Humans: Modeling and Interpretation of Cefatrizine Data" and PPDM 8164, Heatherington et al., "A Pharmacokinetic–Pharmacodynamic Model to Predict Effect of Formulation of Lomustine on Medullat Blastoma Cells in the CSFG:A SAAM II Simulation".

Abstracts of *Pharmaceutical Research* (1992) vol. 9, No. 10, p. S–170—PDD 7005, Crison et al., "The Effect of Particle Size Distribution on Drug Dissolution: A Mathematical Model for Predicting Dissolution and Absorption of Suspensions in the Small Intestine" and PDD 7006, Kurihara–Bergstrom et al., "Transdermal Delivery of Buprenorphine in Man".

Carell et al., Abstract of "WO 95/19359," Jul. 20, 1995, Derwent Database.

Gex–Farby et al., "Considerations on Data Analysis Using Computer Methods and Currently Available Software for Personal Computers," *Pharmacokinetics of Drugs*, Edited by Welling et al., Berlin: Springer–Verlag, pp. 507–527, 1994.

Rossum et al., "Pharmacokinetic: A Dynamic Systems Approach," *Drug Metabolism and Distribution*, Edited by Lamble, Amsterdam: Elsiver Press, pp. 159–167, 1983.

Harvey, "Drug Absorption, Action and Disposition," Remington's Pharmaceutical Sciences, Easton Pennyslvania: Mack Publishing Co., Chap. 35 pp. 697–724, 1990.

Harvey et al., "Basic Pharmacokinetics," Remington's Pharmaceutical Sciences, Easton Pennsylvania: Mack Publishing Co., Chap. 36, pp. 725–745, 1990.

Rollins, "Clinical Pharmacokinetics," Remington's Pharmaceutical Sciences, Easton Pennsylvania: Mac Publishing Co., Chap. 37, pp. 746–756, 1990.

West Database Search Report for U.S. Pat. No. 5,770,384 (Androphy et al.).

West Database Search Report for U.S. Pat. No. 5,789,160 (Eaton et al.).

Seydel, J.K. et al., "Quantitative Structure–Pharmacokinetic Relationships and Drug Design", *Pharma. Ther.* (1982), vol. 15, pp. 131–181.

Enstein, Kurt, "The Future of Toxicity Prediction with QSAR", *In Vitro Toxicology A Journal of Molecular and Cellular Toxicology*, (1993) vol. 6, No. 3 pp. 162–169.

Abstract from *Pharmaceutical Research* (1994) vol. 11, No. 10—APQ 1113, Kuhfeld et al., "An Automated In Vitro Permeability Screen Using Robotics", p. S–39.

Notification of Transmittal of the International Search Report or the Declaration, Nov. 1, 2000, International Application No. PCT/US99/21001.

Written Opinion, Feb. 26, 2001, PCT/US99/21001.

Notification of Transmittal of International Preliminary Examination Report, Dec. 14, 2000, International Application No. PCT/US99/21151.

Written Opinion, Jul. 7, 2000, International Application No. PCT/US99/21151.

Notification of Transmittal of the International Search Report or the Declaration, Feb. 4, 2000, International Application No. PCT/US99/21151.

Abstract: Holford, N.H.G. "Drugmodel", 1981.

Abstract: Agrafiotis D. K.; Myslik J. C.; Salemme F. R., "Advances in diversity profiling and combinational series design", Accession No. 1999254287, 1999.

Abstract: Ajay; Bemis, Guy W.; Murcko, Mark A., "Designing Libraries with CNA Activity", 1999.

Abstract: Cho S J; Zheng W; Tropsha A, "Focus–2D: a new approach to the design of targeted combinatorial chemical libraries", 1998, Accession No. 1998362517.

Abstract: Hopfinger A. J.; Duca J.S.; "Extraction of pharmacophore information from high–throughput screens".

Abstract: Klebe, Gerhard, "Recent developments in structure–based drug design", 2000, Accession No. 2000:377851 BIOSIS.

Abstract: Konings D A M; Wyatt J R; Ecker D J; Freier S M, "Strategies for rapid deconvolution of combinatorial libraries: Comparative evaluation using a model system", 1997, Accession No. 1998:59476.

Abstract: Muller, G., "Toward 3D structures of G protein–coupled receptors; a multidisciplinary approach", 2000, Accession No. 2000456233.

Abstract: Olson A J: Goodsell D S, "Automated docking and the search for HIV protease inhibitors", 1998, Accession No. 1998182948.

Abstract: Parks C A; Crippen G M; Topless J G, "The measurement of Molecular diversity by receptor site interaction simulation"; 1998 Accession No. 10999051971.

Abstract: Sadowski, Jens; Wagener, Markus; Gasteiger, Johann, "Assessing similarity and diversity of combinatorial libraries by spatial autocorrelation functions and neural networks", 1996, Accession No. 1996:48099.

Abstract: Stahura F L; Xue L; Godden J W; Bajorath J., "Molecular scaffold–based design and comparison of combinatorial libraries focused on the ATP–binding site of protein kinases." 1999 Accession No. 2000126742.

Abstract: Zheng W F; Cho, S. J.; Trophas A, "Rational design of a targeted combinatorial chemical library with opiatelike activity", 1998, Accession No. 1998:494993.

Abstract: Zheng W; Cho S J; Tropsha A, "Rational combinatorial library design. 1. Focus–2D: a new approach to the design of targeted combinatorial chemical libraries", 1998, Accession No. 1998199335.

Abstract: Zheng, Weifan; Cho, Sung Jin; Waller, Chris L.; Tropsha, Alexander, "Rational Combinatorial Library Design 3. Simulated Annealing Guided Evaluation (SAGE) of Molecular Diversity: A Novel Computational Tool for Universal Library Design and Database Mining", 1999, Accession No. 1999:354936.

Nicholas H.G. Holford, "DRUGMODEL".

* cited by examiner

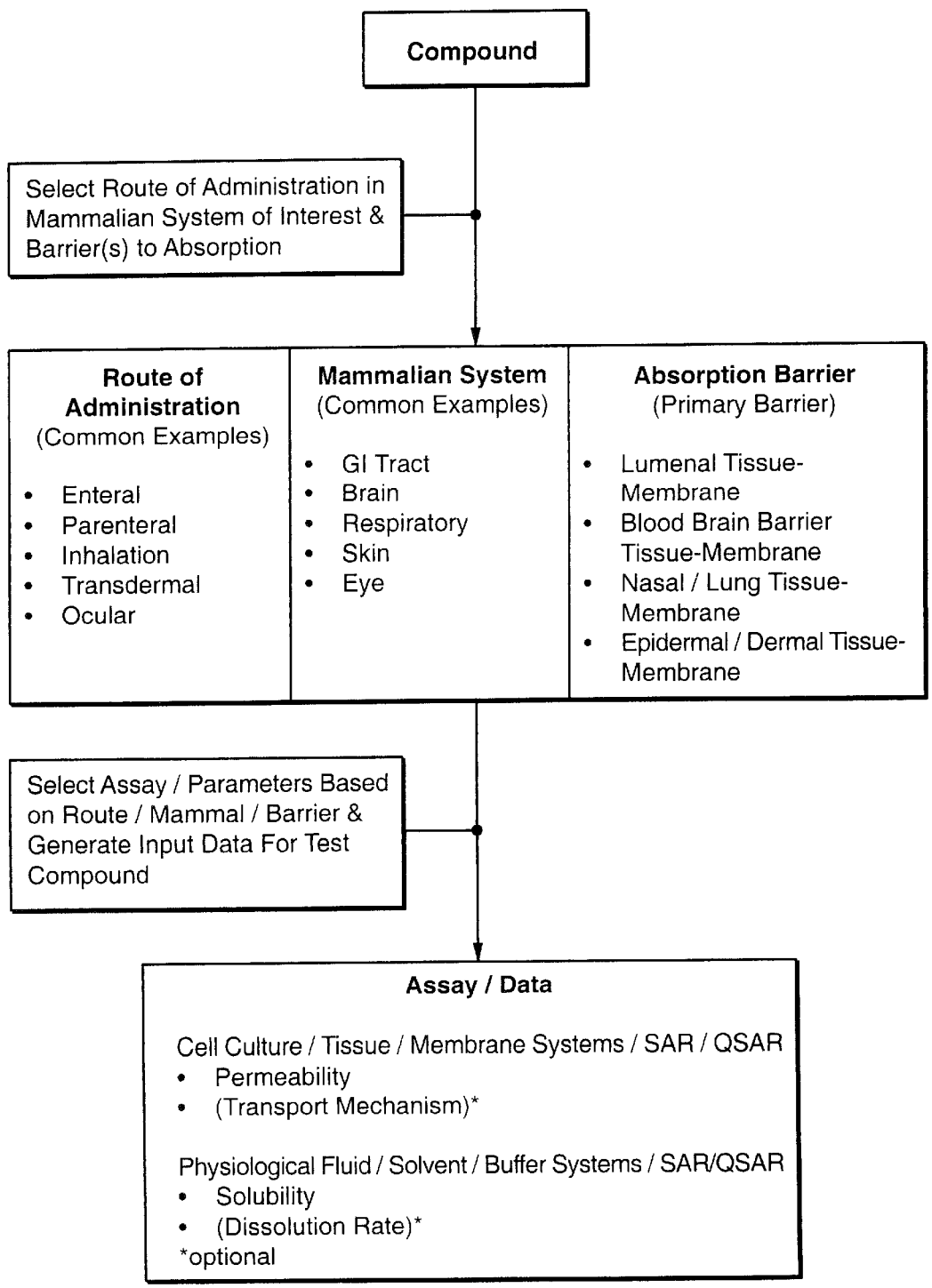
FIG._1

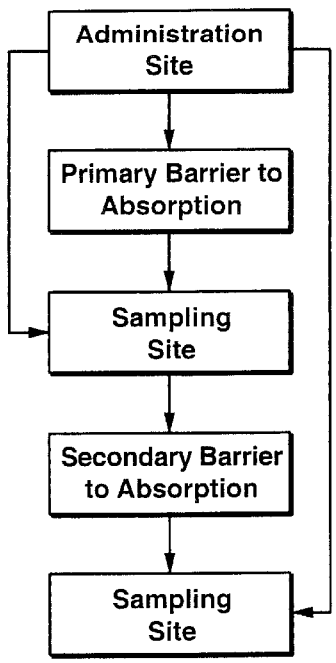
FIG._2
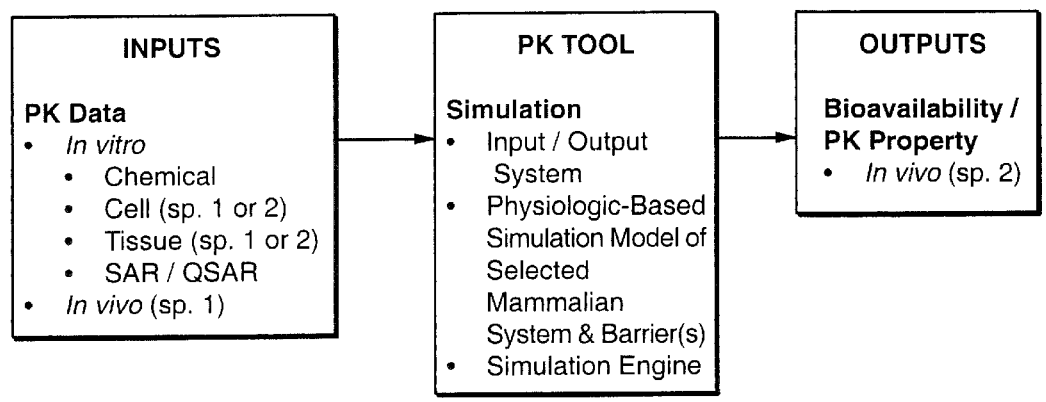
FIG._3

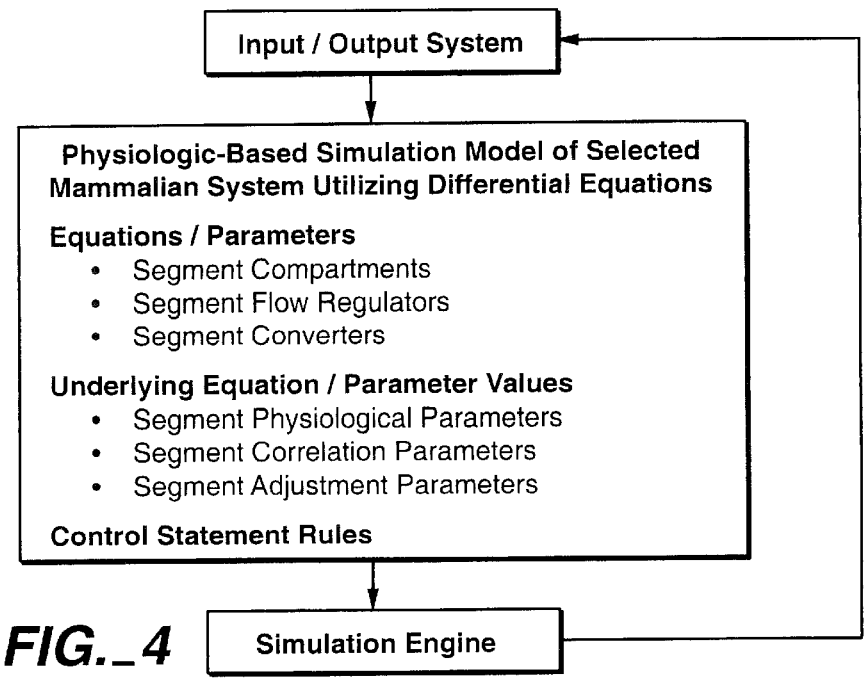
FIG._4
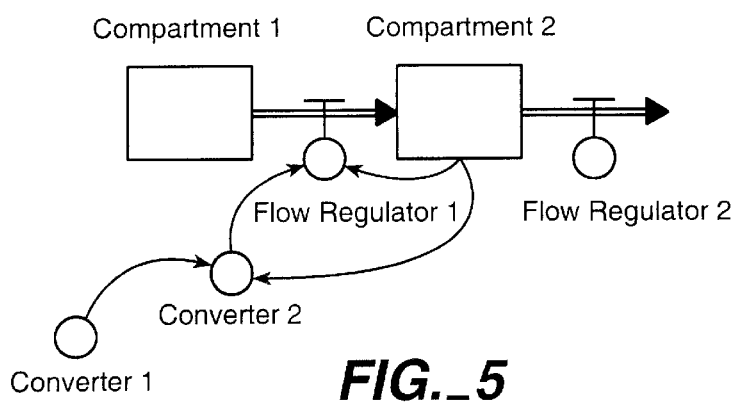
FIG._5
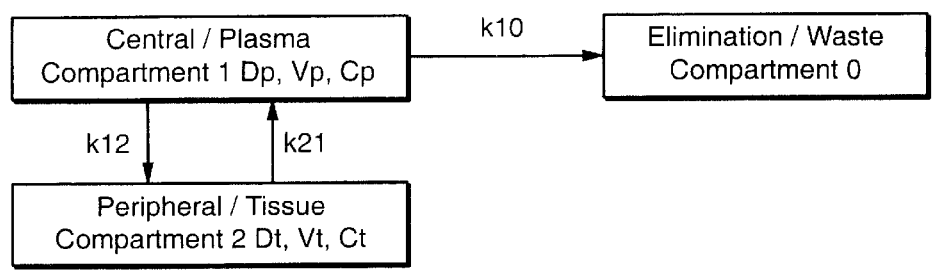
FIG._7

| Symbol | Name | Time-Dependent Function |
|---|---|---|
| □ | Compartment | Equation or value for amount of substance stored. |
| ⇒ (with regulator) | Flow Regulator | Rate equation for amount of substance transferred. |
| ○ | Converter | Equation or pre-defined value for (i) input into flow regulator; (ii) input into another converter; and / or (iii) storing value. |
| ↝ | Input Link | Directs input values. |
FIG._6
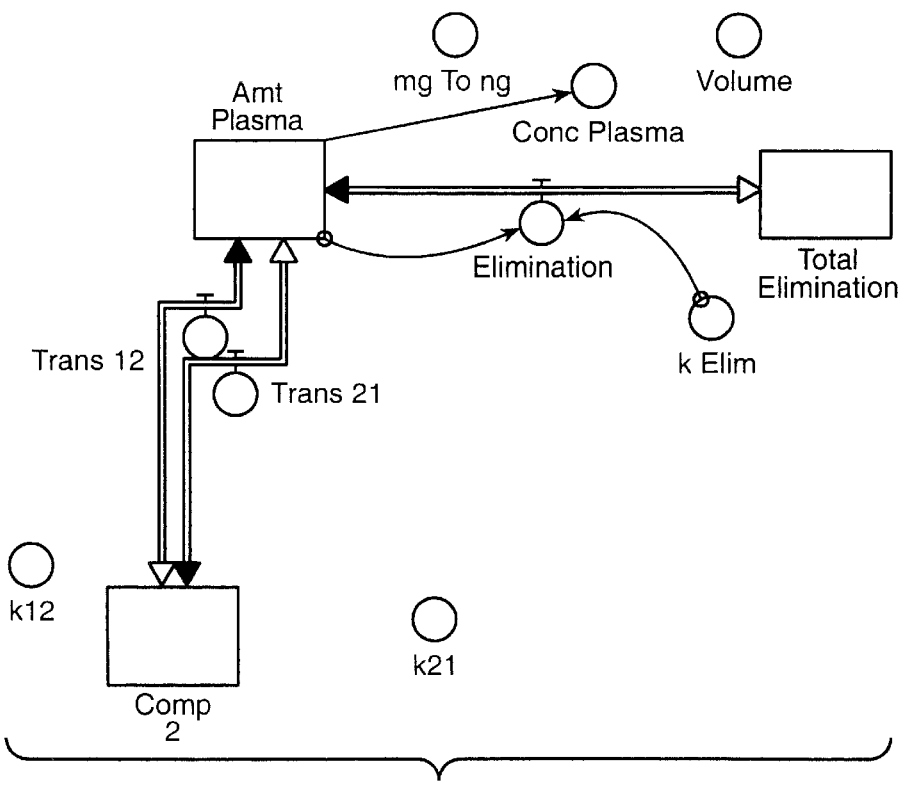
FIG._8

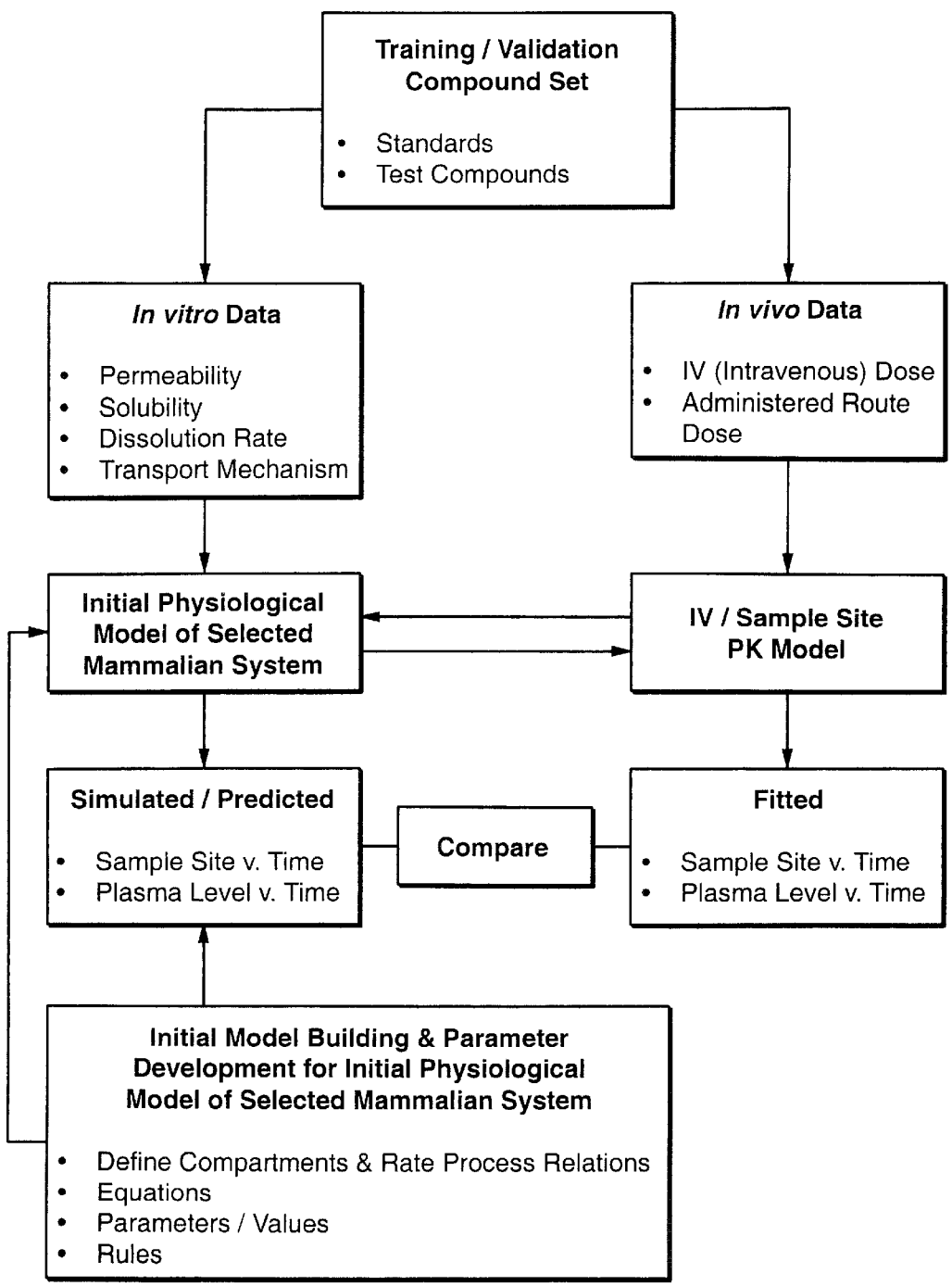
FIG._9

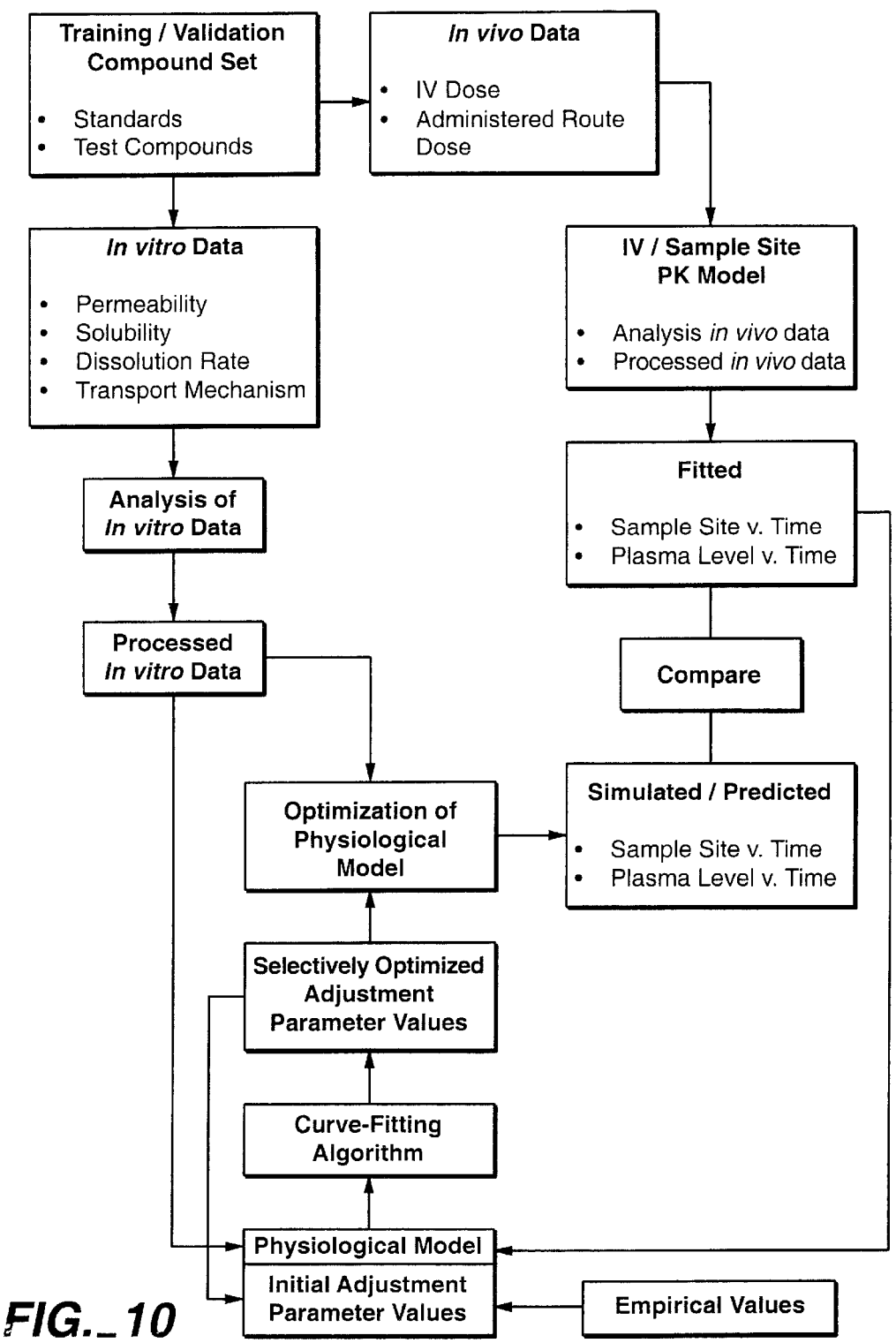
FIG._10

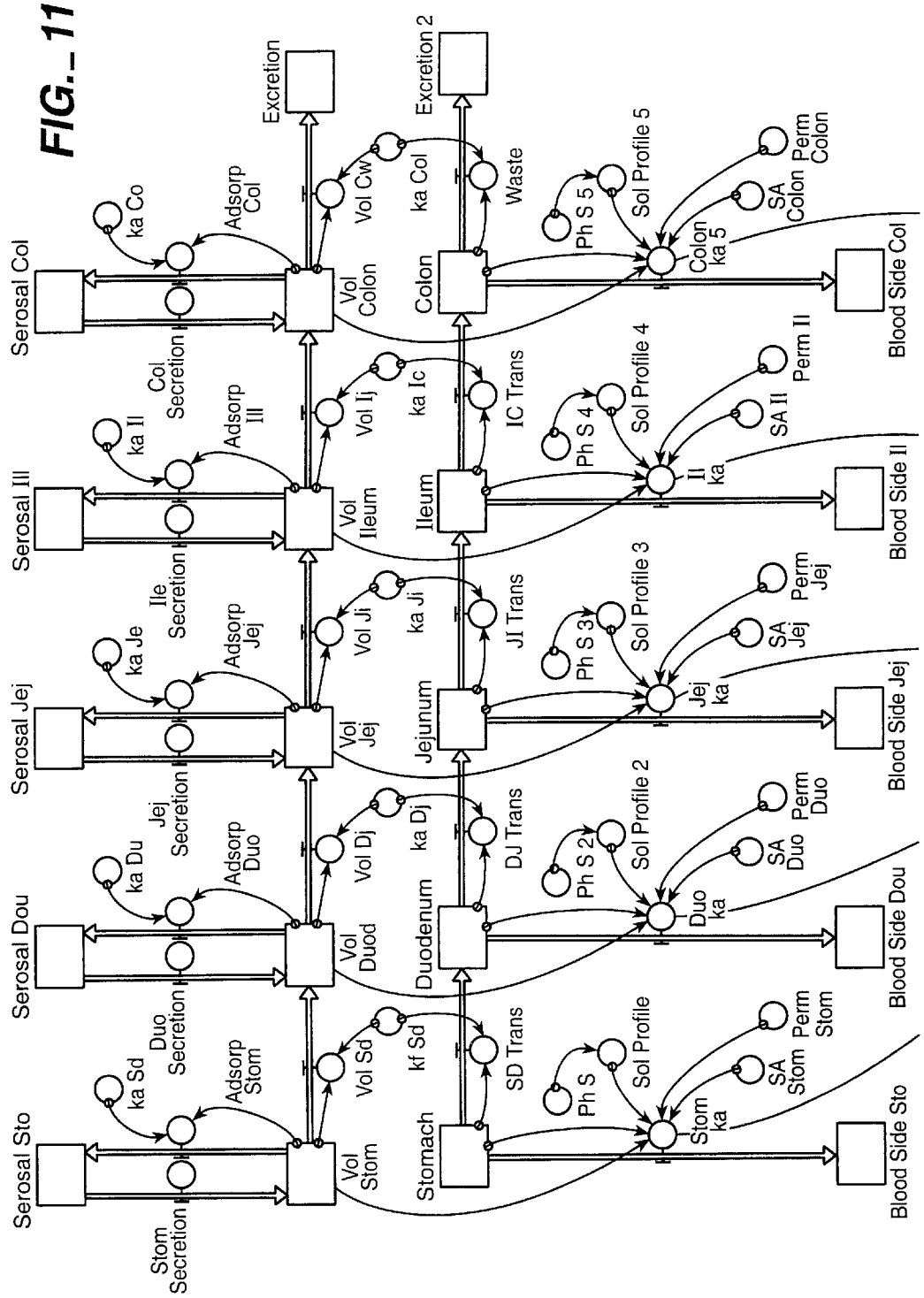
FIG. _11-A

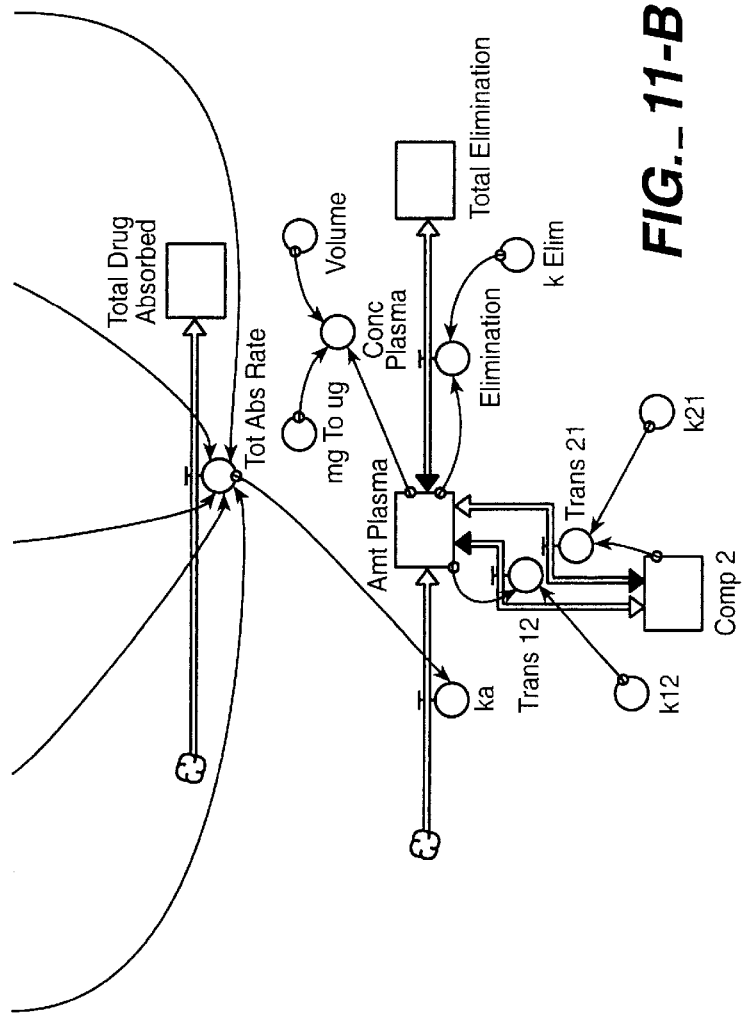
FIG._11-B

Mass-Volume GI Tract Model

- GI Segment Compartments
  - Fluid Volume
  - Fluid Absorption
  - Insoluble Mass
  - Soluble Mass Absorption

- GI Segment Flow Regulators
  - Fluid Volume Absorption Rate
  - Fluid Volume Secretion Rate
  - Fluid Volume GI Transit Rate
  - Insoluble Mass GI Transit Rate
  - Soluble Mass Absorption Rate

- GI Segment Converters
  - Rate Constant
  - pH
  - Solubility
  - Surface Area
  - Permeability

FIG._12

Mass-Volume GI Tract Model

- GI Segment Compartments & Flow Regulators
  - Fluid Volume
    - *Fluid Volume Absorption Rate*
    - *Fluid Volume Secretion Rate*
    - *Fluid Volume GI Transit Rate*
  - Fluid Volume Absorption
    - *Fluid Volume Absorption Rate*
    - *Fluid Volume Secretion Rate*
  - Insoluble Mass
    - *Insoluble Mass GI Transit Rate*
    - *Soluble Mass Absorption Rate*
  - Soluble Mass Absorption
    - *Soluble Mass Absorption Rate*

FIG._13

Mass-Volume GI Tract Model

- **GI Segment Flow Regulators & *Converters***
  - Fluid Volume Absorption Rate
    - *Fluid Volume Absorption Rate Constant*
  - Fluid Volume Secretion Rate
    - *Fluid Volume Secretion Rate Constant*
  - Fluid Volume GI Transit Rate
    - *Fluid Volume GI Transit Rate Constant*
  - Insoluble Mass GI Transit Rate
    - *Insoluble Mass GI Transit Rate Constant*
  - Soluble Mass Absorption Rate
    - *Fluid Volume*
    - *Insoluble Mass*
    - *Mass Solubility Profile*
      - *pH*
    - *Permeability*
    - *Surface Area*

FIG._14

Mass-Volume GI Tract Model

- GI Segment Converters
  - Rate Constant
  - pH
  - Solubility
  - Surface Area
  - Permeability

FIG._15

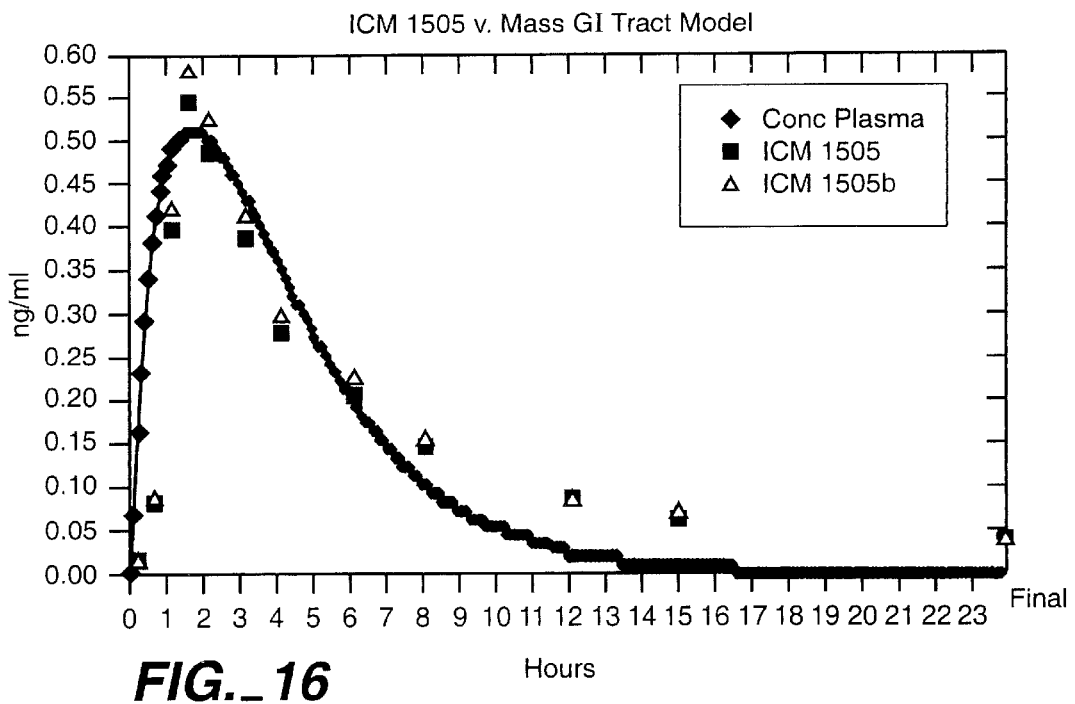
FIG._16
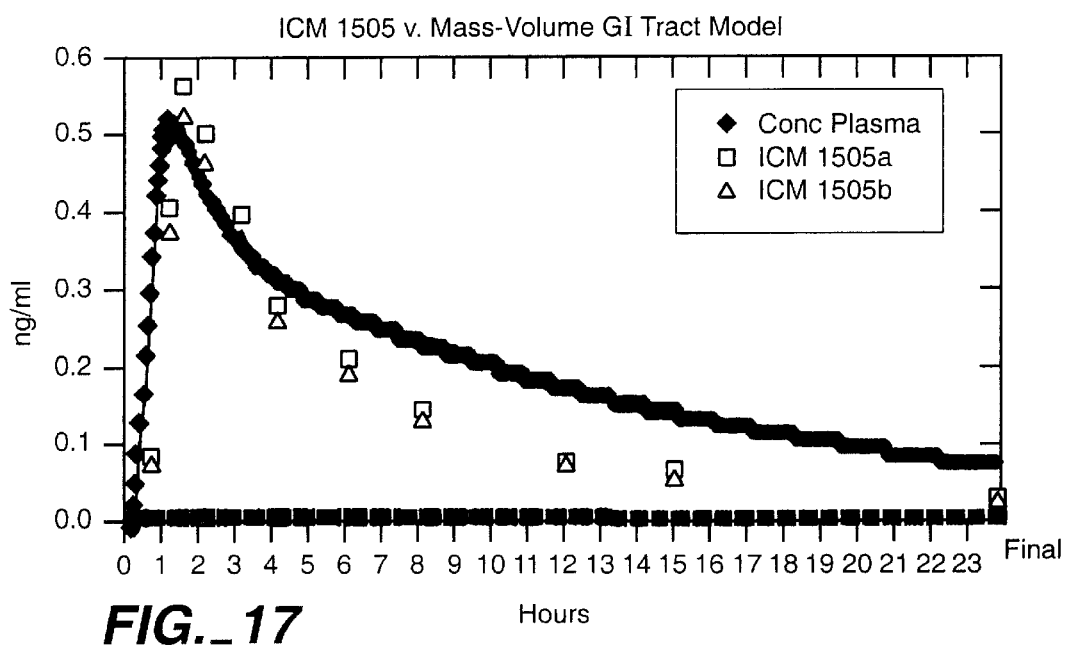
FIG._17

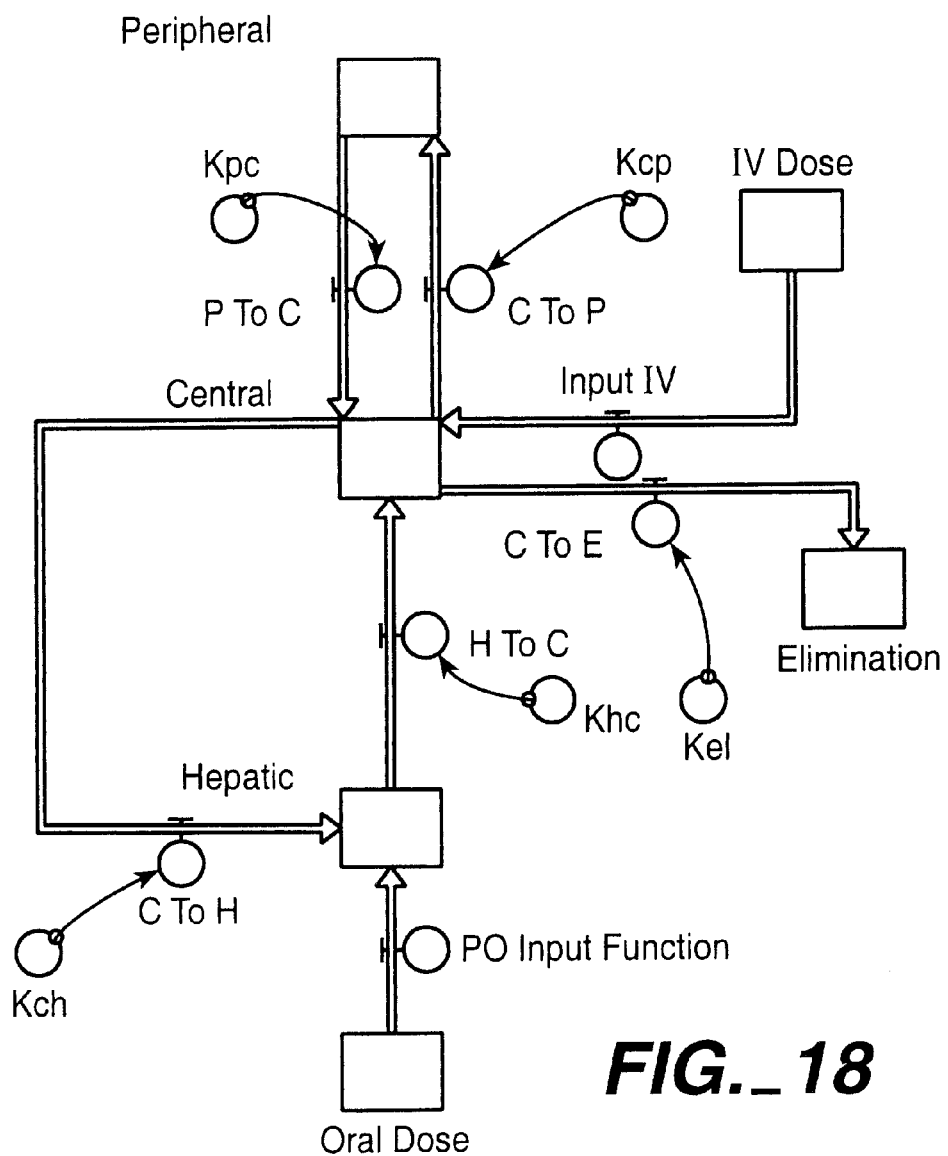
FIG._18

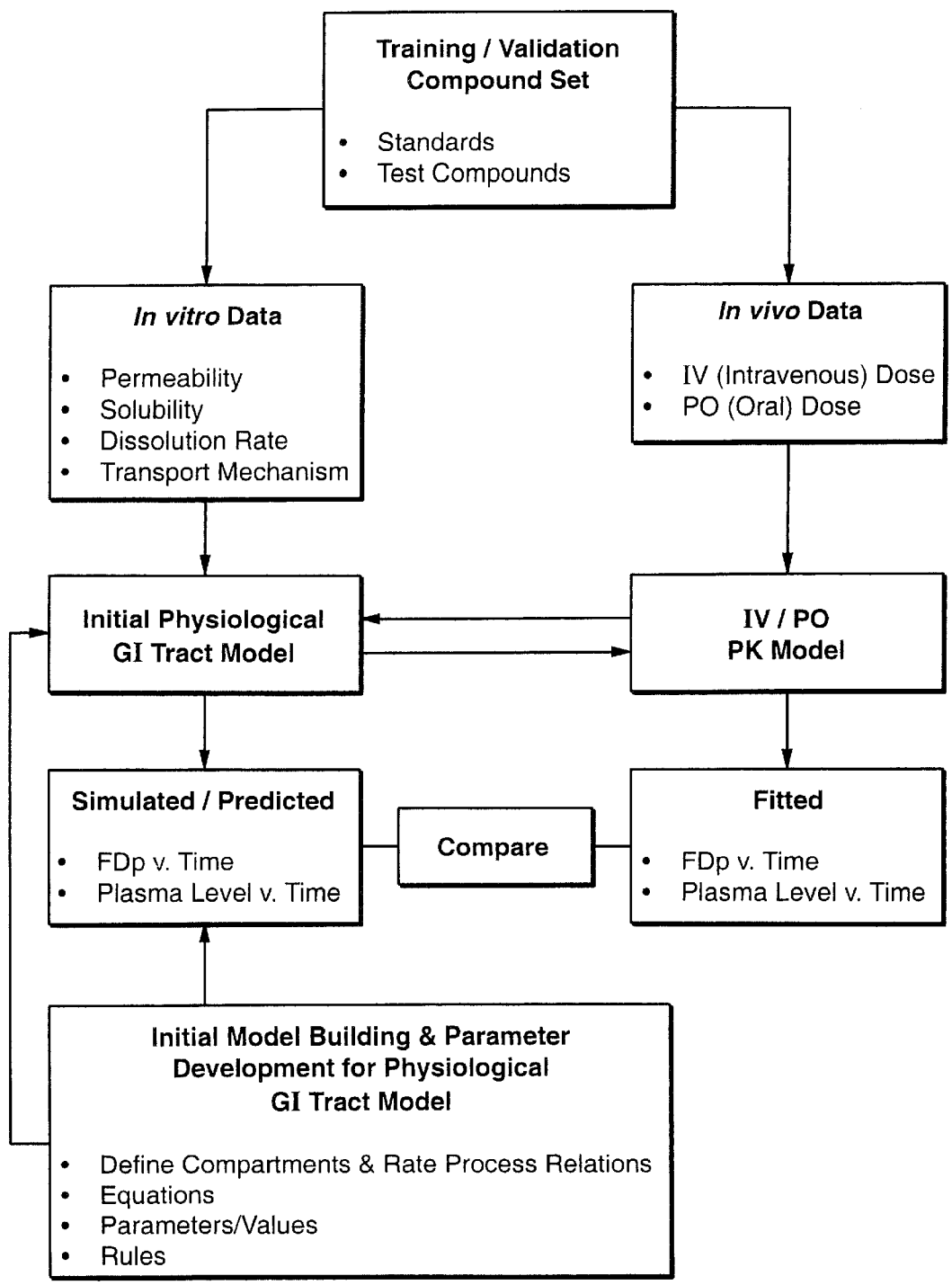
FIG._19

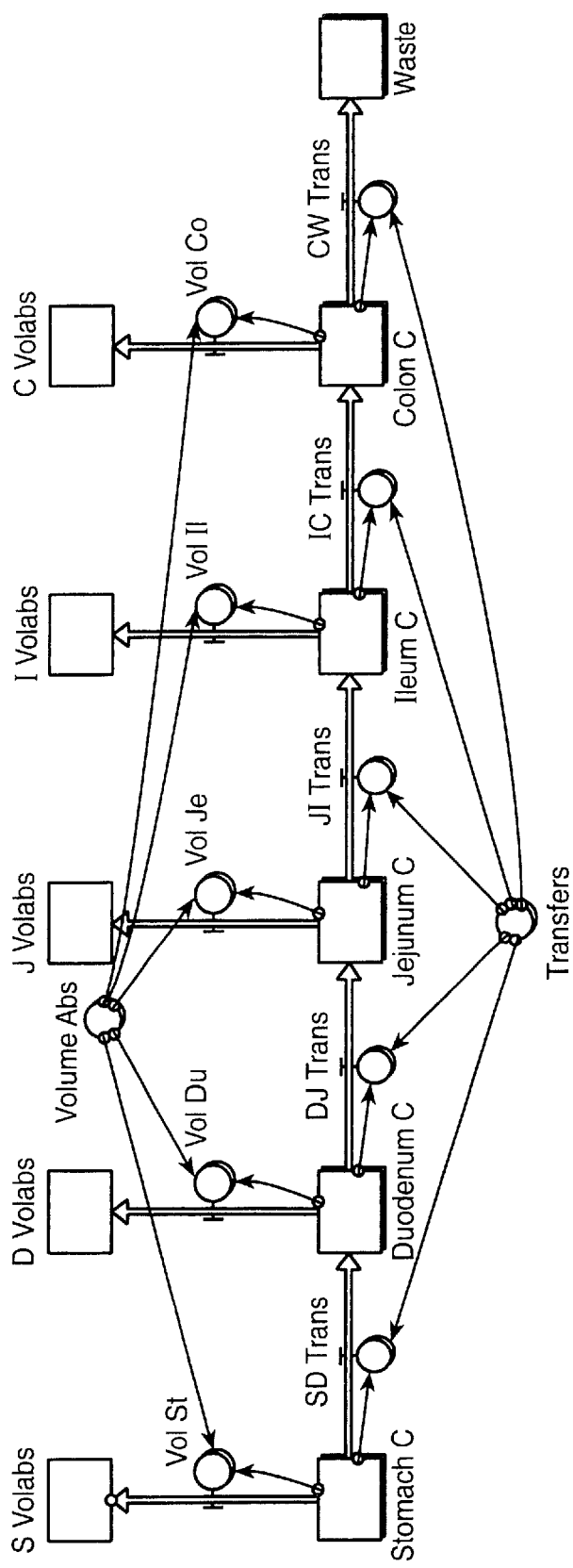
FIG._20

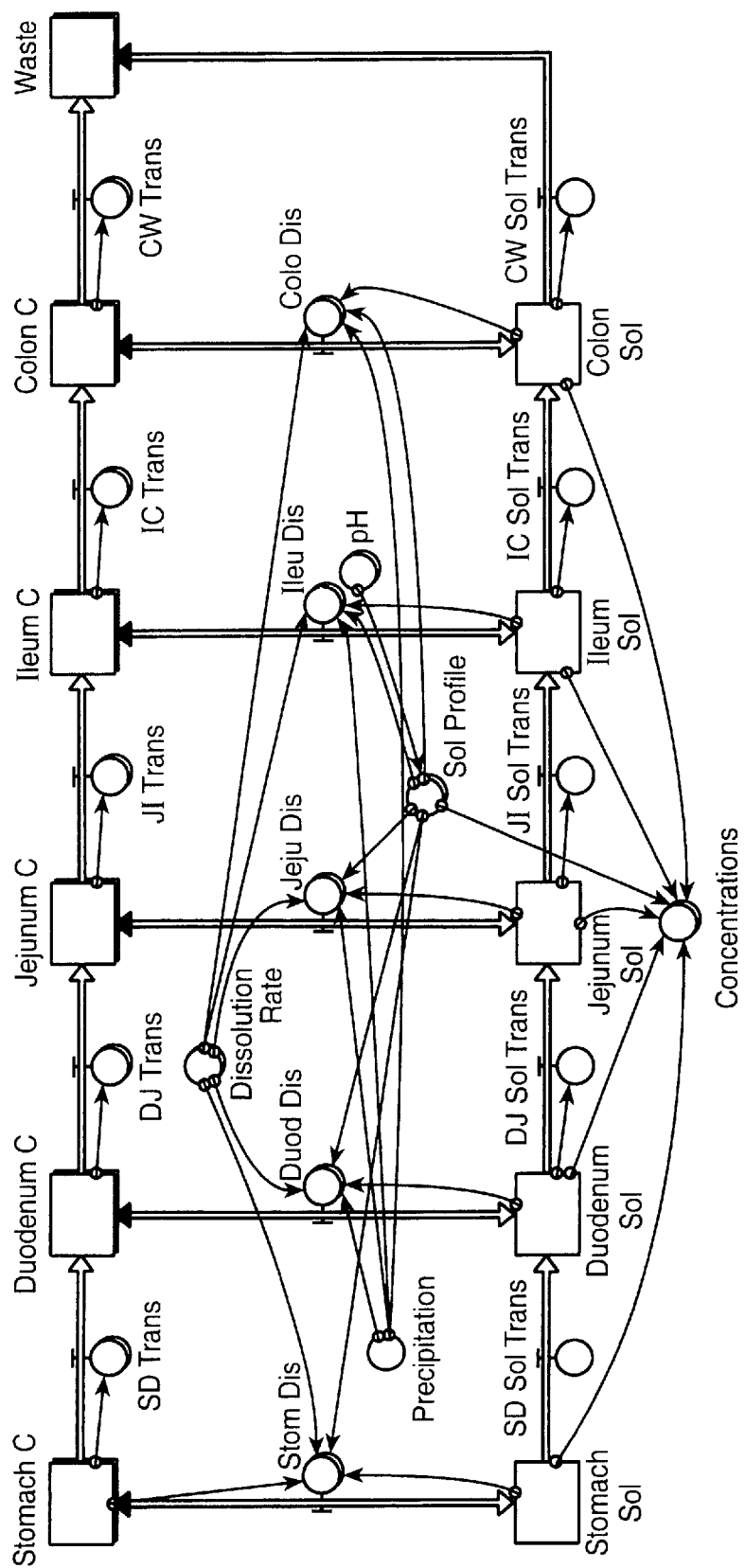
FIG._21  pH Dependent Solubility And Dissolution

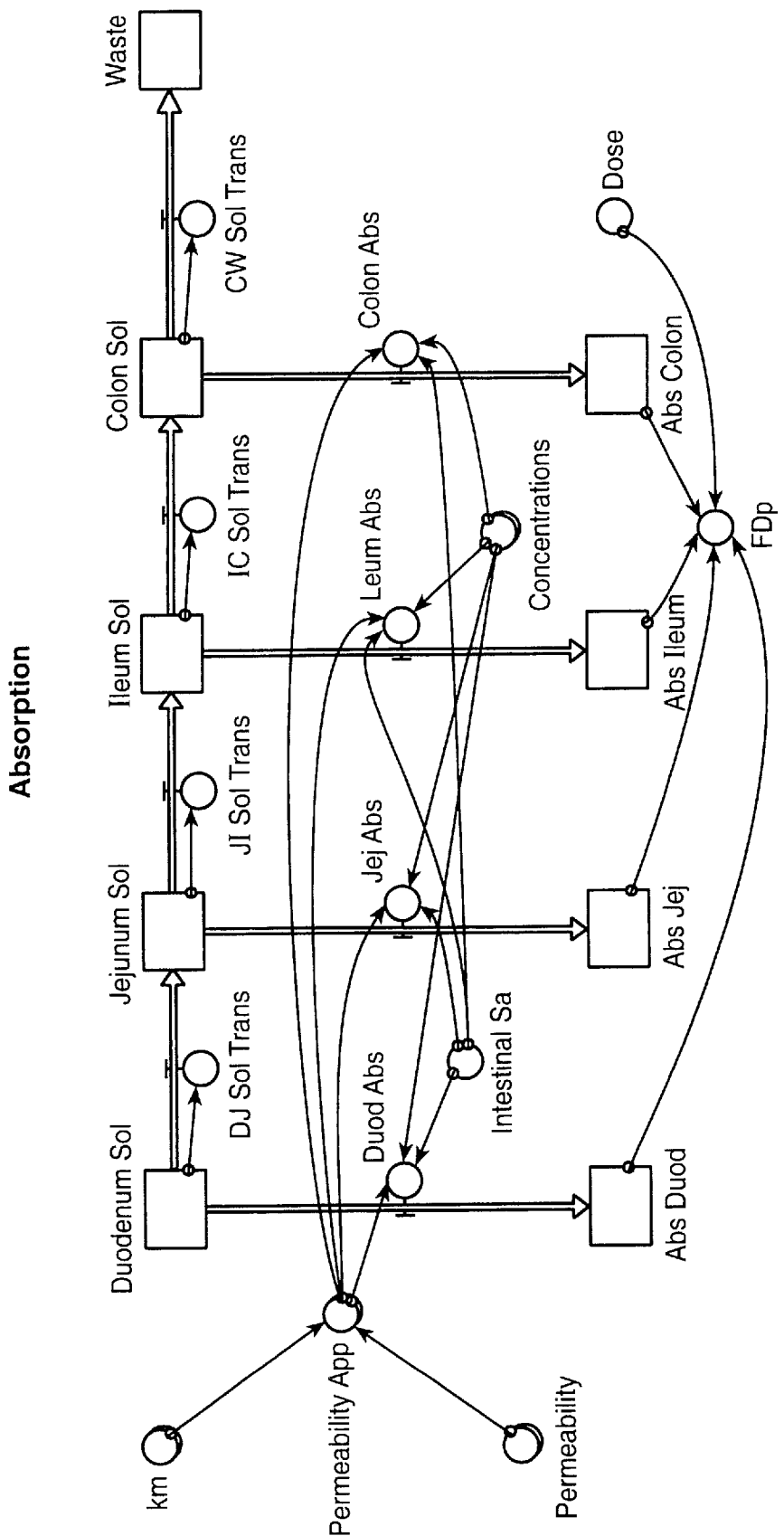
FIG._22

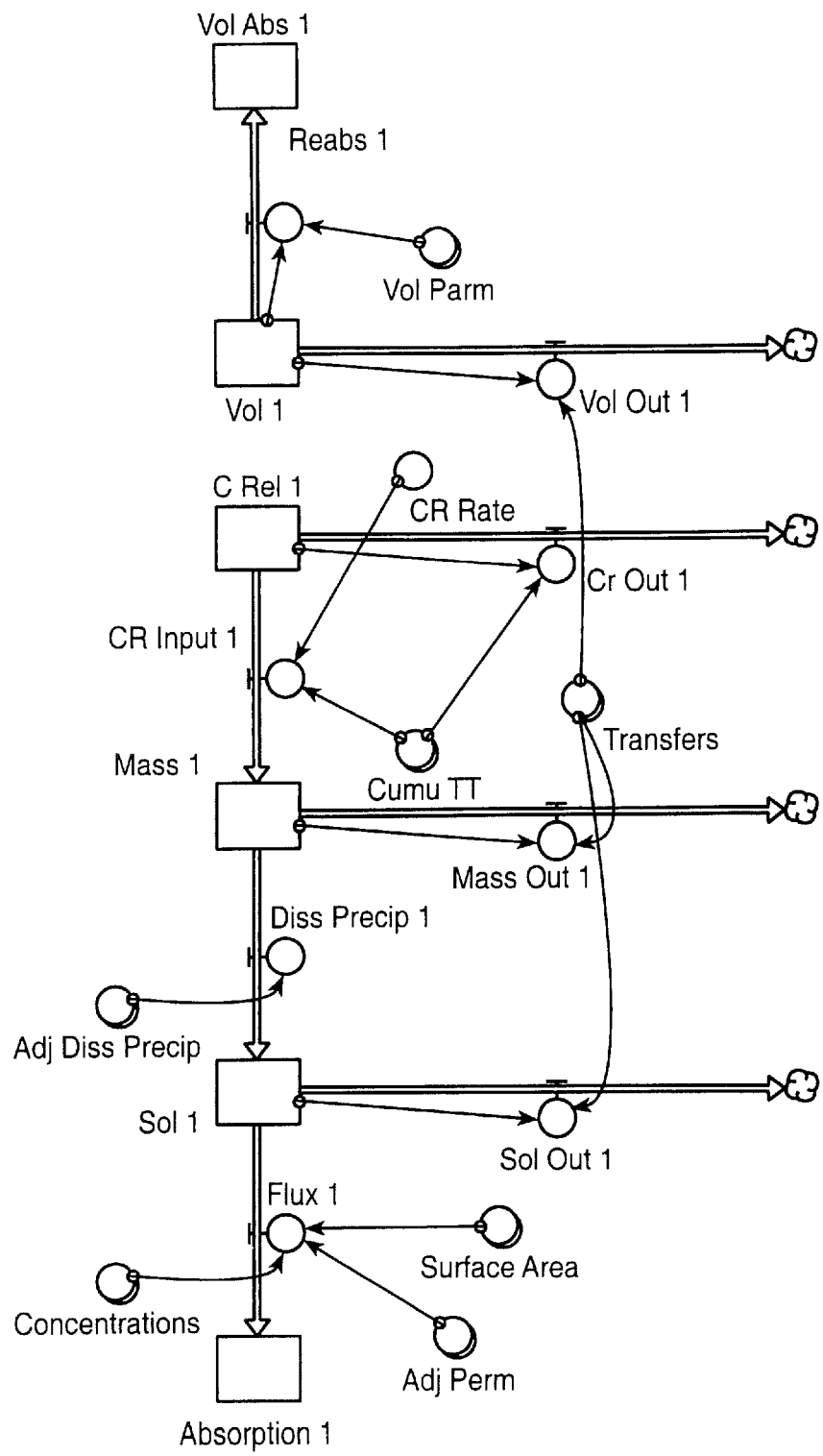
FIG._23

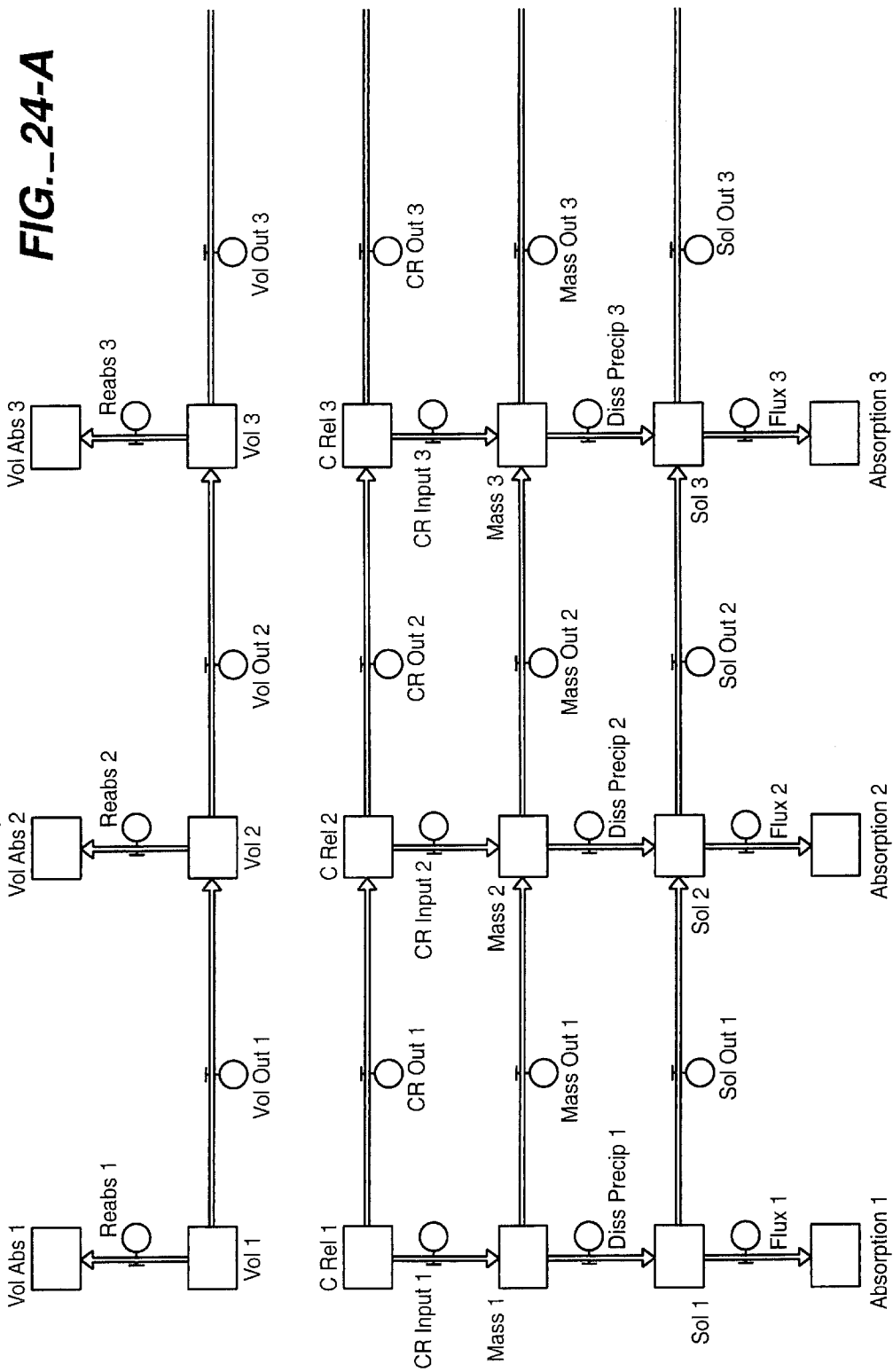
FIG._24-A

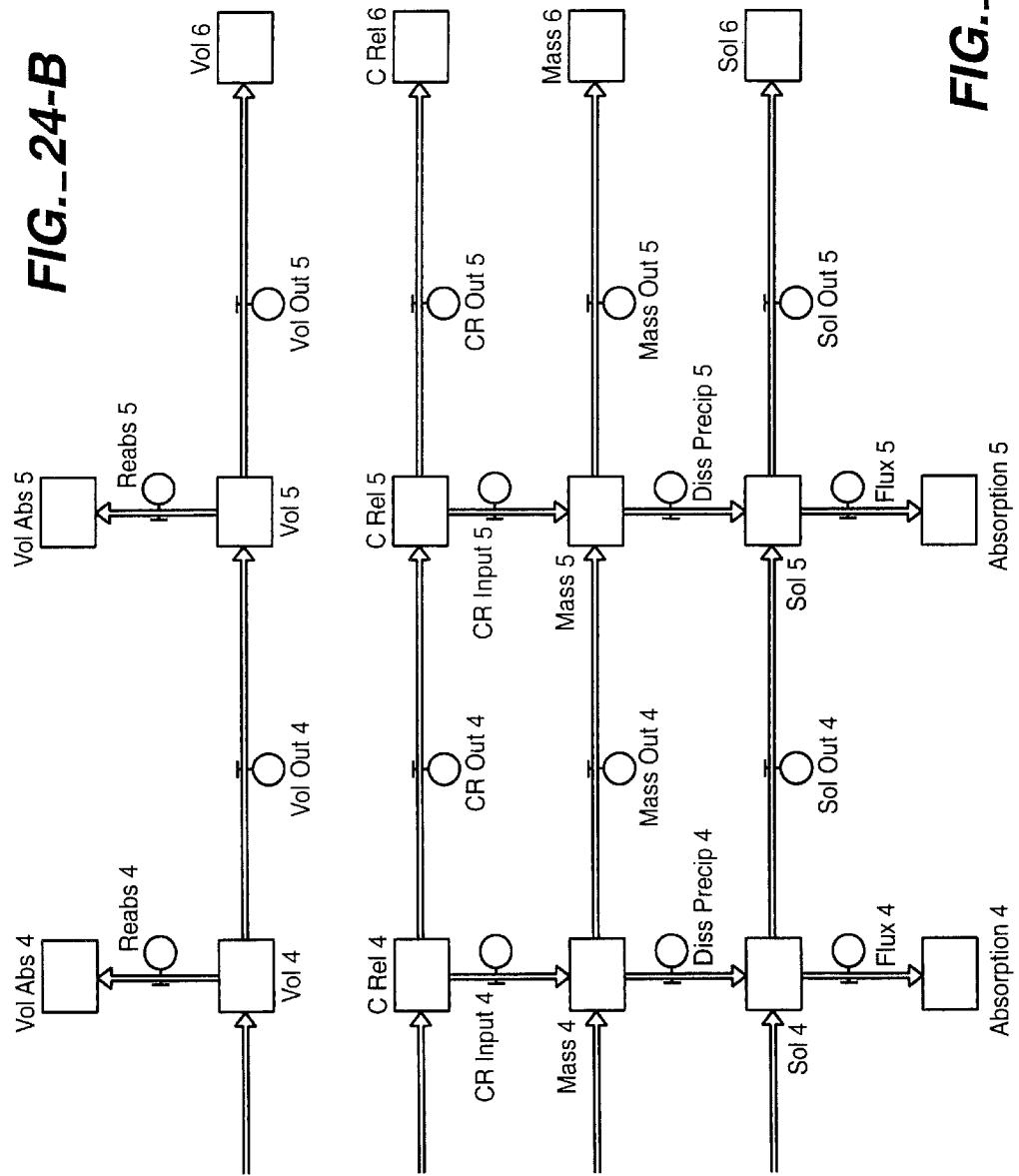

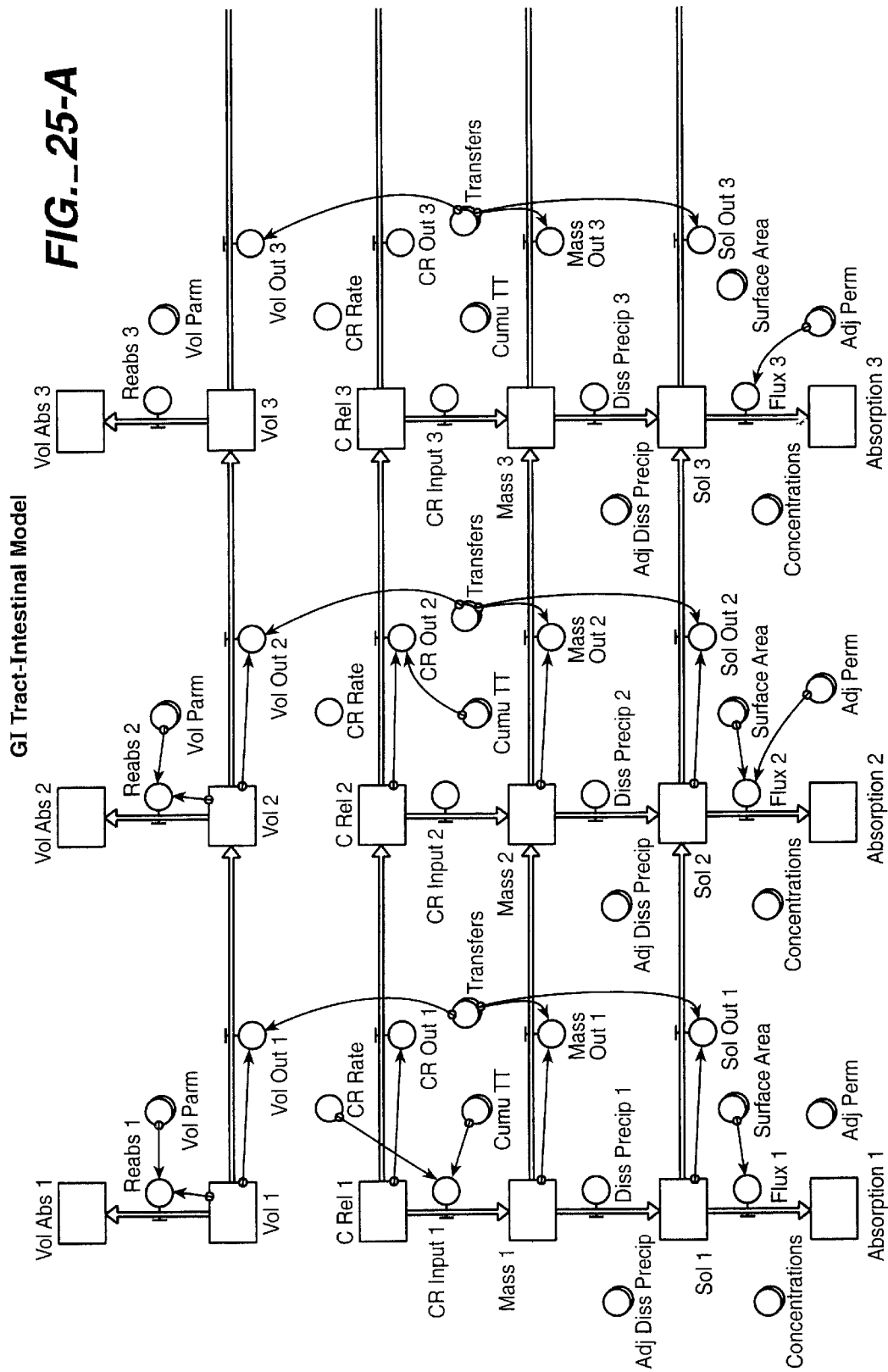
FIG._25-A

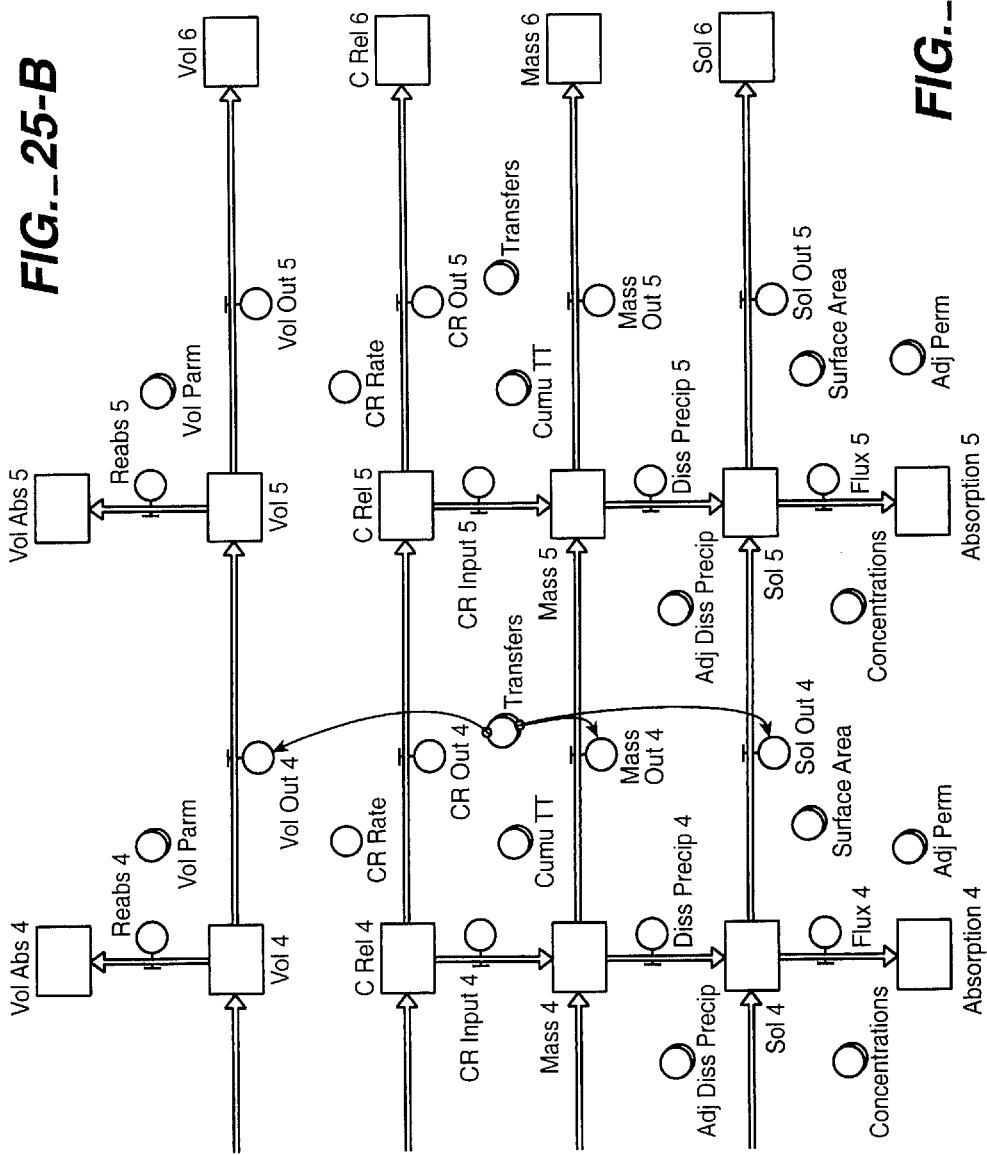

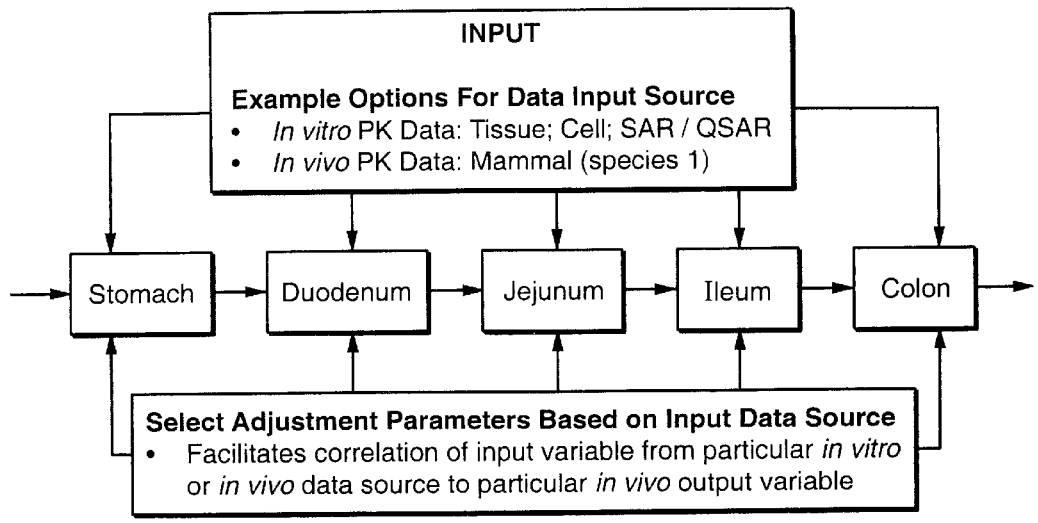
FIG._27
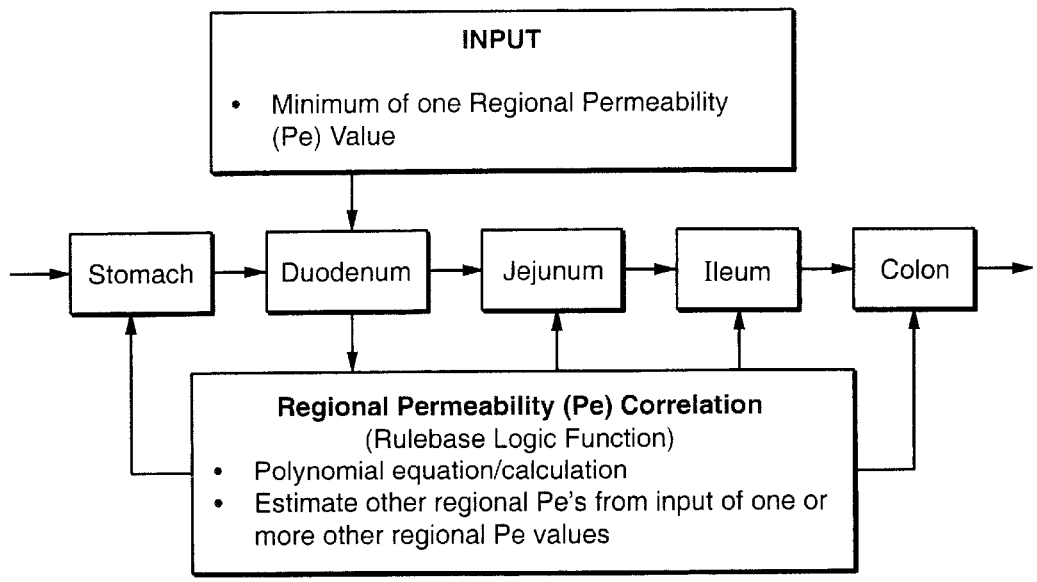
FIG._28

Parameters
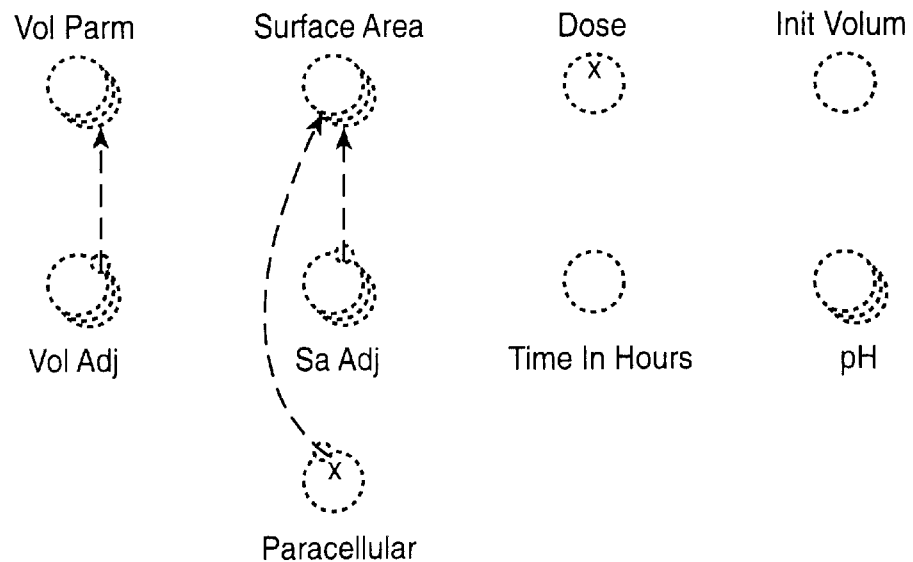
FIG._29
Transit Time
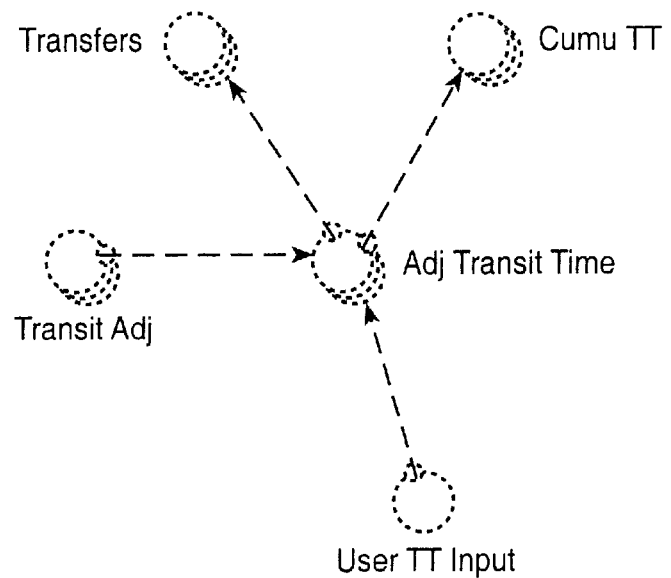
FIG._30

Permeability Calculation
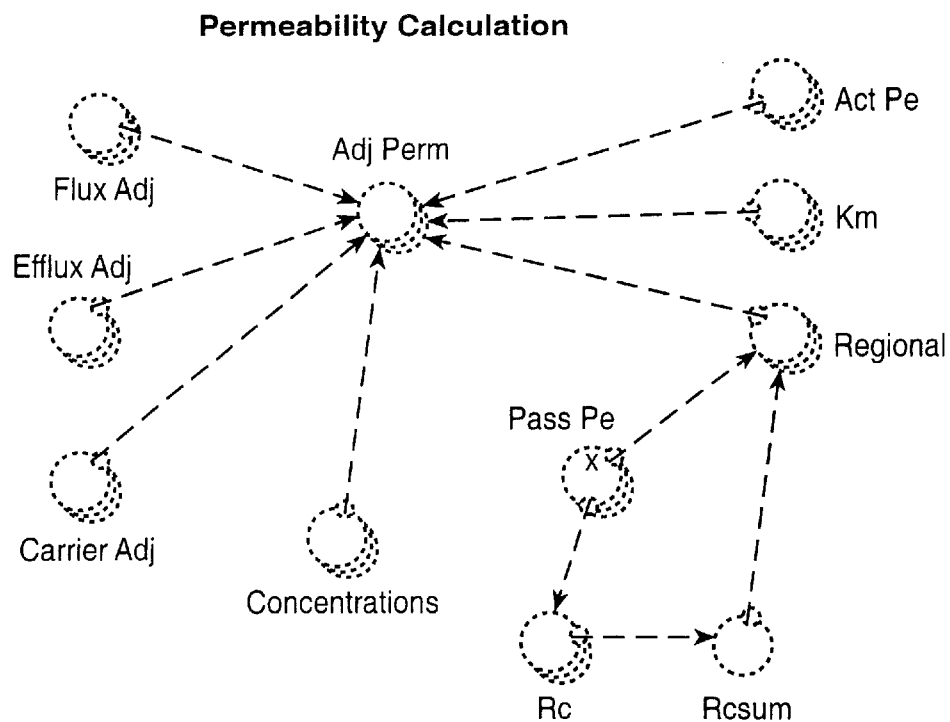
FIG._31
Solubility Calculation
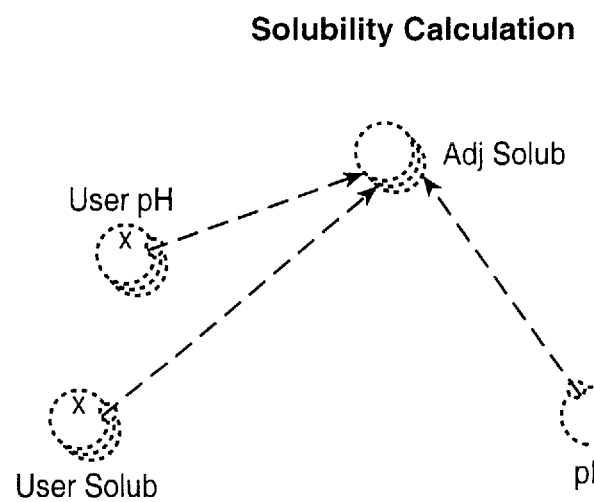
FIG._32

Control Release Calculation
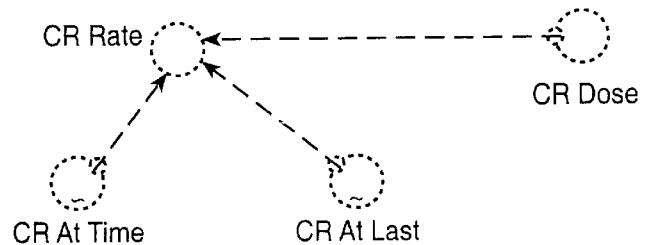
FIG._33
Concentration Calculation
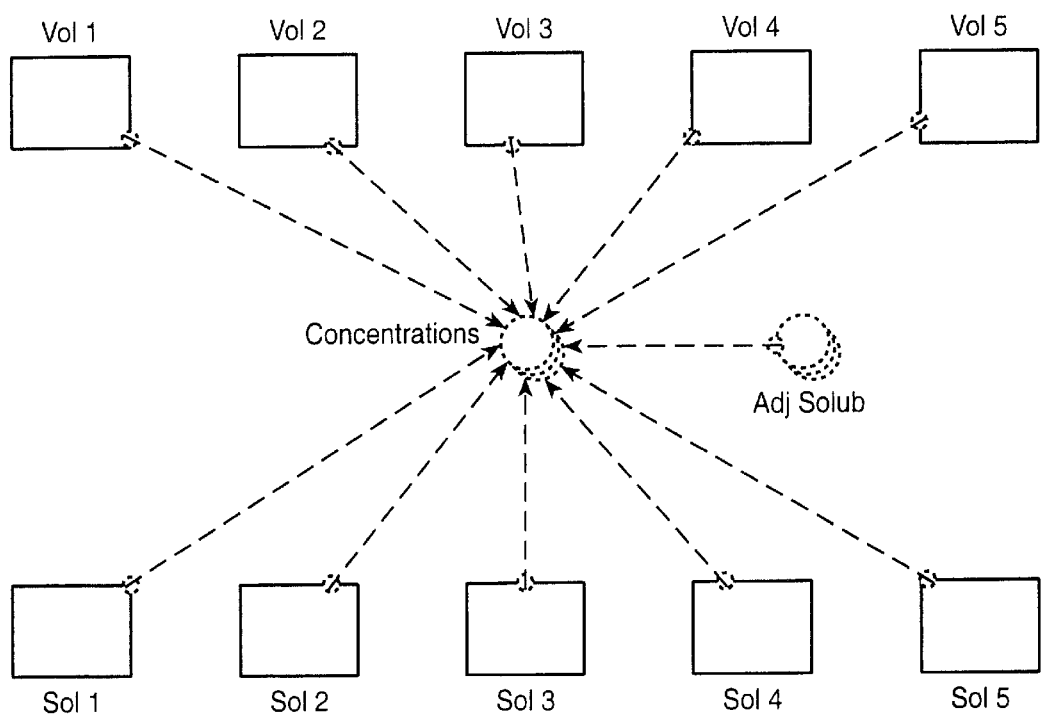
FIG._34

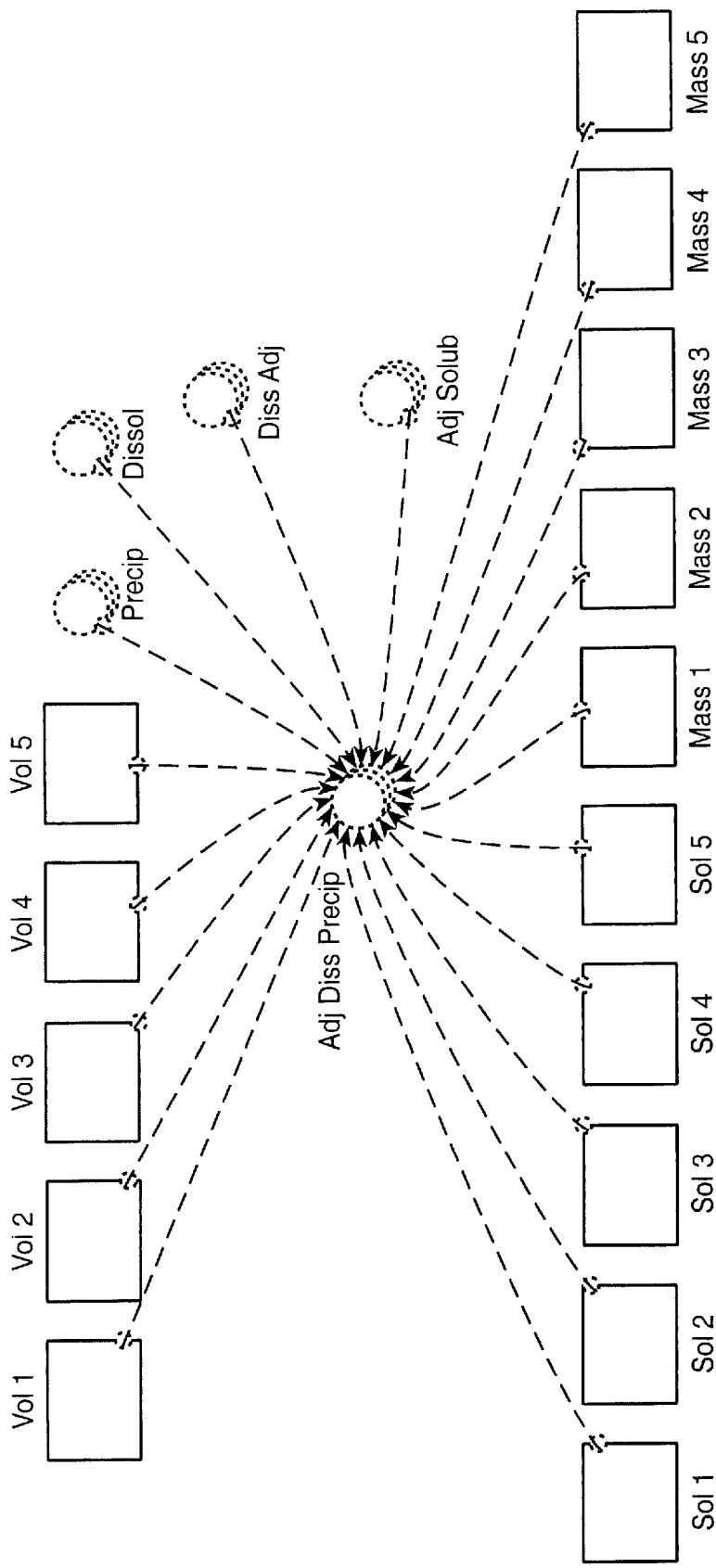
FIG._35

Output Calculations
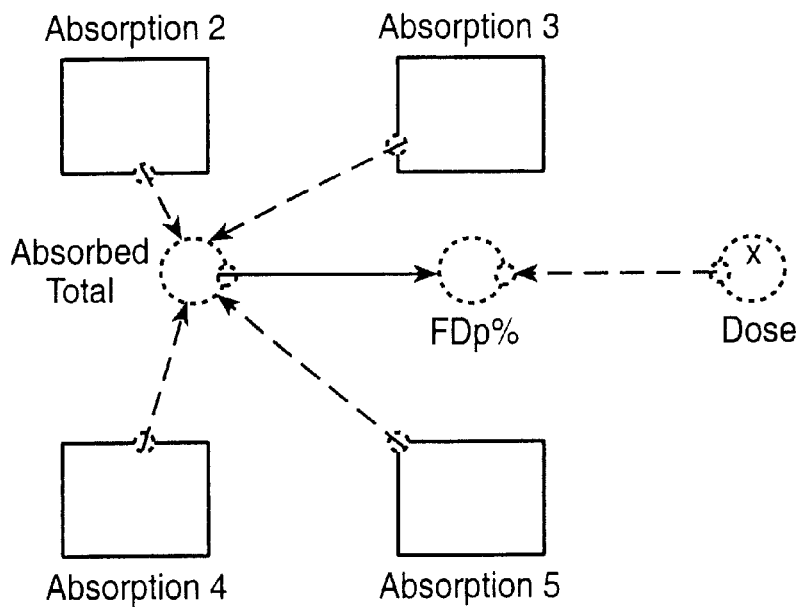
FIG._36
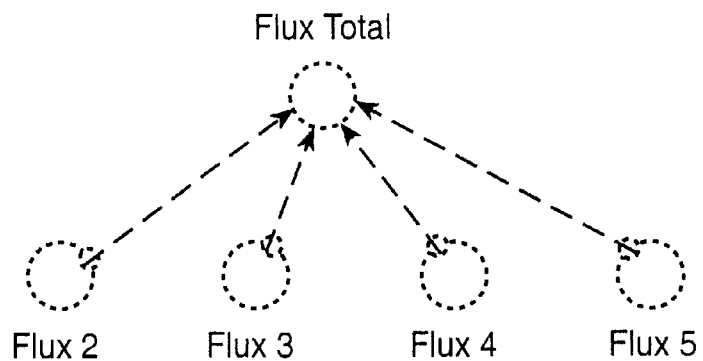
FIG._37

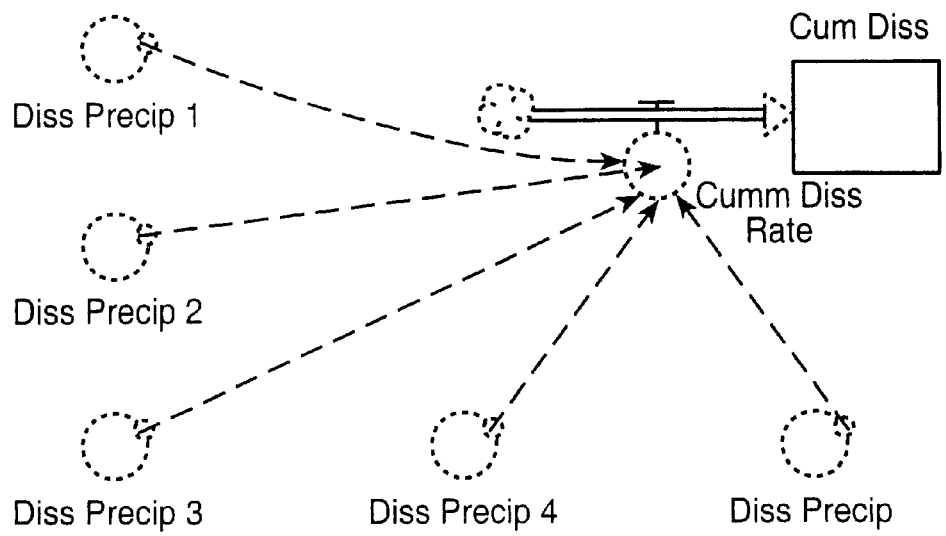
FIG._38
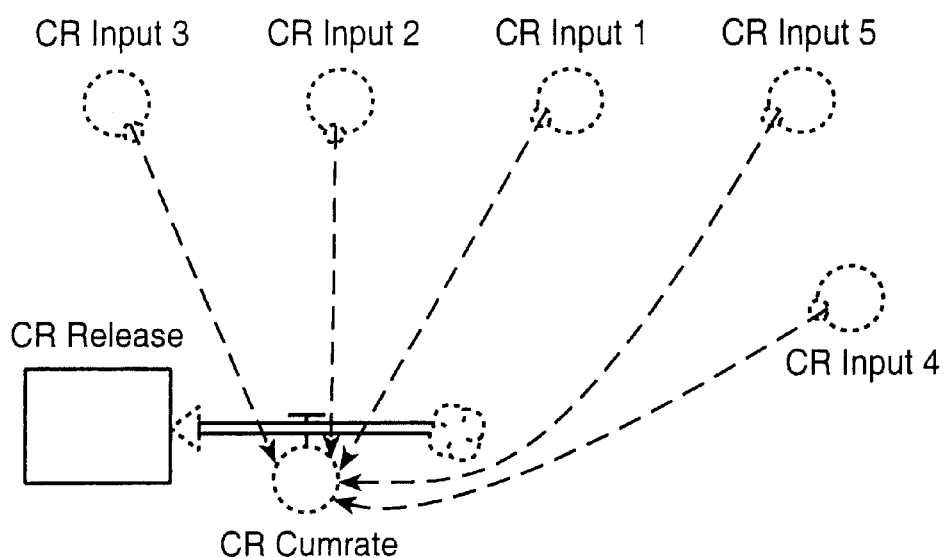
FIG._39

Physiological GI Tract Model

Database
- GI Segment Compartments
  - Fluid Absorption
  - Fluid Volume
  - Insoluble Mass
  - Soluble Mass
  - Soluble Mass Absorption
  - Dosage Form Mass

- GI Segment Flow Regulators
  - Fluid Absorption Rate
  - Fluid Volume Transit Rate
  - Insoluble Mass Transit Rate
  - Insoluble Mass Dissolution Rate
  - Soluble Mass Transit Rate
  - Soluble Mass Absorption Rate
  - Dosage Form Disintegration / Release Rate

- GI Segment Converters
  - Fluid Volume Absorption Rate Constant
  - GI Transit Rate Constant
  - Adjusted Dissolution Rate Constant
  - Dissolved Drug Concentration
  - Adjusted Surface Area
  - Adjusted Permeability

Rulebase
- GI Transit
- Dissolution
- Absorption
- Permeability Calculations
- Concentration Calculations
- Computational Error Corrections

FIG._40

Physiological GI Tract Model

- GI Segment Compartments & *Flow Regulators*
  - Fluid Absorption
    - *Fluid Absorption Rate*
  - Fluid Volume
    - *Fluid Volume Absorption Rate*
    - *Fluid Volume Transit Rate*
  - Insoluble Mass
    - *Insoluble Mass Transit Rate*
    - *Insoluble Mass Dissolution Rate*
  - Soluble Mass
    - *Insoluble Mass Dissolution Rate*
    - *Soluble Mass Transit Rate*
    - *Soluble Mass Absorption Rate*
  - Soluble Mass Absorption
    - *Soluble Mass Absorption Rate*

FIG._41

Physiological GI Tract Model

- GI Segments Flow Regulators & *Converters*
  - Fluid Absorption Rate
    - *Fluid Volume*
    - *Fluid Volume Absorption Rate Constant*
  - Fluid Volume Transit Rate
    - *Fluid Volume*
    - *Fluid Volume Transit Rate Constant*
  - Insoluble Mass Transit Rate
    - *Insoluble Mass*
    - *Insoluble Mass Transit Rate Constant*
  - Insoluble Mass Dissolution Rate
    - *Insoluble Mass*
    - *Dissolution Rate Constant*
  - Soluble Mass Transit Rate
    - *Soluble Mass*
    - *Soluble Mass Transit Rate Constant*
  - Soluble Mass Absorption Rate (Flux)
    - *Surface Area*
    - *Dissolved Mass Concentration*
    - *Permeability*

FIG._42

Physiological GI Tract Model

- Converters
  - Permeability
    - Passive Absorption Adjustment Parameter
      - Efflux / Secretion Adjustment Parameter
      - Active Absorption Adjustment Parameter
      - Active or Carrier Mediated Absorptive Permeability
      - Km
      - Passive Permeability / Regional Correlation
        - Passive Permeability
        - Logic Function For Regional Correlation
          - Passive Permeability
          - Logic Function For Regional Correlation
      - Dissolved Mass Concentrations
  - Dissolved Mass Concentration
    - Fluid Volume
    - Solubility
      - pH
      - Solubility
  - Dissolution Rate Constant
    - Fluid Volume
    - Precipitation Rate Constant
    - Dissolution Rate Adjustment Parameter
    - Solubility
    - Insoluble Mass
    - Soluble Mass
  - Surface Area
    - Surface Area Adjustment Parameter
    - Transport Mechanism
  - Transit Rate
    - Transit Time Adjustment Parameter
    - User Adjusted Transit Time
  - Fluid Volume Absorption Rate Constant
    - Fluid Volume Adjustment Parameter

FIG._43

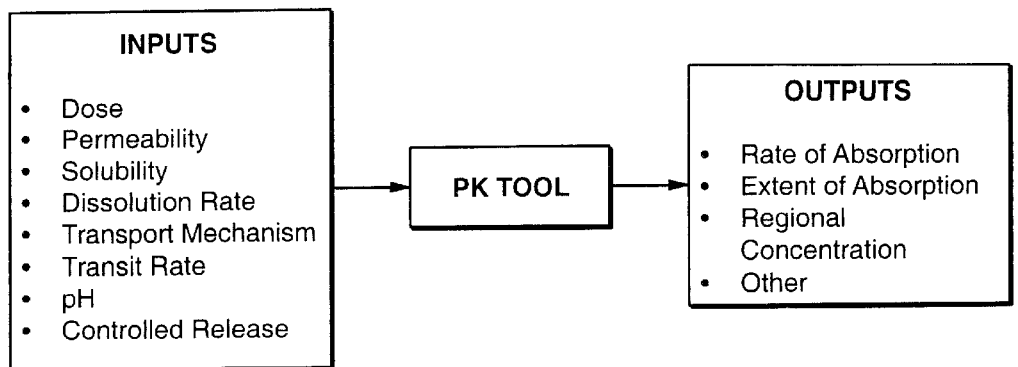
FIG._44
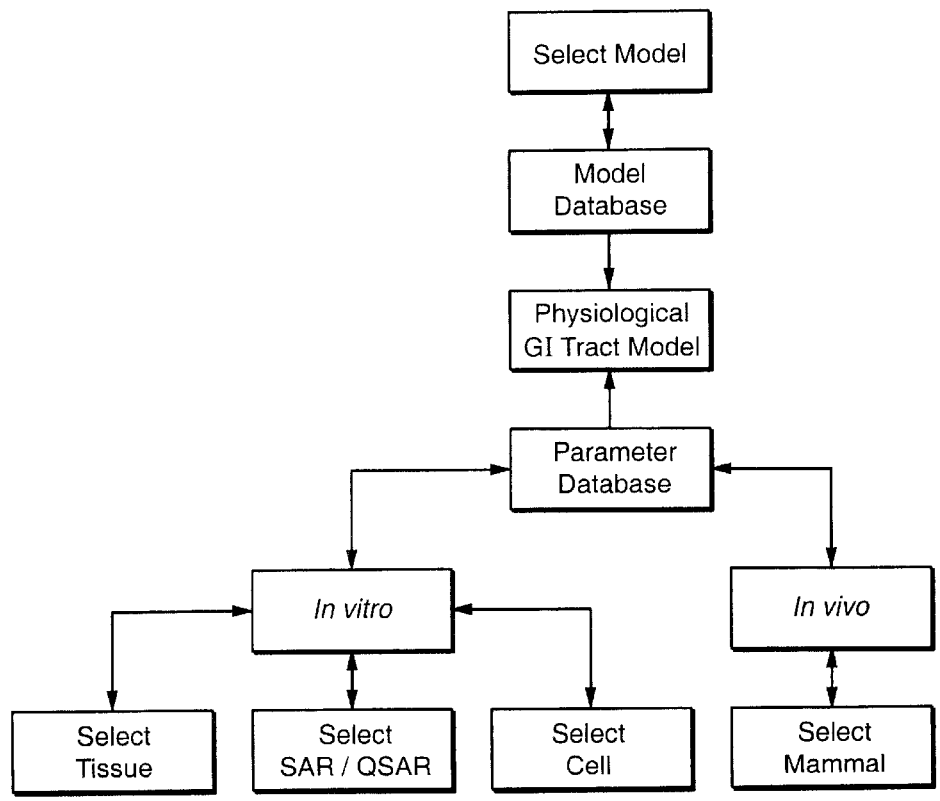
FIG._45

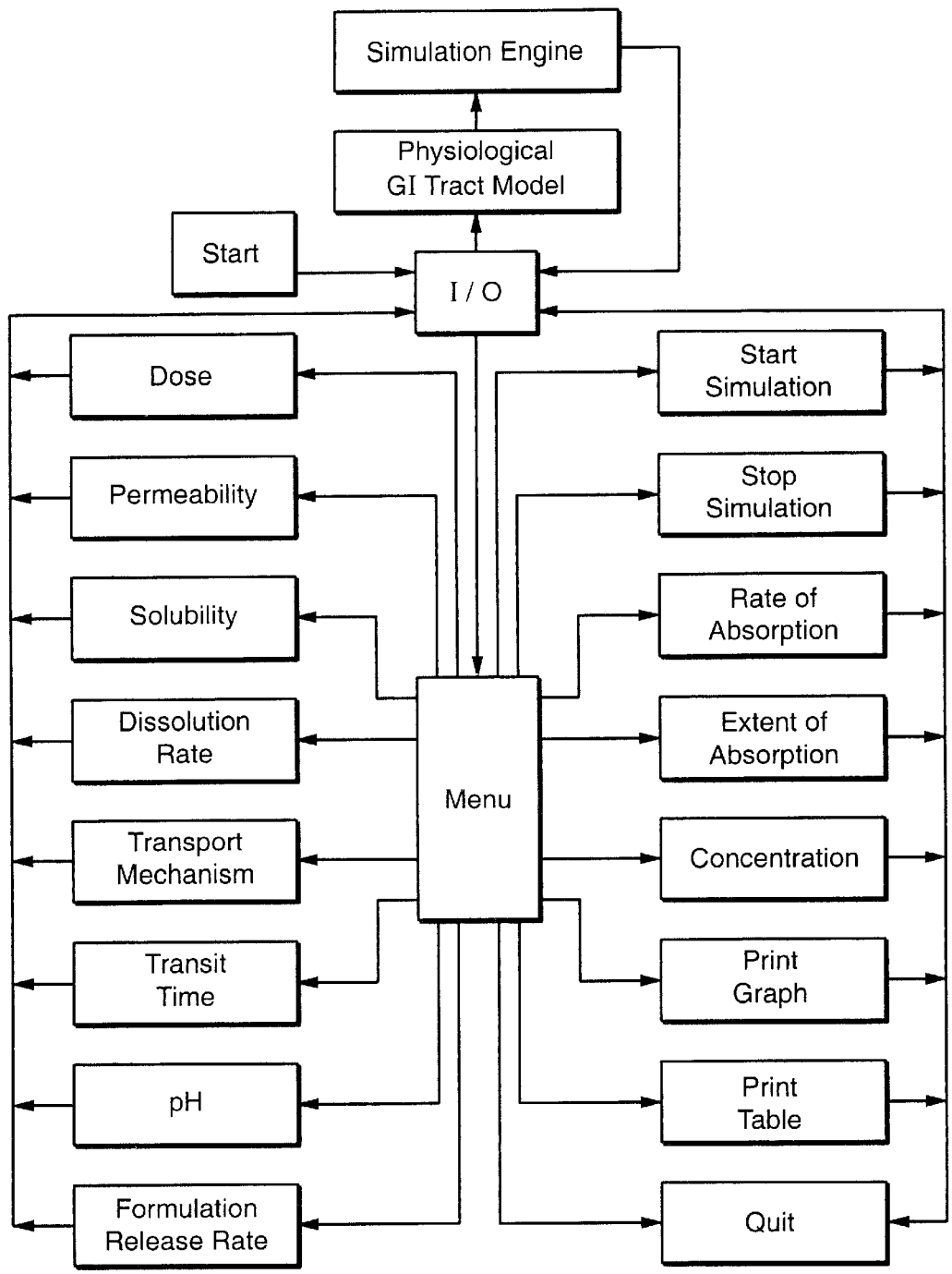
FIG._46

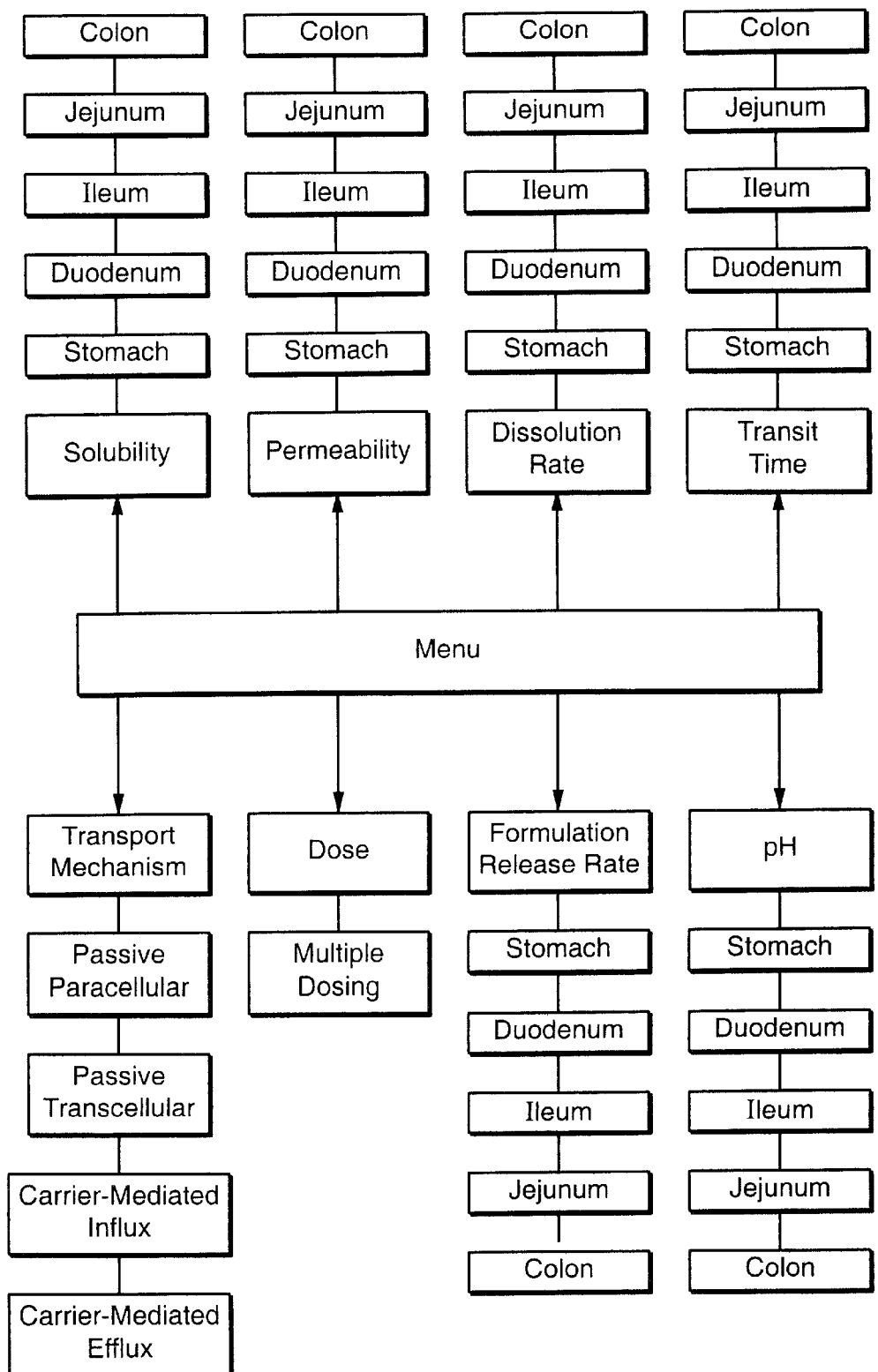
FIG._47

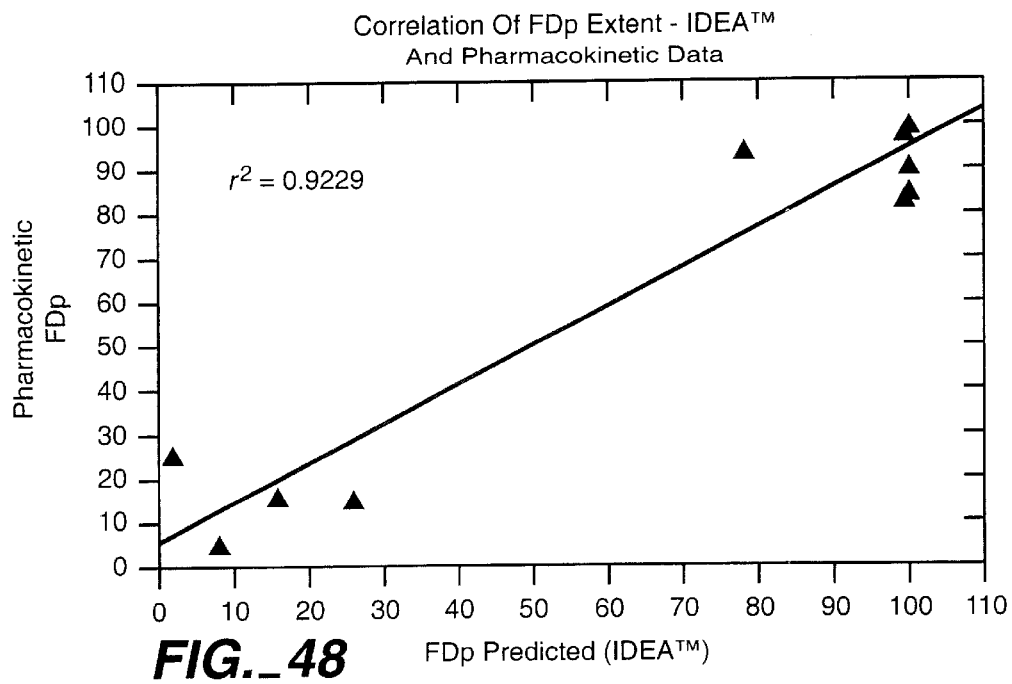
FIG._48
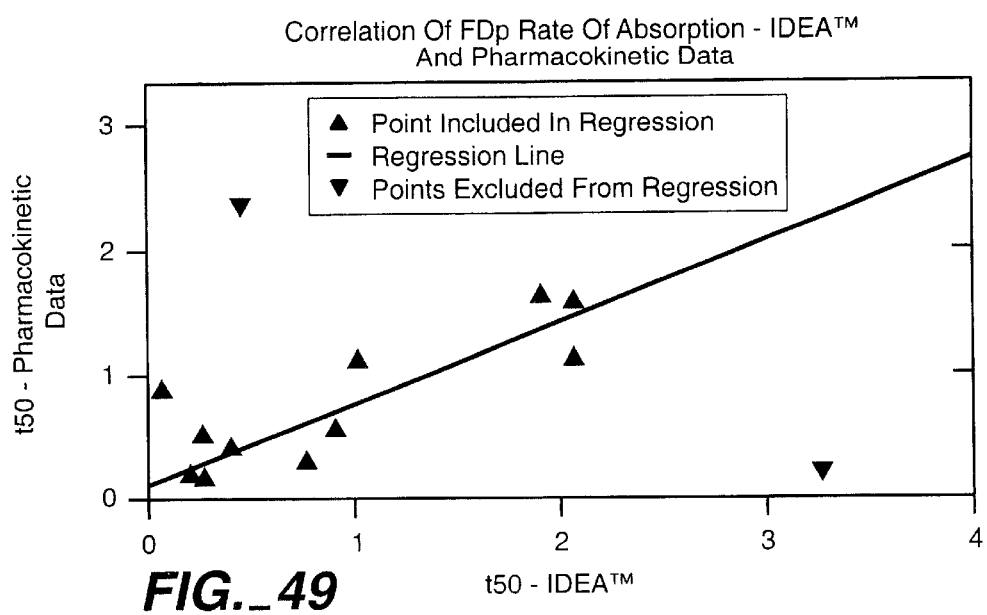
FIG._49

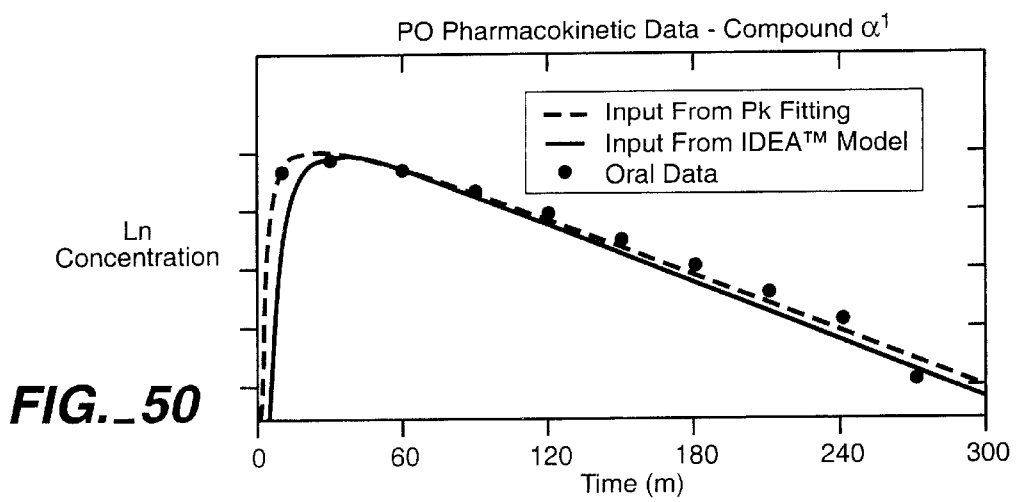
FIG._50
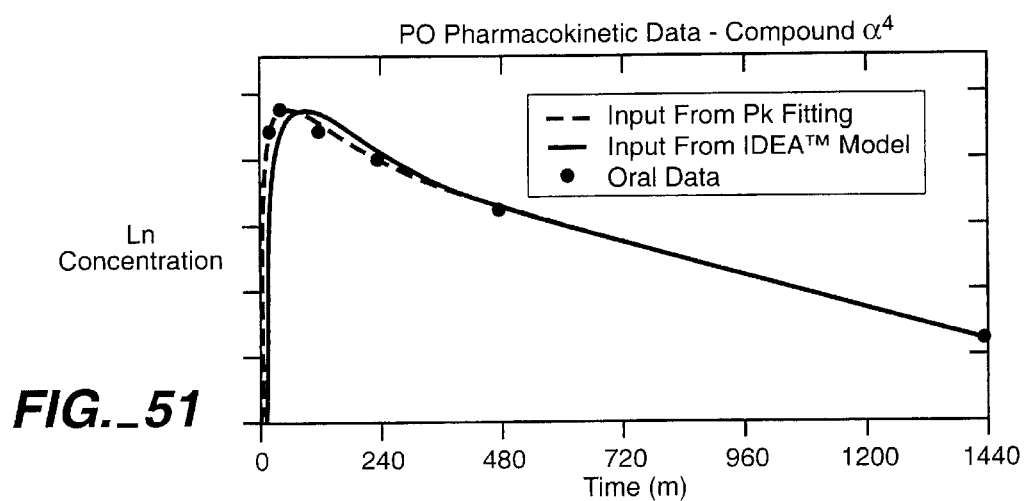
FIG._51
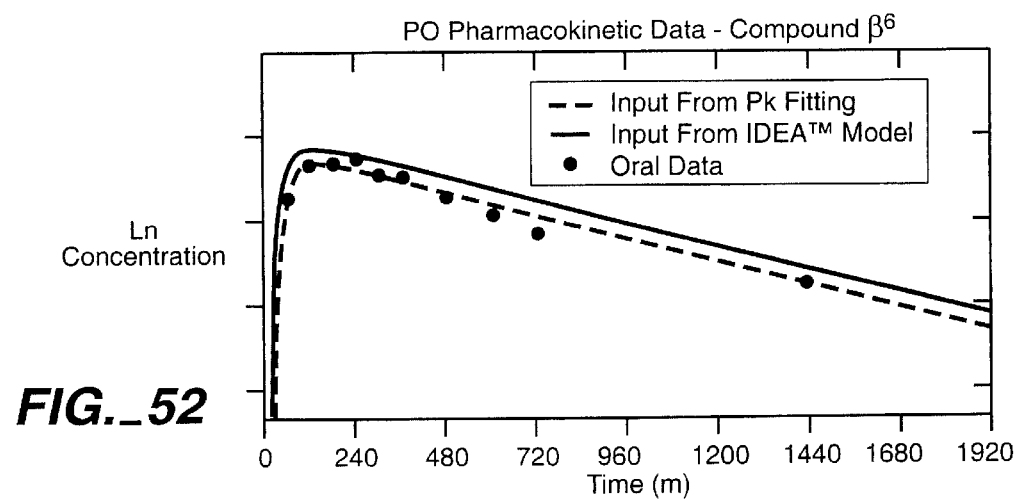
FIG._52

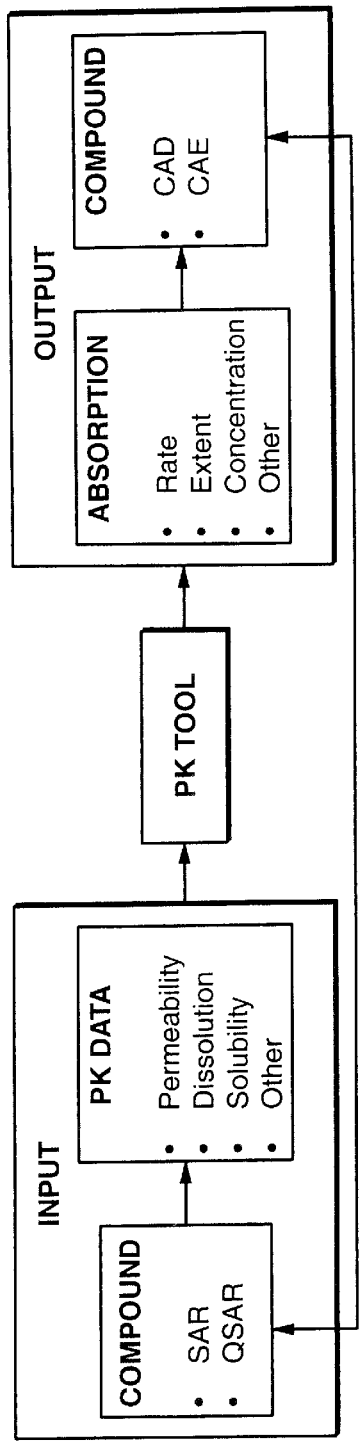
FIG._53
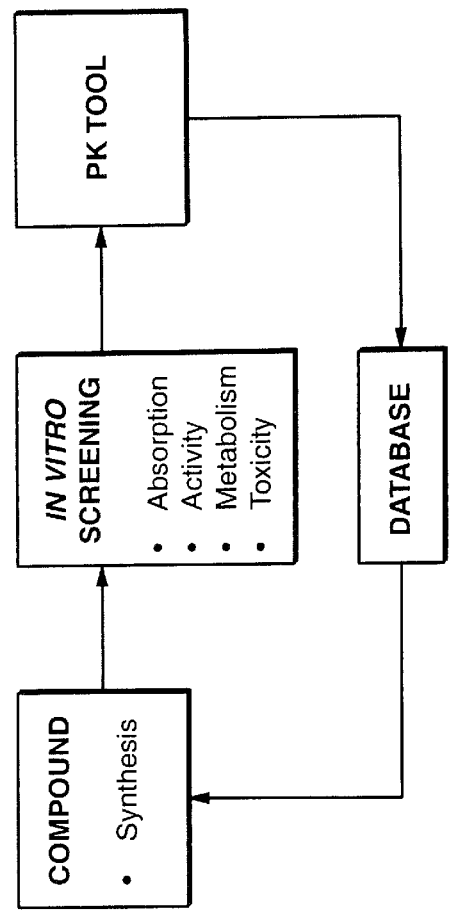
FIG._54

PHARMACOKINETIC-BASED DRUG DESIGN TOOL AND METHOD

CROSS REFERENCE TO RELATED APPLICATIONS

This application claims benefit of to the following U.S. Provisional Applications Ser. Nos. 60/100,224, filed Sep. 14, 1998; 60/109,234 filed Nov. 18, 1998, 60/100,290, filed Sep. 14, 1998; and 60,109,232, filed Nov. 18, 1998.

INTRODUCTION

1. Technical Field

The present invention relates to computer-implemented pharmacokinetic simulation models and drug design.

2. Background

A. Pharmacokinetic Modeling

Pharmacodynamics refers to the study of fundamental or molecular interactions between drug and body constituents, which through a subsequent series of events results in a pharmacological response. For most drugs the magnitude of a pharmacological effect depends on time-dependent concentration of drug at the site of action (e.g., target receptor-ligand/drug interaction). Factors that influence rates of delivery and disappearance of drug to or from the site of action over time include absorption, distribution, metabolism, and elimination. The study of factors that influence how drug concentration varies with time is the subject of pharmacokinetics.

In nearly all cases the site of drug action is located on the other side of a membrane from the site of drug administration. For example, an orally administered drug must be absorbed across a membrane barrier at some point or points along the gastrointestinal (GI) tract. Once the drug is absorbed, and thus passes a membrane barrier of the GI tract, it is transported through the portal vein to the liver and then eventually into systemic circulation (i.e., blood and lymph) for delivery to other body parts and tissues by blood flow. Thus how well a drug crosses membranes is of key importance in assessing the rate and extent of absorption and distribution of the drug throughout different body compartments and tissues. In essence, if an otherwise highly potent drug is administered extravascularly (e.g., oral) but is poorly absorbed (e.g., GI tract), a majority of the drug will be excreted or eliminated and thus cannot be distributed to the site of action.

The principle routes by which drugs disappear from the body are by elimination of unchanged drug or by metabolism of the drug to a pharmacologically active or inactive form(s) (i.e., metabolites). The metabolites in turn may be subject to further elimination or metabolism. Elimination of drugs occurs mainly via renal mechanisms into the urine and to some extent via mixing with bile salts for solubilization followed by excretion through the GI tract, exhaled through the lungs, or secreted through sweat or salivary glands etc. Metabolism for most drugs occurs primarily in the liver.

Each step of drug absorption, distribution, metabolism, and elimination can be described mathematically as a rate process. Most of these biochemical processes involve first order or pseudo-first order rate processes. In other words, the rate of reaction is proportional to drug concentration. For instance, pharmacokinetic data analysis is based on empirical observations after administering a known dose of drug and fitting of the data by either descriptive equations or mathematical (compartmental) models. This permits summarization of the experimental measures (plasma/blood level-time profile) and prediction under many experimental conditions. For example after rapid intravenous administration, drug levels often decline mono-exponentially (first-order elimination) with respect to time as described in Equation 1, where $Cp(t)$ is drug concentration as a function of time, $Cp(0)$ is initial drug concentration, and k is the associated rate constant that represents a combination of all factors that influence the drug decay process (e.g., absorption, distribution, metabolism, elimination).

$$Cp(t) = Cp(0)e^{-kt} \quad \text{(Eq. 1)}$$

This example assumes the body is a single "well-mixed" compartment into which drug is administered and from which it also is eliminated (one-compartment open model). If equilibrium between drug in a central (blood) compartment and a (peripheral) tissue compartment(s) is not rapid, then more complex profiles (multi-exponential) and models (two- and three-compartment) are used. Mathematically, these "multi-compartment" models are described as the sum of equations, such as the sum of rate processes each calculated according to Equation 1 (i.e., linear pharmacokinetics).

Experimentally, Equation 1 is applied by first collecting time-concentration data from a subject that has been given a particular dose of a drug followed by plotting the data points on a logarithmic graph of time versus drug concentration to generate one type of time-concentration curve. The slope (k) and the y-intercept (C0) of the plotted "best-fit" curve is obtained and subsequently incorporated into Equation 1 (or sum of equations) to describe the drug's time course for additional subjects and dosing regimes.

When drug concentration throughout the body or a particular location is very high, saturation or nonlinear pharmacokinetics may be applicable. In this situation the capacity of a biochemical and/or physiological process to reduce drug concentration is saturated. Conventional Michaelis-Menten type equations are employed to describe the non-linear nature of the system, which involve mixtures of zero-order (i.e., saturation:concentration independent) and first-order (i.e., non-saturation:concentration dependent) kinetics. Experimentally, data collection and plotting are similar to that of standard compartment models, with a notable exception being that the data curves are nonlinear. Using a time versus concentration graph to illustrate this point, at very high drug concentration the data line is linear because the drug is being eliminated at a maximal constant rate (i.e., zero-order process). The data line then begins to curve in an asymptotic fashion with time until the drug concentration drops to a point where the rate process becomes proportional to drug concentration (i.e., first-order process). For many drugs, nonlinear pharmacokinetics applies to events such as dissolution of the therapeutic ingredient from a drug formulation, as well as metabolism and elimination. Nonlinear pharmacokinetics also can be applied to toxicological events related to threshold dosing.

Classical one, two and three compartment models used in pharmacokinetics require in vivo blood data to describe time-concentration effects related to the drug decay process, i.e., blood data is relied on to provide values for equation parameters. For instance, while a model may work to describe the decay process for one drug, it is likely to work poorly for others unless blood profile data and associated rate process limitations are generated for each drug in question. Thus, such models are very poor for predicting the in vivo fate of diverse drug sets in the absence of blood data and the like derived from animal and/or human testing.

In contrast to the standard compartment models, physiological-based pharmacokinetic models are designed to integrate basic physiology and anatomy with drug distribution and disposition. Although a compartment approach also is used for physiological models, the compartments correspond to anatomic entities such as the GI tract, liver, lung etc., which are connected by blood flow. Physiological modeling also differs from standard compartment modeling in that a large body of physiological and physicochemical data usually is employed that is not drug-specific. However, as with standard compartment models the conventional physiological models lump rate processes together. Also, conventional physiological models typically fail to incorporate individual kinetic, mechanistic and physiological processes that control drug distribution and disposition in a particular anatomical entity, even though multiple rate processes are represented in vivo. Physiological models that ignore these and other important model parameters contain an underlying bias resulting in poor correlation and predictability across diverse data sets. Such deficiencies inevitably result in unacceptable levels of error when the model is used to describe or predict drug fate in animals or humans. The problem is amplified when the models are employed to extrapolate animal data to humans, and worse, when in vitro data is relied on for prediction in animals or humans.

For instance, the process of drug reaching the systemic circulation for most orally administered drugs can be broken down into two general steps: dissolution and absorption. Since endocytotic processes in the GI tract typically are not of high enough capacity to deliver therapeutic amounts of most drugs, the drugs must be solubilized prior to absorption. The process of dissolution is fairly well understood. However, the absorption process is treated as a "black box." Indeed, although bioavailability data is widely available for many drugs in multiple animal species and in humans, in vitro and or in vivo data generated from animal, tissue or cell culture permeability experiments cannot allow a direct prediction of drug absorption in humans, although such correlations are commonly used.

B. Computer Systems and Pharmacokinetic Modeling

Computers have been used in pharmacokinetics to bring about easy solutions to complex pharmacokinetic equations and modeling of pharmacokinetic processes. Other computer applications in pharmacokinetics include development of experimental study designs, statistical data treatment, data manipulation, graphical representation of data, projection of drug action, as well as preparation of written reports or documents.

Since pharmacokinetic models are described by systems of differential equations, virtually all computer systems and programming languages that enable development and implementation of mathematical models have been utilized to construct and run them. Graphics-oriented model development computer programs, due to their simplicity and ease of use, are typically used for designing multi-compartment linear and non-linear pharmacokinetic models. In essence, they allow a user to interactively draw compartments and then link and modify them with other iconic elements to develop integrated flow pathways using pre-defined symbols. The user assigns certain parameters and equations relating the parameters to the compartments and flow pathways, and then the model development program generates the differential equations and interpretable code to reflect the integrated system in a computer-readable format. The resulting model, when provided with input values for parameters corresponding to the underlying equations of the model, such as drug dose and the like can then be used to simulate the system under investigation.

While tools to develop and implement pharmacokinetic models exist and the scientific literature is replete with examples, pharmacokinetic models and computer systems developed to date have not permitted sufficient predictability of the pharmacokinetic fate of extravascularly administered drugs in a mammal from in vitro cell, tissue or compound structure-activity relationship (SAR/QSAR) data. A similar problem exists when attempting to predict absorption of a compound in one mammal (e.g., human) from data derived from a second mammal (e.g., dog). For example, existing pharmacokinetic models of oral absorption use several different approaches to predict oral absorption and fraction dose absorbed (Amidon et al., *Pharm. Res.*, (1988) 5:651–654; Chiou, W. L., *Int. J. Clin. Pharmacol. Ther.*, (1994) 32:474–482; Chiou, W. L., *Biopharm. Drug Dispos.*, (1995) 16:71–75; Dressman et al., *J. Pharm. Sci.*, (1985) 74:588–589; Lennernas et al., *J. Pharm. Pharmacol.*, (1997) 49:682–686; Levet-Trafit et al., *Life Sciences.*, (1996) 58:PL359–63; Sinko et al., *Pharm. Res.*, (1991) 8:979–988; and Soria et al., *Biopharm. Drug Dispos.*, (1996) 17:817–818). Unfortunately, these models are flawed as they make mathematical assumptions that limit prediction to particular compounds, and the correlation function is sigmoidal in shape (i.e., high/steep slope). Therefore the predictive power of such models for compounds outside a relatively small group is very limited. This is particularly true for collections of compounds possessing variable ranges of dosing requirements and of permeability, solubility, dissolution rates and transport mechanism properties. Other drawbacks include use of drug-specific parameters and values in pharmacokinetic models from the outset of model development, which essentially limits the models to drug-specific predictions. These and other deficiencies also impair generation of rules that universally apply to drug disposition in a complex physiological system such as the GI tract.

Extravascular administration of drugs is the preferred route for physicians, patients, and drug developers alike due to lower product price, increased patient compliance, ease of administration. Current assessment of the bioavailability of extravascularly administered drugs and lead drug compounds, as well as bioavailability of intravascularly administered compounds relative to specialized barriers to absorption such as the blood brain barrier, is limited in large part to animal and human testing. The economic and medical consequences of problems with drug absorption and variable bioavailability are immense. Failing to identify promising or potentially problematic drug candidates during the discovery and pre-clinical stages of drug development is one of the most significant consequences of problems with drug bioavailability. Accordingly, there is a need to develop a comprehensive, physiologically-based pharmacokinetic model and computer system capable of predicting drug bioavailability and variability in humans that utilizes relatively straightforward input parameters. Furthermore, considering the urgent need to provide the medical community with new therapeutic alternatives and the current use of high throughput drug screening for selecting lead drug candidates, a comprehensive biopharmaceutical computer-based tool that employs a modeling approach for predicting bioavailability of compounds and compound formulations is needed.

Relevant Literature

Various publications review gastrointestinal anatomy and physiology including motility, secretion, absorption, and digestion, as well as gastrointestinal pharmacology and physiology in gastrointestinal diseased individuals (See, e.g., L. Johnson ed., *Physiology of the Gastrointestinal Tract*, Second edition, Vol. 2, Ravind Press (1987); Kutchai, *Gastrointestinal System, Part IV, Principles of Physiology*, Mosby Press (1996); and Sleisenger, *Gastrointestinal Disease*, 3$^{rd}$ edition, Saunders (1983)). Sharget et al. (*Physiological Factors Related to Drug Absorption*, Applied Biopharmaceutics and Pharmacokinetics (1993)) review pharmacokinetics and compartment modeling. Various pharmacokinetic models of oral drug absorption are disclosed in Grass, G. (*Advanced Drug Delivery Reviews* (1997) 23:199–219); Amidon et al., (*Pharm. Res.* (1988) 5:651–654); Chiou, W. L., (*Int. J. Clin. Pharmacol. Ther.*, (1994) 32:474–482); Chiou, W. L., (*Biopharm. Drug Dispos.*, (1995) 16:71–75); Dressman et al., (*J. Pharm. Sci.*, (1985) 74:588–589); Lennernas et al., (*J. Pharm. Pharmacol.*, (1997) 49:682–686); Levet-Trafit et al., (*Life Sciences.*, (1996) 58:PL359–63); Sinko et al., (*Pharm. Res.*, (1991) 8:979–988); and Soria et al.,. (*Biopharm. Drug Dispos.*, (1996) 17:817–818)).

SUMMARY OF THE INVENTION

The present invention relates to a pharmacokinetic-based design and selection tool (PK tool) and methods for predicting absorption of a compound in a mammalian system of interest. The methods utilize the tool, and optionally a separately operable component or subsystem thereof.

The PK tool comprises as computer-readable components: (1) input/output system; (2) physiologic-based simulation model of one or more segments of a mammalian system of interest having one or more physiological barriers to absorption that is based on the selected route of administration; and (3) simulation engine having a differential equation solver, and optionally, a control statement module. The physiologic-based simulation model of the PK tool of the invention is a multi-compartment mathematical model comprising as operably linked components: (i) differential equations for one or more of fluid transit, fluid absorption, mass transit, mass dissolution, mass solubility, and mass absorption for one or more segments of the mammalian system of interest; and (ii) initial parameter values for the differential equations corresponding to physiological parameters and selectively optimized adjustment parameters, and optionally regional correlation parameters, for one or more segments of the mammalian system of interest; and, optionally, (iii) control statement rules for one or more of transit, absorption, permeability, solubility, dissolution, concentration, and mathematical error correction for one or more segments of the mammalian system of interest.

The computer-readable input/output system, physiologic-based simulation model, and simulation engine of the PK tool are capable of working together to carrying out the steps of: (1) receiving through the input/output system data comprising dose, permeability and solubility data of a compound of interest for one or more segments of the mammalian system of interest; and (2) applying the physiologic-based simulation model and simulation engine to generate an absorption profile for the compound characterized by one or more of concentration, rate of absorption, and extent of absorption relative to a selected sampling site that is across a physiological barrier for one or more segments of the mammalian system of interest.

The present invention also provides a database for utilization in the PK tool and method of the invention. The database includes one or more physiologic-based simulation models of the invention. Additional databases are provided for simulation model parameters, and may be integrated or separate from a database having a simulation model of the invention. The database(s) includes one or more of (i) differential equations for one or more of fluid transit, fluid absorption, mass transit, mass dissolution, mass solubility, and mass absorption for one or more segments of the mammalian system of interest; (ii) initial parameter values for the differential equations corresponding to physiological parameters and selectively optimized adjustment parameters, and optionally regional correlation parameters, for one or more segments of the mammalian system of interest; and (iii) control statement rules for one or more of transit, absorption, permeability, solubility, dissolution, concentration, and mathematical error correction for one or more segments of the mammalian system of interest. The database(s) have a compartment-flow data structure that is portable into and readable by a simulation engine for calculating time-dependent rate of absorption, extent of absorption, and concentration of a compound at a sampling site across a physiological barrier of one or more segments of the mammalian system of interest.

The invention also includes a method for selectively optimizing a pharmacokinetic-based simulation model for use in the PK tool of the invention. This method permits the PK tool of the invention to accurately predict one or more in vivo pharmacokinetic properties of a compound in a mammalian system of interest from input data derived from a selected in vitro or in vivo data source. The method includes the steps of (i) generating initial adjustment parameter values for one or more independent parameters of the simulation model by utilizing a curve-fitting algorithm to simultaneously fit to the model one or more input variables corresponding to a pharmacokinetic property of a compound test set derived from (a) a first data source corresponding to the mammalian system of interest, and (b) a second data source corresponding to a system other than the mammalian system of interest; (ii) selecting adjustment parameter values that permit correlation of one or more of the input variables from the first data source to one or more input variables from the second data source; (iii) repeating steps (i) and (ii) one or more times for one or more additional independent parameters of the simulation model until deviation of the correlation is minimized; and (iv) utilizing the selected adjustment parameters as constants for the independent parameters in the simulation model.

The present invention further includes a method for producing a pharmacokinetic-based simulation model for use in the PK tool that facilitates estimation of a selected parameter value in a first segment of mammalian system of interest utilizing input data for the selected parameter that corresponds to a second segment of the mammalian system of interest. The method involves (i) providing a logic function module in the simulation model that includes a set of regional correlation parameter values for at least first and second segments of the mammalian system of interest that facilitates estimation of a selected parameter value in the first segment of the mammalian system of interest utilizing input data for the selected parameter that corresponds to the second segment of the mammalian system of interest; and (ii) providing a control statement in the simulation model which initiates the regional correlation estimation function of the logic function module when a value for the first segment is not supplied as input into the model.

The present invention also provides a method for generating formulation profiles for a compound of interest utilizing the PK tool of the invention.

The PK tool of the invention may be provided as a computer system, as an article of manufacture in the form of a computer-readable medium, or a computer program product and the like. Subsystems and individual components of the PK tool also can be utilized and adapted in a variety of disparate applications for predicting the fate of an administered compound. The PK tool and methods of the invention can be used to screen and design compound libraries, select and design drugs, as well as predict drug efficacy in mammals from in vitro and/or in vivo data of one or more compounds of interest. The PK tool and methods of the invention also finds use in selecting, designing, and preparing drug compounds, and multi-compound drugs and drug formulations (i.e., drug delivery system) for preparation of medicaments for use in treating mammalian disorders.

DEFINITIONS

Absorption: Transfer of a compound across a physiological barrier as a function of time and initial concentration. Amount or concentration of the compound on the external and/or internal side of the barrier is a function of transfer rate and extent, and may range from zero to unity.

Bioavailability: Fraction of an administered dose of a compound that reaches the sampling site and/or site of action. May range from zero to unity. Can be assessed as a function of time.

Compound: Chemical entity.

Computer Readable Medium: Medium for storing, retrieving and/or manipulating information using a computer. Includes optical, digital, magnetic mediums and the like; examples include portable computer diskette, CD-ROMs, hard drive on computer etc. Includes remote access mediums; examples include internet or intranet systems. Permits temporary or permanent data storage, access and manipulation.

Data: Experimentally collected and/or predicted variables. May include dependent and independent variables.

Dissolution: Process by which a compound becomes dissolved in a solvent.

Input/Output System: Provides a user interface between the user and a computer system.

Permeability: Ability of a physiological barrier to permit passage of a substance. Refers to the concentration-dependent or concentration-independent rate of transport (flux), and collectively reflects the effects of characteristics such as molecular size, charge, partition coefficient and stability of a compound on transport. Permeability is substance and barrier specific.

Physiologic Pharmacokinetic Model: Mathematical model describing movement and disposition of a compound in the body or an anatomical part of the body based on pharmacokinetics and physiology.

Production Rule: Combines known facts to produce ("infer") new facts. Includes production rules of the "IF . . . THEN" type.

Simulation Engine: Computer-implemented instrument that simulates behavior of a system using an approximate mathematical model of the system. Combines mathematical model with user input variables to simulate or predict how the system behaves. May include system control components such as control statements (e.g., logic components and discrete objects).

Solubility: Property of being soluble; relative capability of being dissolved.

Transport Mechanism: The mechanism by which a compound passes a physiological barrier of tissue or cells. Includes four basic categories of transport: passive paracellular, passive transcellular, carrier-mediated influx, and carrier-mediated efflux.

BRIEF DESCRIPTION OF DRAWINGS

FIG. 1 shows schematic of method to generate input data for selected route of administration, mammalian system, and at least one primary barrier to absorption.

FIG. 2 shows schematic of method for selecting sampling site relative to administration site and barrier to absorption.

FIG. 3 is a high level INPUT/PROCESS/OUTPUT diagram of the PK tool of the invention.

FIG. 4 is a high level flow chart and structure chart of the PK tool and method of the invention.

FIG. 5 is a graphical diagram illustrating generic compartment-flow simulation model and exemplary symbolic relationships among compartments, flow regulators, converters and input links.

FIG. 6 is a key for FIG. 5.

FIG. 7 is a graphical diagram illustrating generic pharmacokinetic first-order two-compartment open plasma model for intravenous injection. D is total drug, V is apparent volume of distribution, and C is drug concentration for either plasma (p) or tissue (t). k12 and k21 represent first-order rate transfer constants for movement of drug from compartment 1 to compartment 2 (k12) and from compartment 2 to compartment 1 (k21). k10 represents first-order rate transfer constant for movement (elimination) of drug from compartment 1 to compartment 0.

FIG. 8 is a graphical compartment-flow diagram illustrating the plasma simulation model of FIG. 7 and exemplary relationships among compartments, flow regulators, converters and input links.

FIG. 9 shows schematic of a method of the invention for development of an initial physiologic-based simulation model for PK tool and method of the invention.

FIG. 10 shows schematic of a method of the invention for development of a physiologic-based simulation model having selectively optimized adjustment parameters.

FIG. 11 shows graphical compartment-flow diagram illustrating the mass-volume GI tract simulation model of the invention linked to a training/validation plasma model.

FIG. 12 illustrates compartment, flow regulator and converter components of the mass-volume GI tract simulation model of the invention.

FIG. 13 illustrates structural relationship among compartment and flow regulator components for the mass-volume GI tract simulation model of the invention.

FIG. 14 illustrates structural relationship among flow regulator and converter components for the mass-volume GI tract simulation model of the invention.

FIG. 15 illustrates structural relationship among converter components for the mass-volume GI tract simulation model of the invention.

FIG. 16 compares plasma concentration profiles derived from clinical studies of gancyclovir and simulation using volume GI tract simulation model of the invention.

FIG. 17 compares plasma concentration profiles derived from clinical studies of gancyclovir and simulation using mass-volume GI tract simulation model of the invention.

FIG. 18 shows graphical compartment-flow diagram illustrating the in vivo data analysis-processing IV/PO PK model (intravenous/oral administration) of the invention.

FIG. 19 shows schematic of method for development of initial integrated physiologic-based GI tract simulation model of PK tool and method of the invention.

FIG. 20 shows graphical compartment-flow diagram illustrating the GI tract fluid transit model component of the PK tool and method of the invention.

FIG. 21 shows graphical compartment-flow diagram illustrating the GI tract solubility-dissolution model component of the PK tool and method of the invention.

FIG. 22 shows graphical compartment-flow diagram illustrating the GI tract absorption model component of the PK tool and method of the invention.

FIG. 23 shows graphical compartment-flow diagram illustrating integration of the GI tract fluid transit model, solubility-dissolution model, and absorption model components for one GI segment of the PK tool and method of the invention.

FIG. 24 shows graphical compartment-flow diagram illustrating integrated GI tract simulation model components (without converters or input link connectors) of the PK tool and method of the invention.

FIG. 25 shows graphical compartment-flow diagram illustrating integrated GI tract simulation model components (with converters and input link connectors) of the PK tool and method of the invention.

FIG. 27 shows schematic of method for selection of model parameters for utilization in a given physiologic-based GI tract simulation model of PK tool and method of the invention.

FIG. 28 shows schematic of method for regional (segmental) calculation/estimation of permeability from one or more user input values for permeability of a given GI tract region/segment. Regional permeability (Pe) correlation based on input of Pe value for duodenum is illustrated.

FIG. 29 shows graphical converter diagram illustrating volume, surface area, dose, time and pH parameters and calculations for integrated GI tract simulation model components of the PK tool and method of the invention.

FIG. 30 shows graphical converter diagram illustrating GI tract transit time parameters and calculations for integrated GI tract simulation model components of the PK tool and method of the invention.

FIG. 31 shows graphical converter diagram illustrating GI tract permeability parameters and calculations for integrated GI tract simulation model components of the PK tool and method of the invention.

FIG. 32 shows graphical converter diagram illustrating GI tract solubility parameters and calculations for integrated GI tract simulation model components of the PK tool and method of the invention.

FIG. 33 shows graphical converter diagram illustrating GI tract control release formulation parameters and calculations for integrated GI tract simulation model components of the PK tool and method of the invention.

FIG. 34 shows graphical compartment-converter diagram illustrating GI tract concentration parameters and calculations for integrated GI tract simulation model components of the PK tool and method of the invention.

FIG. 35 shows graphical compartment-converter diagram illustrating GI tract dissolution parameters and calculations for integrated GI tract simulation model components of the PK tool and method of the invention.

FIG. 36 shows graphical compartment-converter diagram illustrating GI tract output calculations for absorption for integrated GI tract simulation model components of the PK tool and method of the invention.

FIG. 37 shows graphical converter diagram illustrating GI tract output calculations for soluble mass absorption rate (flux) for integrated GI tract simulation model components of the PK tool and method of the invention.

FIG. 38 shows graphical compartment-flow-converter diagram illustrating GI tract output calculations for cumulative dissolution rate and amount for integrated GI tract simulation model components of the PK tool and method of the invention.

FIG. 39 shows graphical compartment-flow-converter diagram illustrating GI tract output calculations for cumulative control release formulation rate and amount for integrated GI tract simulation model components of the PK tool and method of the invention.

FIG. 40 illustrates database and rulebase compartment, flow regulator and converter components for the integrated physiologic-based GI tract simulation model of the invention.

FIG. 41 illustrates structural relationship among compartment and flow regulator components for the integrated physiologic-based GI tract simulation model of the invention.

FIG. 42 illustrates structural relationship among flow regulator and converter components for the integrated physiologic-based GI tract simulation model of the invention.

FIG. 43 illustrates structural relationship among converter components for the integrated physiologic-based GI tract simulation model of the invention.

FIG. 44 is a high level INPUT/PROCESS/OUTPUT diagram of the PK tool of the invention as presented to a user of the carrying out a method of the invention, with inputs provided by the user and outputs provided by the PK tool.

FIG. 45 illustrates a flow chart and structure chart of a subsystem of the PK tool and method of the invention for selection of a physiological GI tract model from a model database and a parameter database.

FIG. 46 is a flow chart and structure chart of the system of the PK tool and method of the invention.

FIG. 47 is a flow chart and structure chart of a menu of the system of the PK tool and method of the invention.

FIG. 48 illustrates correlation of extent of absorption for fraction of the dose absorbed in portal vein (FDp), as predicted using physiologic-based GI tract simulation model and PK tool of the invention, to FDp derived from human clinical data for 12 compounds.

FIG. 49 illustrates correlation of rate of absorption for fraction of the dose absorbed in portal vein (FDp), as predicted using integrated physiologic-based GI tract simulation model and PK tool of the invention, to FDp derived from human clinical data for 12 compounds.

FIG. 50 compares plasma levels as predicted using integrated physiologic-based GI tract simulation model and PK tool of the invention, to plasma levels derived from human clinical data for a test compound.

FIG. 51 compares plasma levels as predicted using integrated physiologic-based GI tract simulation model and PK tool of the invention, to plasma levels derived from human clinical data for a test compound.

FIG. 52 compares plasma levels as predicted using integrated physiologic-based GI tract simulation model and PK tool of the invention, to plasma levels derived from human clinical data for a test compound.

FIG. 53 shows high level INPUT/PROCESS/OUTPUT diagram of the PK tool of the invention for SAR/QSAR and CAD/CAE compound design and synthesis.

FIG. 54 shows high level flow and structure chart for screening method of the invention utilizing the PK tool and method of the invention.

DESCRIPTION OF SPECIFIC EMBODIMENTS

Figure 26:
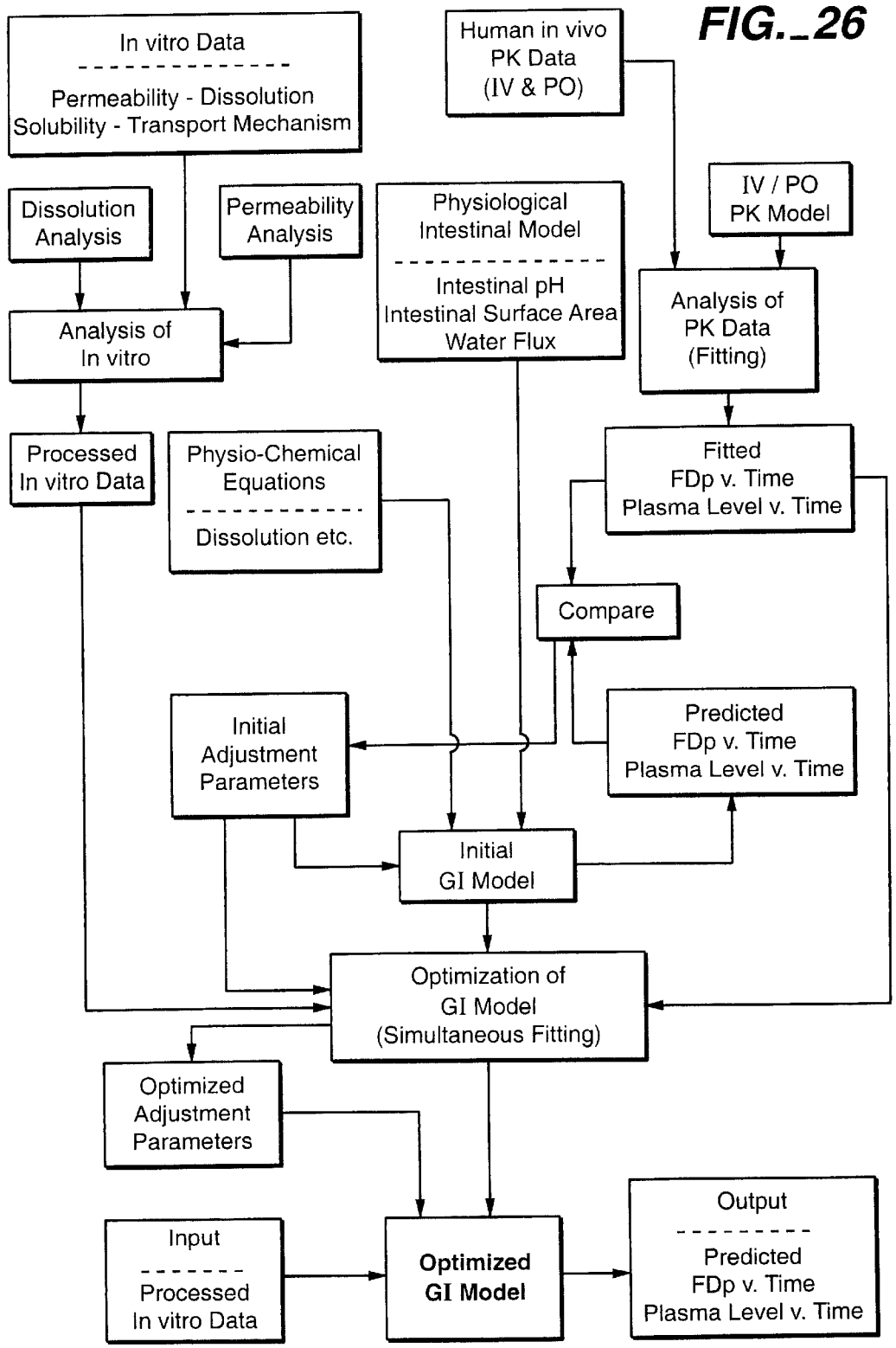
FIG. 26 shows schematic of method for development of selectively optimized adjustment parameters and for optimization of the integrated physiologic-based GI tract simulation model of PK tool and method of the invention.

A pharmacokinetic tool (PK tool) and method is provided for predicting absorption of a compound relative to a physiological barrier of a mammalian system of interest, including extravascularly administered compounds. This includes, but is not limited to, prediction of rate, extent and/or concentration of a compound. The mammal is a human or a non-human animal. The method utilizes the PK tool, and optionally separately operable subsystems or components thereof. The PK tool and method of the invention also facilitates prediction of the fate of a compound in a mammal based on absorption and one or more additional bioavailability parameters including distribution, metabolism, elimination, and optionally toxicity.

The PK tool includes as computer-readable components, an input/output system, a physiologic-based simulation model of a mammalian system of interest, and a simulation engine. The input/output system may be any suitable interface between user and computer system, for input and output of data and other information, and for operable interaction with a simulation engine and a simulation model.

Input data into the PK tool and method of the invention is dose, permeability and solubility data for a test compound of interest, and optionally one or more of dissolution rate, transport mechanism, transit time, pH, delivery system rate such as controlled release rate or formulation release rate (delivery system referred to herein as "formulation"), dosing schedule, and simulation run time. The input data may be derived from in vitro or in vivo sources. In vitro data includes tissue and cell and natural and artificial preparations thereof, physicochemical, molecular structure and molecular structure-activity relationship (SAR) and quantitative-SAR (QSAR) data. In vivo data includes mammal data. The input data corresponds to one or more given physiological segments/regions of the mammalian system of interest.

The simulation output includes an absorption profile characterized by one or more of rate of absorption, extent of absorption, and concentration of the compound relative to a selected sampling site of interest located across a physiological barrier of the mammalian system of interest, i.e., rate and/or extent of transfer of a test sample from an external site (e.g., apical) across a physiological barrier (e.g., epithelium) to an internal site (e.g., basolateral) of that barrier. This can include prediction of rate, extent and/or concentration of a compound at the site of action when the selected sampling site is the site of action. Transfer rate and/or extent are generated utilizing initial dose data for the test compound and in vitro and/or in vivo derived data including permeability and solubility data, and optionally dissolution rate and transport mechanism data (i.e., passive paracellular, passive transcellular, carrier-mediated influx, carrier-mediated efflux) for the test compound. Solubility and dissolution rate are interrelated and effect the ability of the compound to be solubilized at a rate sufficient for absorption to occur across a particular membrane. Permeability refers to the concentration-dependent or concentration-independent rate of transport (flux), and collectively reflects the effect of molecular size, charge, partition coefficient and stability of a compound on absorption for a particular physiological barrier, where the physiological barrier(s) depends on the selected route of administration. Molecular size, charge and partition coefficient determines in large part whether a compound is transported via a paracellular or transcellular mechanism. Stability is a general feature that relates to whether the compound remains intact long enough to be absorbed. Together, dose, solubility and permeability data, and optionally dissolution rate and transport mechanism data, are primary bioavailability factors utilized by the PK tool and method of the invention to generate an absorption profile for a test compound of interest.

An absorption profile generated by the PK tool and method of the invention can be uni- or multi-dimensional output that reflects one or more simulated parameters of the mammalian system of interest relative to the sampling site. The sampling site, for example, portal vein, plasma, tissue, organ and the like, is chosen depending on the intended end use of the PK tool and method of the invention. Output of the method and PK tool can be utilized to profile or rank the compound by a selected absorption parameter, and optionally, absorption and one or more additional bioavailability parameters and toxicity.

The simulation engine comprises a differential equation solver and, optionally, a system control statement module. This includes various computer-readable algorithms for numerical iteration of mathematical equations over interval dt and for processing rules, scenarios and the like that direct a simulation.

The simulation model corresponds to a physiologic-based multi-compartment model of a mammalian system of interest, where the mammalian system represents a physiological barrier to absorption that is based on a selected route of administration, i.e., the location at which the compound is introduced to a mammal. More particularly, the physiologic-based simulation model of the PK tool and method of the invention is a mathematical model comprising as operably linked components: (i) differential equations for calculating one or more of fluid transit, fluid absorption, mass transit, mass dissolution, mass solubility, and mass absorption of a test compound for one or more physiological segments of the mammal system of interest; and (ii) initial parameter values for the differential equations corresponding to physiological parameters and selectively optimized adjustment parameters, and optionally one or more regional correlation parameters, for one or more physiological segments of the mammal system of interest; and optionally (iii) control statement rules for one or more of absorption, permeability, solubility, dissolution, concentration, and mathematical error correction, for one or more physiological segments of the mammal system of interest. The simulation model also may include one or more smoothing functions that facilitate calculation of transitional parameter values occurring between one or more of the physiological segments.

The differential equations of a selected simulation model of a mammalian system of interest describe the rate processes of absorption, and optionally other events, of that model, which in turn describe compound concentrations in the system as a function of time. (See, e.g., Shargel et al., *Applied Biopharmaceutics and Pharmacokinetics*, Appelton & Lange, East Norwalk, Conn., 1993). Thus, the differential equations are selected for a particular model.

The initial physiological parameter values of a given simulation model can be generated de novo or obtained from existing sources including the literature. The selectively optimized adjustment parameter values of a given simulation model of the invention represent regression or stochastic analysis derived values that are used as constants for one or more independent parameters of the model. In particular, the selectively optimized adjustment parameter values are obtainable by using a stepwise fitting and selection process that employs regression- or stochastic-based curve-fitting algorithms to simultaneously estimate the change required in a value assigned to an initial absorption parameter of the model in order to change an output variable. The input variables utilized for fitting include a combination of in vitro data (e.g., permeability, solubility) and in vivo pharmacokinetic data (e.g., fraction of dose absorbed, plasma levels)

for a compound test set having compounds exhibiting a diverse range of in vivo absorption properties. Thus, the input variables used for regression- or stochastic-based fitting are derived from (a) a first data source corresponding to the mammalian system of interest (e.g., in vivo pharmacokinetic data from human for the compound test set), and (b) a second data source corresponding to a system other than the mammalian system of interest (e.g., in vitro solubility data and in vitro permeability data from rabbit tissue for the compound test set). A fitted adjustment parameter value for a given independent parameter is then selected that, when supplied as a constant in the model, permits correlation of one or more of the input variables from the first data source to one or more input variables from the second data source. The process is repeated one or more times for one or more additional independent parameters of the simulation model until deviation of the correlation is minimized. These "selectively optimized" adjustment parameters are then provided to a given simulation model as constants or ranges of constants or functions that modify the underlying equations of the model. The selectively optimized adjustment parameters facilitate accurate correlation of in vitro data derived from a particular type of assay corresponding to the second data source (e.g., Caco-2 cells, segment-specific rabbit intestinal tissue sections etc.) to in vivo absorption for a mammalian system of interest corresponding to the first data source (e.g., segment-specific portions of the human GI tract) for diverse test sample data sets. Selectively optimized adjustment parameters also can be utilized to facilitate accurate correlation of in vivo data derived from a first species of mammal (e.g., rabbit) to a second species of mammal (e.g., human).

For a simulation model representing two or more anatomical segments of a given mammalian system, the model will preferably include regional correlation parameters. The regional correlation parameters permit estimation of a selected parameter value for a first segment of the mammalian system from correlation using a value of the selected parameter for a second segment of the mammalian system. The regional correlation parameters represent a collection of empirically derived values or selectively optimized adjustment parameter values for various segments of the mammalian system of interest, for example, permeability values. The regional (i.e., segmental) correlation is performed by logic function of the model, which when activated utilizes a function/transformation algorithm to estimate the parameter value for the second segment from (1) the corresponding regional correlation parameters, and (2) a user provided input value for the same parameter, but for a different segment. The regional correlation logic function of the model is activated when a user does not supply an input value for a particular parameter. For example, when a user of the PK tool supplies a single permeability value as input into a GI tract simulation model of the invention, such as a permeability value derived from Caco-2 cells that corresponds to colon, then regional permeability correlation is performed by the PK tool to estimate permeability in the other GI tract segments, such as duodenum, jejunum, and ileum.

The control statement rules include various logic elements utilized for providing guidance as to how a given simulation is to proceed. For instance, a control statement rule would include "IF . . . THEN" production rules. An example of a production rule would be "IF solubility of compound is zero THEN absorption is zero." The production rules are based on rules of thumb (heuristics) and the like, and may be generated by correlation of parameters and simulation runs. Rules can be added, modified or removed to change how a simulation model responds to incoming data.

The input/output system, simulation engine and simulation model of the PK tool are capable of working together to carry out the steps of (1) receiving as input data, the initial dose of a test compound at the site of administration and permeability and solubility, and optionally dissolution rate and transfer mechanism data; and (2) applying the simulation engine and the simulation model to generate as output data a simulated in vivo absorption profile for the test compound that reflects rate, extent and/or concentration of the test sample at a given sampling site for a selected route of administration in a mammalian system of interest. This includes uni- and multi-dimensional output profiles that collectively reflect parameters of absorption, which can be directly or indirectly utilized for characterizing in vivo absorption, as well as one or more additional bioavailability parameters including distribution, metabolism, elimination, and optionally toxicity.

The selected routes of administration include enteral (e.g., buccal or sublingual, oral (PO), rectal (PR)), parenteral (e.g., intravascular, intravenous bolus, intravenous infusion, intramuscular, subcutaneous injection), inhalation and transdermal (percutaneous). The preferred route of administration according to the method of the invention is oral administration. The selected route of administration determines the type and/or source of assay or structure-property parameters employed for obtaining a set of input data utilized for generating a simulated in vivo absorption profile. That is, artificial, cell or tissue preparations and the like derived from or representative of a physiological barrier to absorption for a selected route of administration are chosen to generate the relevant input data for use as input into the PK tool. For instance, input data for simulating fate of a test sample following oral administration can be based on cell culture and/or tissue assays that employ biological preparations derived from or representative of the gastrointestinal tract of a mammal of interest, e.g., gastrointestinal epithelial cell preparations for permeability and transfer mechanism data, and physiological/anatomical fluid and admixing conditions corresponding to the relevant portions of the gastrointestinal tract for solubility and dissolution rate assays. Assays for collecting input data for specialized physiological barriers such as the blood brain barrier may initially assume intravascular delivery and thus instantaneous absorption as a first step. In this situation an assay is selected to generate input data relative to the blood brain barrier, which include for instance cell culture and/or tissue assays that employ biological preparations derived from or representative of the interface between systemic blood and the endothelial cells of the microvessels of the brain for a mammal of interest, e.g., blood-brain-barrier microvessel endothelial cell preparations for permeability and transfer mechanism data, and physiological/anatomical fluid and admixing conditions corresponding to the relevant portions of the blood membrane barrier for solubility and dissolution rate assays. A series of assays may be employed to collect input data for two or more barriers to absorption. As an example, oral, hepatic, systemic and blood brain barrier assays may be utilized to obtain input data for screening compound libraries for orally delivered compounds that target brain tissue.

The sampling site relates to the point at which absorption parameters are evaluated for a test sample of interest. This is the site at which rate, extent and/or concentration of a test sample is determined relative to a selected site of administration, and separated from the site of administration by at least one physiological barrier to absorption. For generating simulated absorption profiles, the sampling site preferably is separated from the site of administration by an individual primary barrier to absorption, which can be utilized to evaluate additional absorption events by secondary barriers to absorption so as to sequentially and collectively reflect the summation of absorption events at other sampling sites of interest. As an example, the sampling site selected for oral delivery may be the portal vein where the primary barrier to absorption is the gastrointestinal lumenal membrane, or systemic blood where a secondary barrier to systemic absorption is the liver after the test sample passes from the portal vein through the liver to systemic circulation. Thus the type of physiological barrier(s) residing between a site of administration and a sampling site reflects the type of assay(s) employed for generating the desired input data for use as input data into the PK tool of the invention.

As the selected route of administration determines the barrier(s) to absorption and the physiological parameters that affect absorption events following administration, it also determines the physiologic-based pharmacokinetic simulation model employed in the PK tool for generation of the simulated in vivo absorption profile. By way of example, if the proposed route of administration is oral, then a primary barrier to absorption is the lumenal membrane of the gastrointestinal tract, and a secondary event affecting systemic bioavailability is first pass metabolism by the liver. Thus, a given simulation model and its associated parameters for simulating the fate of a compound selected for oral delivery is chosen to represent this scenario. The model would include therefore relevant components of the gastrointestinal tract for administration and absorption (i.e., stomach, duodenum, jejunum, ileum, and colon) and a primary sampling site (i.e., portal vein) from which to evaluate a primary absorption event. In this instance a secondary barrier to absorption for oral delivery is the liver and a secondary sampling site is systemic blood/plasma. This basic approach to choosing a physiologic-based pharmacokinetic model also applies to models employed to simulate absorption by target organs and the like, where a physiological barrier to absorption is the tissue and/or membrane separating systemic blood from the target organ, such as the blood brain barrier. In this situation if oral delivery is selected as the preferred route of administration for a compound targeting brain tissue, then a gastrointestinal tract model and blood brain barrier model may be implemented separately and/or combined through a complementary plasma component of the models for screening purposes.

The physiological models are selected from a repository of delivery route-specific models stored in a memory, a database, or created de novo. Physiological models of the invention include those corresponding to common routes of administration or barriers to absorption, such as oral (GI tract), ocular (eye), transdermal (skin), rectal, intravenous, rectal, subcutaneous, respiratory (nasal, lung), blood brain barrier and the like. For constructing a model de novo, the basic approach is to identify and isolate a primary barrier to a specific absorption event from secondary events so that each barrier to absorption can be tested and validated in isolation. This involves selecting a site of administration that is separated from a sampling site by a primary physiological barrier to absorption and then building a developmental physiological model that incorporates rate process relations and limitations to describe the isolated absorption event. If desired, the secondary events can be added sequentially so that each additional layer of complexity to the model can be tested and validated in isolation from other components of the initial model.

The invention also relates to a method and PK tool for designing compounds based on absorption. This aspect of the invention utilizes output of the method and PK tool as the input to a structure-activity relationship (SAR) or quantitative SAR (QSAR) design/selection process, e.g., a SAR and/or QSAR computer-assisted design/engineering/selection (CAD/CAE (collectively "CAD")) process. Output of the CAD process is then optionally used as input for the method and PK tool of the invention. SAR and QSAR information may then be incorporated into a database for subsequent iterative design and selection in the CAD process. For instance, compounds designed using a CAD process may be tested in vitro and/or in vivo for absorption parameters such as permeability, solubility, dissolution, and transport mechanism, and optionally one or more additional bioavailability parameters, and the data employed as input into the PK tool and method of the invention (i.e., iterative design). Alternatively, the parameters can be predicted from SAR or QSAR information and utilized as input for the method and PK tool of the invention. In this aspect of the invention, the user also is allowed to vary input parameters for "What if" analysis.

In the forward mode of operation, the user can predict absorption, individual parameters of absorption, as well as one or more other bioavailability parameters of a compound from relatively few input variables including dose, permeability and solubility. Additionally, the user can evaluate alternatives by changing any of the parameters and constants of the system, and observe the ripple effect of the change in one or more parameters on all other parameters. For instance, the user can evaluate alternative absorption profiles using "What if" analysis with any parameter of the system.

In the backward mode of operation, the user specifies one or more objective absorption parameters of a formulation of interest and the PK tool and method of the invention generates alternatives to satisfy the objective. In this aspect of the invention, well-defined properties of the compound (and the formulation base minus the compound) are utilized by the PK tool and method to evaluate alternative dosing and formulation profiles for a given compound. The user also is allowed to vary input dosing and formulation parameters for "What if" analysis. Simulated absorption profiles can then be utilized for preparing suitable formulations and/or dosing regimes. Solubility, permeability, doses and the like also may be estimated in the backward mode of operation.

The PK tool and method of the invention is exemplified by physiologic-based simulation model for predicting oral absorption of a compound in one or more segments of the GI tract of a mammal. The segments include the stomach, duodenum, jejunum, ileum, and colon. The simulation model includes differential equations for calculating one or more of fluid transit, fluid absorption, mass transit, mass dissolution, mass solubility, and mass absorption for one or more segments of the GI tract of a mammal of interest. It also includes initial parameter values for the differential equations that correspond to physiological parameters and selectively optimized adjustment parameters for one or more segments of the GI tract of the mammal of interest. The initial parameter values of simulation model also include one or more regional correlation parameter values, which are optional, but preferred for inclusion. The simulation model of the GI tract also includes control statement rules for one or more of transit, absorption, permeability, solubility, dissolution, concentration, and mathematical error correction for one or more segments of the GI tract of the mammal of interest.

The physiologic-based simulation model of the GI tract corresponds to a compartment-flow simulation model of the GI tract of a mammal characterized by one or more of fluid volume, fluid absorption, insoluble mass, soluble mass, and soluble mass absorption compartments. The compartments of the compartment-flow simulation model are operably linked by one or more flow regulators characterized by fluid absorption rate, fluid volume transit rate, insoluble mass transit rate, insoluble mass dissolution rate, soluble mass transit rate, and soluble mass absorption rate. The flow regulators of the compartment-flow simulation model are modified by one or more converters characterized by fluid volume, fluid volume absorption rate constant, fluid volume transit rate constant, insoluble mass, insoluble mass transit rate constant, dissolution rate constant, soluble mass, soluble mass transit rate constant, surface area, dissolved mass concentration and permeability.

The PK tool and method of this invention accelerate selection and design of compounds for treatment of mammalian disorders, allowing same day response time. The invention optimizes the drug development process in terms of bioavailability parameters, and uses simple in vitro parameters for predicting the in vivo fate of an administered compound. The PK tool and method of the invention also permits utilization of in vivo data from one type of mammal (e.g. rabbit) to predict absorption in a different type of mammal (e.g. human). The invention also is particularly well suited for iterative selection and design of compounds based on structure-bioavailability relationships using a SAR/QSAR approach. This reduces total drug development time, and optimizes the drug design and selection process for animal studies and human clinical trials. Moreover, the PK tool and method of the invention allows separate or concurrent consideration of bioavailability parameters and/or biological drug-receptor activity early in the drug development process. The invention also permits a broad range of in vitro to interspecies correlation, thereby facilitating optimal selection of an animal model for drug development.

PK Tool and System:

The PK tool of the invention is utilized to generate a simulated in vivo absorption profile from dose, solubility and permeability data, and optionally in vitro dissolution rate and transport mechanism data for a test compound. The PK tool includes as computer-readable components, an input/output system suitable for data input and data output, a simulation engine having a differential equation solver, and a physiologic-based simulation model comprising a pharmacokinetic model of the mammalian system to be simulated. In vitro or in vivo data for the test compound is provided through the input/output system, and then the simulation engine and simulation model are applied to facilitate a simulation run so as to generate a user selected in vivo absorption profile for the test sample. Together, the simulation engine and simulation model are employed to simulate the fate of a test sample in the system under investigation.

The PK tool is based on a compartment-flow simulation model system. The compartment-flow model employs compartments, flow regulators, and converters that collectively regulate flow among the compartments. The model components are represented by a series of differential equations which when run through the simulation engine are solved at each time increment dt based on the initial underlying values of the equations, the input values supplied by the user, and calculations performed by various subsystems of the model when activated in a particular scenario.

The PK tool optionally comprises a repository of different pharmacokinetic models and initial parameter values for a given model. The repository preferably resides in a database of the PK tool, and/or is accessible through an acquisition module. The PK tool also may include one or more curve-fitting algorithms for generation of absorption parameters and constants for correlation of in vitro data to in vivo data, or in vivo data from one species of a mammal to in vivo data of a second species of mammal based on a selected route of administration. The curve-fitting algorithms include regression-based and stochastic-based algorithms.

1. Input/Output System

With regard to the components of the PK tool, the input/output system provides a user interface between the user and the PK tool of the invention. The input/output system may be any suitable interface between user and computer system, for input and output of data and other information, and for operable interaction with a simulation engine and a simulation model. For instance, the input/output system may provide direct input form measuring equipment. The input/output system preferably provides an interface for a standalone computer or integrated multi-component computer system having a data processor, a memory, and a display. Input into the method and PK tool of the invention is in vitro or in vivo data derived from an assay corresponding to a selected route of administration and mammalian system of interest. For example, the user enters the initial parameter values for a test compound, e.g., dose, permeability, and solubility derived from the assay, and then optionally indicates the transport mechanism, e.g., passive transcellular, passive paracellular, carrier-mediated influx, or carrier-mediated efflux. When transport mechanism is not indicated, the PK tool can be designed to employ a default transport mechanism, such as passive transcellular. When set to the paracellular mechanism, the absorption of the compound is adjusted to compensate for the lower surface area available for absorption via the paracellular pathway. The model also may incorporate an operation by which the mechanism of absorption can be predicted using the permeability, solubility, molecular structure or other information. This allows the model to automatically compensate for paracellular and/or other absorption mechanisms without requiring prior input and knowledge from the user. Depending on the objective, the user also may specify the pH, delivery system rate such as controlled release rate or formulation release rate (delivery system referred to herein as "formulation"), dosing schedule, and simulation run time, as well as physiologic system specific parameters such as GI transit time when a GI tract model is employed. If values for these parameters are not entered, the PK tool provides default values.

Data may be entered numerically, as a mathematical expression or as a graph that represents a physiological or pharmacokinetic parameter, or alpha such as transcellular, paracellular, passive, active, etc. An advantage of entering data as a graph is that it removes any requirement to define the mathematical relationship between a dependent and an independent variable. The interface output displays and/or compares parameters related to absorption, such as graphs or tables corresponding to rate of absorption, extent of absorption, and concentration profiles, and the like.

The absorption parameters include concentration, rate and/or extent of absorption of a test sample. As can be appreciated, absorption parameters can be represented in multiple different ways that relate time, mass, volume, concentration variables, fraction of the dose absorbed and the like. Examples include rate "dD/dt" and "dc/dt" (e.g., mass/time-mg/hr; concentration/time-$\mu$g/ml/hr), concentration "C" (e.g., mass/volume-$\mu$g/ml), area under the curve "AUC" (e.g., concentration·time, $\mu$g·hr/ml), and extent/ fraction of the dose absorbed "F" (e.g., no units, 0 to 1). Other examples include the maximum concentration ($C_{max}$), which is the maximum concentration reached during the residence of a compound at a selected sampling site; time to maximum concentration ($T_{max}$), which is the time after administration when the maximum concentration is reached; and half-life ($t_{1/2}$), e.g., the time where the concentration reaches ½ its maximum at a selected sampling site. Other examples of output include individual simulated parameters such as permeability, solubility, dissolution, and the like for individual segments, as well as cumulative values for these and/or other parameters.

2. Simulation Engine

The simulation engine comprises a differential equation solver that uses a numerical scheme to evaluate the differential equations of a given physiologic-based simulation model of the invention. The simulation engine also may include a system control statement module when control statement rules such as IF. THEN type production rules are employed. The differential equation solver uses standard numerical methods to solve the system of equations that comprise a given simulation model. These include algorithms such as Euler's and Runge-Kutta methods. Such simulation algorithms and simulation approaches are well known (See, e.g., Acton, F. S., *Numerical Methods that Work*, New York, Harper & Row (1970); Burden et al., *Numerical Analysis*, Boston, Mass., Prindle, Weber & Schmidt (1981); Gerald et al., Applied Numerical Analysis, Reading, Mass., Addison-Wesley Publishing Co., (1984); McCormick et al., Numerical Methods in Fortran, Englewood Cliffs, N.J., Prentice Hall, (1964); and Benku, T., The Runge-Kutta Methods, BYTE Magazine, April 1986, pp. 191–210).

Many different numerical schemes exist for the evaluation of the differential equations. There are literally 100's of schemes that currently exist, including those incorporated into public commercially available computer applications, private industrial computer applications, private individually owned and written computer applications, manual hand-calculated procedures, and published procedures. With the use of computers as tools to evaluate the differential equations, new schemes are developed annually. The majority of the numerical schemes are incorporated into computer applications to allow quick evaluation of the differential equations.

Computer application or programs described as simulation engines or differential equation solver programs can be either interpretive or compiled. A compiled program is one that has been converted and written in computer language (such as C++, or the like) and are comprehendible only to computers. The components of an interpretive program are written in characters and a language that can be read and understood by people. Both types of programs require a numerical scheme to evaluate the differential equations of the model. Speed and run time are the main advantages of using a compiled rather than a interpretive program.

A preferred simulation engine permits concurrent model building and simulation. An example is the STELLA® program (High Performance Systems, Inc.). STELLA® is an interpretive program that can use three different numerical schemes to evaluate the differential equations: Euler's method, Runge-Kutta 2, or Runge-Kutta 4. The program KINETICA™ (InnaPhase, Inc.) is another differential equation solving program that can evaluate the equations of the model. By translating the model from a STELLA® readable format to a KINETICA™ readable format, physiological simulations can be constructed using KINETICA™, which has various fitting algorithms. This procedure can be utilized when the adjustment parameters are being optimized in a stepwise fashion.

3. Simulation Model

The simulation model is a mathematical model of a multi-compartment physiological model of a mammalian system (e.g., GI tract) that corresponds to the selected route of administration (e.g., oral). A given physiological model is represented by series of differential equations that describe rate process interactions among anatomical segments for the physiological system under investigation. The individual segments or compartments are represented mathematically as a one, two and/or three compartment kinetic system. The segments are linked in a stepwise fashion so as to form an integrated physiological model describing absorption of a compound relative to the anatomical segments and at least one sampling site for assessing an absorption event in isolation. For a model simulating oral delivery, anatomical segments of the GI tract are provided, which can include the stomach, duodenum, jejunum, ileum and colon. A sampling site for the GI tract may be the portal vein and/or plasma. The rectum and colon would be applicable for modeling a rectal route of delivery. Segments and sampling site for buccal or sublingual delivery routes can include the mouth, cheek/tongue tissue and plasma. For ocular routes, this can include aqueous humor, conjunctival sac, tear duct, nasal cavity and plasma. For the lung routes, this can include respiratory bronchioles zone and plasma. For delivery via the nose, this can include nasal cavity and plasma. For the topical and transdermal routes, this can include epidermal, dermal, subcutaneous tissue, muscle and plasma. Other systems adhere to these basic designs.

Of course compartments representing a particular anatomical segment can be added or removed depending on the model's intended end use, such as when an isolated segment is examined, or when it is desired to account for parameters affecting bioavailability at additional sampling sites. For example, compartments can be added to account for both pre- or post-absorptive protein binding or complex formation to account for reversible association of a compound to the proteins (albumin and al-acid glycoprotein) of blood, or more usually plasma. Other compartments that may be added would include those that account for phase I and/or phase II hepatic metabolism. Formulation compartments that account for variable compound formulations also can be added, such as time-release, extended release or otherwise controlled release formulations. Another example is inclusion of kidney compartments to account for renal clearance.

The compartments can be modified by factors that influence absorption such as mass, volume, surface area, concentration, permeability, solubility, fluid secretion/absorption, fluid transit, mass transit and the like, depending on the physiological system under investigation. As a rule of thumb, compartment modifiers relate to input variables. For instance, where transport mechanism and dissolution rate are variables considered for generating an absorption profile, then the physiological model will include compartments and parameters that account for these variables.

When represented as a compartment-flow simulation model, the anatomical segments of a physiological model typically include one or more central and peripheral compartments that reversibly communicate through a flow regulator. A central compartment represents the interior or mucosal side of an anatomical segment. A peripheral compartment represents the blood side of the segment. The central and peripheral compartments are connected by a flow regulator representing a physiological barrier through which material from the central compartment "flows" or is transferred to the peripheral compartment at some empirically defined or calculated transfer rate "k12" applied by a converter, which allows calculation of parameters using compartment values. Transfers ("flows") between compartments can be zero order, first order, second order and/or mixed order processes. As an example, a first order transfer from central compartment 1 to peripheral compartment 2 can be defined by a finite difference equation connecting inputs (e.g., rate constant k12 and amount of compound in central compartment=amount+dt*(−elimination−k12+k21)) to the flow controller between the compartments (e.g., k12) and setting it as the product of the two variables. Thus the underlying equations of the model are utilized to calculate the amount of a compound in each compartment, and standard differential equations interrelate the system of compartments and their equations. This permits the model to simulate movement of a compound through each compartment according to the calculated rates at each time increment (dt). Since all movement between compartments is in units of mass, the blood side and transferred test compound concentration is calculated from the amount of compound in the blood side (peripheral compartment) and volume of the mucosal side (central compartment). A model cycle is entered through the input/output user interface as incremental pulses (to simulate ramp, plug flow/lag times) or as a fixed time range to initiate and effectuate cycling of a test compound of interest.

The basic structure of a physiological model and mathematical representation of its interrelated anatomical segments can be constructed using any number of techniques. The preferred techniques employ graphical-oriented compartment-flow model development computer programs such as STELLAR®, Kinetica™ and the like. Many such programs are available, and most employ graphical user interfaces for model building and manipulation. In essence, symbols used by the programs for elements of the model are arranged by the user to assemble a diagram of the system or process to be modeled. Each factor in the model may be programmed as a numerical constant, a linear or non-linear relationship between two parameters or as a logic statement. The model development program then generates the differential equations corresponding to the user constructed model. For example, STELLA®) employs five basic graphic tools that are linked to create the basic structure of a model: (1) stocks; (2) flows; (3) converters; (4) input links; and (5) infinite stocks (See, e.g., Peterson et al., STELLA® II, Technical Documentation, High Performance Systems, Inc., (1993)). Stock are boxes that represent a reservoir or compartment. Flows or flow regulators control variables capable of altering the state of compartment variables, and can be both uni- and bi-directional in terms of flow regulation. Thus, the flow/flow regulators regulate movement into and out of compartments. Converters modify flow regulators or other converters. Converters function to hold or calculate parameter variable values that can be used as constants or variables which describe equations, inputs and/or outputs. Converters allow calculation of parameters using compartment values. Input links serve as the internal communication or connective "wiring" for the model. The input links direct action between compartments, flow regulators, and converters. In calculus parlance, flows represent time derivatives; stocks are the integrals (or accumulations) of flows over time; and converters contain the micro-logic of flows. The stocks are represented as finite difference equations having the following form: Stock(t)=Stock(t−dt)+(Flow)*dt. Rewriting this equation with timescripts and substituting t for dt: $Stock_t = Stock_{t-\Delta t} + \Delta t^*(Flow)$. Re-arranging terms: $(Stock_t - Stock_{t-\Delta t})/\Delta t = Flow$, where "Flow" is the change in the variable "Stock" over the time interval "t." In the limit as $\Delta t$ goes to zero, the difference equation becomes the differential equation: d(Stock)/dt=Flow. Expressing this in integral notation: Stock=∫ Flow dt. For higher-order equations, the higher-order differentials are expressed as a series of first-order equations. Thus, computer programs such as STELLA® can be utilized to generate physiologic-based multi-compartment models as compartment-flow models using graphical tools and supplying the relevant differential equations of pharmacokinetics for the given physiologic system under investigation. An example of iconic tools and description, as well as graphically depicted compartment-flow models generated using STELLA® and their relation to a conventional pharmacokinetic IV model is illustrated in FIGS. 5–8.

The model components may include variable descriptors. Variable descriptors for STELLA®, for example, include a broad assortment of mathematical, statistical, and built in logic functions such as boolean and time functions, as well as user-defined constants or graphical relationships. This includes control statements, e.g., AND, OR, IF . . . THEN . . . ELSE, delay and pulsing, that allow for development of a set of production rules that the program uses to control the model. Variable descriptors are inserted into the "converters" and connected using "input links." This makes it is possible to develop complex rule sets to control flow through the model. The amount of time required to complete one model cycle is accomplished by inputting a total run time and a time increment (dt). The STELLA® program then calculates the value of every parameter in the model at each successive time increment using Runge-Kutta or Euler's simulation techniques. The preferred simulation technique is Runge-Kutta. Once a model is built, it can be modified and further refined, or adapted or reconstructed by other methods, including manually, by compiling, or translated to other computer languages and the like depending on its intended end use.

A preferred method of the invention for constructing a physiological model for in vivo prediction from in vitro input data is depicted in FIG. 9. This method employs a two-pronged approach that utilizes a training set of standards and test compounds having a wide range of dosing requirements and a wide range of permeability, solubility, transport mechanisms and dissolution rates to refine the rate process relations and generate the initial values for the underlying equations of the model. The first prong employs the training/validation set of compounds to generate in vivo pharmacokinetic data (e.g., human plasma profiles). The second prong utilizes the training/validation set of compounds to generate in vitro permeability, solubility, transport mechanism and dissolution rate data that is employed to perform a simulation with the developmental physiological model. The in vivo pharmacokinetic data is then compared to the simulated in vivo data to determine how well a developmental model can predict the actual in vivo values from in vitro data. The developmental model is adjusted until it is capable of predicting in vivo absorption for the training set from in vitro data input. Then the model can then be validated using the same basic approach and to assess model performance.

In particular, three primary sets of data are generated from the training set for the comparison. The first set of data is empirically derived in vivo plasma data from animals or humans. The second set of data is obtained from conversion of the in vivo plasma data to a form corresponding to the primary sampling site of the developmental physiological model. The third set of data is empirically derived in vitro data including permeability, solubility, dissolution rate and transport mechanism data. The raw data points are preferably collected and statistically analyzed to provide the best fit data. The best fit data may be obtained by any number of curve-fitting approaches, including standard regression techniques.

The in vivo plasma data is utilized to judge how well a developmental simulation model is able to predict absorption of the training set of compounds relative to the empirically derived in vivo plasma values. Plasma data also is utilized to calculate absorption at the relevant primary sampling site of the developmental physiological model. For instance, in order to use in vivo plasma data in a developmental physiological model, the plasma data must first be converted to data corresponding to the primary sampling site of the model. If plasma is the primary sampling site then no conversion is needed. However, if plasma is not the primary sampling site, then a pharmacokinetic training/validation model relating the primary sampling site and the in vivo plasma data is utilized. For example, when the developmental model is of the gastrointestinal tract, the portal vein can be selected as a primary sampling site and plasma selected as a secondary sampling site. Thus in this instance the in vivo plasma data is converted to portal vein data so that the parameters affecting secondary bioavailability events are separated from the primary absorption event resulting from passage of the test sample across the gastrointestinal lumen. This is accomplished by adding a plasma-portal vein conversion/validation model that relates in vivo plasma data to portal vein data. This plasma-portal vein conversion/validation model can be separate or integrated with the developmental model. In most cases, the plasma-portal vein model is based on a standard central-peripheral pharmacokinetic compartment approach for data conversion. The third set of data, the in vitro derived data, is utilized to run the developmental model, and the simulated absorption profile from this data set is compared to the in vivo derived plasma and simulated sampling site data. The developmental physiological model is modified until the simulated absorption profiles are in agreement with the in vivo derived plasma and simulated sampling site data.

As the number of parameters for evaluation increase it becomes more important to isolate and test each component of the model building process by validation using a standard validation set of compounds. The validation set of compounds should contain a diverse set of compounds that represent a broad range of absorption profiles for which both in vitro permeability, solubility, dissolution rate, and transport mechanism data, and in vivo plasma data is available. Statistical criteria such as sum of squares of the deviations between experimental data and calculated values obtained from the developmental physiological model are used to determine how well the model fits the data. If the developmental physiological model does not predict a good fit for the data, then the model is adjusted by isolating or including additional rate processes by an iterative approach.

Parameter values utilized in the underlying equations of a given physiological model may be provided in a database for ready access and manipulation by the PK tool of the invention, or provided with a model. The parameter values may include values for physiological parameters, such as rate constants and various other values employed in the PK tool. The rate constants correspond to time-dependent (or time-independent) numerical constants describing rate processes (e.g., k12 and k21). The physiological parameters include rate constants, permeability, solubility, transport mechanism and dissolution rate variables, and the like, as well as pH, volume, surface area, transit times, transit rates, and the like, that are based on the physiology of a given anatomical segment represented in a selected physiological model.

To account for differences between in vitro and in vivo conditions, as well as differences between in vivo conditions of different type of mammals, adjustment parameters that modify one or more of the underlying equations of given simulation model can be utilized to significantly improve predictability. The adjustment parameters include constants or ranges of constants that are utilized to correlate in vitro input parameter values derived from a particular in vitro assay system (e.g., rabbit intestinal tissue, Caco-2 cells) to a corresponding in vivo parameter value employed in the underlying equations of a selected physiological model (e.g., human GI tract). The adjustment parameters are used to build the correlation between the in vitro and in vivo situations, and in vivo (species 1) to in vivo (species 2). These parameters make adjustments to the equations governing the flow of drug and/or calculation of parameters. Generally, the parameters are geometric scaling parameters, as exemplified by the general equations described below for a GI tract simulation model of the invention. This aspect of the invention permits modification of existing physiologic-based pharmacokinetic models as well as development of new ones so as to enable their application for diverse compound data sets.

The adjustment parameters of the PK tool and method of the invention are obtainable from iterative rounds of simulation and simultaneous "adjustment" of one or more empirically derived absorption parameters (e.g., physiological parameters for different anatomical segments) until the in vitro data from a given type of assay (e.g., Caco-2 cell data) can be used in the model to accurately predict in vivo absorption in the system of interest (e.g., human GI). In particular; the adjustment parameters are obtained by a stepwise selective optimization process that employs a curve-fitting algorithm that estimates the change required in a value assigned to an initial absorption parameter of a developmental physiological model in order to change an output variable corresponding to the simulated rate, extent and/or concentration of a test sample at a selected site of administration for a mammalian system of interest. The curve-fitting algorithm can be regression- or stochastic-based. For example, linear or non-linear regression may be employed for curve fitting, where non-linear regression is preferred. Stepwise optimization of adjustment parameters preferably utilizes a concurrent approach in which a combination of in vivo pharmacokinetic data and in vitro data for a diverse set of compounds are utilized simultaneously for fitting with the model. A few parameters of the developmental physiological model are adjusted at a time in a stepwise or sequential selection approach until the simulated absorption profiles generated by the physiological model for each of the training/validation compounds provides a good fit to empirically derived in vivo data. An example of this approach is depicted in FIGS. 10 and 26. Utilization of adjustment parameters permits predictability of diverse data sets, where predictability ranges from a regression coefficient ($r^2$) of greater than 0.40, 0.45, 0.50, 0.55, 0.60, 0.65, 0.60, 0.65, 0.70, or 0.75 for 80% of compounds in a compound test set having a diverse range of dose requirements and a diverse range of permeability, solubility and transport mechanisms. The preferred predictability ranges from a regression coefficient ($r^2$) of greater than 0.60, with a regression coefficient ($r^2$) of greater than 0.75 being more preferred, and greater than 0.80 being most preferred. Adjustment parameters utilized for in vivo to in vitro prediction (e.g. dog to human) employs the same basic approach.

The regional correlation parameters of the PK tool include constants or ranges of constants that are utilized to estimate a selected parameter value of a first segment of the mammalian system under investigation when that value is not supplied by the user. The model performs this estimation by utilizing a function/transformation algorithm (e.g., utilizing polynomial, exponential, logarithm, or any other variety of transformation approaches) in which (1) regional correlation parameter values, and (2) one or more values for the parameter that is supplied by the user for a second segment of the mammalian system, are utilized to estimate the value for the first segment. The regional correlation parameters may be empirically derived values or adjustment parameter values for various segments of the mammalian system of interest such as for permeability. A preferred regional correlation approach employs a polynomial-based correlation. The polynomial is based on the particular parameter to be estimated. The regional correlation is performed by logic function of the model, which when activated utilizes the function/transformation algorithm to perform the estimation. The regional correlation logic function of the model is activated when a value is missing for the selected parameter. The estimated value(s) are then utilized as input variables for the particular parameter in question. The model then proceeds by employing the estimated value for subsequent simulation. Various regional correlation parameters can be used, such as permeability, solubility, dissolution rate, transport mechanism and the like. The preferred correlation parameters are for permeability. This permits the PK tool of the invention to predict absorption of a test sample from minimal input permeability values, such as when the simulation model is a GI tract simulation model and when cell-based assays are employed to provide permeability data corresponding to a given GI segment (e.g., Caco-2 cells and colon).

The above described methodology for in vivo prediction from in vitro input also is followed for in vivo prediction for a first species of mammal from in vivo input data derived from a second species of mammal.

Since the parameter values are specific for a given physiological model (e.g., GI model-parameters, Ocular model-parameters, Blood-Brain-Barrier-parameters, etc.), parameter values are chosen accordingly. These values are obtainable de novo from experiments or from the literature, and adjustment parameters and regional correlation parameters derivable therefrom. The preferred values are based on a diverse collection of training/validation compounds for which in vivo pharmacokinetic data is available.

The various physiological models also may reside in a database, in part or in whole, and may be provided in the database with or without the initial parameter values. The database will preferably provide the differential equations of the model in a compartment-flow data structure that is readily portable as well as executable by the simulation engine.

An integrated physiological model corresponding to the GI tract of a mammal constructed using STELLA® and the above-described methodology is illustrated in FIGS. 24–25, and 29–39. An example of information provided by the database is illustrated in Appendix 4 for the gastrointestinal model depicted in FIGS. 24–25 and 29–39.

A physiologic-based simulation model of the PK tool and method of the invention may optionally include a training/validation model. This aspect of the invention can be used for determining whether the model is specific and accurate with respect to compounds of known membrane transport mechanism (e.g., passive transcellular, passive paracellular, transporter involved for absorption and secretion) and/or with respect to known drug solubility/dissolution rate limitations.

A validation model can be linked to the physiological model of the invention as illustrated in FIG. 11. The linked system is then run to access the specificity and accuracy computed values for rate and extent of absorption. These values are then compared to empirically measured plasma values. If computed values fall outside of an acceptable range the model can be reevaluated for these compounds and adjustments made to the model.

Data Acquisition:

Input data utilized to generate an absorption profile for a test sample include permeability and solubility parameters, and optionally transport mechanism and dissolution parameters. Input data can be generated de novo following any number of techniques, or obtained from public or existing sources where available. The input data can be derived from chemical, and/or biological assays as well as theoretical predictions. By way of example, the in vitro assays may employ artificial (synthetic) or naturally occurring biological preparations. This includes chemical, cell and/or tissue preparations. Assays for generating input data involve screening a plurality of test samples containing isolated compounds and/or isolated mixtures of compounds per test sample in an assay characterized by measurement of (1) permeability and optionally transport mechanism for a test sample; and (2) solubility and optionally dissolution for a test sample. Methods and materials for performing the assays are based on the selected route of administration, the associated barrier(s) to absorption and proposed sampling site(s). For instance, if oral delivery is proposed for simulation and an initial sampling site is selected to be the portal vein (so as to isolate gastrointestinal absorption events from hepatic metabolism) then the input data is collected from an in vitro assay that best approximates the luminal barrier and segmental physiology of the gastrointestinal tract.

Examples of some common cell and tissue sources for permeability and transport mechanism assays for a selected route of administration are provided below in Table 1.

TABLE 1

Permeability and Transport Mechanism.

| Route/Tissue | Cell Culture |
| --- | --- |
| Oral/Intestinal | Caco-2 cells |
| | HT-29 cells |
| | T84 cells |
| | Intestinal epithelial cells (IEC) |
| | SV40 T Immortalized cells |
| | Organ culture/co-culture |
| | Primary culture |
| Inhalation/Nasal | SV40 T immortalized cells |
| | Primary culture |
| Ocular/Corneal | RCE1 cells |
| | Primary cultures |
| | SV40 T immortalized cells |
| Oral-Buccal/Cheek | Primary cultures |
| Topical/Transdermal | HaCat cells |
| | Primary/co-cultures |
| IV/Hepatic | Hepatic carcinoma cell lines |
| | Primary cultures |
| | Co-cultures |
| | SV40 T immortalized cells |
| IV/Blood Brain Barrier | Primary culture |
| | SV40 immortalized cells |

Examples of some common parameters for solubility and dissolution assays for a given route of administration are provided below in Table 2.

TABLE 2

Solubility and Dissolution Parameters.

| Route/Anatomy/Physiology | | In vitro Parameters |
|---|---|---|
| Oral | Gastrointestinal (GI) tract | pH |
| | Stomach | Temperature |
| | Duodenum | Concentration of test sample |
| | Jejunum | Volume |
| | Ileum | Osmotic pressure |
| | Colon | Admixing conditions |
| | | Physiologic Fluid/Buffer/solvent system |
| Buccal/Sublingual | Mouth | Excipients |
| | Cheek | Other Additives |
| | Tongue | Test chamber composition |
| Rectal | Lower GI tract | |
| | Colon | |
| | Rectum | |
| Parenteral | Skin | |
| | Muscles | |
| | Veins | |
| Aerosol | Respiratory system | |
| | Nose | |
| | Lungs | |
| | Mouth | |
| Transdermal | Skin | |
| | Topical | |
| | Ear | |

In vitro and in vivo techniques for collecting permeability and transport mechanism data using cell- and/or tissue-based preparation assays are well known in the art (Stewart et al., Pharm. Res. (1995) 12:693–699; Andus et al., Pharm. Res. (1990) 435–451; Minth et al., Eur. J. Cell. Biol. (1992) 57:132–137; Chan et al., DDT 1(11):461–473). For instance, in vitro assays characterizing permeability and transport mechanisms include in vitro cell-based diffusion experiments and immobilized membrane assays, as well as in situ perfusion assays, intestinal ring assays, intubation assays in rodents, rabbits, dogs, non-human primates and the like, assays of brush border membrane vesicles, and everted intestinal sacs or tissue section assays. In vivo assays for collecting permeability and transport mechanism data typically are conducted in animal models such as mouse, rat, rabbit, hamster, dog, and monkey to characterize bioavailability of a compound of interest, including distribution, metabolism, elimination and toxicity. For high-throughput screening, cell culture-based in vitro assays are preferred. For high-resolution screening and validation, tissue-based in vitro and/or mammal-based in vivo data are preferred.

Cell culture models are preferred for high-throughput screening, as they allow experiments to be conducted with relatively small amounts of a test sample while maximizing surface area and can be utilized to perform large numbers of experiments on multiple samples simultaneously. Cell models also require fewer experiments since there is no animal variability. An array of different cell lines also can be used to systematically collect complementary input data related to a series of transport barriers (passive paracellular, active paracellular, carrier-mediated influx, carrier-mediated efflux) and metabolic barriers (protease, esterase, cytochrome P450, conjugation enzymes).

Cells and tissue preparations employed in the assays can be obtained from repositories, or from any higher eukaryote, such as rabbit, mouse, rat, dog, cat, monkey, bovine, ovine, porcine, equine, humans and the like. A tissue sample can be derived from any region of the body, taking into consideration ethical issues. The tissue sample can then be adapted or attached to various support devices depending on the intended assay. Alternatively, cells can be cultivated from tissue. This generally involves obtaining a biopsy sample from a target tissue followed by culturing of cells from the biopsy. Cells and tissue also may be derived from sources that have been genetically manipulated, such as by recombinant DNA techniques, that express a desired protein or combination of proteins relevant to a given screening assay. Artificially engineered tissues also can be employed, such as those made using artificial scaffolds/matrices and tissue growth regulators to direct three-dimensional growth and development of cells used to inoculate the scaffolds/matrices.

Epithelial and endothelial cells and tissues that comprise them are employed to assess barriers related to internal and external surfaces of the body. For example, epithelial cells can be obtained for the intestine, lungs, cornea, esophagus, gonads, nasal cavity and the like. Endothelial cells can be obtained from layers that line the blood brain barrier, as well as cavities of the heart and of the blood and lymph vessels, and the serious cavities of the body, originating from the mesoderm.

One of ordinary skill in the art will recognize that cells and tissues can be obtained de novo from a sample of interest, or from existing sources. Public sources include cell and cell line repositories such as the American Type Culture Collection (ATCC), the Belgian Culture Collections of Microorganisms (BCCM), or the German Collection of Microorganisms and Cell Cultures (DSM), among many others. The cells can be cultivated by standard techniques known in the art.

Preferred assays for collecting permeability data utilize devices and methods that measure change in resistance or conductivity of a membrane system by ion flux. Any device suitable for such studies can be employed. These include voltage-clamp type devices and methods that employ either cell cultures or precision tissue slices. Diffusion chamber systems utilizing cultured cells grown on permeable supports to measure permeability are preferred. More preferred devices are readily adapted for high-throughput and automated screening. Examples of such devices are known and exemplified in U.S. Pat. No. 5,599,688; WO 96/13721; and WO 97/16717. These devices also can be adapted for examining transport mechanisms. As can be appreciated, however, measurement of resistance, conductivity and/or ion flux is not required to determine permeability of compounds. Many other techniques are available and can be employed in the invention. For instance, permeability data also may be predicted using theoretical models to approximate this parameter, for example, from SAR/QSAR (e.g., log P, molecular weight, H-bonding, surface properties).

Transport mechanism of a test sample of interest can be determined using cell cultures and/or tissue sections following standard techniques. These assays typically involve contacting cells or tissue with a compound of interest and measuring uptake into the cells, or competing for uptake, compared to a known transport-specific substrate. These experiments can be performed at short incubation times, so that kinetic parameters can be measured that will accurately characterize the transporter systems, and minimize the effects of non-saturating passive functions. (Bailey et al., Advanced Drug Delivery Reviews (1996) 22:85–103); Hidalgo et al., Advanced Drug Delivery Reviews (1996) 22:53–66; Andus et al., Pharm. Res. (1990) 7(5):435–451). For high-throughput analyses, cell suspensions can be employed utilizing an automated method that measures gain or loss of radioactivity or fluorescence and the like such as described in WO 97/49987.

In a preferred embodiment, transport mechanism is determined using high-throughput transporter screening cell lines and assays. In this aspect of the invention a cell line is selected and/or manipulated to over-express one or more transporter proteins, and/or enzymes. The cells are then used to rapidly identify the mechanism(s) by which a compound is transported across the physiological barrier of interest. Transporters of interest represent the basic categories of transport including uptake and efflux transporters. These transporters aid in the movement of materials in biological systems, into and out of cells and across cellular layers. Natural combination(s) of enzyme(s) and transporter(s) also can provide the basis of a high-throughput transport mechanism screening assay. For instance, certain enzymes or transporters require secondary enzymes or transporters to function in a normal physiological mode, i.e., cytochrome P4503A is co-regulated with P-glycoprotein. These proteins share the same substrate and their genes are co-regulated. Thus multiple artificial combination(s) of transporter(s) and enzyme(s) can be employed for characterizing transport mechanism of a test sample of interest. Examples of possible combinations of a transporter and/or enzyme in a host cell of interest include cell-transporter-enzyme, cell-transporter, cell-enzyme, cell-enzyme-enzyme, and cell-transporter-transporter. Examples of transporters that can be used to transfect the host cell of interest include peptide transporters (PepT1), amino acid transporters, organic cation transporters (OCT1), organic anion transporters, nucleotide transporters (N1, N2, N3, ES, EI), glucose transporters (SGLT1, GLUT 1 through GLUT 7), monocarboxylate transporters (MCT1), and multi-drug transporters (LRP, MDR, MRP, PGP). Examples of enzymes that can be used to transfect the host cell are Phase I and II enzymes, cytochrome P450, 3A, 2D and the like.

Nucleic acid and/or amino acid sequences for transporters/enzymes can be identified in various genomic and protein related databases. Examples of publicly accessible databases include GenBank (Benson et al., *Nucleic Acids Res* (1998)26(1):1–7; USA National Center for Biotechnology Information, National Library of Medicine, National Institutes of Health, Bethesda, Md., USA), TIGR Database (The Institute for Genomic Research, Rockville, Md., USA), Protein Data Bank (Brookhaven National Laboratory, USA), and the ExPASy and Swiss-Protein database (Swiss Institute of Bioinformatics, Geneve, Switzerland).

Any number of known techniques can be used to prepare nucleic acid encoding a transporter(s) and/or enzyme(s) of interest. To express a target protein in a host cell the nucleotide sequence coding for the polypeptide is inserted into an appropriate expression vector, i.e., a vector that contains the necessary elements for the transcription and translation of the inserted coding sequence. The host cell line can be stably or transiently transfected by methods known in the art. Examples of transient transfection methods include calcium phosphate, electroploration, lipofectamine, and DEAE dextran. A cell line can be stably transfected using methods known in the art such as calcium phosphate. In addition, the host cell can be infected with a retrovirus containing a target protein of interest, resulting in stable expression of the desired target protein. Host cells that express the target gene product can be identified by standard techniques. These include, but are not limited to, detection of the protein as measured by immunoprecipitation and Western blot analysis or by measuring a specific biological response.

For synthesis in a cell, a target transporter/enzyme protein can be generated by standard techniques. Cells that naturally express a target protein can be employed. Transfection and transformation of a host cell with DNA encoding a protein of interest also can be used. For example, a polymerase chain reaction (PCR) based strategy may be used to clone a target DNA sequence encoding all or part of a target membrane polypeptide of interest. (See, e.g., "PCR Cloning Protocols: From Molecular Cloning to Genetic Engineering," B. A. White, ed., Humana Press, Methods in Molecular Biology, Vol. 67, 1997). For example, PCR can be used for cloning through differential and subtractive approaches to cDNA analysis, performing and optimizing long-distance PCR, cloning unknown neighboring DNA, and using PCR to create and screen libraries. PCR also can be used to introduce site-specific and random mutations into DNA encoding a target protein of interest.

For general cloning purposes, complementary and/or degenerate oligonucleotides corresponding to conserved motifs of the target membrane polypeptide may be designed to serve as primers in a cDNA and/or PCR reaction. Templates for primer design can be obtained from any number of sources. For example, sequences, including expressed sequence tags (ESTs) can be obtained from various databases, such as GenBank, TIGR, ExPASy and Swiss-Protein databanks. Homology comparisons performed using any one of a number of alignment readily available programs that employ search engines to find the best primers in a sequence based on various algorithms. Any number of commercially available sequence analysis packages, such as Lasergene, GeneWorks, DNASIS, Gene Jockey II, Gene Construction Kit, MacPlasmap, Plasmid ARTIST, Protein Predictor, DNA/RNA Builder, and Quanta. (See, e.g., "Sequence Data Analysis Guidebook," Simon R. Swindell, ed., Humana Press, 1996). The information can be used to design degenerate primers, nested/multiplex primers, site-directed mutagenesis, restriction enzyme sites etc. Primers can be designed from homology information, and computer programs can be used for primer design as well. Examples include "Primer Premier 4.0" for automatic primer selection (CloneTech, Inc.). The amplified cDNA and/or PCR fragment may be used to isolate full-length clones by radioactive or non-radioactive labeling of the amplified fragment and screening a library.

Alternatively, transporter/enzyme DNA cloned from one source may be utilized to obtain a corresponding DNA sequence from other sources. Specifically, a genomic and/or cDNA library constructed from DNA and/or RNA prepared from a cell known or expected to express the target transporter/enzyme may be used to transform a eukaryotic or prokaryotic host cell that is deficient in the putative gene. Transformation of a recombinant plasmid coding for the protein into a deficient host cell would be expected to provide the cell with a complement product corresponding to the protein of interest. In some cases, a host cell can be selected to express a particular phenotype associated with the target polypeptide and thus may be selected by this property. For a review of cloning strategies which may be used, see e.g., Sambrook et al., 1989, Molecular Cloning, A Laboratory Manual, Cold Springs Harbor Press, New York; and Ausubel et al., 1989, Current Protocols in Molecular Biology, Green Publishing Associates and Wiley Interscience, New York.

To express a target transporter/enzyme in a host cell the nucleotide sequence coding for the protein, or a functional equivalent for modular assembly as described above, is inserted into an appropriate expression vector, i.e., a vector which contains the necessary elements for the transcription and translation of the inserted coding sequence. Host cells containing the coding sequence and that express the target gene product may be identified by standard techniques. For example, these include but are not limited to DNA-DNA or DNA-RNA hybridization; the presence or absence of "marker" gene functions; assessing the level of transcription as measured by the expression of MRNA transcripts in the host cell; and detection of the gene product as measured by immunoassay or by its biological activity.

Once a clone producing the target transporter/enzyme is identified, the clone may be expanded and used to over express the protein(s). If desired, the proteins may be purified using techniques well-known in the art including, but not limited to immunoaffinity purification, chromatographic methods including high performance liquid chromatography or cation exchange chromatography, affinity chromatography based on affinity of the polypeptide for a particular ligand, immunoaffinity purification using antibodies and the like. The purified proteins can then be bound to an artificial membrane matrix and utilized for assessing interaction of compounds to the transporter/enzyme of interest.

Some commonly used host cell systems for expression of transport proteins and enzymes include *E. coli*, Xenopus oocytes, baculovirus, vaccinia, and yeast, as well as many higher eukaryotes including transgenic cells in culture and in whole animals and plants. (See, e.g., G. W. Gould, "Membrane Protein Expression Systems: A User's Guide," Portland Press, 1994, Rocky S. Tuan, ed.; and "Recombinant Gene Expression Protocols," Humana Press, 1996). For example, yeast expression systems are well known and can be used to express and recover target transporter/enzyme systems of interest following standard protocols. (See, e.g., Nekrasova et al, *Eur. J. Biochem.* (1996) 238:28–37; Gene Expression Technology Methods in Enzymology 185: (1990); Molecular Biology and Genetic Engineering of Yeasts CRC Press, Inc. (1992); Herescovics et al., FASEB (1993) 7:540–550; Larriba, G. *Yeast* (1993) 9:441–463; Buckholz, R. G., *Curr Opinion Biotech* (1993) 4:538–542; Mackett, M, "Expression of Membrane Proteins in Yeast Membrane Protein Expression Systems: A Users Guide," pp. 177–218, Portland Press, (1995).

For high-resolution screening and validation, tissue-based assays may be employed to characterize transport mechanisms. For example, of the cytochrome P450 superfamily, CYP3A enzymes represent the most abundant isoforms in the liver and they are responsible for the metabolism of compounds of diverse chemical structure. The uptake of a compound into hepatocytes can be mediated by passive or carrier processes. Once in the parenchymal cell of the liver, the drug can be metabolized or bind to intracellular proteins. The drug or its metabolite(s) may return to the circulation or exit from the hepatocyte into the bile canaliculus, again by passive or carrier-mediated transport, before secretion in bile. Experimental systems have been devised to study these processes in isolation. Examples of such systems include isolated perfused rat liver (IPRL), and bile duct cannulated (BDC) rat models. (Chan et al., DDT (1996) 1:461–473).

Tissue from transgenic animals designed to express particular transport properties in one or more particular tissues also may be utilized to characterize transport mechanisms. In this aspect of the invention, an animal can be genetically manipulated to express or not express one or more specific proteins in a tissue of interest, e.g. transporter protein in duodenum tissue. Tissue from the genetically engineered animal can then be used to examine transport mechanisms in a tissue-based assay. Transgenic animal methodologies are well known (Gordon et al., Hum. Cell (1993) 6(3):161–169; and Jaenisch, R., Science (1998) 240:1468–1474).

Artificially engineered tissue also can be used for permeability assays, such as tissues generated ex vivo for use as skin grafts, transplants, and the like. Such tissues can be obtained using standard techniques. See, for example, U.S. Pat. Nos. 5,759,830; 5,770,193; and 5,770,417.

Solubility and dissolution data can be obtained in an in vitro assay by testing each sample of interest in an appropriate physiologic fluid/buffer system that best approximates the particular physiological system selected as the barrier to absorption. A solubility profile is a plot of solubility of a test sample at various physiological conditions. As an example, the natural pH environment of the gastrointestinal tract varies from acidic in the stomach to slightly alkaline in the small intestine and fluid composition for each segment may vary as well. The solubility profile provides an estimation of the completeness of dissolution of a test sample in a particular physiological compartment or anatomical entity. In this instance, a panel of test wells each having different pHs and physiological fluid composition can be employed to generate a solubility profile for each test sample. Solubility and dissolution data can also be predicted using theoretical models to approximate these values, for example, from SAR/QSAR information.

In vitro dissolution assays measure the rate and extent of dissolution of a test sample in an aqueous solution. Various parameters are considered when performing a dissolution assay and are well known in the art. These parameters include size of the experimental vessel, amount of agitation and nature of the stirrer, temperature and nature of the dissolution medium, pH, viscosity, and design of the dissolution apparatus. Standard methods known in the art for measuring dissolution include rotating basket, paddle, rotating bottle, flow-through dissolution, intrinsic dissolution, and peristalsis methods. These methods can be adapted and used as a guide for high-throughput solubility and dissolution testing.

For high-throughput collection of solubility and dissolution data, automated methods of solid and liquid handling are employed. This method involves addition of samples to a multi-well or multi-tube/plate system. The data associated with these tubes/plates, such as physiologic fluid/buffer system, volume, concentration, pH and tube/plate maps, is transferred into an inventory system. The inventory system generates codes containing updated information pertaining to the aliquoting, diluting, or pooling methods applied to the original tubes/plates. Tasks created in the database are then carried out physically in coded tubes/plates. Aliquots are then distributed to designated screen sites. After testing, the solubility profiles are generated and ported to a database for access and analysis.

Properties in addition to absorption that can be utilized as input into the PK tool and method of the invention when adapted with the appropriate compartments include metabolism, distribution, and elimination, and optionally toxicity. As with absorption, assays to characterize the relevant data are based on the selected route of administration. Metabolism or biotransformation refers to the biochemical transformation of a compound to another chemical form. The biotransformation process typically results in a metabolite that is more polar (water-soluble) than the original parent molecule.

Most tissues have some metabolizing capacity but the liver is by far the most important organ, on the basis of size if not always concentration of target compound metabolizing enzyme. Phase I reactions are defined as those that introduce a functional group to the molecule and phase II reactions are those that conjugate those function groups with endogenous moieties.

Since metabolism is a drug clearance process, metabolism of a compound contributes to elimination of the compound. Thus, compounds can be tested for metabolism in order to generate input data that considers disposition of a test compound after or concurrent with administration using standard techniques known in the art. (See, e.g., Sakuma & Kamataki, Drug metabolism research in the development of innovative drugs, In: Drug News & Perspectives (1994) 7 (2):82–86).

Metabolism assays for high-throughput screening preferably are cell-based (cells and cellular preparations), whereas high resolution screening can employ both cell and tissue-based assays. In particular, test samples from compound libraries can be screened in cell and tissue preparations derived from various species and organs. Although liver is the most frequently used source of cells and tissue, other human and non-human organs, including kidney, skin, intestines, lung, and blood, are available and can be used to assess extra-hepatic metabolism. Examples of cell and tissue preparations include subcellular fractions (e.g., liver S9 and microsomes), hepatocytes (e.g., collagenase perfusion, suspended, cultured), renal proximal tubules and papillary cells, re-aggregate brain cells, bone marrow cell cultures, blood cells, cardiomyocytes, and established cell lines as well as precision-cut tissue slices.

Examples of in vitro metabolism assays suitable for high-throughput screening include assays characterized by cytochrome P450 form-specific metabolism. These involve assaying a test compound by P450 induction and/or competition studies with form-specific competing substrates (e.g., P450 inhibitors), such as P450 enzymes CYP1A, 3A, 2A6, 2C9, 2C19, 2D6, and 2E1. Cells expressing single or combinations of these or other metabolizing enzymes also may be used alone or in combination with cell-based permeability assays. A high-throughput cell-based metabolism assay can include cytochrome P450 induction screens, other metabolism marker enzymes and the like, such as with measurement of DNA or protein levels. Suitable cells for metabolism assays include hepatocytes in primary culture. Computer-implemented systems for predicting metabolism also may be employed.

For distribution and elimination data, in vitro assays can be performed to assess protein binding to a test compound, since protein binding can affect compound distribution and elimination. In general, it is free compound that diffuses into cells and tissues. Binding can be classified as restrictive or permissive with regard to elimination, or quantitatively defined in terms of affinity. Affinity of the binding is defined as low or high when reversible, or more unusually when irreversible binding occurs. The biological half-life of a test compound will increase due to its interaction with a protein. Usually, the higher the affinity the lower the elimination that may be observed. Albumin is by far the most frequent contributors to plasma protein binding since it comprises about one half of the total plasma proteins. The a1-Acid glycoprotein also plays an important role in the protein binding of a compound since it has an affinity for bases (many drugs are weak bases). It is an acute phase reactant and its concentration rises in inflammatory processes, malignant disease and stress. Lipoproteins (HDL, LDL or VLDL) bind drugs that are highly liposoluble and a fairly specific ligand-protein interaction occurs between certain steroids and gamma globulins. Thus, in vitro protein binding assays that employ one or more of albumin, a1-acid glycoprotein, lipoprotein, steroid and gamma globulins may be utilized to collect distribution and elimination data that can be utilized for further data collection.

Similarly, toxicity of a test compound may also be assayed and used to generate relevant toxicity data for a test compound. Any number of techniques in the art may be employed for this purpose. Preferred methods are in vitro. Examples include determination of toxicity mechanisms, determination of cytotoxic potentials in cell and tissues of target organs, estimation of therapeutic indices from in vitro data, cytotoxicity screening of closely related drug compounds in cells from the same mammal or from different species, detection and quantification of peroxisome proliferation, screening of agents to prevent or reverse cytotoxicity, and specialized studies on target cells using co-incubation systems, e.g., red blood cells and hepatocytes.

Toxicity assays may utilize any technique that provides a toxicity parameter as an endpoint. For high-throughput screening, cell based assays are preferred. This includes gene expression (e.g., protein or nucleic acid based) enzymatic activity, and morphology screens and the like. Examples of cell-based assays include in vitro peroxisome proliferation studies, which can be used to assay palmitoyl CoA-oxidation in primary hepatocyte culture, with or without concurrent measurement of DNA or protein levels. Cytotoxicity assays in primary cultures also can be utilized, and include screening for cytotoxicity in hepatocytes or renal proximal tubules, enzyme release (lactate dehydrogenase), and MTT conversion (mitochondrial function) following standard techniques. Computer-implemented SAR/QSAR models for predicting toxicity also may be employed, such as when structural information is available.

PK Tool and System Structure:

The PK tool and system of the invention has the structure shown in FIG. 4. The I/O system provides the user's inputs to the simulation model of the mammalian system of interest. The simulation engine in turn computes one or more of the bioavailability parameters of the compound in the context of one or more physiologic-based segments of the mammalian system under investigation. The output of the simulation engine is then provided to the I/O system.

Operations of the PK tool and system are exemplified in FIGS. 3 and 44–46. After start, the first block is the I/O block (1), where the user enters the inputs and outputs to the system. The I/O system includes I/O panels, for example graphical user interfaces. This may include sub-panels depending on the selected model (see, e.g. FIG. 47). The I/O system may optionally include one or more databases of simulation models and/or parameters for a given simulation model that the user may access as illustrated in FIG. 45. The PK tool and system starts with the user inputs and then computes and displays the results in the output space. The input and output space can be selected, e.g., by toggling, or by a menu. It is to be understood that on-line helps also are available to give a user information, and to guide the user through the PK tool and system user interface.

For input, the Menu function presents various choices to the user. These choices include dose, permeability, and solubility among others. The user then enters the relevant values corresponding to a given physiological segment of the selected mammalian system in question. Depending on the simulation model that the user chooses, the Menu function will provide options for data input, such as pH, transit time, run time, and formulation release rate.

The Menu function also presents various choices to the user after the results for a simulation have been obtained. The choices open to the user include one or more of the functions "Rate of Absorption," "Extent of Absorption," "Concentration," "Print Graph," "Print Table," and "Quit" among others.

For predicting absorption parameters, input of the data is the first operation that the PK tool and system of the invention performs when activated. In this operation, the user enters the appropriate value of each input variable into the input panel in a form readable or convertible by the system to a readable form and obtains complete results in the output panel. Alternatively, the PK tool and system can be adapted to receive structural information that the system, or a separate interfaced system converts to the relevant input parameter values. For this function the user inputs the compound structure in a form readable or convertible by the system to a readable form. This includes standard chemical formulas, chemical names, SMILE strings, as well as two-dimensional and/or three-dimensional structures.

After the user inputs the initial data, the Start Simulation function is selected. In the simulation function, the simulation engine is activated. The user may then choose to invoke the Stop Simulation function, to terminate the simulation, or allow the simulation engine to proceed with until a user specified or system default time point is reached. The user may then view, print, save and/or export then results using output functions, including printing of the I/O panel. This includes numerical, tabular, and graphical formats. These options are selected by the user through the Menu function.

The Quit function exits the PK tool and system. One aspect of the output functions and the Quit function is to save the generated information in a format that allows them to be an input to other programs, such as the SAR or QSAR CAD program.

Forward Mode Operation of the PK Tool:

In the forward mode operation mode, the user enters the input data, and the PK tool reacts as described above. In one embodiment, the PK tool displays a numerical representation or graphic of the test compound or selected PK profile thereof. Also displayed are parameters that can effect fate of the compound in one or more compartments of the mammal, e.g., the dose, formulation, pH, fluid volume, fluid absorption (fluid secretion), dissolution rate, cumulative dissolution, transit, pH-dependent solubility and dissolution and the like. Other variables may also be available, e.g., through a data box.

The forward mode operation of the simulation engine displays the resulting PK parameters, such as absorption. Changing any parameter causes recalculation of the PK quantities, invoking the the simulation engine and its associated simulation model. The forward mode operation provides either, or both, a display or a printout of the PK parameters for a test compound.

Backward Mode Operation of the PK Tool:

In backward mode operation of the PK tool, the user is allowed to assess formulations for a compound. In this aspect of the invention, the user specifies the required absorption profile, or absorption parameter for a compound. The tool then generates the formulation release rates for the compound that meets the requirements. The user can then compare the solution set, against previously qualified compounds and formulation designs drawn from a database and new, unqualified designs created by the tool and method of the invention.

Predictability:

The PK tool and method of the invention permit a high level of accuracy in predicting bioavailability of molecules from the following four classes of compounds: a) passive transcellular; b) passive paracellular; c) transcellular transporter involved; d) apically recycled. The evaluation is based on the difference between bioavailability values predicted by the model and known bioavailability values. For example, conformation of predictability for human GI absorption values for passive transcellular molecules is evaluated with dissolution rate limitations and solubility limitations. If the computed values fall outside of an acceptable range ($r^2>0.75$ predictability), the PK model is reevaluated for these compounds and adjustments made to the model. Similarly, absorption measures that deviate from known values are reevaluated and appropriate modifications made to the model (e.g. iterative process).

The PK model can be used to predict bioavailability in a mammal using dose (actual or estimated) and various input data. Examples include (1) permeability data alone; (2) permeability data together with solubility and dissolution data; (3) permeability data together with animal data; and/or (4) permeability, animal and human clinical data. Validation of the model is defined as follows, where greater than 80% of the compounds tested will fall within the following prediction criteria.

1. Predictability of the PK tool using permeability data alone with limits for dose and elimination rate ($r^2>0.75$ predictability).
2. Predictability of the PK tool using permeability and solubility data along with limits for dose and elimination rate ($r^2>0.75$ predictability).
3. Predictability of the PK tool using permeability data together with animal data for pharmacokinetics together with limits for dose ($r^2>0.85$ predictability).
4. Predictability of the PK tool using permeability and animal or human IV data to predict absorption values for molecules with solubility limitations ($r^2>0.85$ predictability).

The correlation coefficient can be calculated using data from the predicted line from pharmacokinetic fitting as the observed data points and as the predicted fit, and the output of physiologic-based simulation model coupled to the systemic kinetics for that compound. The prediction power of a given physiological simulation model can be demonstrated by simulating the plasma levels in compounds. Other methods can be utilized to assess the predictive power of the model to achieve the same end result (i.e., evaluation of model performance).

The method and PK tool of the invention allows the drug developer to go from a set of user inputs, to predicting the fate of the compound in a mammalian system of interest, to selection of a compound design input to a SAR or QSAR CAD tool, and to chemical synthesis development, validation and high level drug development. The PK tool and system may advantageously be interfaced with other databases and/or systems. For example, the system may be built around an expert system-database manager path. The menu can invoke the on-line documentation, the database, and any member of the expert system-database system.

The PK tool and method of the invention can be used to predict the rate and extent of absorption of compounds as well as regional concentrations relative to one or more selected sampling sites across a physiological barrier of a mammalian system of interest. The PK tool and method of the invention also can be used in combination with prediction of additional bioavailability parameters such as distribution, metabolism and elimination, as well as toxicity. Thus this information can be used to supplement and significantly reduce animal testing during pre-clinical testing. The PK tool and method of the invention also are particularly useful for screening compounds earlier in the drug discovery process. For instance, the PK tool and method may be employed in the screening and ranking of compounds before, during and/or after receptor activity testing, thus increasing the odds of selecting a lead compound that will survive clinical studies, resulting in decreased development costs, faster approval time, and consequent lower drug prices. This permits selection and ranking of lead compounds that not only have optimal receptor activity, but also exhibit optimal bioavailability.

The following Examples are intended to illustrate various aspects of the invention and are not intended to limit the scope of the invention.

EXAMPLES

Example 1

Introduction to Model Design and Development

A physiologic-based simulation model for predicting oral absorption of a compound in a mammal from in vitro (e.g., tissue, cell and SAR/QSAR) and in vivo data (e.g., human) was constructed in two primary stages. The first stage involved development of a mass-based multi-compartment simulation model (mass model), a volume-based multi-compartment simulation model (volume model) and an integrated mass-volume multi-compartment simulation model (mass-volume model). These models were individually tested and validated for five segments of the GI tract: the stomach, the duodenum, the jejunum, the ileum, and the colon. The second stage involved development of an integrated multi-compartment physiological model of the GI tract (GI model). The models were developed using a combination of in vitro data and in vivo data.

A computer-based mathematical model development tool with a graphical user interface was employed to design and construct the initial simulation models. The computer program STELLA(®) was selected as suitable for this purpose since it permitted compartment model building and mathematical equation modification and at each stage of the build, as well as calculation of flow between compartments at user-specified time intervals (dt) with user-specified input functions and values. An example of iconic tools and description, as well as graphically depicted compartment-flow models generated using STELLA® and their relation to a conventional pharmacokinetic IV model is illustrated in FIGS. 5–8.

Example 2

Compound Data Sets

Compound data sets for development, and thus building, testing, training and validation of the models were obtained from various sources including the literature and cell, tissue, animal and human tests as described herein. The data sets included relevant physiological parameters related to absorption of a compound including GI tract related parameters (e.g., pH, initial volumes, surface area, average transit time, volume transfer rates, new water absorption etc.) and physicochemical compound related parameters (e.g., dissolution, permeability, solubility etc.).

Data sets were selected for compounds that permitted development and isolated testing and validation for each stage of the build. Compounds suitable for this purpose were chosen as follows. For the mass, volume and integrated mass-volume simulation models, a candidate compound was chosen based on the premise that the best candidate compound for model development would not be a drug that is highly correlated pharmacokinetically between cell, tissue, animal and humans, but one that is poorly correlated. That is, a compound predicted to have high total absorption in humans based on pre-clinical studies, but ultimately exhibited poor absorption in humans when tested in clinical trials was chosen. Additionally, a compound was selected that is not subject to pre-absorptive or hepatic metabolism so as to isolate absorption components of the models from pre-absorptive and metabolic factors. Gancyclovir (9-(1,3-dihydroxy-2-propoxymethyl)guanine, monosodium salt (DHPG) or Cytovene) was suitable for this purpose. Also, significant animal and human clinical data was publicly available for Gancyclovir (Jacobson et al., *Antimicrobial Agents and Chemotherapy*, Vol. 31, No. 8, p. 1251–1254 (1987); New Drug Application for Gancyclovir Sodium (Syntex, Inc. USA), obtained from the Food & Drug Administration; Drew et al., *New England Journal of Medicine*, (1995) 333:615–610; and Anderson et al., *Clinical Therapeutics*, (1995) 17:425–432 (1995)).

For development and testing of the integrated GI model, a set of training and testing lead drug compounds in various stages of human clinical testing were selected. This test set included compounds having diverse dosage requirements and ranges of permeability, solubility, dissolution and transport mechanisms, as shown below in Table 3.

TABLE 3

Compound Test Set

| Compound | Permeability | Solubility | Dose | Mechanism of Absorption |
|---|---|---|---|---|
| α1 | ++++ | ++++ | +++++ | active |
| α2 | ++ | +++ | +++++ | paracellular |
| α3 | + | + | ++++ | unclassified |
| α4 | + | ++++ | ++ | transcellular |
| α5 | + | +++ | ++++ | paracellular |
| α6 | ++++ | ++ | ++++ | transcellular |
| α10 | ++++ | +++++ | + | transcellular |
| β1 | +++++ | +++++ | + | transcellular |
| β2 | ++++ | ++ | ++ | transcellular |
| β3 | + | + | +++ | paracellular |
| β5 | ++++ | ++ | +++ | unclassified |
| β6 | + | +++++ | +++ | unclassified |

+++++ = greatest value & + = lowest value

Example 3

Experimental Data Collection and Processing

Experimentally derived in vivo and in vitro data was obtained as follows. To ensure quality data was used for training and validation, experimental conditions were specific enough to ensure proper data collection techniques, but flexible to allow minor and insignificant variations in individual protocols. Data sets used for model development included individual data points, i.e., raw data, that was analyzed and processed by stepwise regression analysis using a least squares minimization technique or similar fitting tool. In particular, data processing for permeability involved separation of compounds by absorption mechanism and into training and validation sets. pH dependent solubility profiles were interpolated to obtain complete profiles. For dissolution, data points were fit to determine dissolution rates. For human clinical data, data analysis and processing employed a pharmacokinetic IV/PO model and weighted least-squares regression analysis (See FIG. 18). The IV/PO model includes a central compartment in equilibrium with a peripheral compartment, a pre-systemic compartment re-circulated with the central compartment and for input PO doses (error function input), a hepatic compartment, as well as an IV dose and first-order elimination compartment. The plasma sample is taken from the central compartment, and the FDp sample from the hepatic compartment.

A. Human In vivo Data—Oral (PO)

Plasma levels following oral administration (PO) in humans were used to determine the amount of compound input to the hepatic vein (FDp) as a function of time. Plasma levels of drug in humans following oral administration of drug solution or suspension after an overnight fast were used as a data set. If no solutions or suspensions were administered, formulated dosage form data were used. The PO profiles included individual data points for each patient enrolled in the study from the time of administration through 24 hours to 32 hours after administration, along with dosage. If multiple dose regimens were administered, plasma profiles for all doses were used.

B. Human In vivo Data—Intravenous Administration (IV)

Plasma levels following intravenous administration (IV) in humans were used to determine the amount of drug input to the hepatic vein (FDp) as a function of time. IV profiles included individual data points for each patient enrolled in the study from the time of administration through 24 hours to 32 hours after administration, along with the dose. If multiple dosage regimens were administered, plasma profiles for all doses were used.

C. In vitro Permeability Data

In vitro permeability data was used to calculate drug fluxes across various regions of the intestinal mucosa. This included rabbit intestinal tissue from one or more of duodenum, jejunum, ileum and colon, and Caco-2 cells. The mechanism of transport, such as passive transcellular or paracellular, carrier-mediated absorption, carrier-mediated secretion, or mixed mechanism, was determined for several test compounds and permeabilities for each mechanism and assessed as listed in Table 4. Protocols for permeability assays are described in Example 4.

TABLE 4

Transport mechanism permeabilities and parameters for each GI region.

| Mechanism | Permeabilities | Parameters |
|---|---|---|
| Passive transcellular | Apical to basolateral (AP to BL) | $P_e$ |
| Passive paracellular | AP to BL | $P_e$ |
| Carrier-mediated absorption | AP to BL without inhibition | $K_m$, $P_c$, and $P_m$, or $P_e$ at entire concentration range |
| Carrier-mediated secretion | AP to BL and BL to AP without inhibition | $P_m$, $P_c$, and $P_m$, or $P_e$ at entire concentration range |

D. Solubility Data

Solubilities of test compounds as a function of pH were determined from pH 1.5 to 8.2 in increments of 0.1 pH units. Protocols describing conditions for solubility determination are found in Example 4. Alternatively, solubility at each pH unit from 1.5 to 8.0 was used, with a minimum of 5 data points at pH 1.5, 6.0, 6.5, 7.0, and 7.5. These solubilities were used to calculate the amount of soluble compound available for absorption across the intestinal mucosal barrier.

E. Dissolution Data

The dissolution of test compounds as a function of pH were determined at pH 1.5, 6.0, 6.5, 7.0, and 7.5. Protocols describing conditions for dissolution determination are found Example 4. The dissolution of powdered compound, and alternatively, dissolution/disintegration data for the formulated dosage form used to collect oral plasma profiles were used. The dissolution data were used with solubility data to calculate the amount of drug available for absorption across the intestinal mucous within each region of the intestine.

Example 4

Protocols for Data Collection

Provided below are detailed protocols utilized for collecting and calculating data described in Example 3. These protocols were employed to ensure the quality of the data provided for development of the simulation models.

A. In vitro Permeability Protocols

1. Diffusion Chambers

Permeability data is determined using intestinal tissue in vertical diffusion chambers similar in design to NaviCyte 8×24 mm, 9 mm Low-volume, or 9 mm round tissue diffusion chambers. The chamber system used maintains the tissue as well as the donor and receiver buffers at 37° C. Both the donor and receiver buffers within the chamber are continuously mixed throughout the experiment.

2. Mathematical Calculations

Effective permeability (Pe) is calculated using Equation 2.

$$P_e = \frac{V}{AC_0} \cdot \frac{dC}{dt} \quad \text{(Eq. 2)}$$

where V is the volume of the receiver chamber (ml), A is the surface area available for diffusion (1.78 cm2 for 8×24 mm chambers, 0.64 cm2 for 9 mm round and Low-volume chambers), $C_0$ is the donor concentration, and dC/dt is calculated as the slope of the regression line of the corrected receiver concentration (see Sampling) v. time plot. Two conditions must be satisfied for this equation to apply: (1) sink conditions in the receiver chamber, i.e. the accumulated concentration, must be virtually zero when compared to the donor concentration; and (2) the donor concentration must be constant ($C_0$) throughout the experiment.

The parameters for carrier-mediated absorption and secretion are calculated using Equation 3.

$$P_e = \frac{P_c}{1 + \frac{C_0}{K_m}} + P_m \quad \text{(Eq. 3)}$$

where Pc is the carrier-mediated permeability, Pm is the passive permeability, Km is the affinity of the drug for the carrier, and $C_0$ is the donor concentration. Pc, Pm, and Km are calculated using non-linear regression, Pe is calculated using Equation 2, and $C_0$ is given as part of the experimental conditions. To obtain valid parameter values, Pe is determined for a sufficient number of $C_0$'s to determine Km using Equation 3 (a minimum of 6 $C_0$'s is recommended ranging between the analytical limit and the solubility limit). If Pe values are provided, the variability of the mean as well as the number of experiments performed for each concentration are provided to allow accurate regression analysis.

3. Experimental Conditions a. Buffers

Experiments are performed in appropriate, non-cytotoxic, physiological saline iso-osmotic buffers at pH 7.4 (basolateral/serosal side) or pH 6.5 (apical/mucosal side).

Preferred buffers are Ringer's buffer (pH 7.4), Ringer's with glucose (pH 7.4), MES ringer's buffers (pH 6.5), or MES Ringer's with glucose (pH 6.5) (Table 5).

TABLE 5

Formulas for Ringer's buffer and Ringer's with glucose buffer.

| Chemical | Ringer's buffer (mM) | Ringer's with glucose (mM) | MES Ringers Buffer (mM) | MES Ringer's With glucose (mM) |
|---|---|---|---|---|
| KCI | 5 | 5 | 5 | 5 |
| $Na_2HPO_4$ | 1.15 | 1.15 | — | — |
| $Na_2HPO_4$ | 0.3 | 0.3 | — | — |
| $NaHCO_3$ | 25 | 25 | — | — |
| $MgSO_4$ | 1.1 | 1.1 | 1.1 | 1.1 |
| $CaSO_4$ | 1.25 | 1.25 | 1.25 | 1.25 |
| NaCI | qs iso-osmotic | qs iso-osmotic | qs iso-osmotic | qs iso-osmotic |
| MES | — | — | 25 | 25 |
| Glucose | — | 25 | — | 25 | pH adjusted with 1 N HCI or 1 N NaOH b. Sampling

Samples are collected from the receiver chamber beginning once steady state has been achieved and continuing for at least 90 minutes. Four to six (preferred) samples are collected to allow accurate determination of dC/dt (Equation 2). The volume removed from the receiver chamber at each time point is replaced with buffer containing no drug to maintain constant volume in the receiver chamber. The dilution of the receiver concentration due to the addition of buffer is corrected during data analysis and Pe calculation. The concentration may be corrected by: (1) adding the mass removed at each sampling time to the mass removed from the receiver chamber at all prior sampling times, by summing calculated mass absorbed and adding to mass for sample calculation; and (2) using Equation 4 (preferred).

$$\frac{1}{X} = -\sum_{n}^{k} (-1)n\beta \frac{(S)^{n-1}}{n \, (V)} \quad \text{(Eq. 4)}$$

where the corrected receiver chamber concentration is obtained by dividing the collected sample concentration by Equation 4 (1/x), S is the volume of sample withdrawn, V is the receiver chamber volume, k is the sequential sample number, i.e., k=1 for the first sample time, k=2 for the second sample time, k–3 for the third sample time, etc., and β is the corresponding number from Pascal's triangle (Table 6).

TABLE 6

Pascal's Triangle for determining β coefficients.

| Sample | $1^{st}$ term | $2^{nd}$ term | $3^{rd}$ term | $4^{th}$ term | $5^{th}$ term | $6^{th}$ term |
|---|---|---|---|---|---|---|
| 1 | 1 | | | | | |
| 2 | 1 | 1 | | | | |
| 3 | 1 | 2 | 1 | | | |
| 4 | 1 | 3 | 3 | 1 | | |
| 5 | 1 | 4 | 6 | 4 | 1 | |
| 6 | 1 | 5 | 10 | 10 | 5 | 1 |

Donor concentration ($C_0$) is determined by sampling the donor buffer containing the test compound with subsequent analysis directly from the donor chamber, or from a stock solution of donor buffer provided binding and absorption to the interior of the chambers does not occur.

c. Intestinal Tissue

Rabbit intestinal tissue is used for permeability experiments. During mounting of tissue onto chambers, intestinal muscles are stripped off the mucosa and discarded. Care should be taken to ensure integrity of the tissue. A minimum of three chambers are used to determine $P_e$ values for each region, concentration and compound. The mean $P_e$ and Standard Error of the Mean are provided for each study.

d. Cell Monolayers

Caco-2 cell monolayer Pe is determined in diffusion chambers similar to NaviCyte Snapwell™ diffusion chambers and follow all procedures described above except the recommended buffers are Ringer's with glucose or MES Ringer's with glucose as listed in Table 6.

Caco-2 cells are grown using DMEM media supplemented with 10% FBS, 5% PCN-STEP, and 1% NEAA under 95–100% humidity and 5% $CO_2$ at 37° C. Cells are grown in flasks and the culture split at 85–95% confluence. Snapwells™ are seeded at 65,000 cell/$cm^2$ and used in the permeability experiment within 21–28 days post seeding to allow for differentiation.

4. Determination of Absorption Mechanism

Absorption mechanism for a compound is determined by one of the following methods. Determination of $P_e$ in both the apical-basal (AB) to basal-lateral (BL) and BL to AB directions using Equation 2, or determination of $P_e$ in the AB to BL direction at concentrations, (a) close to the analytical limit, and (b) close to the solubility limit.

Similar $P_e$ values in both the AB to BL and BL to AB indicate a passively absorbed compound and no further studies are required. AB to BL $P_e$ greater than BL to AB indicates carrier-mediated absorption and $P_e$ must be determined for 5 additional $C_0$ in the AB to BL direction. BL to AB $P_e$ greater than AB to BL indicates carrier mediated secretion and $P_e$ determined for 5 additional $C_0$'s in the BL to AB direction.

Similar $P_e$ values at low and high concentrations indicate a passively absorbed compound, and no further studies are required. Low concentration $P_e$ higher than high concentration $P_e$ indicates carrier-mediated absorption and $P_e$ is determined for 5 additional $C_0$'s in the AB to BL direction. High concentration $P_e$ higher than low concentration $P_e$ may indicate carrier-mediated secretion. BL to AB $P_e$ is then determined at the low concentration and the mechanism determined as described above.

B. Solubility Determination

Solubility of a compound is determined using an accurate and scientifically sound method similar to the Phase Rule and Phase-solubility analysis as described in Remington's: The Science and Practice of Pharmacy, $19^{th}$ edition, Chapter 16.

The solubility is determined at pH 1.5 using Simulated Gastric Fluid (USP XXII) minus pepsin. Solubility at pH 6.0, 6.5, 7.0, and 7.5 is determined in Simulated Intestinal Fluid (USB XXII) minus pancreatin. Parameters are for data collection are carefully monitored by ensuring purity of the test compound and accuracy of the Simulated Gastrointestinal fluids. A temperature of 37° C. is maintained accurately during the course of the determination. Complete saturation and accurate analysis of saturated solutions are employed.

C. Dissolution Determination

The dissolution rates are determined using the equipment, apparatus, and methods described in USP XXII, <711> dissolution. The dissolution rate at pH 1.5 is determined in Simulated Gastric Fluid (USP XXII) minus pancreatin. Concentrations are collected and analyzed for drug compound from the vessel for a sufficient time (6 hours, preferable) to allow the initial slope of the concentration v. time curve to be determined. The slope (dissolution rate) is determined using the initial linear portion of the concentration v. time plot if non-sink conditions exist. Under sink conditions, the entire plot are used to calculate the slope. The slope is reported as the dissolution rate. Explanations of the dissolution rate, sink and non-sink conditions, and equations for calculation are given in Remington's: the Science and Practice of Pharmacy, 19th edition, Chapter 34.

If a formulated dosage form is used for dissolution testing, the dissolution protocols described are used to determine the dissolution rate for drug compound from the formulated dosage form.

Example 5

Standards and Protocols for Evaluating Permeability Data Collection

This example provides detailed protocols for controlling the quality of permeability data collection described in Examples 3 and 4. Compounds listed in Table 7 are used as standards for monitoring permeability data collection and quality. The compounds were chosen to represent each intestinal transport mechanism (passive transcellular, passive paracellular, carrier-mediate influx, or carrier-mediated efflux).

TABLE 7

Permeability Standards

| Transport mechanism | Compounds |
| --- | --- |
| Passive Paracellular | mannitol |
| Passive Transcellular | hydrocortisone |
| Carrier-mediated Influx | D-glucose |
| Carrier-mediated Efflux | etoposide |

Mannitol, hydrocortisone, D-glucose, and etoposide also were chosen since they are widely used as markers for intestinal transport across rabbit tissue and other systems with well characterized Pe values. These compounds also are available commercially as either 3H-labeled or 14C-labeled.

Permeability data for standards is compared to the values for rabbit listed in Table 8 (or other standard values) using basic statistical analyses. If the data is significantly different (p-value>0.05) for any of the standard compounds, data collection is repeated.

TABLE 8

Transport Characteristics of Permeability Standards*

| Compound (donor concentration) | Pe (cm/s) | | | |
| --- | --- | --- | --- | --- |
| | Duodenum | Jejunum | Ileum | Colon |
| mannitol (1 mM)5 | $1.73 \times 10^{-6}$ | $3.54 \times 10^{-6}$ | $4.02 \times 10^{-6}$ | $5.53 \times 10^{-6}$ |
| hydrocortisone (0.01 µM)5 | $3.00 \times 10^{-7}$ | $1.31 \times 10^{-6}$ | $2.91 \times 10^{-6}$ | $3.85 \times 10^{-6}$ |
| D-glucose (10 mM)5 | $4.55 \times 10^{-6}$ | $1.02 \times 10^{-5}$ | $1.45 \times 10^{-5}$ | $9.28 \times 10^{-6}$ |
| etoposide (100 µM) | | | | |

*Note: permeability values are representative of ranges. Other values or extended ranges may be used.

A. Experimental Conditions

Protocols, conditions and calculations for permeability evaluation of standards are as described in Example 4, with the following modifications.

Permeability experiments are performed using Ringer's buffer at pH 7.4 on both the apical/mucosal and basolateral/serosal sides. Ringer's buffer is as described above excepting that glucose is substituted with mannitol when Pe values for glucose are being measured.

Samples are collected from the receiver chamber beginning 30 minutes after experiment initiation and continuing every 15 minutes until 6 samples have been collected (105 minutes). One-half ml is removed from each receiver chamber at each time point and compound concentration determined. The volume removed from the receiver chamber is replaced with buffer containing no drug to maintain constant volume in the receiver chamber. The dilution of the receiver concentration due to the addition of buffer should be corrected during data analysis and Pe calculation. The concentration is corrected by using Equation 5.

$$\frac{1}{X} = \sum_{n=1}^{k} (-1)^{n-1} \frac{\beta}{k+1} \left(\frac{S}{V}\right)^{n-1} \quad \text{(Eq. 5)}$$

Where the corrected receiver chamber concentration is obtained by dividing the collected sample concentration by Equation 5 (1/x), S is the volume of sample withdrawn, V is the receiver chamber volume, k is the sequential sample number, i.e. k=1 for the first sample time, k=2 for the second sample time, k=3 for the third sample time, etc., and β is the corresponding number from the modified Pascal's triangle below (Table 9). Note: Since the sample intervals are not even (i.e. the 1st interval is 30 minutes, all others 15 minutes) Equation 5 as well as the β coefficients are modified from those listed in Example 4.

TABLE 9

Modified Pascal's Triangle for determining β coefficients.

| Sample | 1st term | 2nd term | 3rd term | 4th term | 5th term | 6th term |
| --- | --- | --- | --- | --- | --- | --- |
| 1 | 2 | | | | | |
| 2 | 3 | 2 | | | | |
| 3 | 4 | 5 | 2 | | | |
| 4 | 5 | 9 | 7 | 2 | | |
| 5 | 6 | 14 | 16 | 9 | 2 | |
| 6 | 7 | 20 | 30 | 27 | 11 | 2 |

The donor concentration $C_0$ is determined by sampling 0.02 ml of the donor buffer containing drug (with subsequent analysis) directly from the donor chamber. Potential binding of drugs to the chambers also is monitored. Donor samples (0.02 ml) are taken at experiment initiation and at experiment conclusion. If a significant decrease in drug concentration has occurred (>10%) the experiment is repeated using procedures which compensate for the drug loss in the donor chamber. It is recommended that the donor chamber solution be removed and replaced with fresh donor buffer containing drug at appropriate intervals. The intervals and volumes to be used are determined using sound scientific judgment. Adequate data is collected to show the donor drug concentration has remained constant throughout the experiment.

For tissue-based permeability assays, during mounting of tissue onto chambers, intestinal muscles should be stripped off the mucosa and discarded. Care should be taken to ensure integrity of the tissue.

Animals donating tissue are euthanized immediately prior to experiment initiation. The small intestine is excised from the animal and kept in ice cold Ringer's buffer pH 7.4 until mounted in diffusion chambers. As soon as possible after excision, the tissue is cut into an appropriately sized piece and placed over the diffusion chamber pins with the mucosal side down. The muscle layers are carefully stripped away using forceps. After the tissue is mounted the two half chambers are placed together and the donor and receiver sides filled with the appropriate pre-warmed (37° C.) buffer. If NaviCyte chambers are used, the gas lift system is connected with 95% $O_2$/5% $CO_2$ flowing at ~5–15 ml/min (depending upon chamber volume) into each half chamber to maintain pH and mixing. Sampling begins 30 minutes after connection of the gas lift system.

The mean Pe and Standard Error of the Mean are determined for each study. Permeabilities from at least 6 chambers from 3 different animals are used in calculating the mean and Standard Error of the Mean.

In addition, the Pe of radiolabeled mannitol is determined simultaneously with the standard compound as a marker of intestinal integrity. Mannitol Pe values may be determined by concurrent diffusion using a donor buffer containing mannitol and the standard drug compound, or by continuing the experiment for 60 minutes after the last standard compound sample is collected using donor buffer containing mannitol and fresh receiver buffer containing no compounds.

Special experimental conditions are followed for certain standard compounds. This includes such conditions as a proton gradient, a sodium gradient, presence of glucose, etc. These conditions are listed in Table 10 and are substituted or added to the general conditions listed above.

TABLE 10

Experimental Conditions

| Standard Compound | Donor Concentration | Special Conditions |
|---|---|---|
| mannitol | 1 mM | |
| D-glucose | 10 mM | |
| hydrocortisone | 0.01 µM | |
| etoposide | 100 µM | drug dissolved in DMSO, DMSO concentration in buffer <0.1% |

Example 6

Physiologic-Based Mass Simulation Model

A. Design

A multi-compartment physiologic-based mass simulation model (the "mass model") was designed to integrate mass-flow relationships among GI compartments representing the stomach, duodenum, jejunum, ileum, and colon, and thus throughout the GI tract, and to characterize drug movement in units of mass into peripheral compartments. Converters that interrelated transfer rates and associated rate constants (k), which in turn were modified by various factors including pH, solubility profiles, compartment surface area and drug permeability were incorporated to account for drug movement among compartments. A plasma kinetics model also was included for validation purposes and for correlating clinical plasma data to the mass model. Converters also were used for unit conversion.

Gancyclovir was chosen to develop and test the mass model. Gancyclovir exhibits no in vivo biotransformation and is poorly absorbed. Thus, the mass model assumes no metabolism or protein binding. Additionally, dissolution rate and delivery system were not used in the mass model as modifying parameters of drug absorption, i.e., drug assumed to be completely dissolved in the stomach and solubilized according to its solubility profile.

Surface area values for each compartment of the mass model represented a "functional surface area," as opposed to an absolute value. A functional surface area was utilized since (1) fluids entering the gastrointestinal compartments do not cover the surfaces of the compartment instantaneously, but rather over a time course; and (2) solubilized drug within the fluid is not ideally presented to all absorptive areas. Functional surface areas for each compartment were calculated by solving Equation 6 for the area using various data inputs from the literature.

$$P \cdot A \cdot S_p = \partial M / \partial t \qquad \text{(Eq. 6)}$$

Where P is the permeability coefficient, A is the surface area of the membrane, $S_p$ is the solubility of the drug in the relevant segment of the intestine, and $\partial M/\partial t$ is drug flux, where flux $\partial M/\partial t$ is determined from the permeability of the drug in the particular intestinal compartment, the surface area covered by drug solution and the solubility of at the pH of the intestinal compartment.

For example, several studies have been conducted comparing permeability of various compounds (Rubas et al., *Pharmaceutical Research*, Vol. 10, No. 1 (1993)). Mannitol, which has similar physicochemical properties to Gancyclovir, also has similar permeability characteristics and a bioavailability of approximately 10% in humans when it is orally administered. For mannitol, permeability is well characterized. Thus, data obtained from the literature related to permeability in each compartment, pH-dependent solubility and mass concentration relationships was used to solve Equation (6) for area. Thus, it was this area, and not the theoretical total surface area of each compartment, that was used as the functional area of a compartment, which represented a good approximation of in vivo surface area relationships for initial model building.

Permeability values were obtained from published in vitro cell diffusion experiments and were accounted for by converters that modified luminal and peripheral flow (K12) for each compartment. For solubility, a solubility curve was used based on experimental data available in the literature. pH was then isolated in a separate converter to modify the solubility curve for the particular compartment. In contrast, for validation purposes, an absolute solubility value was used and pH was entered as 1 to isolate that converter from the validation model.

Absorption "transfer" rates among each two compartment sub-system were collected into a separate flow representing total absorption rate, which in turn was collected into a compartment representing the total amount of drug absorbed for each GI tract compartment, namely, stomach, duodenum, jejunum, ileum, and colon. Absorption rates among stomach, duodenum, jejunum, ileum, and colon modules were connected by flows modified by the associated rate constants between each GI segment.

For validation purposes, a plasma kinetics model was integrated with the mass-flow compartments by linking the total absorption rate to a flow representing the absorption rate constant, which in turn fed into the central plasma compartment. A standard two-compartment plasma kinetics model (Ramsay, *European Journal of Pharmaceutics and Biopharmaceitucs*, Vol. 37, No. 3 (1991)) was used for this purpose. (See FIGS. 5 and 6) The plasma kinetics model incorporated first order transfers between the blood compartment and peripheral compartment. Two flows were used and set up as first order systems and thus different rate constants were applied in each direction. Compartment values were represented as mass units. Blood volume was input in a converter, which modified a converter for concentration along with the mass compartment. An elimination rate constant was also obtained form the literature in a first order process. In addition, while most drugs are given in milligram doses, plasma concentrations are reported in microgram or nanogram per milliliter. This is done since compounds are distributed rapidly into a large volume after entering the blood resulting in a concentration of drug in systemic circulation that is quite low with respect to the concentration at the site of administration. Accordingly, an additional converter was added to convert milligram units to nanogram or microgram units expected for concentrations of the test compound based on human bioavailability data. A compartment also was added to collect elimination data.

B. Mass Model Parameters

Parameters and associated values of the mass model include pH, solubility, permeability, and intestinal transit, and are illustrated in Table 11.

TABLE 11

| Mass Model Parameters/Values | |
|---|---|
| Parameter | Value |
| Dose | 1000 mg |
| dt | 0.125 |
| Run Time | 24 hrs |
| ka assumed (mass transit) | 2.8 or 3 |
| Stomach | |
| Area | 50 cm² |
| Solubility | 31 mg/ml |
| Permeability | $1.1 \times 10^{-6}$ cm/sec |
| Duodenum | |
| Area | 125 cm² |
| Solubility | 3.65 mg/ml |
| Permeability | $1.1 \times 10^{-6}$ cm/sec |
| Jejunum | |
| Area | 182 cm² |
| Solubility | 3.65 mg/ml |
| Permeability | $2.17 \times 10^{-6}$ cm/sec |
| Ileum | |
| Area | 102 cm² |
| Solubility | 3.65 mg/ml |
| Permeability | $4.06 \times 10^{-6}$ cm/sec |
| Colon | |
| Area | 138 cm² |
| Solubility | 3.65 mg/ml |
| Permeability | $3.80\ 10^{-6}$ cm/sec |
| Plasma Kinetics | |
| $k_{12}$ | 0.839 |
| $k_{21}$ | 0.670 |
| $k_{elim}$ | 0.161 |
| Fluid Volume | 76,800 ml |

The mass model also was tested by inputting values derived from the literature (Gibaldi et al., *Pharmacokinetics*, pp. 284–288, Marcell Dekker (1975)) into the plasma kinetics model. These values are shown in Table 12.

TABLE 12

| Values for Plasma Kinetic Module | |
|---|---|
| Dose | 1 g |
| 1505a | 2.718 h⁻¹ |
| 1505b | 0.254 h⁻¹ |
| $k_{21}$ | 0.3737 h⁻¹ |
| $k_{12}$ | 0.7509 h⁻¹ |

TABLE 12-continued

| Values for Plasma Kinetic Module | |
|---|---|
| Dose | 1 g |
| $k_{10}$ | 1.3474 h⁻¹ |
| $V_p$ | 20.1241 |

Example 7

Testing and Validation Mass Model

The mass model was tested using parameters shown in Table 11 with an initial dose of 1000 mg over a time course of 24 hours. AUC, $C_{max}$, $T_{max}$, and $T_{1/2}$ were simulated using various doses (New Drug Application for Gancyclovir Sodium, Syntex (USA), (obtained from the FDA under the Freedom of Information Act (FIA)) and compared to human clinical data obtained for Gancyclovir. Bioavailability simulated by the mass model for Gancyclovir was approximately 6%. Compared to human clinical data, obtained for two Phase I clinical studies (designated here as ICM 1505 and 1505b), bioavailability of fasted patients in clinical trials typically ranged from 3–20%. The mass model also was tested using a plasma kinetics validation model illustrated in FIG. 8.

FIG. 16 shows the area under the concentration time curve for a 1000 mg dose of Gancyclovir, Tmax=1.4 hrs, Cmax= 0.51 ng/ml., using the mass model, as compared to clinical study data of ICM 1505 and 1505b. The results demonstrate that the mass model underestimated plasma concentration during the post-absorptive period. Table 13 shows comparison of some values between clinical studies and those predicted by the mass model. The clinical studies also used a 70 Kg body weight for normalization of concentrations.

TABLE 13

| Comparison of Mass Model to Clinical data | | | |
|---|---|---|---|
| Parameter | Mass Model | Clinical 1505a | Clinical 1505b |
| Cmax (mcg/ml) | 0.51 | 0.55 | 0.59 |
| Tmax (hrs) | 1.40 | 1.43 | 1.43 |

Example 8

Physiologic-Based Volume Simulation Model

A. Design

A physiologic-based simulation model for incorporating fluid volume flux and GI transit (the "volume model") was developed for integration with the mass model to account for changes in absorption resulting from fluid absorption/ secretion and transit, and thus apparent drug concentration. The volume model was constructed so that fluid enters a compartment and was absorbed by a first order process based on an absorption rate for that fluid. Movement of fluid between compartments was dependent on a zero or first order fluid transit rate.

B. Volume Model Parameters

As a starting point for the volume model, values were obtained from literature that described in general terms absorption and secretion of fluid throughout the body (Change et al., *Gastrointestinal, Hepatobiliary and Nutritional Physiology*, Chapter 5, p. 92, Lippincott-Raven (1996)). Values representing total intake of fluid per day and total secretion of fluid per day were modeled into the system normalized linearly to increments of dt for the model. To permit for changes in dt for the model, the values were entered as pulses. Values used in the volume model are shown in Table 14.

TABLE 14

Volume Model Parameters/Values

| Source | ml/24 hrs | ml/0.1 hrs |
|---|---|---|
| Intake/Secretion | | |
| Stomach | 6500 | 27.08 |
| Orally | 2000 | 8.33 |
| Salivary Glands | 1500 | 6.25 |
| Stomach | 2500 | 10.42 |
| Duodenum | 2000 | 8.33 |
| Bile | 500 | 2.08 |
| Pancreas | 1500 | 6.25 |
| Jejunum/Ileum | 1000 | 4.17 |
| Jejunum | 641 | 2.67 |
| Ileum | 359 | 1.50 |
| Colon | 0 | 0 |
| Total | 9000 | 337.57.5 |
| Absorption | | |
| Duodenum | 2598 | 10.82 |
| Jejunum | 3783 | 15.76 |
| Ileum | 2120 | 8.83 |
| Colon | 400 | 1.67 |
| Total | 8900 | 37.09 |

Note: Values for compartments based on % total intestinal area

Where data was only available for a series of compartments, values were assigned to each compartment based on the percentage of the total area for that series (e.g. secretions for jejunum and ileum and absorption for parts of the small intestine). The model was set as two flows between the blood (serosal) side of the compartment and the compartment itself. Each flow represented the rate constant for secretion and fluid absorption.

For development purposes, absorption and stomach secretion were assumed to be zero order when using values from Table 14 for both flows. Also, daily volume for fluid entry into the stomach was entered as a pulse according to the dt values shown in Table 14. Thus, total intake and secretions of fluid was modeled as a pulse occurring every 6 minutes throughout a 24 hour period. Initial volume in the stomach also was set up as a pulse of the total oral intake, salivary excretion, and stomach secretion over each dt increment.

Example 9

Testing and Validation of Volume Model

To test movement of fluid between compartments the volume model was modified to approximate zero order fluid transit or emptying and isolated from the mass component of the model. Initial values of 1000 ml and 250 ml were used for testing.

Example 10

Physiologic-Based Mass-Volume Simulation Model

A. Design

A physiologic-based simulation model integrating the mass and volume models (the "mass-volume model") was constructed to integrate complex mass and fluid flow relationships. The integrated mass-volume model also included compartments to characterize drug movement into peripheral compartments. A plasma kinetics model for training/validation purposes also was included. The basic design for the integrated mass-volume model, linked to the plasma kinetics model shown in FIG. 8, is illustrated in FIG. 11.

Volume for a compartment was added as a product to obtain the amount of drug solubilized at a time increment volume. Additionally, an "IF . . . THEN . . . ELSE" control statement was added to prevent the equation from indicating that more drug was solubilized than dosed. Thus, the integrated mass-volume model shows the mass of drug in the stomach connected to the absorption rate constant as well as the volume compartment.

Mass and fluid transit rate constants of 2.8 and 3 for the stomach were calculated from values obtained from the literature for Gancyclovir (Syntex, Clinical Studies ICM 1653 and 1774, FDA NDA available data and Bachrach et al., Functional and Diagnostic Aspects of the Upper Digestive Tract, Digestive System, Part I, Upper Digestive Tract, Netter (1989)), and determined for each of the remaining compartments to approximate mass and fluid movement.

B. Mass-Volume Model Parameters

Parameters and associated values and equations were systematically varied or as described above for individual mass and volume models; an example of the equations and parameters employed in the mass-volume model are shown in Appendix 1. Dissolution rate and delivery system (controlled release device/formulation) were excluded from in the mass-volume model, and thus the model assumes a test compound is immediately in solution in the stomach.

Example 11

Testing and Validation of Mass-Volume Model

The mass-volume model was tested using the equations and parameters shown in Appendix 1. These parameters included the pulsed estimate of fluid absorption and gastrointestinal secretions, and rate constants extracted from the literature. Alternate sets of parameters for fluid absorption and secretions also were tested. For example, simple zero and first order rate constants of 1 or a sequential integer and various doses were evaluated for comparison to human clinical data.

FIG. 17 shows the area under the concentration time curve for a 1000 mg dose of Gancyclovir, Tmax=1.1875 hrs, Cmax=0.54 mcg/ml., using the mass-volume model of FIG. 11 with the estimated absorption and secretion rates, relationships, and values of Appendix 1, as compared to clinical study data of ICM 1505 and 1505b. The data is now less favorable for Tmax but more favorable for AUC compared to the mass model. These results demonstrate that the mass model underestimated plasma concentration during the post-absorptive period, while the combined mass-volume model appeared to overestimate it.

The mass-volume model was modified to incorporate simple zero and first order absorption and secretion. This model was then run using an initial volume of 250 ml and also 4 administrations of 250 ml water as done during clinical studies. Results were similar to the results shown in FIG. 17, but with slightly higher absorption.

The mass-volume model also was run using the following combinations of data input: (1) doses of 500 mg, 750 mg, 1000 mg at qid, bid, and tid dosing; (2) initial volumes of 250 ml, 500 ml, 1000 ml; (3) varying absorption and secretion rates based on differing assumptions for daily secretion and fluid intake; (4) varying pH values in the various compartments; and (5) simulation of food intake and fasting conditions. Correlation was very good with some clinical data and less than optimal with others. Correlation with theoretical estimations also varied from very good to poor.

Collectively, the mass-volume model represented an improvement over the individual mass and volume models in that it provided a better approximation of in vivo conditions. While the simpler mass-model correlated better with clinical data, the integrated mass-volume model was more sensitive to changes in the various input parameters, physiological conditions and underlying constants, and thus a more rigorous model of the GI tract.

Example 12

Physiologic-Based GI Tract Simulation Model

A. Design

The mass-volume model was selectively improved in a stepwise fashion to create an integrated physiologic-based simulation model of the GI tract of a mammal (the "GI model") capable of compound-independent prediction of oral absorption with a high level of accuracy. The model was developed to be flexible. That is, it was designed so that additional physiological factors that influence oral absorption could be identified and incorporated into the model as needed to improve the quality of the prediction for a diverse set of test compounds. Additionally, the GI model was developed to minimize input data requirements.

The basic approach involved generation, testing and integration of a GI transit model (FIG. 20), a pH-dependent solubility and dissolution model (FIG. 21), and an absorption model (FIG. 22), as well as underlying equations and parameters, constants, calculated parameters, and rules by which a given simulation is to proceed. A controlled release device and formulation compartment also was included. A graphical compartment-flow model of the integrated GI model is illustrated in FIG. 24 (without converters, ghost or connectors) and FIG. 25 (with converters, ghost and connectors). Parameter inputs, calculations and outputs are illustrated in FIGS. 29–39. An abbreviation key for the GI model is provided as Appendix 3.

The GI model also incorporated additional features to improve the predictive power and versatility of the simulation model. One feature was the development and incorporation of regression analysis derived adjustment parameters based on analysis and processing of human clinical data and in vitro data for a diverse set of compounds. The adjustment parameters were utilized as constants in the GI model, and thus modify underlying equations of the model. A second feature was development and incorporation of regional permeability correlation parameters and equations that permitted estimation of values for segments of the model that were missing user provided input values for corresponding parameters. This facilitates prediction of oral drug absorption when permeability values or other parameter for a given compound are provided for a limited number of GI segments, for example, when cell-based input data, such permeability data derived from Caco-2 cells is used to provide permeability input data of colon. Another feature was development and incorporation of parameters and calculations to account for transport mechanism and thus transport-specific variations in compound absorption. Another feature was incorporation of the ability to isolate and evaluate specific regional absorption events related to dissolution and mass transit. Also, the GI model was developed to separate absorption into the portal vein (FDp) from hepatic metabolism, so as to account for individual primary barriers to absorption.

B. GI Model Equations, Rules and Parameters

1. General Equations for GI Model:

Various differential equations and rules utilized for the GI tract model are provided below. For the equations, adjustment parameters are designated by the letter Z.

Transit Time:

First Order Transit Process $$\frac{dA}{dt} = k_{TT}[A] \quad \text{(Eq. 7)}$$

dA/dt=rate of transit (or absorption), $k_{TT}$=rate of constant, A=amount (compound or water) in proximal compartment.

Rate Constant Calculation $$k_{TT} = \frac{\ln 10}{TT_{ADJ}} \quad \text{(Eq. 8)}$$

$TT_{ADJ}$=adjusted transit time $$TT_{ADJ} = (TT_p \cdot Z_{TT} \cdot User_{TT}) \quad \text{(Eq. 9)}$$

$TT_p$=physiological transit time, $Z_{TT}$=transit time adjustment parameter, $User_{TT}$=User controlled adjustment to transit time.

$K_{TT}$ is a regionally dependent parameter, i.e. different rate constants are used for each region of the GI tract.

Fluid Volume Absorption/Resorption:

$$\frac{dA}{dt} = k_{VA}[A] \quad \text{(Eq. 10)}$$

dA/dt=rate of absortpion, $k_{VA}$=rate constant, A=amount of fluid (water) in the compartment $$k_{VAZ} = k_{emp} \cdot Z_{VA} \quad \text{(Eq. 11)}$$

$Z_{VA}$=volume absorption adjustment parameter, $k_{emp}$ is determined emperically to match human fluid absorption in vivo.

Dissolution and Solubility:

Dissolution Rate (Regionally Dependent)

$$\frac{d(A)}{dt} = k_D \cdot Z_D \cdot Mass \cdot (S_{ADJ} - C) \quad \text{(Eq. 12)}$$

A=Amount dissolved, $k_D$=User supplied dissolution rate constant, $Z_D$=Dissolution rate adjustment parameter, $S_{ADJ}$=solubility, C=concentration Solubility (Regionally Dependent)

$$S_{ADJ} = \frac{(s_N - s_{n-1})}{(pH_n - pH_{n-1})}(pH - pH_{n-1}) + S_{n-1} \quad \text{(Eq. 13)}$$

$S_{ADJ}$=Solubility, $S_n$=user supplied solubility $\{S_1 \ldots S_5\}$, $pH_n$=user supplied pH values $\{pH_1 \ldots pH_5\}$ corresponding to user supplied solubilities, pH=pH value appropriate to region of the system, such as GI tract. n is selected such that $pH_n > pH$, and $pH_{n-1} < pH$. If any of $pH_1 \ldots pH_5$ are equal to pH, the corresponding $S_n$ is used as the solubility.

Concentration (Regionally Dependent)

$$C = \frac{S_{ADJ}}{V} \quad \text{(Eq. 14)}$$

C=concentration of soluble drug, V=volume of fluid
Flux/Absorption:

$$J = P_{ADJ} \cdot SA_{ADJ} \cdot C \quad \text{(Eq. 15)}$$

J=flux, $P_{ADJ}$=Adjusted permeability, $SA_{ADJ}$=Adjusted surface area available for absorption, C=concentration $$P_{ADJ} = \left(\frac{2}{1+Z_{EFF}}\right) \cdot P_m \cdot Z_F \cdot 3600 + \frac{Z_{ACT} \cdot P_c \cdot 3600}{1 + \frac{C}{K_m}} \quad \text{(Eq. 16)}$$

$Z_{EFF}$=Efflux transport adjustment parameter, $P_m$=passive membrane permeability, $Z_F$=passive permeability or flux adjustment parameter, $Z_{ACT}$=active permeability adjustment parameter, $P_c$=active carrier permeability, C=concentration, $K_m$=Michaelis-Menten kinetic parameter.

Regional Permeability Correlation
Any regional permeability, $P_m$, can be calculated using any number of other provided permeabilities.

$$\ln P_a = C + A \cdot \ln\frac{1}{P_b} + B \cdot \ln\left(\frac{1}{P_b}\right)^2 \quad \text{(Eq. 17)}$$

$P_a$=permeability calculated using the regional correlation, $P_b$=permeability provided by the user, and A, B, and C=correlation coefficients fitted to determine correlation.

By way of example, rules utilized for a GI tract model of the PK tool and method of the invention include the following general processes.

2. General Processes for Rule Generation:
1. GI transit. The transit of drug compound and fluid volume are somewhat controlled and the transit of formulations and/or controlled release devices is much more strictly controlled.
2. Controlled Drug Release. The release of drug from the dosage form must be controlled such that drug is released into the correct intestinal region at the appropriate time.
3. Dissolution. A comparison between the concentration and the solubility must be made to determine if additional insoluble compound will dissolve, or if compound already dissolved must precipitate to insoluble drug due to solubility limitations.
4. Absorption. Mathematically, absorption may occur when physiologically it is impossible, e.g. when the volume in the colon becomes low enough that any dissolved drug will be within fluid contained in other solid waste also present in the colon and therefore unavailable for absorption. IF . . . THEN production rules control these situations.
5. Permeability calculations. To estimate unprovided permeability values from provided permeability values logical evaluations must be made to determine the correct equations necessary to make the correlations.
6. Concentration calculations. The concentration in the intestine cannot exceed the solubility for that particular region. If it does, an incorrect flux will be calculated. IF . . . THEN production rules are used to ensure the correct concentration is used in the flux calculation.
7. Mathematical anomalies. At certain times during the simulation (especially early and late in the simulation) some compartments, flow regulators, or converters used in other calculations may have a value of 0 which will result in a computational error, e.g. division by 0. Production of rules are used to identify these situations and avoid the errors.

The following table lists the specific processes, conditions, results that control statement rules, e.g., IF . . . THEN production rules, are used to control. Generally, separate rules used for each region of the GI tract and are combined into one line in the table.

TABLE 15

Rules for Physiologic-Based GI tract Simulation Model

| Process | Condition | Result in True | Result if False | Comments |
|---|---|---|---|---|
| GI Transit of drug compound or fluid volume | Time <4 hours | No transit to waste | Transit to waste by first order proces | Applies to GI regions using different values for the condition. |
| GI Transit of formulations or controlled release devices | Time cumulative physiol. transit time | no transit to next compartment | Immediate transit to next compartment | The rate constant for first order transit is set exceedingly large to provide near instantaneous transit. |
| Controlled release | Time to reach GI region <Time< Time to exit GI region | Drug is released from dosage form to GI region | No drug release into that GI region | Drug is released according to user provided release profile. |
| Dissolution | Soluble drug/volume (concentration) < Solubility | Drug moves from insoluble to soluble compartment according to dissolution rate | Drug moves from soluble to insoluble compartment according to precipitation rate | Precipitation rate is set to provide near instantaneous precipitation without causing "overshoot". |
| Absorption | Volume <1 × $10^{-6}$ ml AND Mass <1 × $10^{-8}$ mg | No absorption, i.e. concentration = 0 | Absorption by flux equation | |
| Permeability Calculations | Duodenum, Jejunum, and Ileum Permeabilites all provided | Use provided Permeabilities | Estimate unprovided permeabilities from provided permeabilities | 1 or 2 permeabilities can be used to calculate unprovided permeabilities |

TABLE 15-continued

Rules for Physiologic-Based GI tract Simulation Model

| Process | Condition | Result in True | Result if False | Comments |
|---|---|---|---|---|
| Concentration Calculation Mathematical anomalies | Concentration < Solubility Volume = 0 | Concentration used in flux equation Dissolution rate = 0 | Solubility used in flux equation Dissolutioin rate calculated by Noyes-Whitney equation | Dissolution given as an example. Similar condications are provided for concentration calculations and other processes. |

Exemplary equations, rules, parameters and initial values for the graphical compartment-flow model and various sub-models of the integrated GI model illustrated in FIGS. 20–25 and 29–39 are provided in Appendix 4, as related to the abbreviation key provided as Appendix 3. Various aspects of the physiological, adjustment and regional correlation parameters employed in the GI model and their development are described in further detail below.

1. Physiological Parameters

Physiological parameters of the GI model included physiological ranges reported in the literature (Table 17) as well as specific values utilized in the model and compiled for each of five regions of the gastrointestinal tract (stomach, duodenum, jejunum, ileum and colon)(Table 16). These included values related to pH, transit time, surface area, and volume parameters.

TABLE 16

Physiological Parameters Employed In GI Model

| | pH[a] | Initial Volumes (ml) | Surface Area (cm$^2$)[b] | Average Transit time (hr)[c] | Volume Transfer Rates ($t_{90}$) (hr$^{-1}$)[c] | New Water Absorption Rates* (hr$^1$)[d] |
|---|---|---|---|---|---|---|
| Stomach | 1.5 | 100 | NA | 0.5 | 4.6 | 0 |
| Duodenum | 6.0 | 0 | 150 | 0.225 | 10.8 | 0 |
| Jejunum | 6.5 | 0 | 1000 | 1.5 | 1.54 | 1.75 |
| Ileum | 7.0 | 0 | 1000 | 1.5 | 1.54 | 1.75 |
| Colon | 6.5 | 0 | 850 | 24 | 0.094 | 0.1 |

*Water absorption rate parameters were set so that cumulative water absorption from each region using the GI model were in agreement with values listed in Table 17.

TABLE 17

Physiological Parameters Employed In GI Model

| | pH[a] | Initial Volumes (ml) | Surface Area (cm$^2$)[b] | Average Transit time (hr)[c] | Volume Transfer Rates ($t_{90}$) (hr$^{-1}$)[c] | New Water Absorption Rates* (hr$^1$)[d] |
|---|---|---|---|---|---|---|
| Stomach | 1.0–2.5 | 100 | NA | 0.5–3.0 | 0.8–4.6 | 0 |
| Duodenum | 4.0–6.4 | 0 | 147–168 | 0.20–0.25 | 9.2–11.5 | 0 |
| Jejunum | 4.4–6.4 | 0 | 913.5–1044 | 1.0–2.0 | 1.15–2.3 | 4.0–4.5 |
| Ileum | 6.8–7.4 | 0 | 913.5–1044 | 1.2–1.5 | 1.54–1.9 | 2.4–2.7 |
| Colon | 5.5–7.0 | 0 | 763–18–36 872 | | 0.064–0.13 | 1.4–1.6 |

[a]Lui et al. J Pharm Sci 1986; 75(3): 271–4; Youngberg et al. Dig Dis Sci 1987; 32(5): 472–80; Charman et al. J Pharm Sci 1997; 86(3): 269–82; Langguth et al. Biopharm Drug Dispos 1994; 15(9): 719–46; Kararli TT. Biopharm Drug Dispos 1995; 16(5): 351–80;
[b]Wagner JG. J Pharm Sci 1961; 50(5): 59–87; Ho NF, Park JY, Ni PF, et al. Crouthamel W, Sarapu AC, editors. Animal Models For Oral Drug Delivery In Man: In Situ And In vivo Approaches. Washington, D.C. American Pharmaceutical Association, 1983; 2, Advancing quantitative and mechanistic approaches in interfacing gastrointestinal drug absorption studies in animals and humans. p. 27–106;
[c]Ho et al. Crouthamel W, Sarapu AC, editors. Animal Models For Oral Drug Delivery In Man: In Situ And In vivo Approaches. Washington, D.C. American Pharmaceutical Association, 1983; 2, Advancing quantitative and mechanistic approaches in interfacing gastrointestinal drug absorption studies in animals and humans. p. 27–106; Oberle et al. Journal of Pharmacokinetics & Biopharmaceutics 1987;15: 529–44; Davis SS. STP Pharma 1986; 22: 1015–22; Davis et al. Gut 1986; 27: 886–92;
[d]Turnberg LA. Digestion (1973)9:357–81.

2. Adjustment Parameters

Differences between in vitro and in vivo conditions, as well as differences between in vivo conditions for one species of mammal and a second hamper accurate prediction of absorption using a simulation approach. For example, in vitro dissolution rate may or may not be comparable to dissolution rates existing in vivo, or, the permeability in rabbits may or may not be comparable to the permeability in humans.

To compensate for such differences, a set of selectively optimized adjustment parameters were developed. These parameters were designed to be utilized as constants that modify the underlying equations of specific compartments of the GI model to permit automatic correlation of input data to output data as well as facilitate accurate prediction of oral absorption for a diverse set of compounds. For example, the differential equation utilized to calculate fluid volume absorption/resorption employs a rate constant obtained from an equation that is modified by a volume absorption adjustment parameter $ZV_A$ (see Eq. 11) Listed below (Table 18) are examples of parameters that can be used to adjust parameters and equations as well as those which can be added or removed to a given model if necessary.

TABLE 18

Adjustment Parameters

| Compartment | Segment |
|---|---|
| Regional fluid absorption | stomach |
| | duodenum |
| | jejunum |
| | ileum |
| | colon |
| Flux/Permeability | duodenum |
| | jejunum |
| | ileum |
| | colon |
| Active/Carrier mediated Transport (absorption) | duodenum |
| | jejunum |
| | ileum |
| | colon |
| Compound Efflux (secretion) | duodenum |
| | jejunum |
| | ileum |
| | colon |
| Transfer rates | stomach to duodenum |
| | duodenum to jejunum |
| | jejunum to ileum |
| | ileum to colon |
| | colon to waste |
| Surface Area | duodenum |
| | jejunum |
| | ileum |
| | colon |

The adjustment parameters were developed and optimized using a stepwise selective optimization process. Initial adjustment parameters were developed for correlation between humans and rabbit as follows. Two primary sets of data were used: 1) FDp and best fit plasma profiles from in vivo clinical pharmacokinetic (PK) data, and 2) simulated FDp and plasma profiles generated from the GI model. The FDp and best fit plasma profiles from in vivo PK data was obtained by analyzing and processing IV and PO data from humans for the test set of compounds described in Example 2 using a regression-based curve fitting algorithm to determine the best fit curve that matched the actual clinical plasma profiles. The second set of data was generated using a developmental GI model.

In vitro data (permeability, solubility, dissolution rate, and dose) were used as inputs into the GI model with the adjustment parameters set to some initial value previously determined to provide reasonably predictable values for FDp. The GI model was used to provide FDp data for each test compound. The FDp data generated from the GI model also was used as input data into an IV/PO PK model, such as the one shown in FIG. 18, to determine plasma profiles.

The PO input to the IV/PO PK model of FIG. 18 used for fitting clinical data is an error function and shown in Equation 18.

$$F = \frac{D \cdot FD_P}{2} \left| 1 - erf \left| \frac{1 - \frac{t}{t_{50}}}{\frac{1}{P_e} \cdot \sqrt{\frac{t}{t_{50}}}} \right| \right| \quad \text{(Eq. 18)}$$

Where D is the dose of drug delivered to the intestine, t is time in minutes, t50 is the time for 50% of the drug to be absorbed, and Pe is a parameter (Peclet number) related to the slope of the linear portion of the absorption curve.

When fitting the data, all available in vivo PK data (multiple intravenous (IV) dosing and multiple oral (PO) dosing) was analyzed simultaneously using the IV/PO PK model of FIG. 18. The data were weighted by 1/Standard Error of the Mean (SEM) or by 1/Concentration$^2$.

The initial adjustment parameter values were determined empirically. Using a limited set of compounds and corresponding in vitro data from rabbit tissue, the adjustment parameters were manually varied to obtain FDp values that were reasonably consistent with the actual PK data. After the initial values were determined, the GI model developed using STELLA® was converted to a program file readable by a program having fitting algorithm, such as KINETICA™. The initial adjustment parameters were then simultaneously fit using non-linear regression analysis in a stepwise manner to determine optimized values (i.e., best fit values) for the adjustment parameters. Within each step, a few parameters were selected for optimization by simultaneous fitting. The fitting was approached using an iterative process, where selected adjustment parameters were varied systematically such that the deviation of the GI model determined absorption from the actual PK determined absorption was minimized. Once the deviation was reduced to a satisfactory level, few more parameters were then selected and optimized. The process was continued until all parameters were successfully optimized. The new parameters were then placed into the GI model and the FDp determined for each compound which is compared to the PK FDp to establish the goodness of fit. This process was repeated until an acceptable goodness of fit was established. Using this approach, adjustment parameters were developed to correlate, for example, in vitro solubility, dissolution, dose and permeability in rabbits to in vivo human absorption. Although FDp was employed as the reference for deviation, the actual measurement of absorption can be evaluated using any number of parameters, such as plasma levels, absorption constants, or others. Moreover, it will be appreciated that many sets of adjustment parameters may be developed and established. For instance, other sets of adjustment parameters may be established to correlate dog, rat, monkey or other species permeability data to human, dog, rat, rabbit, monkey, or other animal in vivo absorption.

3. Regional Permeability Correlation Parameters

Since Pe in all intestinal regions may not be available, for instance when cell monolayer data is employed to determine Pe in colon, a correlation was developed that provides a reasonable prediction of unknown Pe values in the other intestinal regions.

An objective was to establish a correlation between regional permeabilities that allowed prediction of permeability in the duodenum, jejunum or ileum using known permeabilities in one or two of the other regions.

Correlation development involved obtention of regional permeability values in intestinal tissue from the literature and experimentally using methods consistent with the experimental protocols as described in Examples 4–5.

The regional correlation parameters were estimated using a polynomial equation developed for this purpose (Equation 17). Any regional permeability, $P_m$, can be calculated using any number of other provided permeabilities.

The regional correlation parameter function was incorporated into the GI model using a logic function module. A control statement was utilized to regulate activation of the regional correlation parameter estimation function when a user provides less than the total number of permeability values for the segments of the GI tract.

The following (Table 19) shows correlations that were established along with the corresponding correlation coefficient. Correlations were accomplished by data transformation and fitting to a non-linear function.

TABLE 19

Results of Regional Correlation

| Variable | | |
|---|---|---|
| Dependent | Independent | Correlation Coefficient |
| Duodenum | Jejunum | 0.870 |
| Duodenum | Ileum | 0.906 |
| Jejunum | Duodenum | 0.858 |
| Jejunum | Ileum | 0.914 |
| Ileum | Duodenum | 0.855 |
| Ileum | Jejunum | 0.894 |

As an example of the capability of the correlation, two of the above correlations were evaluated by estimating the permeability in the duodenum and jejunum using ileum Pe values. The compounds chosen were those for which complete Pe values were available.

The error and % error for the permeability calculations were determined by comparing predicted values to the known permeabilities (Table 20).

TABLE 20

Evaluation of Regional Correlations

| | Intestinal Region | | | |
|---|---|---|---|---|
| | Duodenum | | Jejunum | |
| Compound | Error | % Error | Error | % Error |
| Compound α1 | −4.64E-07 | −46.36 | 2.42E-07 | 35.03 |
| Compound α2 | 6.37E-08 | 5.79 | −1.11E-07 | −5.14 |
| Compound α3 | 3.10E-07 | 114.91 | −8.38E-07 | −45.28 |
| Compound α4 | 1.18E-05 | 196.00 | −5.40E-06 | −16.38 |

The above results demonstrate that the regional correlation parameter function of the GI model was able to accurately predict Pe values for compounds within the initial data set (i.e., high $r^2$).

Example 13

Validation and Testing of GI Model

To demonstrate that the physiological parameters of the model were operating in a logical manner consistent with expected behavior in vivo, the parameters were varied and the effect on output monitored. For example, a decrease in the surface area available for absorption should result in a decrease in the amount of compound absorbed. Thus, the physiological parameters of the model were varied by increasing and/or decreasing their values. The effect of these variations on the rate, as measured by T50 (time for 50% absorption), and extent, as measured by FDp, were simulated. Table 21 shows the physiological parameters that were varied and the expected effect on FDp and T50.

TABLE 21

Physiological Parameter Variations*

| Parameter | Range evaluated | Expected effect | |
|---|---|---|---|
| Surface Area or Permeability | 0.05 to 10 × Normal* | Increase in: Surface Area or | Increase FDp |
| | $1 \times 10^{-7}$ to $1s10^{-5}$ cm/s | Permeability | Decrease T50 |
| GI Transit | 0.05 to 10 × Normal* | Increase in: | Increase FDp |

TABLE 21-continued

Physiological Parameter Variations*

| Parameter | Range evaluated | Expected effect | |
|---|---|---|---|
| | | Time | GI Transit Time |
| | | | Increase T50 |
| Dissolution Rate | 0.05 to 10 × Normal* | Increase in: Dissolution Rate | Increase FDp |
| | | | Decreased T50 |
| Solubility | 1 to 100 mg/ml | Increase in: Solubility | Increase FDp |
| | | | Decrease T50 |

*Normal values used in the model are listed in Example 12. In each case, only the parameter chosen was varied, all other parameters were held constant.

All effects on FDp and T50 were as expected with the changes in the physiological parameters. While not all of the ranges were in the physiological range, the lower part of the range was included to assure that the model would limit to zero FDp as the various parameters approached zero.

The basic structure of the GI model also was assessed by comparing its ability to predict, from dose and in vitro solubility and rabbit tissue permeability data, the rate and extent of oral drug absorption in humans and dogs for several drugs, including atenolol, ganciclovir, verapamil, and naproxin. These compounds were chosen for their well known and diverse in vivo absorption properties and interspecies absorption variability. By changing the physiological parameter values of the simulation model so that they corresponded to the species under investigation, but not changing the model structure, i.e., compartment, flow regulator, converter relationships, efficacy of the model structure could be evaluated. Initial parameter values for dog and human were derived from the literature. Adjustment parameters were used to build the correlation between the in vitro data and in vivo absorption. For all four drugs, the GI model accurately predicted FDp for both dog and human.

To assess the basic power of the GI model for predicting oral drug absorption, the model was tested by simulating FDp as a function of time so as to separate absorption across intestinal tissue from first pass metabolism and drug concentration in systemic circulation. Accordingly, methods were developed and used to determine FDp from clinical plasma data so that transport across the intestinal tissue could be determined. This was accomplished by simultaneously fitting clinical pharmacokinetic data (PO and IV) to the two compartment open IV/PO PK model illustrated as a compartment-flow model in FIG. 18. Elimination was from the central compartment. Input from oral doses was into a pre-systemic compartment (for metabolism) which was in equilibrium with the central compartment. FDp was determined simultaneously for each oral dose. Clinical pharmacokinetic data fitted to the IV/PO PK model demonstrated the ability of the model to accurately determine blood levels in the central compartment.

The fitted clinical FDp data for a test set of compounds was then compared to FDp predicted by the GI model using both experimental in vitro values for permeability as input as well as estimated permeability values calculated by the model using the regional permeability correlation function. The permeability source of the test compounds are shown in Table 22 below.

TABLE 22

Permeability Source of Test Compounds

| Compound | Permeability source* |
|---|---|
| α1 | experimental |
| α2 | experimental |
| α3 | experimental |
| α4 | experimental |
| α5 | estimation |
| α6 | experimental |
| α10 | estimation |
| β1 | estimation |
| β2 | estimation |
| β3 | estimation |
| β5 | estimation |
| β6 | estimation |

*Experimental-permeability values for all intestinal segments were submitted. Estimation-permeability values were calculated using regional permeability correlation parameters.

FIGS. 48–52 are illustrative of the results of these tests. The physiological model was found to accurately predict FDp for the test set of compounds. The accuracy of the prediction is based on both rate and extent of absorption. Correlation of FDp extent between the clinical data and as predicted by the model for the test set of compounds yielded a collective regression coefficient ($r^2$) of greater than 0.92.

Example 14

Smoothing Functions for GI Model

In the in vivo physiological situation, permeability and pH do not change at distinct points or places with the GI tract (with the exception of the gastro-duodenal junction). For example, permeability of a drug in the duodenum may be measured at $1.5 \times 10^{-6}$ cm/s and $2.5 \times 10^{-6}$ cm/s in the jejunum, but there is no distinct point in the intestine where such an abrupt change exist. Since the GI model simulates five regions or segments of the GI tract, and each segment utilizes its own set of initial permeability and pH values, an abrupt change, as opposed to an incremental transition, is simulated for a dosage form or dissolved drug as it passes distally through the segmented GI tract.

To account for this phenomenon, and to generate a GI model that is as physiologically accurate as possible, smoothing functions were incorporated into the model. Pairs of exponential functions were used to adjust the permeability and pH values in each segment of the intestine. The functions were developed to be time/position dependent using the mean cumulative transit time as cues for adjustment. For example, prior to the cumulative transit time to reach the ileum ($C_{TT}I$), the ileum permeability will be equal to the user provided or regional correlation estimated jejunum permeability. As time approaches $C_{TT}I$, the ileum permeability will correspond to the exact average of the jejunum and ileum permeability at that point. Immediately after $C_{TT}I$, the ileum permeability continues to gradually decrease/increase exponentially until it reaches the user provided, or estimated, ileum permeability.

Two exponential functions were used in combination to effectively smooth the permeability and pH values. The GI model was adapted to employ Equation 19 as the time approaches a mean cumulative transit time ($C_{TT}$), and Equation 20 immediately after $C_{TT}$.

$$P = A - ke^{(\alpha t)} \quad \text{(Eq. 19)}$$

$$P = B + ke^{-\alpha(t-TT)} \quad \text{(Eq. 20)}$$

Where A=permeability or pH in the previous intestinal region or segment, B=permeability or pH in the latter region, k is defined in Equation 21, α=a constant used to determine the steepness of the transition between regions and is inversely proportional to the transit time of the region, t=time, and TT=cumulative transit time to exit the previous region.

$$k = 0.5(A-B)/e^{\alpha TT} \quad \text{(Eq. 21)}$$

These smoothing functions were utilized to adjust permeability and pH at junctions of the stomach/duodenum, duodenum/jejunum, jejunum/ileum, and ileum/colon.

APPENDIX 1

Abbreviation Key for Mass-Volume Model

| Abbreviation | |
|---|---|
| Kf sd = | associated rate constant for stomach and duodenum |
| Ka dj = | associated rate constant for duodenum and jejunum |
| Ka ji = | associated rate constant for jejunum and ileum |
| Ka ie = | associated rate constant for ileum and colon |
| Ka co = | associated rate constant for colon and excretion |
| SD trans = | transfer rate between stomach and duodenum |
| DJ trans = | transfer rate between duodenum and jejunum |
| JL trans = | transfer rate between jejunum and ileum |
| IC trans = | transfer rate between ileum and colon |
| Waste = | transfer rate between colon and excretion |
| pH s = | pH stomach |
| pH s2 = | pH duodenum |
| pH s3 = | pH jejunum |
| pH s4 = | pH ileum |
| pH s5 = | pH colon |
| sol profile = | solubility profile for stomach |
| sol profile 2 = | solubility profile for duodenum |
| sol profile 3 = | solubility profile for jejunum |
| sol profile 4 = | solubility profile for ileum |
| sol profile 5 = | solubility profile for colon |
| stom ka = | associated rate constant for stomach compartments 1 and 2 |
| dua ka = | associated rate constant for duodenum compartments 1 and 2 |
| Jej ka = | associated rate constant for jejunum compartments 1 and 2 |
| Il ka = | associated rate constant for ileum compartments 1 and 2 |
| Colon ka = | associated rate constant for colon compartments 1 and 2 |
| SA stom = | surface area of stomach |
| SA duo = | surface area of duodenum |
| SA jej = | surface area of jejunum |
| SA il = | surface area of ileum |
| SA colon = | surface area of colon |
| Perm stom = | permeability of stomach |
| Perm duo = | permeability of duodenum |
| Perm jej = | permeability of jejunum |
| Perm il = | permeability of ileum |
| Perm colon = | permeability of colon |
| Ka sd = | associated rate construct for stomach fluid absorption |
| Ka du = | associated rate construct for duodeunm fluid absorption |
| Ka je = | associated rate construct for jejunm fluid absorption |
| Ka il = | associated rate construct for ilenum fluid absorption |
| Ka co = | associated rate construct for colon fluid absorption |

Note: other abbreviations adhere to above descriptors and are self explanatory

Appendix 2: Equations, Parameters and Values For Mass-Volume Model amt_plasma(t)=amt_plasma(t-dt)+(trans_21+ka-elimination-trans_12) * dt
INIT amt_plasma=0
INFLOWS:
trans_21=k21*comp_2
ka=tot_abs_rate
OUTFLOWS:
elimination=amt_plasma*k_elim trans_12k12*amt_plasma
blood_side_col(t)=blood_side_col(t−dt)+(colon_ka_5) * dt
INIT blood_side_col=0
INFLOWS:
colon_ka_5= IF Vol_colon*sol_profile_5>=Colon THEN
Colon*SA_colon*perm_colon*3600 ELSE
Vol_colon*sol_profile_5*SA_colon*perm_colon*3600
blood_side_dou(t)=blood_side_dou(t−dt)+(duo_ka) * dt
INIT blood_side_dou=0
INFLOWS:
duo_ka= IF Vol_duod*sol_profile_2>=duodenum THEN
duodenum*SA_duo*permduo*3600 ELSE
Vol_duod*sol_profile_2*SA_duo*perm_duo*3600
blood_side_il(t)=blood_side_il(t−dt)+(Il_ka) * dt
INIT blood_side_il=0
INFLOWS:
Il_ka= IF Vol_ileum*sol_profile_4>=Ileum THEN
Ileum*SA_Il*perm_Il*3600 ELSE
Vol_ileum*sol_profile_4*SA_Il*perm_Il*3600
blood_side_jej(t)=blood_side_jej(t−dt)+(Jej_ka) * dt
INIT blood_side_jej=0
INFLOWS:
Jej_ka= IF Vol_jej*sol_profile_3>=Jejunum THEN
Jejunum*SA_jej*perm_jej *3600
ELSE Vol_jej*sol_profile_3*SA_jej*perm_jej*3600
blood_side_sto(t)=blood_side_sto(t−dt)+(stom_ka) * dt
INIT blood_side_sto=0
INFLOWS:
stom_ka= IF Vol_stom*sol_profile>=Stomach THEN
Stomach*SA_stom*perm_stom*3600 ELSE
Vol_stom*sol_profile*SA_stom*perm_stom*3600
Colon(t)=Colon(t−dt)+(IC_trans−Waste−colon_ka_5) * dt
INIT Colon=0
INFLOWS:
IC_trans=ka_ic*Ileum
OUTFLOWS:
Waste=ka_col*Colon
colon_ka_5= IF Vol_colon*sol_profile_5>=Colon THEN
Colon*SA_colon*perm_colon*3600 ELSE
Vol_colon*sol_profile_5*SA_colon*perm_colon*3600
comp_2(t)=comp_2(t−dt)+(trans_12−trans_21) * dt
INIT comp_2=0
INFLOWS:
trans_12=k12*amt_plasma
OUTFLOWS:
trans_21=k21*comp_2
duodenum(t)=duodenum(t−dt)+(SD_trans−duo_ka−DJ_trans) * dt
INIT duodenum=0
INFLOWS:
SD_trans=if Stomach>0 then kf_sd*Stomach else 0
OUTFLOWS:
duo_ka= IF Vol_duod*sol_profile_2>=duodenum THEN
duodenum*SA_duo*perm_duo*3600 ELSE
Vol_duod*sol_profile_2*SA_duo*perm_duo*3600
DJ_trans=ka_dj*duodenum
excretion(t)=excretion(t−dt)+(vol_cw) * dt
INIT excretion=0
INFLOWS:
vol_cw=Vol_colon*ka_col
excretion_2(t)=excretion_2(t−dt)+(Waste) * dt
INIT excretion_2=0
INFLOWS:
Waste=ka_col*Colon
Ileum(t)=Ileum(t−dt)+(JL_trans−IC_trans−Il_ka) * dt
INIT Ileum=0
INFLOWS:
JL_trans=ka_ji*Jejunum
OUTFLOWS:
IC_trans=ka_ic*Ileum
Il_ka= IF Vol_ileum*sol_profile_4>=Ileum THEN
Ileum*SA_Il*perm_Il*3600 ELSE
Vol_ileum*sol_profile_4*SA_Il*perm_Il*3600
Jejunum(t)=Jejunum(t=dt)+(DJ_trans−JL_trans−Jej_ka) * dt
INIT Jejunum=0
INFLOWS:
DJ_trans=ka_dj*duodenum
OUTFLOWS:
JL_trans=ka_ji*Jejunum
Jej_ka= IF Vol_jej*sol_profile_3>=Jejunum THEN
Jejunum*SA_jej*perm_jej *3600
ELSE Vol_jej*sol_profile_3*SA_jej*perm_jej*3600
serosal_col(t)=serosal_col(t−dt)+(Adsorp_col−col_secretion) * dt
INIT serosal_col=0
INFLOWS:
Adsorp_col=PULSE(1.67,0,.1)+0*Vol_colon*ka_co
OUTFLOWS:
col_secretion=0
serosal_dou(t)=serosal_dou(t−dt)+(Adsorp_Duo−duo_secretion) * dt
INIT serosal_dou=0
INFLOWS:
Adsorp_Duo=PULSE(10.82,0,.1)+0*Vol_duod*ka_du
OUTFLOWS:
duo_secretion=PULSE(10.82,0,.1)
serosal_ill(t)=serosal_ill(t−dt)+(Adsorpt_ill−ile_secretion) * dt
INIT serosal_ill=0
INFLOWS:
Adsorpt_ill=PULSE(8.83,0,.10)+0*Vol_ileum*ka_il
OUTFLOWS:
ile_secretion=PULSE(1.50,0,.1)
serosal_jej(t)=serosal_jej(t−dt)+(Adsorp_jej−jej_secretion) * dt
INIT serosal_jej=0
INFLOWS:
Adsorp_jej=PULSE(15.76,0,.1)+0*Vol_jej*ka_je
OUTFLOWS:
jej_secretion=PULSE(2.67,0,.1)
serosal_sto(t)=serosal_sto(t−dt)+(Adsorp_Stom−Stom_Secretion) * dt
INIT serosal_sto=0
INFLOWS:
Adsorp_Stom=0*Vol_stom*ka_sd
OUTFLOWS:
Stom_Secretion=PULSE(16.67,0,.1)
Stomach(t)=Stomach(t−dt)+(−SD_trans−stom_ka) * dt
INIT Stomach=1000
OUTFLOWS: SD_trans=if Stomach>0 then kf_sd*Stomach else 0
stom_ka= IF Vol_stom*sol_profile>=Stomach THEN
Stomach*SA_stom*perm_stom*3600 ELSE
Vol_stom*sol_profile*SA_stom*perm_stom*3600
total_drug_absorbed(t)=total_drug_absorbed(t−dt)+ (tot_abs_rate) * dt
INIT total_drug_absorbed=0
INFLOWS:
tot_abs_rate=stom_ka+duo_ka+Jej_ka+Il_ka+colon_ka_5

Total_Elimination(t)=Total_Elimination(t−dt)+
    (elimination) * dt
INIT Total_Elimination=0
INFLOWS:
elimination=amt_plasma*k_elim
Vol_colon(t)=Vol_colon(t−dt)+(vol_ij+col_secretion−
    vol_cw−Adsorp_col) * dt
INIT Vol_colon=0
INFLOWS:
vol_ij=Vol_ileum*ka_ic
col_secretion=0
OUTFLOWS:
vol_cw=Vol_colon*ka_col
Adsorp_col=PULSE(1.67,0,.1)+0*Vol_colon*ka_co
Vol_duod(t)=Vol_duod(t−dt)+(vol_sd+duo_secretion−
    voil_dj−Adsorp_Duo) * dt
INIT Vol_duod=0
INFLOWS:
vol_sd=kf_sd*Vol_stom
duo_secretion=PULSE(10.82,0,.1)
OUTFLOWS:
voil_dj=Vol_duod*ka_dj
Adsorp_Duo=PULSE(10.82,0,.1)+0*Vol_duod*ka_du
Vol_ileum(t)=Vol_ileum(t−dt)+(vol_ji+ile_secretion−
    Adsorpt_ill−vol_ij) * dt
INIT Vol_ileum=0
INFLOWS:
vol_ji=Vol_jej*ka_ji
ile_secretion=PULSE(1.50,0,.1)
OUTFLOWS:
Adsorpt_ill=PULSE(8.83,0,.10)+0*Vol_ileum*ka_il
vol_ij=Vol_ileum*ka_ic
Vol_jej(t)=Vol_jej(t−dt)+(voil_dj+jej_secretion−vol_ji−
    Adsorp_jej) * dt
INIT Vol_jej=0
INFLOWS:
voil_dj=Vol_duod*ka_dj
jej_secretion=PULSE(2.67,0,.1)
OUTFLOWS:
vol_ji=Vol_jej*ka_ji
Adsorp_jej=PULSE(15.76,0,.1)+0*Vol_jej*ka_je
Vol_stom(t)=Vol_stom(t−dt)+(Stom_Secretion−vol_sd−
    Adsorp_Stom) * dt
INIT Vol_stom=PULSE(8.33,0,.1)
INFLOWS:
Stom_Secretion=PULSE(16.67,0,.1)
OUTFLOWS:
vol_sd=kf_sd*Vol_stom
Adsorp_Stom=0*Vol_stom*ka_sd
conc_plasma=(amt_plasma/volume)*mg_to_ug
k12=.839
k21=.67
ka_co=1
ka_col=3
ka_dj=3
ka_du=1
ka_ic=3
ka_il=8.83
ka_je=1
ka_ji=3
ka_sd=1
kf_sd=2.8
k_elim=.161
mg_to_ug=1000 perm_colon=3.80e-6
perm_duo=1.10e-6
perm_Il=4.06e-6
perm_jej=2.17e-6
perm_stom=1.10e-6
ph_s=1.5
ph_s2=6.6
ph_s_3=6.6
ph_s_4=7.5
ph_s_5=6.6
SA_colon=138
SA_duo=125
SA_Il=102
SA_jej=182
SA_stom=50
volume=4*19200
sol_profile=GRAPH(ph_s)
(1.00, 63.0), (1.50, 25.0), (2.00, 10.0), (2.50, 5.00), (3.00, 4.00), (3.50, 3.80), (4.00, 3.65), (4.50, 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)
sol_profile_2=GRAPH(ph_s_2)
(1.00, 63.0), (1.50, 25.0), (2.00, 10.0), (2.50, 5.00), (3.00, 4.00), (3.50, 3.80), (4.00, 3.65), (4.50, 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)
sol_profile_3=GRAPH(ph_s_3)
(1.00, 63.0), (1.50, 25.0), (2.00, 10.0), (2.50, 5.00), (3.00, 4.00), (3.50, 3.80), (4.00, 3.65), (4.50, 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)
sol_profile_4=GRAPH(ph_s_4)
(1.00, 63.0), (1.50, 25.0), (2.00, 10.0), (2.50, 5.00), (3.00, 4.00), (3.50, 3.80), (4.00, 3.65), (4.50, 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)
sol_profile_5=GRAPH(ph_s_5)
(1.00, 63.0), (1.50, 25.0), (2.00, 10.0), (2.50, 5.00), (3.00, 4.00), (3.50, 3.80), (4.00, 3.65), (4.50, 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)

APPENDIX 3

Abbreviation Key For GI Model

The legend/key has been divided into sub-sections corresponding to the sub-sections of the model diagram
Numbered suffixes (1, 2, 3, 4, 5, 6) have been assigned to distinguish between intestinal regions (stomach, duodenum, jejunum, ileum, colon, and waste, respectively).

| | |
|---|---|
| 1 | stomach |
| 2 | duodenum |
| 3 | jejunum |
| 4 | ileum |
| 5 | colon |
| 6 | waste |

APPENDIX 3-continued

Abbreviation Key For GI Model

For example, VOL 1 is the volume in the stomach, MASS 3 is the insoluble mass in the jejunum. In the equations, COMP 1 indicates the stomach, COMP 2 the duodenum, COMP 3, the jejunum, etc. Ghosts are listed under the sub-section containing the original reservoir, flow regulator, or converter.
Abbreviations listed in italics are regionally dependent and set up as arrays to allow independent values for each intestinal region.
In general, ADJ as a prefix indicates a calculated parameter value (ADJ = adjusted), while ADJ as a suffix indicates and adjustment parameter (ADJ = adjustment).
Intestinal model Reservoirs/Compartment

| | |
|---|---|
| VOL ABS | Fluid volume absorbed |
| VOL | Fluid volume |
| C REL | Mass of drug contained with a formulation or controlled release device |
| MASS | Insoluble mass of drug (not contained within the formulation or controlled release device |
| SOL | Soluble mass of drug |
| ABSORPTION | Mass of drug absorbed |

Flow regulators

| | |
|---|---|
| REABS | Rate of water absorption |
| VOL OUT | Fluid volume transit rate |
| CR OUT | Formulation or contolled release device transit rate |
| CR INPUT | Drug release rate from formulation or controlled release device |
| MASS OUT | Insoluble drug mass transit rate |
| DISS PRECIP | Dissolution rate |
| SOL OUT | Soluble drug mass transit rate |
| FLUX | Absorption rate |

ADJ PARMS (Adjustment Parameters)

| | |
|---|---|
| VOL ADJ | Fluid volume absorption adjustment parameter |
| DISS ADJ | Dissolution rate adjustment parameter |
| TRANSIT ADJ | Transit time adjustment parameter |
| SA ADJ | Surface area adjustment parameter |
| FLUX ADJ | Passive Absorption adjustment parameter |
| EFFLUX ADJ | Efflux or secretion adjustment parameter |
| CARRIER ADJ | Active absorption adjustment parameter |

PARMS (Parameters)

| | |
|---|---|
| VOL PARM | Fluid volume absorption rate constant |
| SURFACE AREA | Surface area available for absorption |
| DOSE | The administered dose of drug |
| INIT VOLUME | The administered volume of water or fluid |
| TIME IN HOURS | A clock |
| pH | The physiological pH value |
| PARACELLULAR | A user controlled switch used to adjust absorption based on absorption mechanism |

TRANSIT TIME

| | |
|---|---|
| TRANSFERS | GI transit constant |
| CUMU TT | Cumulative transit time |
| ADJ TRANSIT TIME | Adjusted GI transit time incorporating adjustment parameter and user input |
| USER TT INPUT | User controlled adjustments to the GI transit time |

OUTPUT CALCULATIONS

| | |
|---|---|
| ABSORBED TOTAL | Total mass of drug absorbed (sum of ABSORPTION 1 . . . 5) |
| FDp % | Total absorption rate (sum of FLUX 1 . . . 5) |
| CUM DISS | Cumulative drug mass dissolved |
| CR Release | Cumulative drug mass released from formulation |

APPENDIX 3-continued

Abbreviation Key For GI Model

| | |
|---|---|
| CUM DISS RATE | Sum of DISS PRECIP 1 . . . 5 |
| CR cumrate | Summ of CR INPUT 1 . . . 5 |

PERMEABILITY CALCULATION

| | |
|---|---|
| ADJ | Adjusted permeability incorporating all transport mechanisms and relevant adjustment parameters |
| ACT PE | Active or carrier-mediated absorptive permeability |
| Km | Constant from the Micaelis-Menten type permeability equation for active transport |
| REGIONAL | Passive permeability after regional correlation calculation (same as PASS PE if regional correlation is not used) |
| PASS PE | Passive permeability entered by user |
| RC | A logical function used in determining the regional correlation |
| RCSUM | A logical function used in determining the regional correlation |

SOLUBILITY CALCULATION

| | |
|---|---|
| USER pH | User supplied pH value for which a solubility value is available |
| USER SOLUB | User supplied solubility value corresponding to the USER pH value |
| ADJ SOLUB | Solubility calculated (if necessary) at the appropriate pH value using the entered USER pH and USER SOLUB values |

CONTROLLED RELEASE CALCLATION

| | |
|---|---|
| CR RATE | The instantaneous release rate from the formulation |
| CR DOSE | The total dose contained with the formulation |
| CR AT TIME | The cumulative drug mass release profile |
| CR AT LAST | The cumulative drug mass release profile |

Note: CR AT TIME hold the value at the current time value (t), CR AT LAST holds the value at the immediately preceeding time value (T-1)

CONC CALCULATION

| | |
|---|---|
| CONCENTRATIONS | The dissolved drug concentration |

DISSOLUTION CALCULATION

| | |
|---|---|
| PRECIP | Precipitation rate constant |
| DISSOL | Dissolution rate constant |
| ADJ DISS PRECIP | Adjusted rate constant incorporating PRCIP, DISSOL and calculated concentration |

Appendix 4: Equations, Parameters and Values For GI Model

- ADJ PARMS
  - CARRIER_ADJ[COMPS] = 0
  - DISS_ADJ[COMP_1] = 1
  - DISS_ADJ[COMP_2] = 1
  - DISS_ADJ[COMP_3] = 1
  - DISS_ADJ[COMP_4] = 1
  - DISS_ADJ[COMP_5] = 1
  - EFFLUX_ADJ[COMPS] = 1
  - FLUX_ADJ[COMP_1] = 1
  - FLUX_ADJ[COMP_2] = 10
  - FLUX_ADJ[COMP_3] = 8
  - FLUX_ADJ[COMP_4] = 2
  - FLUX_ADJ[COMP_5] = 1
  - SA_ADJ[COMP_1] = 1
  - SA_ADJ[COMP_2] = 1
  - SA_ADJ[COMP_3] = 1
  - SA_ADJ[COMP_4] = 1
  - SA_ADJ[COMP_5] = 1
  - TRANSIT_ADJ[COMP_1] = 1
  - TRANSIT_ADJ[COMP_2] = 1
  - TRANSIT_ADJ[COMP_3] = 1
  - TRANSIT_ADJ[COMP_4] = 1
  - TRANSIT_ADJ[COMP_5] = 1
  - VOL_ADJ[COMP_1] = 1
  - VOL_ADJ[COMP_2] = 1
  - VOL_ADJ[COMP_3] = 1
  - VOL_ADJ[COMP_4] = 1
  - VOL_ADJ[COMP_5] = 1
- CONC CALCULATION
  - CONCENTRATIONS[COMP_1] = if VOL_1=0.0 then 0 else if ADJ_SOLUB[COMP_1]<SOL_1/VOL_1 then ADJ_SOLUB[COMP_1] else SOL_1/VOL_1 + 0*(SOL_2+SOL_5+SOL_3+SOL_4+VOL_3+VOL_2+VOL_4+VOL_5)
  - CONCENTRATIONS[COMP_2] = if VOL_2 = 0.0 then 0 else if (VOL_2<1e-6 AND SOL_2<1e-7) then 0 else if ADJ_SOLUB[COMP_2]<SOL_2/VOL_2 then ADJ_SOLUB[COMP_2] else SOL_2/VOL_2 +0*(SOL_1+SOL_5+SOL_3+SOL_4+VOL_3+VOL_1+VOL_5+VOL_4)
  - CONCENTRATIONS[COMP_3] = if VOL_3 = 0.0 then 0 else if (VOL_3<1e-6 AND SOL_3<1e-7) then 0 else if ADJ_SOLUB[COMP_3]<SOL_3/VOL_3 then ADJ_SOLUB[COMP_3] else SOL_3/VOL_3 +0*(SOL_1+SOL_2+SOL_4+SOL_5+VOL_5+VOL_4+VOL_1+VOL_2)
  - CONCENTRATIONS[COMP_4] = if VOL_4 = 0.0 then 0 else if (VOL_4<1e-6 AND SOL_4<1e-7) then 0 else if ADJ_SOLUB[COMP_4]<SOL_4/VOL_4 then ADJ_SOLUB[COMP_4] else SOL_4/VOL_4 +0*(SOL_1+SOL_2+SOL_3+SOL_5+VOL_1+VOL_2+VOL_3+VOL_5)

- CONCENTRATIONS[COMP_5] = if VOL_5 = 0.0 then 0 else if (VOL_5<1e-6 AND SOL_5<1e-7) then 0 else if ADJ_SOLUB[COMP_5]<SOL_5/VOL_5 then ADJ_SOLUB[COMP_5] else SOL_5/VOL_5
+0*(SOL_1+SOL_4+SOL_3+SOL_2+VOL_3+VOL_1+VOL_2+VOL_4)

CONTROL RELEASE CALCULATION

- CR_DOSE = 0
- CR_RATE = (CR_AT_TIME-CR_AT_LAST)*20*(CR_DOSE/100)
- CR_AT_LAST = GRAPH(TIME-DT)
  (0.00, 0.00), (0.25, 17.7), (0.5, 31.5), (0.75, 42.2), (1.00, 50.6), (1.25, 57.1), (1.50, 62.1), (1.75, 66.1), (2.00, 69.2), (2.25, 71.6), (2.50, 73.4), (2.75, 74.9), (3.00, 76.0), (3.25, 76.9), (3.50, 77.6), (3.75, 78.1), (4.00, 78.5), (4.25, 78.9), (4.50, 79.1), (4.75, 79.3), (5.00, 79.5), (5.25, 79.6), (5.50, 79.7), (5.75, 79.7), (6.00, 79.8), (6.25, 79.8), (6.50, 79.9), (6.75, 79.9), (7.00, 79.9), (7.25, 79.9), (7.50, 80.0), (7.75, 80.0), (8.00, 80.0), (8.25, 80.0), (8.50, 80.0), (8.75, 80.0), (9.00, 80.0), (9.25, 80.0), (9.50, 80.0), (9.75, 80.0), (10.0, 80.0), (10.3, 80.0), (10.5, 80.0), (10.8, 80.0), (11.0, 80.0), (11.3, 80.0), (11.5, 80.0), (11.8, 80.0), (12.0, 80.0), (12.3, 80.0), (12.5, 80.0), (12.8, 80.0), (13.0, 80.0)...
- CR_AT_TIME = GRAPH(TIME)
  (0.00, 0.00), (0.25, 17.7), (0.5, 31.5), (0.75, 42.2), (1.00, 50.6), (1.25, 57.1), (1.50, 62.1), (1.75, 66.1), (2.00, 69.2), (2.25, 71.6), (2.50, 73.4), (2.75, 74.9), (3.00, 76.0), (3.25, 76.9), (3.50, 77.6), (3.75, 78.1), (4.00, 78.5), (4.25, 78.9), (4.50, 79.1), (4.75, 79.3), (5.00, 79.5), (5.25, 79.6), (5.50, 79.7), (5.75, 79.7), (6.00, 79.8), (6.25, 79.8), (6.50, 79.9), (6.75, 79.9), (7.00, 79.9), (7.25, 79.9), (7.50, 80.0), (7.75, 80.0), (8.00, 80.0), (8.25, 80.0), (8.50, 80.0), (8.75, 80.0), (9.00, 80.0), (9.25, 80.0), (9.50, 80.0), (9.75, 80.0), (10.0, 80.0), (10.3, 80.0), (10.5, 80.0), (10.8, 80.0), (11.0, 80.0), (11.3, 80.0), (11.5, 80.0), (11.8, 80.0), (12.0, 80.0), (12.3, 80.0), (12.5, 80.0), (12.8, 80.0), (13.0, 80.0)...

DISSOLUTION CALCULATION

- ADJ_DISS_PRECIP[COMP_1] = if VOL_1=0 then 0 else if (SOL_1/VOL_1<ADJ_SOLUB[COMP_1]) then (DISSOL[COMP_1]*DISS_ADJ[COMP_1]*MASS_1*(ADJ_SOLUB[COMP_1]-SOL_1/VOL_1)) else ((SOL_1/VOL_1)-ADJ_SOLUB[COMP_1])*PRECIP[COMP_1]+
0*(MASS_1+MASS_2+MASS_3+MASS_4+MASS_5+SOL_1+SOL_2+SOL_3+SOL_4+SOL_5+VOL_1+VOL_2+VOL_3+VOL_4+VOL_5)
- ADJ_DISS_PRECIP[COMP_2] = if VOL_2=0 then 0 else if (SOL_2/VOL_2<ADJ_SOLUB[COMP_2]) then (DISSOL[COMP_2]*DISS_ADJ[COMP_2]*MASS_2*(ADJ_SOLUB[COMP_2]-SOL_2/VOL_2)) else ((SOL_2/VOL_2)-ADJ_SOLUB[COMP_2])*PRECIP[COMP_2]
+0*(MASS_1+MASS_2+MASS_3+MASS_4+MASS_5+SOL_1+SOL_2+SOL_3+SOL_4+SOL_5+VOL_1+VOL_2+VOL_3+VOL_4+VOL_5)
- ADJ_DISS_PRECIP[COMP_3] = if VOL_3=0 then 0 else if (SOL_3/VOL_3<ADJ_SOLUB[COMP_3]) then (DISSOL[COMP_3]*DISS_ADJ[COMP_3]*MASS_3*(ADJ_SOLUB[COMP_3]-SOL_3/VOL_3)) else ((SOL_3/VOL_3)-ADJ_SOLUB[COMP_3])*PRECIP[COMP_3]
+0*(MASS_1+MASS_2+MASS_3+MASS_4+MASS_5+SOL_1+SOL_2+SOL_3+SOL_4+SOL_5+VOL_1+VOL_2+VOL_3+VOL_4+VOL_5)

○ ADJ_DISS_PRECIP[COMP_4] = if VOL_4=0 then 0 else if
  (SOL_4/VOL_4<ADJ_SOLUB[COMP_4]) then
  (DISSOL[COMP_4]*DISS_ADJ[COMP_4]*MASS_4*(ADJ_SOLUB[COMP_4]-SOL_4/VOL_4)) else
  ((SOL_4/VOL_4)-ADJ_SOLUB[COMP_4])*PRECIP[COMP_4]
  +0*(MASS_1+MASS_2+MASS_3+MASS_4+MASS_5+SOL_1+SOL_2+SOL_3+SOL_4+SOL_5+V
  OL_1+VOL_2+VOL_3+VOL_4+VOL_5)
○ ADJ_DISS_PRECIP[COMP_5] = if VOL_5=0 then 0 else if
  (SOL_5/VOL_5<ADJ_SOLUB[COMP_5]) then
  (DISSOL[COMP_5]*DISS_ADJ[COMP_5]*MASS_5*(ADJ_SOLUB[COMP_5]-SOL_5/VOL_5)) else
  ((SOL_5/VOL_5)-ADJ_SOLUB[COMP_5])*PRECIP[COMP_5]
  +0*(MASS_1+MASS_2+MASS_3+MASS_4+MASS_5+SOL_1+SOL_2+SOL_3+SOL_4+SOL_5+V
  OL_1+VOL_2+VOL_3+VOL_4+VOL_5)
○ DISSOL[COMP_1] = 1
○ DISSOL[COMP_2] = 1
○ DISSOL[COMP_3] = 1
○ DISSOL[COMP_4] = 1
○ DISSOL[COMP_5] = 1
○ PRECIP[COMP_1] = 10
○ PRECIP[COMP_2] = 10
○ PRECIP[COMP_3] = 10
○ PRECIP[COMP_4] = 10
○ PRECIP[COMP_5] = 10
▣ INPUTS
▣ INTESTINAL MODEL
☐ ABSORPTION_1(t) = ABSORPTION_1(t - dt) + (FLUX_1) * dt
  INIT ABSORPTION_1 = 0
  INFLOWS:
    ⇶ FLUX_1 =
      CONCENTRATIONS[COMP_1]*ADJ_PERM[COMP_1]*SURFACE_AREA[COMP_1]

☐ ABSORPTION_2(t) = ABSORPTION_2(t - dt) + (FLUX_2) * dt
  INIT ABSORPTION_2 = 0
  INFLOWS:
    ⇶ FLUX_2 =
      CONCENTRATIONS[COMP_2]*ADJ_PERM[COMP_2]*SURFACE_AREA[COMP_2]

☐ ABSORPTION_3(t) = ABSORPTION_3(t - dt) + (FLUX_3) * dt
  INIT ABSORPTION_3 = 0
  INFLOWS:
    ⇶ FLUX_3 =
      CONCENTRATIONS[COMP_3]*ADJ_PERM[COMP_3]*SURFACE_AREA[COMP_3]

☐ ABSORPTION_4(t) = ABSORPTION_4(t - dt) + (FLUX_4) * dt
  INIT ABSORPTION_4 = 0
  INFLOWS:

⇶ FLUX_4 = CONCENTRATIONS[COMP_4]*ADJ_PERM[COMP_4]*SURFACE_AREA[COMP_4]

▢ ABSORPTION_5(t) = ABSORPTION_5(t - dt) + (FLUX_5) * dt
INIT ABSORPTION_5 = 0
  INFLOWS:
    ⇶ FLUX_5 = if time<32 then CONCENTRATIONS[COMP_5]*ADJ_PERM[COMP_5]*SURFACE_AREA[COMP_5]*(32-time)/48*(VOL_5/17.2) else 0

▢ C_REL_1(t) = C_REL_1(t - dt) + (- CR_OUT_1 - CR_INPUT_1) * dt
INIT C_REL_1 = CR_DOSE
  OUTFLOWS:
    ⇶ CR_OUT_1 = IF TIME >= CUMU_TT[COMP_1] THEN C_REL_1*10000 ELSE 0
    ⇶ CR_INPUT_1 = if TIME>CUMU_TT[COMP_1] then 0 else CR_RATE ▢ C_REL_2(t) = C_REL_2(t - dt) + (CR_OUT_1 - CR_OUT_2 - CR_INPUT_2) * dt
INIT C_REL_2 = 0
  INFLOWS:
    ⇶ CR_OUT_1 = IF TIME >= CUMU_TT[COMP_1] THEN C_REL_1*10000 ELSE 0
  OUTFLOWS:
    ⇶ CR_OUT_2 = IF TIME >= CUMU_TT[COMP_2] THEN C_REL_2*10000 ELSE 0
    ⇶ CR_INPUT_2 = if TIME>CUMU_TT[COMP_2] then 0 else CR_RATE ▢ C_REL_3(t) = C_REL_3(t - dt) + (CR_OUT_2 - CR_OUT_3 - CR_INPUT_3) * dt
INIT C_REL_3 = 0
  INFLOWS:
    ⇶ CR_OUT_2 = IF TIME >= CUMU_TT[COMP_2] THEN C_REL_2*10000 ELSE 0
  OUTFLOWS:
    ⇶ CR_OUT_3 = IF TIME >= CUMU_TT[COMP_3] THEN C_REL_3*10000 ELSE 0
    ⇶ CR_INPUT_3 = if TIME > CUMU_TT[COMP_3] then 0 else CR_RATE ▢ C_REL_4(t) = C_REL_4(t - dt) + (CR_OUT_3 - CR_OUT_4 - CR_INPUT_4) * dt
INIT C_REL_4 = 0
  INFLOWS:
    ⇶ CR_OUT_3 = IF TIME >= CUMU_TT[COMP_3] THEN C_REL_3*10000 ELSE 0
  OUTFLOWS:
    ⇶ CR_OUT_4 = IF TIME >= CUMU_TT[COMP_4] THEN C_REL_4*10000 ELSE 0
    ⇶ CR_INPUT_4 = if TIME>CUMU_TT[COMP_4] then 0 else CR_RATE ▢ C_REL_5(t) = C_REL_5(t - dt) + (CR_OUT_4 - CR_OUT_5 - CR_INPUT_5) * dt
INIT C_REL_5 = 0
  INFLOWS:
    ⇶ CR_OUT_4 = IF TIME >= CUMU_TT[COMP_4] THEN C_REL_4*10000 ELSE 0
  OUTFLOWS:
    ⇶ CR_OUT_5 = IF TIME >= CUMU_TT[COMP_5] THEN C_REL_5*10000 ELSE 0
    ⇶ CR_INPUT_5 = if TIME>CUMU_TT[COMP_5] then 0 else CR_RATE ▢ C_REL_6(t) = C_REL_6(t - dt) + (CR_OUT_5) * dt
INIT C_REL_6 = 0
  INFLOWS:
    ⇶ CR_OUT_5 = IF TIME >= CUMU_TT[COMP_5] THEN C_REL_5*10000 ELSE 0

```
MASS_1(t) = MASS_1(t - dt) + (CR_INPUT_1 - MASS_OUT_1 - DISS_PRECIP_1) * dt
INIT MASS_1 = DOSE
    INFLOWS:
        CR_INPUT_1 = if TIME>CUMU_TT[COMP_1] then 0 else CR_RATE
    OUTFLOWS:
        MASS_OUT_1 = MASS_1*TRANSFERS[COMP_1]
        DISS_PRECIP_1 = ADJ_DISS_PRECIP[COMP_1]
MASS_2(t) = MASS_2(t - dt) + (MASS_OUT_1 + CR_INPUT_2 - MASS_OUT_2 -
DISS_PRECIP_2) * dt
INIT MASS_2 = 0
    INFLOWS:
        MASS_OUT_1 = MASS_1*TRANSFERS[COMP_1]
        CR_INPUT_2 = if TIME>CUMU_TT[COMP_2] then 0 else CR_RATE
    OUTFLOWS:
        MASS_OUT_2 = MASS_2*TRANSFERS[COMP_2]
        DISS_PRECIP_2 = ADJ_DISS_PRECIP[COMP_2]
MASS_3(t) = MASS_3(t - dt) + (CR_INPUT_3 + MASS_OUT_2 - MASS_OUT_3 -
DISS_PRECIP_3) * dt
INIT MASS_3 = 0
    INFLOWS:
        CR_INPUT_3 = if TIME > CUMU_TT[COMP_3] then 0 else CR_RATE
        MASS_OUT_2 = MASS_2*TRANSFERS[COMP_2]
    OUTFLOWS:
        MASS_OUT_3 = MASS_3*TRANSFERS[COMP_3]
        DISS_PRECIP_3 = ADJ_DISS_PRECIP[COMP_3]
MASS_4(t) = MASS_4(t - dt) + (CR_INPUT_4 + MASS_OUT_3 - MASS_OUT_4 -
DISS_PRECIP_4) * dt
INIT MASS_4 = 0
    INFLOWS:
        CR_INPUT_4 = if TIME>CUMU_TT[COMP_4] then 0 else CR_RATE
        MASS_OUT_3 = MASS_3*TRANSFERS[COMP_3]
    OUTFLOWS:
        MASS_OUT_4 = MASS_4*TRANSFERS[COMP_4]
        DISS_PRECIP_4 = ADJ_DISS_PRECIP[COMP_4]
MASS_5(t) = MASS_5(t - dt) + (CR_INPUT_5 + MASS_OUT_4 - MASS_OUT_5 -
DISS_PRECIP_5) * dt
INIT MASS_5 = 0
    INFLOWS:
        CR_INPUT_5 = if TIME>CUMU_TT[COMP_5] then 0 else CR_RATE
        MASS_OUT_4 = MASS_4*TRANSFERS[COMP_4]
    OUTFLOWS:
        MASS_OUT_5 = if time>4 then MASS_5*TRANSFERS[COMP_5] else 0
        DISS_PRECIP_5 = ADJ_DISS_PRECIP[COMP_5]
MASS_6(t) = MASS_6(t - dt) + (MASS_OUT_5) * dt
INIT MASS_6 = 0
    INFLOWS:
```

```
MASS_OUT_5 = if time>4 then MASS_5*TRANSFERS[COMP_5] else 0
SOL_1(t) = SOL_1(t - dt) + (DISS_PRECIP_1 - SOL_OUT_1 - FLUX_1) * dt
INIT SOL_1 = 0
INFLOWS:
    DISS_PRECIP_1 = ADJ_DISS_PRECIP[COMP_1]
OUTFLOWS:
    SOL_OUT_1 = SOL_1*TRANSFERS[COMP_1]
    FLUX_1 =
        CONCENTRATIONS[COMP_1]*ADJ_PERM[COMP_1]*SURFACE_AREA[COMP_1]

SOL_2(t) = SOL_2(t - dt) + (SOL_OUT_1 + DISS_PRECIP_2 - SOL_OUT_2 - FLUX_2) * dt
INIT SOL_2 = 0

INFLOWS:
    SOL_OUT_1 = SOL_1*TRANSFERS[COMP_1]
    DISS_PRECIP_2 = ADJ_DISS_PRECIP[COMP_2]
OUTFLOWS:
    SOL_OUT_2 = SOL_2*TRANSFERS[COMP_2]
    FLUX_2 =
        CONCENTRATIONS[COMP_2]*ADJ_PERM[COMP_2]*SURFACE_AREA[COMP_2]

SOL_3(t) = SOL_3(t - dt) + (DISS_PRECIP_3 + SOL_OUT_2 - SOL_OUT_3 - FLUX_3) * dt
INIT SOL_3 = 0

INFLOWS:
    DISS_PRECIP_3 = ADJ_DISS_PRECIP[COMP_3]
    SOL_OUT_2 = SOL_2*TRANSFERS[COMP_2]
OUTFLOWS:
    SOL_OUT_3 = SOL_3*TRANSFERS[COMP_3]
    FLUX_3 =
        CONCENTRATIONS[COMP_3]*ADJ_PERM[COMP_3]*SURFACE_AREA[COMP_3]

SOL_4(t) = SOL_4(t - dt) + (DISS_PRECIP_4 + SOL_OUT_3 - SOL_OUT_4 - FLUX_4) * dt
INIT SOL_4 = 0

INFLOWS:
    DISS_PRECIP_4 = ADJ_DISS_PRECIP[COMP_4]
    SOL_OUT_3 = SOL_3*TRANSFERS[COMP_3]
OUTFLOWS:
    SOL_OUT_4 = SOL_4*TRANSFERS[COMP_4]
    FLUX_4 =
        CONCENTRATIONS[COMP_4]*ADJ_PERM[COMP_4]*SURFACE_AREA[COMP_4]

SOL_5(t) = SOL_5(t - dt) + (DISS_PRECIP_5 + SOL_OUT_4 - SOL_OUT_5 - FLUX_5) * dt
INIT SOL_5 = 0

INFLOWS:
```

- DISS_PRECIP_5 = ADJ_DISS_PRECIP[COMP_5]
- SOL_OUT_4 = SOL_4*TRANSFERS[COMP_4]
OUTFLOWS:
- SOL_OUT_5 = if time>4 then SOL_5*TRANSFERS[COMP_5] else 0
- FLUX_5 = if time<32 then CONCENTRATIONS[COMP_5]*ADJ_PERM[COMP_5]*SURFACE_AREA[COMP_5]*(32-time)/48*(VOL_5/17.2) else 0

☐ SOL_6(t) = SOL_6(t - dt) + (SOL_OUT_5) * dt
INIT SOL_6 = 0
INFLOWS:
- SOL_OUT_5 = if time>4 then SOL_5*TRANSFERS[COMP_5] else 0

☐ VOL_1(t) = VOL_1(t - dt) + (- REABS_1 - VOL_OUT_1) * dt
INIT VOL_1 = INIT_VOLUME
OUTFLOWS:
- REABS_1 = VOL_1*VOL_PARM[COMP_1]
- VOL_OUT_1 = VOL_1*TRANSFERS[COMP_1]

☐ VOL_2(t) = VOL_2(t - dt) + (VOL_OUT_1 - VOL_OUT_2 - REABS_2) * dt
INIT VOL_2 = 0
INFLOWS:
- VOL_OUT_1 = VOL_1*TRANSFERS[COMP_1]
OUTFLOWS:
- VOL_OUT_2 = VOL_2*TRANSFERS[COMP_2]
- REABS_2 = VOL_2*VOL_PARM[COMP_2]

☐ VOL_3(t) = VOL_3(t - dt) + (VOL_OUT_2 - VOL_OUT_3 - REABS_3) * dt
INIT VOL_3 = 0
INFLOWS:
- VOL_OUT_2 = VOL_2*TRANSFERS[COMP_2]
OUTFLOWS:
- VOL_OUT_3 = VOL_3*TRANSFERS[COMP_3]
- REABS_3 = VOL_3*VOL_PARM[COMP_3]

☐ VOL_4(t) = VOL_4(t - dt) + (VOL_OUT_3 - VOL_OUT_4 - REABS_4) * dt
INIT VOL_4 = 0
INFLOWS:
- VOL_OUT_3 = VOL_3*TRANSFERS[COMP_3]
OUTFLOWS:
- VOL_OUT_4 = VOL_4*TRANSFERS[COMP_4]
- REABS_4 = VOL_4*VOL_PARM[COMP_4]

☐ VOL_5(t) = VOL_5(t - dt) + (VOL_OUT_4 - VOL_OUT_5 - REABS_5) * dt
INIT VOL_5 = 0
INFLOWS:
- VOL_OUT_4 = VOL_4*TRANSFERS[COMP_4]
OUTFLOWS:
- VOL_OUT_5 = VOL_5*TRANSFERS[COMP_5]
- REABS_5 = VOL_5*VOL_PARM[COMP_5]

☐ VOL_6(t) = VOL_6(t - dt) + (VOL_OUT_5) * dt
INIT VOL_6 = 0

INFLOWS:
  VOL_OUT_5 = VOL_5*TRANSFERS[COMP_5]
VOL_ABS_1(t) = VOL_ABS_1(t - dt) + (REABS_1) * dt
INIT VOL_ABS_1 = 0
  INFLOWS:
    REABS_1 = VOL_1*VOL_PARM[COMP_1]
VOL_ABS_2(t) = VOL_ABS_2(t - dt) + (REABS_2) * dt
INIT VOL_ABS_2 = 0
  INFLOWS:
    REABS_2 = VOL_2*VOL_PARM[COMP_2]
VOL_ABS_3(t) = VOL_ABS_3(t - dt) + (REABS_3) * dt
INIT VOL_ABS_3 = 0
  INFLOWS:
    REABS_3 = VOL_3*VOL_PARM[COMP_3]
VOL_ABS_4(t) = VOL_ABS_4(t - dt) + (REABS_4) * dt
INIT VOL_ABS_4 = 0
  INFLOWS:
    REABS_4 = VOL_4*VOL_PARM[COMP_4]
VOL_ABS_5(t) = VOL_ABS_5(t - dt) + (REABS_5) * dt
INIT VOL_ABS_5 = 0
  INFLOWS:
    REABS_5 = VOL_5*VOL_PARM[COMP_5]
MULTI DOSE CALCULATION
OUTPUT CALCULATIONS
  CR_Release(t) = CR_Release(t - dt) + (CR_cumrate) * dt
  INIT CR_Release = 0
    INFLOWS:
      CR_cumrate = CR_INPUT_1+CR_INPUT_2+CR_INPUT_3+CR_INPUT_4+CR_INPUT_5

CUM_DISS(t) = CUM_DISS(t - dt) + (CUMM_DISS_RATE) * dt
  INIT CUM_DISS = 0
    INFLOWS:
      CUMM_DISS_RATE =
        DISS_PRECIP_1+DISS_PRECIP_2+DISS_PRECIP_3+DISS_PRECIP_4+DISS_PRECIP
        5
  ABSORBED_TOTAL = ABSORPTION_2+ABSORPTION_3+ABSORPTION_4+ABSORPTION_5

FDp% = ABSORBED_TOTAL/DOSE*100
  FLUX_TOTAL = FLUX_2+FLUX_3+FLUX_4+FLUX_5
PARMS
  DOSE = 1000
  INIT_VOLUME = 100
  PARACELLULAR = 1
  pH[COMP_1] = 1.5
  pH[COMP_2] = 5
  pH[COMP_3] = 6.5

- pH[COMP_4] = 7
- pH[COMP_5] = 6.5
- SURFACE_AREA[COMP_1] = if PARACELLULAR =0 then 50*SA_ADJ[COMP_1] else 50*SA_ADJ[COMP_1]
- SURFACE_AREA[COMP_2] = if PARACELLULAR=0 then 150*SA_ADJ[COMP_2] else 7.5*SA_ADJ[COMP_2]
- SURFACE_AREA[COMP_3] = if PARACELLULAR=0 then 1000*SA_ADJ[COMP_3] else 50*SA_ADJ[COMP_3]
- SURFACE_AREA[COMP_4] = if PARACELLULAR=0 then 1000*SA_ADJ[COMP_4] else 50*SA_ADJ[COMP_4]
- SURFACE_AREA[COMP_5] = if PARACELLULAR=0 then 850*SA_ADJ[COMP_5] else 42.5*SA_ADJ[COMP_5]
- TIME_IN_HOURS = TIME
- VOL_PARM[COMP_1] = 0*VOL_ADJ[COMP_1]
- VOL_PARM[COMP_2] = 0*VOL_ADJ[COMP_2]
- VOL_PARM[COMP_3] = 1.75*VOL_ADJ[COMP_3]
- VOL_PARM[COMP_4] = 1.75*VOL_ADJ[COMP_4]
- VOL_PARM[COMP_5] = 0.10*VOL_ADJ[COMP_5]

PERMEABILITY CALCULATION
- ACT_PE[COMPS] = [0 ,
  0 ,
  0 ,
  0 ,
  0 ]
- ADJ_PERM[COMP_1] = (2/(1+EFFLUX_ADJ[COMP_1]))*REGIONAL[COMP_1]*FLUX_ADJ[COMP_1]*3600+(CARRIER_ DJ[COMP_1]*ACT_PE[COMP_1]*3600/(1+(CONCENTRATIONS[COMP_1]/(Km[COMP_1]))))*0

- ADJ_PERM[COMP_2] = (2/(1+EFFLUX_ADJ[COMP_2]))*REGIONAL[COMP_2]*FLUX_ADJ[COMP_2]*3600+(CARRIER_ DJ[COMP_2]*ACT_PE[COMP_2]*3600/(1+(CONCENTRATIONS[COMP_2]/(Km[COMP_2]))))

- ADJ_PERM[COMP_3] = (2/(1+EFFLUX_ADJ[COMP_3]))*REGIONAL[COMP_3]*FLUX_ADJ[COMP_3]*3600+(CARRIER_ DJ[COMP_3]*ACT_PE[COMP_3]*3600/(1+(CONCENTRATIONS[COMP_3]/(Km[COMP_3]))))

- ADJ_PERM[COMP_4] = (2/(1+EFFLUX_ADJ[COMP_4]))*REGIONAL[COMP_4]*FLUX_ADJ[COMP_4]*3600+(CARRIER_ DJ[COMP_4]*ACT_PE[COMP_4]*3600/(1+(CONCENTRATIONS[COMP_4]/(Km[COMP_4]))))

- ADJ_PERM[COMP_5] = (2/(1+EFFLUX_ADJ[COMP_5]))*REGIONAL[COMP_5]*FLUX_ADJ[COMP_5]*3600+(CARRIER_ DJ[COMP_5]*ACT_PE[COMP_5]*3600/(1+(CONCENTRATIONS[COMP_5]/(Km[COMP_5]))))

- Km[COMPS] = [1 ,
  1 ,
  1 ,
  1 ,
  1 ]
- PASS_PE[COMPS] = [0 ,
  1.10E-06 ,
  2.17E-06 ,
  4.06E-06 ,
  3.80E-06 ]
- RC[COMP_1] = PASS_PE[COMP_1]*0
- RC[COMP_2] = IF PASS_PE[COMP_2]>0 THEN 1 ELSE 0
- RC[COMP_3] = IF PASS_PE[COMP_3]>0 THEN 2 ELSE 0
- RC[COMP_4] = IF PASS_PE[COMP_4]>0 THEN 4 ELSE 0
- RC[COMP_5] = PASS_PE[COMP_5]*0
- RCSUM = RC[COMP_2]+RC[COMP_3]+RC[COMP_4]
- REGIONAL[COMP_1] = PASS_PE[COMP_1]+RCSUM*0
- REGIONAL[COMP_2] = if RCSUM=2 then
  (EXP( -9.011926 + 2.594378 *LOGN(1/PASS_PE[COMP_2]) -0.065515
  *LOGN(1/PASS_PE[COMP_2])^2))^(-1) else
  if RCSUM=4 then (EXP(-0.369414*LOGN(1/PASS_PE[COMP_4])+0.23756*LOGN(1/PASS_PE[COMP_4])^2-0.009
  9719*LOGN(1/PASS_PE[COMP_4])^3))^(-1) else
  if RCSUM=6 then
  0.5*(EXP( -9.011926 + 2.594378 *LOGN(1/PASS_PE[COMP_3]) -0.065515
  *LOGN(1/PASS_PE[COMP_3])^2))^(-1)
  +0.5*(EXP( -21.009845 + 4.544238 *LOGN(1/PASS_PE[COMP_4]) -0.140815
  *LOGN(1/PASS_PE[COMP_4])^2))^(-1) else
  PASS_PE[COMP_2]
- REGIONAL[COMP_3] = if RCSUM=1 then
  (EXP( -3.238469 + 1.509131 *LOGN(1/PASS_PE[COMP_2]) -0.022109
  *LOGN(1/PASS_PE[COMP_2])^2))^(-1) else
  if RCSUM=4 then (EXP(-0.093739*LOGN(1/PASS_PE[COMP_4])+0.182344*LOGN(1/PASS_PE[COMP_4])^2-0.00
  23631*LOGN(1/PASS_PE[COMP_4])^3))^(-1) else
  if RCSUM=5 then
  0.5*(EXP( -3.238469 + 1.509131 *LOGN(1/PASS_PE[COMP_2]) -0.022109
  *LOGN(1/PASS_PE[COMP_2])^2))^(-1)
  +0.5*(EXP( -15.415683 + 3.543563 *LOGN(1/PASS_PE[COMP_4]) -0.100318
  *LOGN(1/PASS_PE[COMP_4])^2))^(-1) else
  PASS_PE[COMP_3]

- REGIONAL[COMP_4] = if RCSUM=1 then
  (EXP( 14.455255 -1.264630 *LOGN(1/PASS_PE[COMP_2]) + 0.082015
  *LOGN(1/PASS_PE[COMP_2])^2))^(-1) else
  if RCSUM=2 then
  (EXP( 11.480333 -0.791109 *LOGN(1/PASS_PE[COMP_3]) + 0.066063
  *LOGN(1/PASS_PE[COMP_3])^2))^(-1) else
  if RCSUM=3 then
  0.5*(EXP( 14.455255 -1.264630 *LOGN(1/PASS_PE[COMP_2]) + 0.082015
  *LOGN(1/PASS_PE[COMP_2])^2))^(-1)
  +0.5*(EXP( 11.480333 -0.791109 *LOGN(1/PASS_PE[COMP_3]) + 0.066063
  *LOGN(1/PASS_PE[COMP_3])^2))^(-1) else
  PASS_PE[COMP_4]
- REGIONAL[COMP_5] = PASS_PE[COMP_5] +RCSUM*0

▣ SOLUBILIY CALCULATION
- ADJ_SOLUB[COMP_1] = if USER_pH[COMP_1]>=pH[COMP_1] then USER_SOLUB[COMP_1]
  else
  ((USER_SOLUB[COMP_2]-USER_SOLUB[COMP_1])/(USER_pH[COMP_2]-USER_pH[COMP_1]
  ))*(pH[COMP_1]-USER_pH[COMP_1])+USER_SOLUB[COMP_1]
- ADJ_SOLUB[COMP_2] = if USER_pH[COMP_2]=pH[COMP_2] then USER_SOLUB[COMP_2]
  else if USER_pH[COMP_2]<pH[COMP_2] then
  ((USER_SOLUB[COMP_3]-USER_SOLUB[COMP_2])/(USER_pH[COMP_3]-USER_pH[COMP_2]
  ))*(pH[COMP_2]-USER_pH[COMP_2])+USER_SOLUB[COMP_2] else
  ((USER_SOLUB[COMP_2]-USER_SOLUB[COMP_1])/(USER_pH[COMP_2]-USER_pH[COMP_1]
  ))*(pH[COMP_2]-USER_pH[COMP_1])+USER_SOLUB[COMP_1]
- ADJ_SOLUB[COMP_3] = if USER_pH[COMP_3]=pH[COMP_3] then USER_SOLUB[COMP_3]
  else if USER_pH[COMP_3]<pH[COMP_3] then
  ((USER_SOLUB[COMP_4]-USER_SOLUB[COMP_3])/(USER_pH[COMP_4]-USER_pH[COMP_3]
  ))*(pH[COMP_3]-USER_pH[COMP_3])+USER_SOLUB[COMP_3] else
  ((USER_SOLUB[COMP_3]-USER_SOLUB[COMP_2])/(USER_pH[COMP_3]-USER_pH[COMP_2]
  ))*(pH[COMP_3]-USER_pH[COMP_2])+USER_SOLUB[COMP_2]
- ADJ_SOLUB[COMP_4] = if USER_pH[COMP_4]=pH[COMP_4] then USER_SOLUB[COMP_4]
  else if USER_pH[COMP_4]<pH[COMP_4] then
  ((USER_SOLUB[COMP_5]-USER_SOLUB[COMP_4])/(USER_pH[COMP_5]-USER_pH[COMP_4]
  ))*(pH[COMP_4]-USER_pH[COMP_4])+USER_SOLUB[COMP_4] else
  ((USER_SOLUB[COMP_4]-USER_SOLUB[COMP_3])/(USER_pH[COMP_4]-USER_pH[COMP_3]
  ))*(pH[COMP_4]-USER_pH[COMP_3])+USER_SOLUB[COMP_3]
- ADJ_SOLUB[COMP_5] = if USER_pH[COMP_3]=pH[COMP_3] then USER_SOLUB[COMP_3]
  else if USER_pH[COMP_3]<pH[COMP_3] then
  ((USER_SOLUB[COMP_4]-USER_SOLUB[COMP_3])/(USER_pH[COMP_4]-USER_pH[COMP_3]
  ))*(pH[COMP_3]-USER_pH[COMP_3])+USER_SOLUB[COMP_3] else
  ((USER_SOLUB[COMP_3]-USER_SOLUB[COMP_2])/(USER_pH[COMP_3]-USER_pH[COMP_2]
  ))*(pH[COMP_3]-USER_pH[COMP_2])+USER_SOLUB[COMP_2]
- USER_pH[COMPS] = [1.5 ,
  5 ,
  6.5 ,
  7 ,
  7.5 ]

- USER_SOLUB[COMPS] = [31 ,
  3.65 ,
  3.65 ,
  3.65 ,
  3.65 ,
  3.65 ]
- TRANSIT TIME
  - ADJ_TRANSIT_TIME[COMP_1] = .5*TRANSIT_ADJ[COMP_1]*USER_TT_INPUT
  - ADJ_TRANSIT_TIME[COMP_2] = .25*TRANSIT_ADJ[COMP_2]*USER_TT_INPUT
  - ADJ_TRANSIT_TIME[COMP_3] = 1.5*TRANSIT_ADJ[COMP_3]*USER_TT_INPUT
  - ADJ_TRANSIT_TIME[COMP_4] = 1.5*TRANSIT_ADJ[COMP_4]*USER_TT_INPUT
  - ADJ_TRANSIT_TIME[COMP_5] = 24*TRANSIT_ADJ[COMP_5]*USER_TT_INPUT
  - CUMU_TT[COMP_1] = ADJ_TRANSIT_TIME[COMP_1]
  - CUMU_TT[COMP_2] = ADJ_TRANSIT_TIME[COMP_1]+ADJ_TRANSIT_TIME[COMP_2]
  - CUMU_TT[COMP_3] = ADJ_TRANSIT_TIME[COMP_1]+ADJ_TRANSIT_TIME[COMP_2]+ADJ_TRANSIT_TIME[COMP_3]
  - CUMU_TT[COMP_4] = ADJ_TRANSIT_TIME[COMP_1]+ADJ_TRANSIT_TIME[COMP_2]+ADJ_TRANSIT_TIME[COMP_3]+ADJ_TRANSIT_TIME[COMP_4]
  - CUMU_TT[COMP_5] = ADJ_TRANSIT_TIME[COMP_1]+ADJ_TRANSIT_TIME[COMP_2]+ADJ_TRANSIT_TIME[COMP_3]+ADJ_TRANSIT_TIME[COMP_4]+ADJ_TRANSIT_TIME[COMP_5]
  - TRANSFERS[COMP_1] = LOGN(10)/ADJ_TRANSIT_TIME[COMP_1]
  - TRANSFERS[COMP_2] = LOGN(10)/ADJ_TRANSIT_TIME[COMP_2]
  - TRANSFERS[COMP_3] = LOGN(10)/ADJ_TRANSIT_TIME[COMP_3]
  - TRANSFERS[COMP_4] = LOGN(10)/ADJ_TRANSIT_TIME[COMP_4]
  - TRANSFERS[COMP_5] = LOGN(10)/ADJ_TRANSIT_TIME[COMP_5]
  - USER_TT_INPUT = 1

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of optimizing a model for predicting a pharmacokinetic property of a compound in a mammalian system of interest, the method comprising:
   (i) assigning an initial value to a selected adjustment parameter of the model;
   (ii) inputting first data for a plurality of compounds into the model and running the model to generate output data;
   (iii) comparing the output data with second data for the plurality of compounds;
   (iv) selecting a new value for the selected adjustment parameter such that deviation of the comparison in step (iii) is reduced; and
   (v) replacing the value for the selected adjustment parameter in the model with the new value selected in step (iv).

2. The method of claim 1, wherein the first and second data are stored in the same data source.

3. The method of claim 1, wherein the first data is stored in a first data source and the second data is stored in a second data source.

4. The method of claim 1, wherein the selected adjustment parameter is a plurality of selected adjustment parameters and wherein step (i) assigns an initial value to each of the plurality of selected adjustment parameters, step (iv) selects a new value for one or more of the plurality of selected adjustment parameters, and step (v) replaces the value for the one or more of the plurality of selected adjustment parameters with the new value selected in step (iv).

5. The method of claim 1, wherein the selectively optimized adjustment parameter values are selected from the group consisting of constants, ranges of constants, functions and algorithms.

6. The method of claim 1, further comprising:
   (vi) repeating steps (ii)–(v) one or more times until a difference between the output data and the second data is less than the largest experimental error in the first or second data or less than the largest interday variation in the first or second data.

7. The method of claim 6, wherein the difference is determined by one of the following: normalized difference, collective regression coefficient, normalized arithmetic mean, normalized median, normalized geometric mean, normalized harmonic mean, variance, standard deviation, or coefficient of variation.

8. The method of claim 6, further comprising:
   (vii) storing the selectively optimized adjustment parameter value in a database.

9. The method of claim 8, wherein the selectively optimized adjustment parameter values are stored in a computer-implemented database.

10. The method of claim 1, wherein the model comprises a physiologic pharmacokinetic model of one or more anatomical segments of the mammalian system of interest.

11. The method of claim 10, wherein the physiologic pharmacokinetic model determines the change in one or more physiological parameters of the one or more anatomical segments and the movement and disposition of the compound in the one or more anatomical segments as a function of time.

12. The method of claim 10, wherein the mammalian system of interest is selected from the group consisting of gastrointestinal tract, liver, heart, kidney, eye, nose, lung, skin and brain.

13. The method of claim 10, wherein the mammalian system of interest is human.

14. The method of claim 10, wherein the first data corresponds to one or more in vitro properties for each of the plurality of compounds.

15. The method of claim 14, wherein the first data is derived from testing of each of the plurality of compounds for at least one in vitro property in an assay that generates data, the assay selected from the group consisting of cell, tissue, physicochemical, structure-activity relationship (SAR), and quantitative structure-activity relationship (QSAR).

16. The method of claim 14, wherein the in vitro properties are selected from the group consisting of absorption, distribution, metabolism, elimination, and toxicity.

17. The method of claim 10, wherein the second data corresponds to one or more in vivo properties for each of the plurality of compounds.

18. The method of claim 17, wherein the in vivo properties are selected from the group consisting of absorption, distribution, metabolism, elimination, and toxicity.

19. The method of claim 18, wherein the plurality of compounds include compounds exhibiting different in vivo properties in the mammalian system of interest.

20. The method of claim 19, wherein the in vivo properties are selected from the group consisting of permeability, solubility, dissolution, activity, metabolism, and toxicity.

21. The method of claim 20 wherein the one or more in vivo properties are derived from testing each of the plurality of compounds in the mammalian system of interest for the one or more in viva properties.

22. The method of claim 1, wherein the selecting step comprises a curve-fitting algorithm.

23. The method of claim 22, wherein the curve-fitting algorithm is a regression-based algorithm.

24. The method of claim 22, wherein the curve-fitting algorithm is a plurality of curve fitting algorithms.

25. The method of claim 24, wherein the plurality of curve fitting algorithms are used simultaneously.

26. A computer-implemented method of optimizing a model for predicting an in vivo property of a compound in a mammalian system of interest, the method comprising:
   (i) providing a computer containing the model;
   (ii) assigning an initial value to a selected adjustment parameter of the model;
   (iii) inputting first data for a plurality of compounds into the model on the computer to generate output data;
   (iv) comparing the output data with second data for the plurality of compounds;
   (v) selecting a new value for the selected adjustment parameter such that deviation of the comparison in step (iv) is reduced; and
   (vi) replacing the value for the selected adjustment parameter in the model with the new value selected in step (v).

27. The method of claim 26, wherein the first and second data are stored in the same data source.

28. The method of claim 26, wherein the first data is stored in a first data source and the second data is stored in a second data source.

29. The method of claim 26, further comprising:
(vii) repeating steps (iii)–(vi) one or more times until a difference between the output data and the second data is less than the largest experimental error in the first or second data or less than the largest interday variation in the first or second data.

30. The method of claim 29, wherein the difference is determined by one of the following: normalized difference, collective regression coefficient, normalized arithmetic mean, normalized median, normalized geometric mean, normalized harmonic mean, variance, standard deviation, or coefficient of variation.

31. The method of claim 26, further comprising:
(vii) storing the selected adjustment parameter value in a computer-implemented database.

32. The method of claim 26, wherein the selected adjustment parameter is a plurality of selected adjustment parameters and wherein step (ii) assigns an initial value to each of the plurality of selected adjustment parameters, step (v) selects a new value for one or more of the plurality of selected adjustment parameters and step (vi) replaces the value for the one or more of the plurality of selected adjustment parameters with the new value selected in step (v).

33. The method of claim 26, wherein the selected adjustment parameter value is selected from the group consisting of a constant, a range of constants, a function and an algorithm.

34. The method of claim 26, wherein the model comprises a physiologic pharmacokinetic model of one or more anatomical segments of the mammalian system of interest.

35. The method of claim 26, wherein the mammalian system of interest is selected from the group consisting of gastrointestinal tract, liver, heart, kidney, eye, nose, lung, skin and brain.

36. The method of claim 26, wherein the mammalian system of interest is human.

37. The method of claim 26, wherein the physiologic pharmacokinetic model determines the change in one or more physiological parameters of the one or more anatomical segments and the movement and disposition of the compound in the one or more anatomical segments as a function of time.

38. The method of claim 37, wherein the first data corresponds to one or more in vitro properties for each of the plurality of compounds.

39. The method of claim 38, wherein the first data is derived from testing of each of the plurality of compounds for at least one in vitro property in an assay that generates data, the assay selected from the group consisting of cell, tissue, physicochemical, structure-activity relationship (SAR), and quantitative structure-activity relationship (QSAR).

40. The method of claim 38, wherein the in vitro properties are selected from the group consisting of absorption, distribution, metabolism, elimination, and toxicity.

41. The method of claim 37, wherein the second data corresponds to one or more in vivo properties for each of the plurality of compounds.

42. The method of claim 41, wherein the in vivo properties are selected from the group consisting of absorption, distribution, metabolism, elimination, and toxicity.

43. The method of claim 41, wherein the plurality of compounds include compounds exhibiting different in vivo properties in the mammalian system of interest.

44. The method of claim 43, wherein the in vivo properties are selected from the group consisting of permeability, solubility, dissolution, activity, metabolism, and toxicity.

45. The method of claim 44 wherein the one or more in vivo properties are derived from testing each of the plurality of compounds in the mammalian system of interest for the one or more in vivo properties.

46. The method of claim 26, wherein the selecting step comprises a curve-fitting algorithm.

47. The method of claim 46, wherein the curve-fitting algorithm is a plurality of curve fitting algorithms.

48. The method of claim 47, wherein the provided computer contains the curve fitting algorithms and wherein the plurality of curve fitting algorithms are used simultaneously.

49. The method of claim 46, wherein the curve-fitting algorithm is a regression-based algorithm.

50. The method of claim 49, wherein the provided computer contains the curve fitting algorithm.

51. A computer-implemented method of generating optimized values for adjustment parameters of a physiologic-based model, the model predicting an in vivo property of a compound in a mammalian system of interest from an in vitro property of the compound, the method comprising:
(i) providing a computer having a curve-fitting algorithm and the physiologic-based model of the mammalian system of interest, the model comprising two or more equations, the model having as an output a predicted in vivo property of a compound in the mammalian system as a function of time, and at least two of the two or more equations are each modified by at least one adjustment parameter;
(ii) assigning an initial value to each of a plurality of adjustment parameters of the model;
(iii) inputting data from a first data source into the model and running the model to generate output data, the first data source containing first data for a plurality of compounds;
(iv) comparing the output data with a second data source, the second data source containing second data for the plurality of compounds;
(v) selecting a new value for one or more of the plurality of adjustment parameters such that deviation of the comparison in step (iv) is reduced using at least the curve-fitting algorithm on the computer; and
(vi) replacing the value for the one or more of the plurality of adjustment parameters in the model with the new value selected in step (v).

52. The method of claim 51, further comprising:
(vii) repeating steps (iii)-(vi) one or more times until a difference between the output data and the second data is less than the largest experimental error in the first or second data or less than the largest interday variation in the first or second data.

53. The method of claim 52, wherein the difference is determined by one of the following: normalized difference, collective regression coefficient, normalized arithmetic mean, normalized median, normalized geometric mean, normalized harmonic mean, variance, standard deviation, or coefficient of variation.

54. The method of claim 51, further comprising:
(vii) storing the adjustment parameter values in a database.

55. The method of claim 54, wherein the database is in a computer-implemented database.

56. The method of claim 51, wherein the first data is derived from testing each of the plurality of compounds for an in vitro property in an assay that generates data, the assay selected from the group consisting of cell, tissue, physicochemical, structure-activity relationship (SAR), and quantitative structure-activity relationship (QSAR).

57. The method of claim 51, wherein the second data is derived from testing each of the plurality of compounds for an in vivo property in the mammalian system of interest.

58. The method of claim 51, wherein the first data corresponds to one or more in vitro properties and the second data corresponds to one or more in vivo properties, the in vivo properties selected from the group consisting of absorption, distribution, metabolism, elimination, and toxicity.

59. The method of claim 51, wherein the plurality of compounds include compounds exhibiting different in vivo properties in the mammalian system of interest.

60. The method of claim 59, wherein the in vivo properties are selected from the group consisting of permeability, solubility, dissolution, activity, metabolism, and toxicity.

61. The method of claim 51, wherein the physiologic-based model comprises a physiologic pharmacokinetic model of one or more anatomical segments of the mammalian system of interest.

62. The method of claim 61, wherein the mammalian system of interest is selected from the group consisting of gastrointestinal tract, liver, heart, kidney, eye, nose, lung, skin and brain.

63. The method of claim 61, wherein the mammalian system of interest is human.

64. The method of claim 61, wherein the physiologic pharmacokinetic model calculates the change in one or more physiological parameters of the one or more anatomical segments and the movement and disposition of the compound in the one or more of the anatomical segments as a function of time.

65. The method of claim 64, wherein the second data corresponds to one or more in vivo properties for each compound of the plurality of compounds.

66. The method of claim 65, wherein the in vivo properties are selected from the group consisting of absorption, distribution, metabolism, elimination, and toxicity.

67. The method of claim 51, wherein the curve fitting algorithm fits a plurality of curves and the fitting is simultaneous.

68. The method of claim 51, wherein the curve-fitting algorithm is a regression-based algorithm.

69. A computer-implemented method of generating optimized values for a plurality of selected adjustment parameters of a physiologic-based model, the model predicting an in vivo property of a compound in a first mammalian system from an in vivo property of the compound in a second mammalian system, the method comprising:

(i) providing a computer having a curve-fitting algorithm and the physiologic-based model of the first mammalian system, the model having as an output an in vivo property of a compound in the first mammalian system as a function of time, and wherein the model comprises the plurality of selected adjustment parameters;

(ii) assigning an initial value to each of the plurality of selected adjustment parameters of the model;

(iii) inputting data from first data for a plurality of compounds into the model and running the model to generate output data, the first data containing in vivo data for each of a plurality of compounds in the second mammalian system;

(iv) comparing the output data with second data containing in vivo data for each of the plurality of compounds in the first mammalian system;

(v) selecting a new value for one or more of the plurality of selected adjustment parameters such that deviation of the comparison in step (iv) is reduced using at least the curve-fitting algorithm on the computer; and (vi) replacing the value of the one or more of the plurality of selected adjustment parameters in the model with the new value selected in step (v).

70. The method of claim 69, further comprising:

(vi) repeating steps (iii)–(vi) one or more times until a difference between the output data and the second data is less than the largest experimental error in the first or second data or less than the largest interday variation in the first or second data.

71. The method of claim 70, wherein the difference is determined by one of the following: normalized difference, collective regression coefficient, normalized arithmetic mean, normalized median, normalized geometric mean, normalized harmonic mean, variance, standard deviation, or coefficient of variation.

72. A computer implemented method of generating a selectively optimized adjustment parameter of a physiologic pharmacokinetic model of a mammalian system of interest that corresponds to a second species of mammal for predicting a pharmacokinetic property of a compound in the mammalian system from in vivo data obtained from a first species of mammal, the method comprising:

(i) providing a computer having a physiologic pharmacokinetic model of the mammalian system of interest, the model calculates as one or more output variables a pharmacokinetic property of a compound in the mammalian system as a function of time, wherein the model comprises a selected adjustment parameter;

(ii) assigning an initial value to the selected adjustment parameter of the model;

(iii) inputting data from a first data source into the model and running the model to generate output data, the first data source containing the first data for a plurality of compounds;

(iv) comparing the output data with a second data source, the second data source containing data for the plurality of compounds in the mammalian system of interest;

(v) selecting a new value for the selected adjustment parameter such that deviation of the comparison in step (iv) is reduced using at least the curve-fitting algorithm on the computer; and (vi) replacing the value of the selected adjustment parameter in the model with the new value selected in step (v).

73. The method of claim 72, wherein the plurality compounds comprise compounds having different pharmacokinetic properties in the mammalian system of interest.

74. The method of claim 72, wherein the model comprises equations having one or more input variables.

75. A computer-implemented method for optimizing a physiologic pharmacokinetic model for predicting a pharmacokinetic property of a compound in a mammalian system of interest, the method comprising:

(i) providing a computer having a curve-fitting algorithm and the physiologic pharmacokinetic model of the mammalian system of interest, the model having as an output an in vivo property of a compound in the mammalian system as a function of time, and wherein the model comprises a plurality of selected adjustment parameters;

(ii) assigning an initial value to each of the plurality of selected adjustment parameters of the model;

(iii) inputting first data for a plurality of compounds into the model and running the model to generate output data;

(iv) comparing the output data with second data for the plurality of compounds in the mammalian system of interest;

(v) selecting a new value for one or more of the plurality of selected adjustment parameters such that deviation of the comparison in step (iv) is reduced using at least the curve-fitting algorithm on the computer; and (vi) replacing the value for the one or more of the plurality of selected adjustment parameter values in the model with the new value selected in step (v).

76. The method of claim 75, further comprising:

(vii) repeating steps (iii)–(vi) one or more times until a difference between the output data and the second data is less than the largest experimental error in the first or second data or less than the largest interday variation in the first or second data.

77. A device for selectively optimizing a model for predicting a pharmacokinetic property of a compound in a mammalian system of interest, the device comprising:

assigning means for assigning an initial value to a selected adjustment parameter;

inputting means for inputting first data for a plurality of compounds into the model;

running means for running the model to generate output data;

comparing means for comparing the output data with second data for the plurality of compounds;

selecting means for selecting a new value for the selected adjustment parameter such that deviation of the comparison from the comparison means is reduced; and replacing means for replacing the value of the selected adjustment parameter in the model with the new value selected by the selecting means.

78. The device of claim 77, wherein the first and second data are stored in the same data source.

79. The device of claim 77, wherein the first data is stored in a first data source and the second data is stored in a second data source.

80. The device of claim 77, further comprising:

repeating means for using the inputting means, the running means, the comparing means, the selecting means, and the replacing means one or more times until a difference between the output data and the second data is less than the largest experimental error in the first or second data or less than the largest interday variation in the first or second data.

81. The device of claim 80, wherein the repeating means determines the difference by one of the following: normalized difference, collective regression coefficient, normalized arithmetic mean, normalized median, normalized geometric mean, normalized harmonic mean, variance, standard deviation, or coefficient of variation.

82. The device of claim 77, wherein the selected adjustment parameter is a plurality of selected adjustment parameters and wherein the assigning means assigns an initial value to each of the plurality of selected adjustment parameters, the selecting means selects a new value for one or more of the plurality of selected adjustment parameters, and the replacing means replaces the value for the one or more of the plurality of selected adjustment parameters with the new value selected by the selecting means.

83. The device of claim 77, further comprising:

storing means for storing the value of the selected adjustment parameter in a database.

84. The device of claim 77, wherein the selected adjustment parameter value is selected from the group consisting of a constant, a range of constants, a function and an algorithm.

85. The device of claim 77, wherein the model comprises a physiologic pharmacokinetic model of one or more anatomical segments of the mammalian system of interest.

86. The device of claim 85, wherein the physiologic pharmacokinetic model comprises means for determining the change in one or more physiological parameters of the one or more anatomical segments and the movement and disposition of the compound in the one or more anatomical segments as a function of time.

87. The device of claim 85, wherein the mammalian system of interest is selected from the group consisting of gastrointestinal tract, liver, heart, kidney, eye, nose, lung, skin and brain.

88. The device of claim 85, wherein the mammalian system of interest is human.

89. The device of claim 85, wherein the first data corresponds to one or more in vitro properties for each of the plurality of compounds.

90. The device of claim 89, wherein the first data is derived from testing of each of the plurality of compounds for at least one in vitro property in an assay that generates data, the assay selected from the group consisting of cell, tissue, physicochemical, structure-activity relationship (SAR), and quantitative structure-activity relationship (QSAR).

91. The device of claim 89, wherein the in vitro properties are selected from the group consisting of absorption, distribution, metabolism, elimination, and toxicity.

92. The device of claim 85, wherein the second data corresponds to one or more in vivo properties for each of the plurality of compounds.

93. The device of claim 92, wherein the in vivo properties are selected from the group consisting of absorption, distribution, metabolism, elimination, and toxicity.

94. The device of claim 92, wherein the plurality of compounds include compounds exhibiting different in vivo properties in the mammalian system of interest.

95. The device of claim 94, wherein the in vivo properties are selected from the group consisting of permeability, solubility, dissolution, activity, metabolism, and toxicity.

96. The device of claim 95, wherein the one or more in vivo properties are derived from testing each of the plurality of compounds in the mammalian system of interest for the one or more in vivo properties.

97. The device of claim 77, wherein the selecting means comprises a curve-fitting algorithm.

98. The device of claim 97, wherein the curve-fitting algorithm is a regression-based algorithm.

99. The device of claim 97, wherein the curve-fitting algorithm is a plurality of curve fitting algorithms.

100. The device of claim 99, wherein the plurality of curve-fitting algorithms are a plurality of simultaneous curve-fitting algorithms.

101. A method for predicting a pharmacokinetic property of a compound in a mammalian system of interest, the method comprising:

providing a model, wherein the model comprises a selected adjustment parameter and wherein the selected adjustment parameter comprises a value obtained by:

(i) assigning an initial value to the selected adjustment parameter;

(ii) inputting first data for a plurality of compounds into the model and running the model to generate output data;

(iii) comparing the output data with second data for the plurality of compounds;

(iv) selecting a new value for the selected adjustment parameter such that deviation of the comparison in step (iii) is reduced; and (v) replacing the value of the selected adjustment parameter in the model with the new value selected in step (iv); and using the model to predict a pharmacokinetic property of a particular compound.

102. The method of claim 100, wherein the first and second data are stored in the same data source.

103. The method of claim 100, wherein the first data is stored in a first data source and the second data is stored in a second data source.

104. The method of claim 100, further comprising:
(vi) repeating steps (ii)–(v) one or more times until a difference between the output data and the second data is less than the largest experimental error in the first or second data or less than the largest interday variation in the first or second data.

105. The method of claim 104, wherein the difference is determined by one of the following: normalized difference, collective regression coefficient, normalized arithmetic mean, normalized median, normalized geometric mean, normalized harmonic mean, variance, standard deviation, or coefficient of variation.

106. The method of claim 100, wherein the selected adjustment parameter is a plurality of selected adjustment parameters and wherein step (i) assigns an initial value to each of the plurality of selected adjustment parameters, step (iv) selects a new value for one or more of the plurality of selected adjustment parameters, and step (v) replaces the value for the one or more of the plurality of selected adjustment parameters with the new value selected in step (iv).

107. The method of claim 100, further comprising:
storing the selected adjustment parameter value in a database.

108. The method of claim 100, wherein the selected adjustment parameter value is selected from the group consisting of a constant, a range of constants, a function and an algorithm.

109. The method of claim 100, wherein the model comprises a physiologic pharmacokinetic model of one or more anatomical segments of the mammalian system of interest.

110. The method of claim 109, wherein the physiologic pharmacokinetic model determines the change in one or more physiological parameters of the one or more anatomical segments and the movement and disposition of the compound in the one or more anatomical segments as a function of time.

111. The method of claim 109, wherein the mammalian system of interest is selected from the group consisting of gastrointestinal tract, liver, heart, kidney, eye, nose, lung, skin and brain.

112. The method of claim 109, wherein the mammalian system of interest is human.

113. The method of claim 109, wherein the first data corresponds to one or more in vitro properties for each of the plurality of compounds.

114. The method of claim 113, wherein the first data is derived from testing of each of the plurality of compounds for at least one in vitro property in an assay that generates data, the assay selected from the group consisting of cell, tissue, physicochemical, structure-activity relationship (SAR), and quantitative structure-activity relationship (QSAR).

115. The method of claim 113, wherein the in vitro properties are selected from the group consisting of absorption, distribution, metabolism, elimination, and toxicity.

116. The method of claim 109, wherein the second data corresponds to one or more in vivo properties for each of the plurality of compounds.

117. The method of claim 116, wherein the in vivo properties are selected from the group consisting of absorption, distribution, metabolism, elimination, and toxicity.

118. The method of claim 116, wherein the plurality of compounds include compounds exhibiting different in vivo properties in the mammalian system of interest.

119. The method of claim 118, wherein the in vivo properties are selected from the group consisting of permeability, solubility, dissolution, activity, metabolism, and toxicity.

120. The method of claim 119, wherein the one or more in vivo properties are derived from testing each of the plurality of compounds in the mammalian system of interest.

121. The method of claim 101, wherein the selecting step comprises a curve-fitting algorithm.

122. The method of claim 121, wherein the curve-filling algorithm is a regression-based algorithm.

123. The method of claim 121, wherein the curve-fitting algorithm is a plurality of curve-fitting algorithms.

124. The method of claim 123, wherein the plurality of curve-fitting algorithms are used simultaneously.

125. An article of manufacture comprising:
a computer readable medium; and
a data structure stored on the medium for predicting a pharmacokinetic property of a compound in a mammal of interest, wherein the data structure comprises a computer readable model of a selected mammalian system, wherein the computer readable model comprises a selected adjustment parameter, and wherein the data structure further comprises a value obtained by means for:
(i) assigning an initial value to the selected adjustment parameter of the model;
(ii) receiving first data for a plurality of compounds into the model and running the model to generate output data;
(iii) comparing the output data with second data for the plurality of compounds;
(iv) selecting a new value for the selected adjustment parameter such that deviation of the comparison in (iii) is reduced; and
(v) replacing the value of the selected adjustment parameter in the model with the new value selected in (iv).

126. The article of manufacture of claim 125, wherein the first and second data are stored in the same data source.

127. The article of manufacture of claim 125, wherein the first data is stored in a first data source and the second data is stored in a second data source.

128. The article of manufacture of claim 125, further comprising:
(vi) means for repeating (ii)–(v) one or more times until a difference between the output data and the second data is less than the largest experimental error in the first or second data or less than the largest interday variation in the first or second data.

129. The article of manufacture of claim 128, wherein the repeating means determines the difference by one of the following: normalized difference, collective regression coefficient, normalized arithmetic mean, normalized median, normalized geometric mean, normalized harmonic mean, variance, standard deviation, or coefficient of variation.

130. The article of manufacture of claim 125, wherein the selected adjustment parameter is a plurality of selected adjustment parameters and wherein (i) assigns an initial value to each of the plurality of selected adjustment parameters, (iv) selects a new value for one or more of the plurality of selected adjustment parameters, and (v) replaces the value for the one or more of the plurality of selected adjustment parameters and with the new value selected in (iv).

131. The method of claim 125, wherein the selected adjustment parameter value is selected from the group consisting of a constant, a range of constants, a function, an algorithm, a plurality of algorithms, and a plurality of functions.

132. The article of manufacture of claim 125, wherein the computer readable model comprises a physiologic pharmacokinetic model of one or more anatomical segments of the mammalian system of interest.

133. The article of manufacture of claim 132, wherein the physiologic pharmacokinetic model comprises means for determining the change in one or more physiological parameters of the one or more anatomical segments and the movement and disposition of the compound in the one or more anatomical segments as a function of time.

134. The article of manufacture of claim 125, wherein the mammalian system of interest is selected from the group consisting of gastrointestinal tract, liver, heart, kidney, eye, nose, lung, skin and brain.

135. The article of manufacture of claim 125, wherein the mammalian system of interest is human.

136. The article of manufacture of claim 125, wherein the first data corresponds to one or more in vitro properties for each of the plurality of compounds.

137. The article of manufacture of claim 136, wherein the first data is derived from testing each of the plurality of compounds for at least one in vitro property in an assay that generates data, the assay selected from the group consisting of cell, tissue, physicochemical, structure-activity relationship (SAR), and quantitative structure-activity relationship (QSAR).

138. The article of manufacture of claim 136, wherein the in vitro properties are selected from the group consisting of absorption, distribution, metabolism, elimination, and toxicity.

139. The article of manufacture of claim 135, wherein the second data corresponds to one or more in vivo properties for each of the plurality of compounds.

140. The article of manufacture of claim 139, wherein the in vivo properties are selected from the group consisting of absorption, distribution, metabolism, elimination, and toxicity.

141. The article of manufacture of claim 139, wherein the plurality of compounds include compounds exhibiting different in vivo properties in the mammalian system of interest.

142. The article of manufacture of claim 141, wherein the in vivo properties are selected from the group consisting of permeability, solubility, dissolution, activity, metabolism, and toxicity.

143. The article of manufacture of claim 142, wherein the one or more in vivo properties are derived from testing each of the plurality of compounds in the mammalian system of interest for the one or more in vivo properties.

144. The article of manufacture of claim 125, wherein the selecting means comprises a curve-fitting algorithm.

145. The article of manufacture of claim 144, wherein the curve-fitting algorithm is a regression-based algorithm.

146. The article of manufacture of claim 144, wherein the curve-fitting algorithm is a plurality of curve-fitting algorithms.

147. The article of manufacture of claim 146, wherein the plurality of curve-fitting algorithms are a plurality of simultaneous curve-fitting algorithms.

148. A computer program product for predicting a pharmacokinetic property of a compound in a mammal, the product comprising:
a computer readable medium; and
a program stored on the medium for predicting a pharmacokinetic property of a compound in a mammal of interest, wherein the program comprises a computer readable model of a selected mammalian system, the computer readable model comprises a selected adjustment parameter, and wherein the selected adjustment parameter comprises values obtained by:
(i) assigning an initial value to the selected adjustment parameter of the model;
(ii) inputting data from first data for a plurality of compounds into the model and running the model to generate output data;
(iii) comparing the output data with data from second data for the plurality of compounds;
(iv) selecting a new value for the selected adjustment parameter such that deviation of the comparison in step (iii) is reduced; and
(v) replacing the value of the selected adjustment parameter in the model with the new value selected in step (iv).

149. The product of claim 148, wherein the first and second data are stored in the same data source.

150. The product of claim 148, wherein the first data is stored in a first data source and the second data is stored second data source.

151. The product of claim 148, further comprising:
(vi) repeating steps (ii)–(v) one or more times until a difference between the output data and the second data is less than the largest experimental error in the first or second data or less than the largest interday variation in the first or second data.

152. The product of claim 151, wherein the difference is determined by one of the following: normalized difference, collective regression coefficient, normalized arithmetic mean, normalized median, normalized geometric mean, normalized harmonic mean, variance, standard deviation, or coefficient of variation.

153. The product of claim 148, wherein the selected adjustment parameter is a plurality of selected adjustment parameters and wherein step (i) assigns an initial value to each of the plurality of selected adjustment parameters, step (iv) selects a new value for one or more of the plurality of selected adjustment parameters, and step (v) replaces the value for the one or more of the plurality of selected adjustment parameters and with the new value selected in step (iv).

154. The product of claim 148, wherein the selected mammalian system has one or more physiological barriers to absorption based on a selected route of administration.

155. The product of claim 148, wherein the computer readable model models one or more of fluid transit, fluid absorption, mass transit, mass dissolution, mass solubility, and mass absorption for one or more segments of the selected mammalian system.

156. An article of manufacture for predicting a pharmacokinetic property of a compound in a mammal comprising:

a computer readable medium; and a program stored on the medium for predicting a pharmacokinetic property of a compound in a mammal, wherein the program comprises a computer readable model of a selected mammalian system, the computer readable model comprising a plurality of selectively optimized adjustment parameters, and wherein the selectively optimized adjustment parameters comprise values obtained by:

(i) assigning an initial value to each of the plurality of selected adjustment parameters of the model;

(ii) inputting first data for a plurality of compounds into the model and running the model to generate output data;

(iii) comparing the output data with second data for the plurality of compounds;

(iv) selecting a new value for one or more of the plurality of selected adjustment parameters such that deviation of the comparison in step (iii) is reduced;

(v) replacing the value for one or more of the plurality of selected adjustment parameter values in the model with the new value selected in step (iv).

157. The article of manufacture of claim 156, wherein the first and second data are stored in the same data source.

158. The article of manufacture of claim 156, wherein the first data is stored in a first data source and the second data is stored in a second data source.

159. The article of manufacture of claim 156, further comprising:

(vi) repeating steps (ii)–(v) one or more times until a difference between the output data and the second data is less than the largest experimental error in the first or second data or less than the largest interday variation in the first or second data.

160. The article of manufacture of claim 159, wherein the difference is determined by one of the following: normalized difference, collective regression coefficient, normalized arithmetic mean, normalized median, normalized geometric mean, normalized harmonic mean, variance, standard deviation, or coefficient of variation.

161. The article of manufacture of claim 156, wherein the mammalian system is human.

162. The article of manufacture of claim 156, wherein the mammalian system is selected from the group consisting of gastrointestinal tract, liver, heart, kidney, eye, nose, lung, skin and brain.

163. The article of manufacture of claim 162, wherein the mammalian system is gastrointestinal tract.

164. The article of manufacture of claim 163, wherein the computer readable model models segments of the gastrointestinal tract and the segments are selected from the group consisting of stomach, duodenum, jejunum, ileum and colon.

165. The article of manufacture of claim 156, wherein the first data comprises in vitro data.

166. The article of manufacture of claim 165, wherein the in vitro data is obtained from testing of a compound in one or more assays that generate data selected from the group consisting of cell, tissue, structure-activity relationship (SAR), and quantitative structure-activity relationship (QSAR) data.

167. The article of manufacture of claim 165, wherein the plurality of compounds comprise compounds having different pharmacokinetic properties in the mammalian system.

168. The article of manufacture of claim 156, wherein the first data comprises in vivo data from a first species of mammal and the mammalian system comprises a second species of mammal.

169. The article of manufacture of claim 167, wherein the plurality of compounds comprise compounds having different pharmacokinetic properties in the mammalian system.

170. The article of manufacture of claim 156, wherein the plurality of selected adjustment parameters are applied to one or more of fluid absorption, flux, permeability, transport mechanism, transfer rate, and segment surface area.

171. The article of manufacture of claim 156, wherein input data for the computer readable model comprises data selected from the group consisting of dissolution rate, transport mechanism and formulation release rate.

172. The article of manufacture of claim 156, wherein the computer readable model has equations using one or more input variables corresponding to the input data for calculating as one or more output variables the change in the physiological property.

173. The article of manufacture of claim 156, wherein the pharmacokinetic property is selected from the group consisting of absorption, distribution, metabolism, elimination and toxicity.

174. The article of manufacture of claim 156, wherein the computer readable model uses data selected from the group consisting of concentration permeability, solubility, dissolution rate, transport mechanism, and formulation release rate as input data.

175. The article of manufacture of claim 156, wherein the computer readable model uses models selected from the group consisting of pH, fluid volume, fluid volume transfer rate, fluid absorption, surface area, and transit time.

176. The article of manufacture of claim 156, wherein the computer readable model includes models for one or more of absorption, distribution, metabolism, elimination and toxicity.

177. The article of manufacture of claim 156, wherein the computer readable model includes models for one or more of fluid transit, fluid absorption, mass transit, mass dissolution, mass solubility, and mass absorption for one or more segments of the mammalian system.

178. The article of manufacture of claim 156, wherein the computer readable model comprises rules for one or more of transit, absorption, permeability, solubility, dissolution, and concentration for one or more segments of the mammalian system.

179. The article of manufacture of claim 156, wherein the computer model comprises a model of at least two anatomical segments and comprises a logic function module comprising a regional correlation estimation function and a control statement for initiating the function, wherein the estimation function when initiated generates an estimated value for a selected pharmacokinetic property of the compound in a first anatomical segment when supplied with an input value corresponding to the selected pharmacokinetic property in a second anatomical segment and with a regional correlation coefficient for the selected pharmacokinetic property of the first and second anatomical segments.

180. An article of manufacture comprising:

a computer readable medium; and a program stored on the medium for predicting a pharmacokinetic property of a compound in a mammal of interest, wherein the program comprises a computer readable model of a selected mammalian system, the computer readable model comprises at least one selected adjustment parameter, and wherein at least the one selected adjustment parameter comprises a value obtained by:

(i) assigning an initial value to the at least one selected adjustment parameter of the model;

(ii) inputting first data for a plurality of compounds into the model and running the model to generate output data;

(iii) comparing the output data with second data for the plurality of compounds;

(iv) selecting a new value for the at least one selected adjustment parameter such that deviation of the comparison in step (iii) is reduced;

(v) replacing the value for the at least one selected adjustment parameter in the model with the new value selected in step (iv).

181. The article of manufacture of claim 180, wherein the first and second data are stored in the same data source.

182. The article of manufacture of claim 180, wherein the first data is stored in a first data source and the second data is stored in a second data source.

183. The article of manufacture of claim 180, further comprising:

(vi) repeating steps (ii)–(v) one or more times until a difference between the output data and the second data is less than the largest experimental error in the first or second data or less than the largest interday variation in the first or second data.

184. The article of manufacture of claim 183, wherein the difference is determined by one of the following: normalized difference, collective regression coefficient, normalized arithmetic mean, normalized median, normalized geometric mean, normalized harmonic mean, variance, standard deviation, or coefficient of variation.

185. The article of manufacture of claim 180, wherein the at least one selected adjustment parameter is a plurality of selected adjustment parameters and wherein step (i) assigns an initial value to each of the plurality of selected adjustment parameters, step (iv) selects a new value for one or more of the plurality of selected adjustment parameters, and step (v) replaces the value for the one or more of the plurality of selected adjustment parameters and with the new value selected in step (iv).

186. The article of manufacture of claim 180, wherein the computer readable model is a physiologic pharmacokinetic model of at least two of anatomical segments of the selected mammalian system and a logic function module comprising a regional correlation estimation function and a control statement for initiating the function wherein the estimation function when initiated generates an estimated value for a selected pharmacokinetic property of the compound in a first anatomical segment when supplied with an input value corresponding to the selected pharmacokinetic property in a second anatomical segment and with a regional correlation coefficient for the selected pharmacokinetic property of the first and second anatomical segments.

187. The article of manufacture of claim 186, wherein the mammalian system of interest is selected from the group consisting of gastrointestinal tract, liver, heart, kidney, eye, nose, lung, skin and brain.

188. The article of manufacture of claim 186, wherein the mammalian system of interest is human.

189. The article of manufacture of claim 186, wherein the pharmacokinetic property is selected from the group consisting of absorption, distribution, metabolism, elimination and toxicity.

190. The article of manufacture of claim 186, wherein the pharmacokinetic property is selected from the group consisting of permeability, solubility, dissolution rate and transport mechanism.

191. The article of manufacture of claim 186, wherein the input data comprises in vitro data.

192. The article of manufacture of claim 191, wherein the in vitro data is derived from testing of the compound in an assay that generates data selected from the group consisting of cell, tissue, physicochemical, structure-activity relationship (SAR) and quantitative structure-activity relationship (QSAR) data.

193. The article of manufacture of claim 186, wherein the computer readable model uses equations selected from the group consisting fluid transit, fluid absorption, mass transit, mass dissolution, mass solubility and mass absorption.

194. The article of manufacture of claim 193, wherein one or more of the equations is modified by a selectively optimized adjustment parameter.

195. The article of manufacture of claim 186, wherein the regional correlation estimation function comprises an algorithm.

196. The article of manufacture of claim 195, wherein the algorithm is selected from the group consisting of a polynomial, exponential, and logarithm.

197. An article of manufacture comprising:

a computer readable medium; and a program stored on the medium for predicting absorption of a compound in a mammal of interest, wherein the program comprises a computer readable model of a selected mammalian system, wherein the computer readable model comprises a selected adjustment parameter, and wherein the selected adjustment parameter comprises a value obtained by:

(i) assigning an initial value to the selected adjustment parameter of the model;

(ii) inputting data first data for a plurality of compounds into the model and running the model to generate output data;

(iii) comparing the output data with second data for the plurality of compounds;

(iv) selecting a new value for the selected adjustment parameter such that deviation of the comparison in step (iii) is reduced; and (v) replacing the value of the selected adjustment parameter in the model with the new value selected in step (iv).

198. The article of manufacture of claim 197, wherein the first and second data are stored in the same data source.

199. The article of manufacture of claim 197, wherein the first data is stored in a first data source and the second data is stored in a second data source.

200. The article of manufacture of claim 197, further comprising:

(vi) repeating steps (ii)–(v) one or more times until a difference between the output data and the second data is less than the largest experimental error in the first or second data or less than the largest interday variation in the first or second data.

201. The article of manufacture of claim 200, wherein the difference is determined by one of the following: normalized difference, collective regression coefficient, normalized arithmetic mean, normalized median, normalized geometric mean, normalized harmonic mean, variance, standard deviation, or coefficient of variation.

202. The article of manufacture of claim 197, wherein the mammalian system is selected from the group consisting of gastrointestinal tract, eye, nose, lung, skin and brain.

203. The article of manufacture of claim 202, wherein the mammalian system is the gastrointestinal tract.

204. The article of manufacture of claim 197, wherein the mammal is human.

205. The article of manufacture of claim 197, wherein the selected mammalian system has one or more physiological barriers to absorption of the compound based on a selected route of administration.

206. The article of manufacture of claim 198, wherein the computer readable model models one or more of fluid transit, fluid absorption, mass transit, mass dissolution, mass solubility, and mass absorption for one or more segments of the mammalian system.

207. The article of manufacture of claim 197, wherein the selected adjustment parameter is a plurality of selected adjustment parameters and wherein step (i) assigns an initial value to each of the plurality of selected adjustment parameters, step (iv) selects a new value for one or more of the plurality of selected adjustment parameters, and step (v) replaces the value for the one or more of the plurality of selected adjustment parameters and with the new value selected in step (iv).

208. The article of manufacture of claim 207, wherein the simulation model corresponds to a compartment-flow model comprising compartments that are operably linked through flow regulators modified by one or more converters.

209. The article of manufacture of claim 208, wherein the compartments comprise one or more compartments characterized by a parameter selected from the group consisting of fluid volume, fluid absorption, formulation, insoluble mass, soluble mass, and soluble mass absorption.

210. The article of manufacture of claim 208, wherein the flow regulators are characterized by a parameter selected from the group consisting of fluid absorption rate, fluid transit rate, formulation transit rate, formulation release rate, insoluble mass transit rate, insoluble mass dissolution rate, soluble mass transit rate, and soluble mass absorption rate.

211. The article of manufacture of claim 208, wherein the converters are characterized by a parameter selected from the group consisting of fluid volume, fluid volume absorption rate constant, fluid volume transit rate constant, insoluble mass, insoluble mass transit rate constant, dissolution rate constant, soluble mass, soluble mass transit rate constant, surface area, dissolved mass concentration and permeability.

212. The article of manufacture of claim 208, wherein one or more of the converters are characterized by one or more of the plurality of selected adjustment parameters.

213. The article of manufacture of claim 208, wherein one or more of the converters are characterized by a regional correlation parameter.

214. The article of manufacture of claim 197, wherein the model is a physiological model and the first data includes data selected from the group consisting of soluble mass transfer rate constant, permeability, solubility, dissolution rate, and transport mechanism.

215. The article of manufacture of claim 197, wherein the first data includes data selected from the group consisting of pH, initial fluid volume, surface area, fluid volume transit time, insoluble mass transit time, soluble mass transit time, fluid volume transfer rate, and fluid absorption rate.

216. The article of manufacture of claim 197, where the first and second data is selected from the group consisting of dissolution rate, transport mechanism, transit time, pH and formulation release rate.

217. The article of manufacture of claim 197, wherein the first data is in vitro data.

218. The article of manufacture of claim 217, wherein the in vitro data is permeability data derived from an assay selected from the group consisting of a cell-based assay and a tissue-based assay.

219. The article of manufacture of claim 217, wherein the in vitro data is transport mechanism data derived from an assay selected from the group consisting of a cell-based assay and a tissue-based assay.

220. The article of manufacture of claim 217, wherein the in vitro data is permeability data derived from structure-activity relationship data of the compound.

221. The article of manufacture of claim 217, wherein the in vitro data is dissolution rate data derived from structure-activity relationship data of the compound.

222. The article of manufacture of claim 217, wherein the in vitro data is solubility data derived from structure-activity relationship data of the compound.

223. A computer system for predicting a pharmacokinetic property of a compound in a mammalian system of interest, the computer system comprising:
  a computer; and
  a program implementing a physiologic pharmacokinetic model on the computer, wherein the model comprises a selected adjustment parameter, and wherein the selected adjustment parameter comprises a value obtained by:
    (i) assigning an initial value to the selected adjustment parameter;
    (ii) inputting first data for a plurality of compounds into the model and running the model to generate output data;
    (iii) comparing the output data with second data for the plurality of compounds;
    (iv) selecting a new value for of the selected adjustment parameter such that deviation of the comparison in step (iii) is reduced; and
    (v) replacing the value for the selected adjustment parameter in the model with the new value selected in step (iv).

224. The computer system of claim 223, wherein the first and second data are stored in the same data source.

225. The computer system of claim 223, wherein the first data is stored in a first data source and the second data is stored in a second data source.

226. The computer system of claim 223, further comprising:
  (vi) repeating steps (ii)–(v) one or more times until a difference between the output data and the second data is less than the largest experimental error in the first or second data or less than the largest interday variation in the first or second data.

227. The computer system of claim 226, wherein the difference is determined by one of the following: normalized difference, collective regression coefficient, normalized arithmetic mean, normalized median, normalized geometric mean, normalized harmonic mean, variance, standard deviation, or coefficient of variation.

228. The computer system of claim 223, wherein the selected adjustment parameter is a plurality of selected adjustment parameters and wherein step (i) assigns an initial value to each of the plurality of selected adjustment parameters, step (iv) selects a new value for one or more of the plurality of selected adjustment parameters, and step (v) replaces the value for the one or more of the plurality of selected adjustment parameters and with the new value selected in step (iv).

229. The computer system of claim 223, wherein the selected adjustment parameter value is stored in a database on the computer.

230. The computer system of claim 223, wherein the selected adjustment parameter value is selected from the group consisting of a constant, a range of constants, a function, an algorithm, a plurality of functions, and a plurality of algorithms.

231. The computer system of claim 223, wherein the model comprises a physiologic pharmacokinetic model of one or more anatomical segments of the mammalian system of interest.

232. The computer system of claim 231, wherein the mammalian system of interest is selected from the group consisting of gastrointestinal tract, liver, heart, kidney, eye, nose, lung, skin and brain.

233. The computer system of claim 231, wherein the mammalian system of interest is human.

234. The computer system of claim 231, wherein the physiologic pharmacokinetic model determines the change in one or more physiological parameters of the one or more anatomical segments and the movement and disposition of the compound in the one or more anatomical segments as a function of time.

235. The computer system of claim 231, wherein the first data corresponds to one or more in vitro properties for each of the plurality of compounds.

236. The computer system of claim 235, wherein the first data is derived from testing of each of the plurality of compounds for at least one in vitro property in an assay that generates data, the assay selected from the group consisting of cell, tissue, physicochemical, structure-activity relationship (SAR), and quantitative structure-activity relationship (QSAR).

237. The computer system of claim 235, wherein the in vitro properties are selected from the group consisting of absorption, distribution, metabolism, elimination, and toxicity.

238. The computer system of claim 231, wherein the second data corresponds to one or more in vivo properties for each of the plurality of compounds.

239. The computer system of claim 238, wherein the in vivo properties are selected from the group consisting of absorption, distribution, metabolism, elimination, and toxicity.

240. The computer system of claim 238, wherein the plurality of compounds include compounds exhibiting different in vivo properties in the mammalian system of interest.

241. The computer system of claim 240, wherein the in vivo properties are selected from the group consisting of permeability, solubility, dissolution, activity, metabolism, and toxicity.

242. The computer system of claim 240, wherein the one or more in vivo properties are derived from testing each of the plurality of compounds in the mammalian system of interest for the one or more in vivo properties.

243. The computer system of claim 223, wherein the selecting step comprises a curve-fitting algorithm.

244. The computer system of claim 243, wherein the curve-fitting algorithm is a regression-based algorithm.

245. The computer system of claim 243, wherein the curve-fitting algorithm is a plurality of curve-fitting algorithms.

246. The computer system of claim 245, wherein the plurality of curve-fitting algorithms are used simultaneously.

247. A method of predicting a pharmacodynamic or pharmacokinetic property of a compound in a mammal, the method comprising:
providing a model, wherein the model comprises a selected adjustment parameter, and wherein the selected adjustment parameter comprises a value obtained by:
(i) assigning an initial value to the selected adjustment parameter of the model;
(ii) inputting first data for a plurality of compounds into the model and running the model to generate output data;
(iii) comparing the output data with second data for the plurality of compounds;
(iv) selecting a new value for the selected adjustment parameter such that deviation of the comparison in step (iii) is reduced; and
(v) replacing the value for the selected adjustment parameter in the model with the new value selected in step (iv); and
using the model to predict the property of the compound.

248. The method of claim 247, wherein the first and second data are stored in the same data source.

249. The method of claim 247, wherein the first data is stored in a first data source and the second data is stored second data source.

250. The method claim 247, further comprising:
(vi) repeating steps (ii)–(v) one or more times until a difference between the output data and the second data is less than the largest experimental error in the first or second data or less than the largest interday variation in the first or second data.

251. The method of claim 250, wherein the difference is determined by one of the following: normalized difference, collective regression coefficient, normalized arithmetic mean, normalized median, normalized geometric mean, normalized harmonic mean, variance, standard deviation, or coefficient of variation.

252. The method of claim 250, wherein the selected adjustment parameter is a plurality of selected adjustment parameters and wherein step (i) assigns an initial value to each of the plurality of selected adjustment parameters, step (iv) selects a new value for one or more of the plurality of selected adjustment parameters and step (v) replaces the value for the one or more of the plurality of selected adjustment parameters and with the new value selected in step (iv).

253. The method of claim 247, wherein the selected adjustment parameter value is selected from the group consisting of a constant, a range of constants, a function, an algorithm, a plurality of functions, and a plurality of algorithms.

254. The method of claim 247, further comprising:
storing the selected adjustment parameter value in a database.

255. The method of claim 247, wherein the model comprises a physiologic pharmacokinetic model of one or more anatomical segments of the mammal.

256. The method of claim 255, wherein the mammal is a mammalian system selected from the group consisting of gastrointestinal tract, liver, heart, kidney, eye, nose, lung, skin and brain.

257. The method of claim 255, wherein the mammal is human.

258. The method of claim 255, wherein the physiologic pharmacokinetic model determines the change in one or more physiological parameters of the one or more anatomical segments and the movement and disposition of the compound in the one or more anatomical segments as a function of time.

259. The method of claim 255, wherein the first data corresponds to one or more in vitro properties for each of the plurality of compounds.

260. The method of claim 259, wherein the first data is derived from testing of each of the plurality of compounds for at least one in vitro property in an assay that generates data, the assay selected from the group consisting of cell, tissue, physicochemical, structure-activity relationship (SAR), and quantitative structure-activity relationship (QSAR).

261. The method of claim 259, wherein the in vitro properties are selected from the group consisting of absorption, distribution, metabolism, elimination and toxicity.

262. The method of claim 255, wherein the second data corresponds to one or more in vivo properties for each of the plurality of compounds.

263. The method of claim 262, wherein the in vivo properties are selected from the group consisting of absorption, distribution, metabolism, elimination, and toxicity.

264. The method of claim 255, wherein the plurality of compounds include compounds exhibiting different in vivo properties in the mammal.

265. The method of claim 264, wherein the in vivo properties are selected from the group consisting of permeability, solubility, dissolution, activity, metabolism, and toxicity.

266. The method of claim 265, wherein the one or more in vivo properties are derived from testing each of the plurality of compounds in the mammal for the one or more in vivo properties.

267. The method of claim 247, wherein the selecting step comprises a curve-fitting algorithm.

268. The method of claim 267, wherein the curve-fitting algorithm is a regression-based algorithm.

269. The method of claim 267, wherein the curve-fitting algorithm is a plurality of curve-fitting algorithms.

270. The method of claim 269, wherein the plurality of curve-fitting algorithms are used simultaneously.

271. A computer system for predicting absorption of a compound in a mammalian system of interest, the computer system comprising:
  a computer; and
  a program implementing an absorption model on the computer, wherein the model comprises at least one selected adjustment parameter and wherein the at least one selected adjustment parameter comprises a value obtained by:
    (i) assigning an initial value to the at least one selected adjustment parameter of the model;
    (ii) inputting first data for a plurality of compounds into the model and running the model to generate output data;
    (iii) comparing the output data with second data for the plurality of compounds;
    (iv) selecting a new value for the at least one selected adjustment parameter such that deviation of the comparison in step (iii) is reduced; and
    (v) replacing the value of the at least one selected adjustment parameter value in the model with the new value selected in step (iv).

272. The computer system of claim 271, wherein the first and second data are stored in the same data source.

273. The computer system of claim 271, wherein the first data is stored in a first data source and the second data is stored in a second data source.

274. The computer system of claim 271, further comprising:
  (vi) repeating steps (ii)–(v) one or more times until a difference between the output data and the second data is less than the largest experimental error in the first or second data or less than the largest interday variation in the first or second data.

275. The computer system of claim 271, wherein the difference is determined by one of the following: normalized difference, collective regression coefficient, normalized arithmetic mean, normalized median, normalized geometric mean, normalized harmonic mean, variance, standard deviation, or coefficient of variation.

276. The computer system of claim 274, wherein the at least one selected adjustment parameter is a plurality of selected adjustment parameters and wherein step (i) assigns an initial value to each of the plurality of selected adjustment parameters, step (iv) selects a new value for one or more of the plurality of selected adjustment parameters, and step (v) replaces the value for the one or more of the plurality of selected adjustment parameters and with the new value selected in step (iv).

277. A computer system for predicting oral absorption of a compound in a mammal, the computer system comprising:
  a computer; and
  a program implementing an oral absorption model on the computer, wherein the model comprises a plurality of selected adjustment parameters, and wherein the plurality of selected adjustment parameters comprise values obtained by:
    (i) assigning an initial value the selected adjustment parameter of the model;
    (ii) inputting first data source containing first data for a plurality of compounds into the model and running the model to generate output data;
    (iii) comparing the output data with second data for the plurality of compounds;
    (iv) selecting a new value for one or more of the plurality of selected adjustment parameter such that deviation of the comparison in step (iii) is reduced; and
    (v) replacing the value of the one or more of the plurality of selected adjustment parameters in the model with the new value selected in step (iv).

278. The computer system of claim 277, wherein the first and second data are stored in the same data source.

279. The computer system of claim 277, wherein the first data is stored in a first data source and the second data is stored in a second data source.

280. The computer system of claim 277, further comprising:
  (vi) repeating steps (ii)–(v) one or more times until a difference between the output data and the second data is less than the largest experimental error in the first or second data or less than the largest interday variation in the first or second data.

281. The computer system of claim 280, wherein the difference is determined by one of the following: normalized difference, collective regression coefficient, normalized arithmetic mean, normalized median, normalized geometric mean, normalized harmonic mean, variance, standard deviation, or coefficient of variation.

282. The computer system of claim 277, wherein at least one of the plurality of selected adjustment parameters is applied to one or more of fluid absorption, flux, permeability, transport mechanism, transfer rate, and segment surface area.

283. A computer system of claim 277, wherein the oral absorption model is a compartment-flow model.

284. The computer system of claim 277, wherein the oral absorption model comprises computer-implemented rules for one or more of transit, absorption, permeability, solubility, dissolution, and concentration for one or more segments of the GI tract of the mammal.

285. A computer system for predicting a property of a compound in a mammalian system, the computer system comprising:
- a computer; and
- a program on the computer, wherein the program comprises a plurality of selectively optimized adjustment parameters, the selectively optimized adjustment parameters comprise values obtained by:
  - (i) assigning an initial value to each of the plurality of selected adjustment parameters of the program;
  - (ii) inputting first data for a plurality of compounds into the program and running the program to generate output data;
  - (iii) comparing the output data with second data for the plurality of compounds;
  - (iv) selecting a new value for one or more of the plurality of selected adjustment parameters such that deviation of the comparison in step (iii) is reduced; and
  - (v) replacing the value of the one or more of the plurality of selected adjustment parameters in the program with the new value selected in step (iv).

286. The computer system of claim 285, wherein the first and second data are stored in the same data source.

287. The computer system of claim 285, wherein the first data is stored in a first data source and the second data is stored in a second data source.

288. The computer system of claim 285, further comprising:
- (vi) repeating steps (ii)–(v) one or more times until a difference between the output data and the second data is less than the largest experimental error in the first or second data or less than the largest interday variation in the first or second data.

289. The computer system of claim 288, wherein the difference is determined by one of the following: normalized difference, collective regression coefficient, normalized arithmetic mean, normalized median, normalized geometric mean, normalized harmonic mean, variance, standard deviation, or coefficient of variation.

290. The computer system of claim 285, wherein the mammalian system is human.

291. The computer system of claim 285, wherein the mammalian system is selected from the group consisting of gastrointestinal tract, liver, heart, kidney, eye, nose, lung, skin and brain.

292. The computer system of claim 291, wherein the mammalian system of interest is gastrointestinal tract, the gastrointestinal tract is modeled in segments and the segments are selected from the group consisting of stomach, duodenum, jejunum, ileum and colon.

293. The computer system of claim 285, wherein at least one of the plurality of selected adjustment parameters is applied to one or more of fluid absorption, flux, permeability, transport mechanism, transfer rate, and segment surface area.

294. The computer system of claim 285, wherein input data to the model includes data selected from the group consisting of dissolution rate, transport mechanism and formulation release rate.

295. The computer system of claim 285, wherein the first data is obtained from testing of a compound in one or more assays that generate data selected from the group consisting of cell, tissue, structure-activity relationship (SAR), and quantitative structure-activity relationship (QSAR) data.

296. The computer system of claim 285, wherein the plurality of compounds comprise compounds having diverse pharmacokinetic properties in the mammalian system of interest.

297. The computer system of claim 285, wherein the first data comprises in vivo data from a first species of mammal and the mammalian system comprises a second species of mammal.

298. The computer system of claim 297, wherein the plurality of compounds comprise compounds having different pharmacokinetic properties in the mammalian system.

299. The computer system of claim 298, wherein the program comprises a model of at least two anatomical segments of the mammalian system and a logic function module comprising a regional correlation estimation function and a control statement for initiating the function, wherein the estimation function when initiated generates an estimated value for a selected pharmacokinetic property of the compound in a first anatomical segment when supplied with an input value corresponding to the selected pharmacokinetic property in a second anatomical segment and with a regional correlation coefficient for the selected pharmacokinetic property of the first and second anatomical segments.

300. The computer system of claim 285, wherein the program comprises equations for one or more of fluid transit, fluid absorption, mass transit, mass dissolution, mass solubility, and mass absorption.

301. The computer system of claim 300, wherein the equations use initial parameter values corresponding to a physiological parameter and the plurality of selected adjustment parameters.

302. The computer system of claim 285, wherein the model uses equations and the equations comprise one or more input variables corresponding to the input data for calculating as one or more output variables the change in the property.

303. The computer system of claim 302, wherein the equations comprise one or more input variables corresponding to the input data for calculating as one or more output variables the change in an absorption property.

304. The computer system of claim 285, wherein the program comprises rules for one or more of transit, absorption, permeability, solubility, dissolution, and concentration for the mammalian system.

305. The computer system of claim 285, wherein the property is selected from the group consisting of absorption, distribution, metabolism, elimination, and toxicity.

306. The computer system of claim 285, wherein the property is selected from the group consisting of concentration, permeability, solubility, dissolution rate, transport mechanism, and formulation release rate.

307. The computer system of claim 285, wherein the property is selected from the group consisting of pH, fluid volume, fluid volume transfer rate, fluid absorption, surface area, and transit time.

308. The computer system of claim 285, further comprising a user interface on the computer.

309. A method of predicting a pharmacokinetic property of a compound in a mammalian system of interest, the method comprising:
- providing a computer comprising an input system, an output system and a model, wherein the model comprises a selected adjustment parameter, and wherein the selected adjustment parameter comprises a value obtained by:
  - (i) assigning an initial value to the selected adjustment parameter of the model;
  - (ii) inputting first data for a plurality of compounds into the model and running the model to generate output data;
  - (iii) comparing the output data with second data for the plurality of compounds;

(iv) selecting a new value for one or more of the plurality of selected adjustment parameters such that deviation of the comparison in step (iii) is reduced;

(v) replacing the value for the selected adjustment parameter with the new value selected in set (iv);

entering through the input system input data for the compound;

using the model to predict the pharmacokinetic property of the compound; and outputting a predicted pharmacokinetic property of the compound with the output system.

310. The method of claim 309, wherein the first and second data are stored in the same data source.

311. The method of claim 309, wherein the first data is stored in a first data source and the second data is stored in a second data source.

312. The method of claim 309, further comprising:

(vi) repeating steps (ii)–(v) one or more times until a difference between the output data and the second data is less than the largest experimental error in the first or second data or less than the largest interday variation in the first or second data.

313. The method of claim 312, wherein the difference is determined by one of the following: normalized difference, collective regression coefficient, normalized arithmetic mean, normalized median, normalized geometric mean, normalized harmonic mean, variance, standard deviation, or coefficient of variation.

314. The method of claim 309, wherein the selected adjustment parameter is a plurality of selected adjustment parameters and wherein step (i) assigns an initial value to each of the plurality of selected adjustment parameters, step (iv) selects a new value for one or more of the plurality of selected adjustment parameters and step (v) replaces the value for the one or more of the plurality of selected adjustment parameters and with the new value selected in step (iv).

315. The method of claim 309, wherein the computer further comprises a data processor and a memory and wherein the output system is at least a display.

316. The method of claim 315, wherein the computer is a standalone computer.

317. The method of claim 315, wherein the model is provided as computer readable program code.

318. The method of claim 317, wherein the computer readable program code is embodied in a computer readable medium.

319. The method of claim 317, wherein the computer readable program code is embodied in a memory.

320. The method of claim 315, wherein the input system and the output system comprise a user interface.

321. The method of claim 315, wherein the model models at least one of fluid transit, fluid absorption, mass transit, mass dissolution, mass solubility, and mass absorption.

322. The method of claim 315, wherein the mammalian system of interest is selected from the group consisting of gastrointestinal tract, liver, heart, kidney, eye, nose, lung, skin and brain.

323. The method of claim 315, wherein the first data comprises in vivo data from a first species of mammal and the mammalian system of interest corresponds to a second species of mammal.

324. The method of claim 323, wherein the plurality of compounds comprise compounds having different pharmacokinetic properties.

325. The method of claim 315, wherein the first data is obtained from testing of the compound in one or more assays that generate data selected from the group consisting of cell, tissue, structure-activity relationship (SAR), and quantitative structure-activity relationship (QSAR) data.

326. The method of claim 315, wherein the plurality of compounds comprise compounds having different pharmacokinetic properties.

327. The method of claim 315, wherein the input data is selected from the group consisting of concentration, permeability, solubility, dissolution rate, transport mechanism, and formulation release rate.

328. The method of claim 315, wherein the input data further comprises data selected from the group consisting of dissolution rate, transport mechanism and formulation release rate.

329. The method of claim 315, wherein the pharmacokinetic property is selected from the group consisting of absorption, distribution, metabolism, elimination and toxicity.

330. The method of claim 315, wherein the pharmacokinetic property is selected from the group consisting of pH, initial fluid volume, surface area, transit time, fluid volume transfer rate, and fluid absorption.

331. The method of claim 315, wherein the mammalian system of interest is human.

332. The method of claim 315, wherein the model models one or more of transit, absorption, permeability, solubility, dissolution, and concentration for one or more segments of the mammal system of interest.

333. The method of claim 315, wherein the model includes equations for calculating as one or more output variables the change in the pharmacokinetic property.

334. The method of claim 315, wherein the model includes equations for one or more input variables corresponding to the input data for calculating as one or more output variables the change in an absorption parameter.

335. The method of claim 315, wherein the selected adjustment parameter modifies the portion of the model for one or more of fluid absorption, flux, permeability, transport mechanism, transfer rate, and segment surface area.

336. The method of claim 315, comprising:

reversibly storing in a computer-implemented database data corresponding to a predicted pharmacokinetic property of the compound.

337. The method of claim 315, wherein the model comprises a model of at least two anatomical segments and a logic function module comprising a regional correlation estimation function and a control statement for initiating the function wherein the estimation function when initiated is capable of generating an estimated value for a selected pharmacokinetic property of the compound in a first anatomical segment when supplied with an input value corresponding to the selected pharmacokinetic property in a second anatomical segment and with a regional correlation coefficient for the selected pharmacokinetic property of the first and second anatomical segments.

338. The method of claim 337, wherein the regional correlation estimation function comprises an algorithm.

339. The method of claim 338, wherein the algorithm is selected from the group consisting of a polynomial, exponential, and logarithm.

340. A computer system for predicting a property of a compound in a mammalian system of interest, the computer system comprising:

a computer; and a program on the computer, wherein the program comprises a selected adjustment parameter, and wherein the selected adjustment parameter comprises a value obtained by:

(i) assigning an initial value to the selected adjustment parameter of the program;
(ii) inputting first data for a plurality of compounds into the program and running the program to generate output data;
(iii) comparing the output data with second data for the plurality of compounds;
(iv) selecting a new value for the selected adjustment parameter such that deviation of the comparison in step (iii) is reduced; and
(v) replacing the value of the selected adjustment parameter in the program with the value selected in step (iv).

341. The computer system of claim 340, wherein the first and second data are stored in the same data source.

342. The computer system of claim 340, wherein the first data is stored in a first data source and the second data is stored in a second data source.

343. The computer system of claim 340, further comprising:
(vi) repeating steps (ii)–(v) one or more times until a difference between the output data and the second data is less than the largest experimental error in the first or second data or less than the largest interday variation in the first or second data.

344. The method of claim 343, wherein the difference is determined by one of the following: normalized difference, collective regression coefficient, normalized arithmetic mean, normalized median, normalized geometric mean, normalized harmonic mean, variance, standard deviation, or coefficient of variation.

345. The method of claim 340, wherein the selected adjustment parameter is a plurality of selected adjustment parameters and wherein step (i) assigns an initial value to each of the plurality of selected adjustment parameters, step (iv) selects a new value for one or more of the plurality of selected adjustment parameters, and step (v) replaces the value for the one or more of the plurality of selected adjustment parameters and with the new value selected in step (iv).

346. The computer system of claim 340, wherein the program comprises a compartment-flow model for calculating time-dependent rate of absorption, extent of absorption, and concentration of a compound at a sampling site across a physiological barrier of one or more segments of the mammalian system.

347. The computer system of claim 346, wherein the selected adjustment parameter is selected from the group consisting of regional fluid absorption, permeability, flux, active transport, carrier mediated transport, compound efflux, transfer rate, and surface area.

348. The computer system of claim 346, wherein the property is selected from the group consisting of soluble mass transfer rate constant, permeability, solubility, dissolution rate, transport mechanism, pH, initial volume, surface area, transit time, fluid volume transfer rate, and fluid absorption rate.

349. A computer-implemented model of the gastrointestinal tract of a mammal for predicting a pharmacokinetic property of a compound in the mammal, the model comprising:
a computer; and
a program implementing a physiologic model on the computer, wherein the physiologic model comprises a plurality of selected adjustment parameters, and wherein the plurality of selected adjustment parameters comprise values obtained by:
(i) assigning an initial value to each of the plurality of selected adjustment parameters of the model;
(ii) inputting data from first data for a plurality of compounds into the model and running the model to generate output data;
(iii) comparing the output data with data from second data for the plurality of compounds;
(iv) selecting a new value for one or more of the plurality of selected adjustment parameters such that deviation of the comparison in step (iii) is reduced; and
(v) replacing the value of the one or more of the plurality of the selected adjustment parameters in the model with the new value selected in step (iv),
wherein the physiologic model comprises a compartment-flow model for calculating time-dependent rate of absorption, extent of absorption, and concentration of a compound at a sampling site across a physiological barrier of one or more segments of the mammalian system, wherein
the compartments are characterized by fluid volume, fluid absorption, insoluble mass, soluble mass, and mass absorption for one or more of segments of the GI tract of a mammal, the compartments are operably linked through flow regulators and converters, the flow regulators regulate flow among compartments and the converters modify the flow regulators, and wherein the flow regulators are characterized by fluid absorption rate, fluid transit rate, insoluble mass transit rate, insoluble mass dissolution rate, soluble mass transit rate, and soluble mass absorption rate.

350. The computer-implemented model of claim 349, wherein the first and second data are stored in the same data source.

351. The computer-implemented model of claim 349, wherein the first data is stored in a first data source and the second data is stored in a second data source.

352. The computer-implemented model of claim 349, further comprising:
(vi) repeating steps (ii)–(v) one or more times until a difference between the output data and the second data is less than the largest experimental error in the first or second data or less than the largest interday variation in the first or second data.

353. The computer-implemented model of claim 352, wherein the difference is determined by one of the following: normalized difference, collective regression coefficient, normalized arithmetic mean, normalized median, normalized geometric mean, normalized harmonic mean, variance, standard deviation, or coefficient of variation.

354. The computer-implemented model of claim 349, wherein the converters are characterized by fluid volume, fluid volume absorption rate constant, fluid volume transit rate constant, insoluble mass, insoluble mass transit rate constant, dissolution rate constant, soluble mass, soluble mass transit rate constant, surface area, dissolved mass concentration and permeability.

355. The computer-implemented model of claim 349, which further comprises compartments characterized by formulation and flow regulators characterized by formulation transit rate and formulation release rate.

356. The computer-implemented model of claim 349, further comprising:
compartments characterized by fluid volume and fluid volume absorption for stomach, duodenum, jejunum, ileum and colon that are operably linked through flow regulators and one or more converters that modify one or more of the flow regulators, wherein the flow regulators are characterized by fluid volume absorption rate and fluid volume transit rate, and wherein the converters are characterized by selected adjustment parameter values for one or more of fluid absorption rate constant and fluid volume transit rate constant.

357. A device for predicting a pharmacokinetic property of a compound in a mammalian system of interest, the device comprising:
modeling means for modeling at least one pharmacokinetic property of a compound in a mammal, wherein the modeling means comprises adjustment means for adjusting the model, and wherein the adjustment means is obtained by:
(i) assigning an initial value to the adjustment means;
(ii) inputting first data for a plurality of compounds into the modeling means and running the model to generate output data;
(iii) comparing the output data with second data for the plurality of compounds; and
(iv) selecting a new adjustment means such that deviation of the comparison means in step (iii) is reduced; and
applying means for applying the modeling means to predict a pharmacokinetic property of the compound.

358. The device of claim 357, wherein the first and second data are stored in the same data source.

359. The device of claim 357, wherein the first data is stored in a first data source and the second data is stored in a second data source.

360. The device of claim 357, further comprising:
(v) repeating means for repeating steps (ii)–(v) one or more times until a difference between the output data and the second data is less than the largest experimental error in the first or second data or less than the largest interday variation in the first or second data.

361. The device of claim 360, wherein the repeating means determines the difference by one of the following: normalized difference, collective regression coefficient, normalized arithmetic mean, normalized median, normalized geometric mean, normalized harmonic mean, variance, standard deviation, or coefficient of variation.

362. The device of claim 357, wherein the adjustment means is a plurality of adjustment means and wherein step (i) assigns an initial value to each of the plurality of adjustment means and step (iv) selects a new value for one or more of the plurality of adjustment means.

363. The device of claim 357, wherein the adjustment means is selected from the group consisting of a constant, a range of constants, a function, an algorithm, a plurality of functions, and a plurality of algorithms.

364. The device of claim 357, wherein the modeling means is a physiologic pharmacokinetic model of one or more anatomical segments of the mammalian system of interest.

365. The device of claim 364, wherein the mammalian system of interest is selected from the group consisting of gastrointestinal tract, liver, heart, kidney, eye, nose, lung, skin and brain.

366. The device of claim 364, wherein the mammalian system of interest is human.

367. The device of claim 364, wherein the physiologic pharmacokinetic model comprises means for determining the change in one or more physiological parameters of the one or more anatomical segments and the movement and disposition of the compound in the one or more anatomical segments as a function of time.

368. The device of claim 364, wherein the first data corresponds to one or more in vitro properties for each of the plurality of compounds.

369. The device of claim 368, wherein the first data is derived from testing of each of the plurality of compounds for at least one in vitro property in an assay that generates data, the assay selected from the group consisting of cell, tissue, physicochemical, structure-activity relationship (SAR), and quantitative structure-activity relationship (QSAR).

370. The device of claim 368, wherein the in vitro properties are selected from the group consisting of absorption, distribution, metabolism, elimination, and toxicity.

371. The device of claim 364, wherein the second data corresponds to one or more in vivo properties for each of the plurality of compounds.

372. The device of claim 371, wherein the in vivo properties are selected from the group consisting of absorption, distribution, metabolism, elimination, and toxicity.

373. The device of claim 371, wherein the plurality of compounds include compounds exhibiting different in vivo properties in the mammalian system of interest.

374. The device of claim 373, wherein the in vivo properties are selected from the group consisting of permeability, solubility, dissolution, activity, metabolism, and toxicity.

375. The device of claim 374, wherein the one or more in vivo properties are derived from testing each of the plurality of compounds in the mammalian system of interest for the one or more in vivo properties.

376. The device of claim 357, wherein the selecting step comprises a curve-fitting algorithm.

377. The device of claim 376, wherein the curve-fitting algorithm is a regression-based algorithm.

378. The device of claim 376, wherein the curve-fitting algorithm is a plurality of curve-fitting algorithms.

379. The device of claim 378, wherein the plurality of curve-fitting algorithms are a plurality of simultaneous curve-fitting algorithms.

380. A method of predicting a pharmacokinetic property of a compound in a mammalian system of interest, the method comprising:
providing a computer comprising an input system, an output system, a processor and an absorption model, wherein the model comprises a plurality of selected adjustment parameters, and wherein the selected adjustment parameters comprise values obtained by:
(i) assigning an initial value to each of the plurality of selected adjustment parameters of the model;
(ii) inputting first data for a plurality of compounds into the model and running the model to generate output data;
(iii) comparing the output data with second data for the plurality of compounds;
(iv) selecting a new value for one or more of the plurality of selected adjustment parameters such that deviation of the comparison in step (iii) is reduced; and
(v) replacing the value for the one or more at the plurality of adjustment parameters in the model with the new value selected in step (iv);
entering through the input system input data for the compound;
using the model to predict the absorption of the compound; and outputting an absorption property of the compound with the output system.

381. A method for predicting solubility of a compound in the gastrointestinal (GI) tract of a mammal, the method comprising:

providing a solubility model, wherein the solubility model is a compartment-flow model, the model comprises a plurality of selected adjustment parameters, and wherein the selected adjustment parameters comprise values obtained by:
(i) assigning an initial value to each of the plurality of selected adjustment parameters of the model;
(ii) inputting first data for a plurality of compounds into the model and running the model to generate output data;
(iii) comparing the output data with second data for the plurality of compounds;
(iv) selecting a new value for one or more of the plurality of selected adjustment parameters such that deviation of the comparison in step (iii) is reduced; and
(v) replacing the value for the one or more of the plurality of the selected adjustment parameters in the model with the new value selected in step (iv), wherein
the compartments are characterized by insoluble mass and soluble mass for stomach, duodenum, jejunum, ileum and colon that are operably linked through flow regulators and one or more converters that modify one or more of the flow regulators, wherein the flow regulators are characterized by insoluble mass transit rate, insoluble mass dissolution rate, and soluble mass transit rate, wherein the converters are characterized by insoluble mass, insoluble mass transit rate constant, insoluble mass dissolution rate constant, soluble mass, and soluble mass transit rate constant, and wherein one or more of the converters are characterized by the selected adjustment parameters; and
using the solubility model to predict solubility of a particular compound.

382. A method for predicting absorption of a compound in the gastrointestinal (GI) tract of a mammal to at least the portal vein, the method comprising:

providing an absorption model, the absorption model corresponding to a compartment-flow model, wherein the model comprises a plurality of selected adjustment parameters, and wherein the plurality of selected adjustment parameters comprise values obtained by:
(i) assigning an initial value to each of the plurality of selected adjustment parameters of the model;
(ii) inputting first data for a plurality of compounds into the model and running the model to generate output data;
(iii) comparing the output data with second data for the plurality of compounds;
(iv) selecting a new value for one or more of the plurality of selected adjustment parameters such that deviation of the comparison in step (iii) is reduced; and
(v) replacing the value of the one or more of the plurality of the selected adjustment parameters in the model with the new value selected in step (iv), wherein
compartments in the model are characterized by soluble mass and soluble mass absorption for stomach, duodenum, jejunum, ileum and colon that are operably linked through flow regulators and one or more converters that modify the flow regulators, where the flow regulators are characterized by insoluble mass transit rate, insoluble mass dissolution rate, soluble mass transit rate, soluble mass absorption rate, where the converters are characterized by insoluble mass, insoluble mass dissolution rate constant, soluble mass transit rate constant, surface area, dissolved mass concentration, and permeability, and wherein one or more of the converters are modified by one or more of the plurality of selected adjustment parameters; and
using the absorption model to predict the absorption of a particular compound.

* * * * *